(12) United States Patent
Boman et al.

(10) Patent No.: US 7,749,999 B2
(45) Date of Patent: Jul. 6, 2010

(54) ALPHA-KETOAMIDES AND DERIVATIVES THEREOF

(75) Inventors: Erik Boman, Chula Vista, CA (US); Susana Conde Ceide, San Diego, CA (US); Russell Dahl, Carlsbad, CA (US); Nancy G. J. Delaet, San Diego, CA (US); Justin Ernst, San Diego, CA (US); Antonio Garrido Montalban, San Diego, CA (US); Hiroshi Nakanishi, San Diego, CA (US); Edward Roberts, Fallbrook, CA (US); Eddine Saiah, La Jolla, CA (US); Robert Sullivan, Vista, CA (US); Zhinjun Wang, San Diego, CA (US); Jeffrey Kahl, San Diego, CA (US); Christopher Larson, San Diego, CA (US)

(73) Assignee: Itherx Pharmaceuticals, Inc., San Diego, CA (US)

( * ) Notice: Subject to any disclaimer, the term of this patent is extended or adjusted under 35 U.S.C. 154(b) by 413 days.

(21) Appl. No.: 10/939,324

(22) Filed: Sep. 10, 2004

(65) Prior Publication Data

US 2005/0107399 A1  May 19, 2005

Related U.S. Application Data

(60) Provisional application No. 60/502,569, filed on Sep. 11, 2003, provisional application No. 60/531,234, filed on Dec. 18, 2003, provisional application No. 60/575,704, filed on May 28, 2004, provisional application No. 60/585,012, filed on Jul. 2, 2004.

(51) Int. Cl.
*A61K 31/535* (2006.01)
*C07D 265/30* (2006.01)

(52) U.S. Cl. .................................. 514/231.2; 544/106
(58) Field of Classification Search ................. 544/106; 514/231.2
See application file for complete search history.

(56) References Cited

U.S. PATENT DOCUMENTS

| | | | |
|---|---|---|---|
| 3,546,219 A | 12/1970 | Long et al. | |
| 3,626,008 A | 12/1971 | Biland | |
| 4,029,671 A | 6/1977 | Friedman et al. | |
| 4,761,424 A | 8/1988 | Carethers et al. | |
| 6,143,931 A | 11/2000 | Baldino et al. | |
| 6,197,750 B1 | 3/2001 | Karanewsky et al. | |
| 6,452,050 B1 | 9/2002 | Baldino et al. | |
| 6,525,046 B1 | 2/2003 | Cirillo et al. | |
| 6,562,558 B1 | 5/2003 | Begley et al. | |
| 6,583,282 B1 | 6/2003 | Zhang et al. | |
| 6,734,301 B2 | 5/2004 | Ennis et al. | |
| 6,794,380 B2 | 9/2004 | Brown | |
| 6,797,267 B2 | 9/2004 | Horwitz | |
| 2003/0008868 A1 | 1/2003 | Francesco Cirillo et al. | |
| 2003/0060455 A1 | 3/2003 | Moss et al. | |
| 2003/0068340 A1 | 4/2003 | Cappola et al. | |
| 2003/0125354 A1 | 7/2003 | Hao et al. | |
| 2003/0130309 A1 | 7/2003 | Moss et al. | |
| 2003/0162968 A1 | 8/2003 | Cirillo et al. | |
| 2003/0225089 A1 | 12/2003 | Jung et al. | |
| 2003/0236193 A1 | 12/2003 | Oliner et al. | |
| 2004/0023961 A1 | 2/2004 | Dumas et al. | |
| 2004/0044020 A1 | 3/2004 | Meade et al. | |
| 2004/0048797 A1 | 3/2004 | Miller et al. | |
| 2004/0110755 A1 | 6/2004 | Simianer et al. | |
| 2004/0166111 A1 | 8/2004 | Kaymakcalan et al. | |
| 2004/0192653 A1 | 9/2004 | Munson et al. | |
| 2004/0192748 A1 | 9/2004 | Barbosa, Jr. et al. | |
| 2004/0198697 A1 | 10/2004 | Cohen et al. | |
| 2005/0176687 A1 | 8/2005 | Moussy et al. | |

FOREIGN PATENT DOCUMENTS

| | | |
|---|---|---|
| EP | 190457 | 8/1986 |
| EP | 0 049 0263 | 6/1992 |
| EP | 514264 | 11/1992 |
| EP | 661260 | 7/1995 |
| EP | 747347 | 12/1996 |
| EP | 1022027 | 7/2000 |
| FR | 2834288 | 7/2003 |
| JP | 05201980 | 8/1993 |
| JP | 07224041 | 8/1995 |
| JP | 2001031636 | 2/2001 |
| JP | 2003335733 | 11/2003 |
| WO | WO 92/06948 | 4/1992 |

(Continued)

OTHER PUBLICATIONS

Miller et al., J. Agr. Food Chem., vol. 22, No. 5, 1974, especially p. 854, col. 1.*

(Continued)

*Primary Examiner*—Golam M. M. Shameem
*Assistant Examiner*—Susannah Chung
(74) *Attorney, Agent, or Firm*—Foley & Lardner LLP

(57) ABSTRACT

The present invention provides low molecular weight compounds useful as cytokine inhibitors, and compositions thereof. In particular, compounds of the invention are useful as anti-inflammatory agents. There are further provided methods for the preparation of such agents and their use in preventing or treating conditions mediated by cytokines such as arthritis.

35 Claims, No Drawings

FOREIGN PATENT DOCUMENTS

| | | |
|---|---|---|
| WO | WO 98/09946 | 3/1998 |
| WO | WO 98/46551 | 10/1998 |
| WO | WO 98/46559 | 10/1998 |
| WO | WO 99/23091 | 5/1999 |
| WO | WO 99/32110 | 7/1999 |
| WO | WO 99/32463 | 7/1999 |
| WO | WO 99/51224 | 10/1999 |
| WO | WO 99/55696 | 11/1999 |
| WO | WO 99/64044 | 12/1999 |
| WO | WO 00/16769 | 3/2000 |
| WO | WO 00/18725 | 4/2000 |
| WO | WO 00/18738 | 4/2000 |
| WO | WO 00/43384 | 7/2000 |
| WO | WO 00/50425 | 8/2000 |
| WO | WO 00/55151 | 9/2000 |
| WO | WO 01/01986 | 1/2001 |
| WO | WO 01/10821 | 2/2001 |
| WO | WO 01/12187 | 2/2001 |
| WO | WO 01/12189 | 2/2001 |
| WO | WO 01/36403 | 5/2001 |
| WO | WO 01/47913 | 7/2001 |
| WO | WO 01/47916 | 7/2001 |
| WO | WO 01/55144 | 8/2001 |
| WO | WO 01/58869 | 8/2001 |
| WO | WO 02/08225 | 1/2002 |
| WO | WO 02/32862 | 4/2002 |
| WO | WO 02/42248 | 5/2002 |
| WO | WO 02/42292 | 5/2002 |
| WO | WO 02/066442 | 8/2002 |
| WO | WO 02/072571 | 9/2002 |
| WO | WO 02/083628 | 10/2002 |
| WO | WO 02/085859 | 10/2002 |
| WO | WO 02/092576 | 11/2002 |
| WO | WO 02/096876 | 12/2002 |
| WO | WO 02/098869 | 12/2002 |
| WO | WO 03/000680 | 1/2003 |
| WO | WO 03/005999 | 1/2003 |
| WO | WO 03/010159 | 2/2003 |
| WO | WO 03/022273 | 3/2003 |
| WO | WO 03/049742 | 6/2003 |
| WO | WO 03/068221 | 8/2003 |
| WO | WO 03/068223 | 8/2003 |
| WO | WO 03/072569 | 9/2003 |
| WO | WO 03/084539 | 10/2003 |
| WO | WO 2004/004725 | 1/2004 |
| WO | WO 2004/013127 | 2/2004 |
| WO | WO 2004/022041 | 3/2004 |
| WO | WO 2004/024727 | 3/2004 |
| WO | WO 2004/045607 | 6/2004 |
| WO | WO 2004/058724 | 7/2004 |
| WO | WO 2004/083193 | 9/2004 |

OTHER PUBLICATIONS

Kim et al., Journal of the Chemical Society, Perkin Transactions 1, vol. 3, 1995, 253-9.*
Kim et al., J. Chem. Soc., Perkin Trans 1, vol. 3, 1995, 253-9, especially p. 253.*
Abjil, Atherosclerose en ontsteking: de betekenis van C-reactieve proteine. Ned Tijdschr Geneeskd, 2003, 147(1), 15-20.
Ablamunits, et. al., "Islet T Cells Secreting IFN-γ in NOD Mouse Diabetes: Arrest by p277 Peptide Treatment," J. Autoimmun., 1988, 11, 73-81.
Abu-Amer, et. al., "Tumor Necrosis Factor Receptors Types 1 and 2 Differentially Regulate Osteoclastogenesis," J. Biol. Chem., 2000, 275(35), 27307-10.
Akaike, et. al., "Free radicals in viral pathogenesis: molecular mechanisms involving superoxide and NO," Proc. Soc. Exp. Biol. Med., 1998, 217, 64-73.
Alexander, et. al., "Mechanisms of innate resistance to *Toxoplasma gondii* infection," Philos. Trans. R. Soc. Lond. B. Biol. Sci., 1997, 352, 1355-1359.
Aliev et al., Synthesis and structure of 5-p-ethoxyphenyl-3-methoxycarbonyl-1-p-tolyl-4-p-tolyloxamoylpyrazole. Russian Chemical Bulletin (Translation of Izvestiya Akademil Nauk, Seriya Khimicheskaya), 48(3): 604-607, 1999.
Bacqui, et. al., "Enhanced Interleukin-1β, Interleukin-6 and Tumor Necrosis Factor-α Production By LPS Stimulated Human Monocytes Isolated From HIV+ Patients," Immunopharmacol. Immunotoxicol, 2000, 22(3), 401-421.
Baronzio, et. al., "Proinflammatory and regulatory cytokine levels in AIDS cachexia," In Vivo, 1999, 13(6), 499-502.
Barry, et. al., "A Molecular Rearrangement During the Reduction of Thionaphthenopyrazole Dioxides," J. Chem. Soc., 1956, 4974-4978.
Beisel, "Herman Award Lecture, 1995: infection-induced malnutrition—from cholera to cytokines," Am. J. Clin. Nutr., 1995, 62, 813-819.
Ben-Bassat, "Biological activity of tyrosine kinase inhibitors: Novel agents for psoriasis therapy," Current Opinion in Investigational Drugs, 2001, 2(11), 1539-1545.
Bodor, "Novel Approaches In Prodrug Design," Drugs of the Future, 1981, 6, 165-182.
Bonay, "Characterization of proliferative responses and cytokine mRNA profiles induced by *Vespula* venom in patients with severe reactions to wasp stings," Clin. Exp. Immunol., 1997, 109, 342-350.
Borjesson, et. al., TNF-α stimulates alveolar liquid clearance during intestinal ischemia-reperfusion in rats, Amer. J. Physiol., 2000, 278, L-3-L12.
Bozkurt, "Results of Targeted Anti-Tumor Necrosis Factor Therapy With Etanercept (ENBREL) in Patients With Advanced Heart Failure," Circulation, 2001, Feb. 27, 103(8) 1044-1047.
Branger, et. al., "Anti-Inflammatory Effects of a p38 Mitogen-Activated Protein Kinase Inhibitor During Human Endotoxemia," J. Immunol., 2002, 168(8) 4070-4077.
Bresnihan, et. al., Treatment of rheumatoid arthritis with recombinant human interleukin-1 receptor antagonist, Arthritis. Rheum., 1998, 41:2196-2204.
Bruserud, "Effects of Endogenous Interleukin 1 on Blast Cells Derived From Acute Myelognoeus Leukemia Patients," Leukemia Res., 1996, 20, 65-73.
Burke, et. al., "Early Development of Acute Myelogenous Leukemia Following Kidney Transplantation: Possible Role of Multiple Serum Cytokines," Leuk. Lymphoma., 1995, 19, 173-180.
Chen et al., Rapid synthesis of α-ketoamides using microwave irradiation-simultaneous cooling method. Tetrahedron Lett., 44:8873-8876, 2003.
Chevalier, "Upregulation of enzymatic activity by interleukin-1 in osteoarthritis," Biomed. Pharmacother., 1997, 51, 58-62.
Childs, "Efficacy of Etanercept for Wear Debris—Induced Osteolysis," J. Bone Miner. Res., 2001, 16, 338-347.
Chisari, et. al., "Hepatitis B virus immunology," Sprinter Semin. Immunopathol., 1995, 17, 261-281.
Clarmunt, et. al., "3(5)-(1-Adamantyl)pyrazoles: chemistry and molecular structure," J. Chem. Soc., Perkin Trans., 2(10), 2000, 2049-2053.
Cominelli, et. al., "Interleukin-1 and interleukin-1 receptor antagonist in inflammatory bowel disease," Aliment Pharmacol. Ther., 1996, 10, 49.
Crowe, et. al., GM-CSF and its effects on replication of HIV-1 in cells of macrophage lineage, Journal of Leukocyte Biology, 1997, 62, 41-48.
Dallalio, et. al., "Cytokine and Cytokine Receptor Concentrations in Bone Marrow Supernatant from Patients with HIV: Correlation with Hematologic Parameters," J. Investig. Med., 1999, 47(9), 477-483.
Delima, et. al., "Soluble antagonists to interleukin-1 (IL-1) and tumor necrosis factor (TNF) inhibits loss of tissue attachment in experimental periodontitis," J. Clin. Peridontol., 2001, 28(3), 233-40.
De Sio, "Chemical and photochemical behaviours of 5-benzoylamido-4-diazo-1-methyl-3-phenylphrazole." Heterocycles, 22:2309-2311, 1984.
Dinarello, et. al., "Interleukin-1," Rev. Infect. Diseases, 1984, 6, 51-95.

Dinarello, "Interleukin-1 and Interleukin-1 Receptor Antagonist," Nutrition, 1995, 11, 492-494.

Dischino et al., Synthesis of carbon-14 labeled (R)-3-fluoro-4-(2'-(5'',6'',7'',8''-tetrahydro-5'',5'',8'',8''-tetramethyl-2''-naphthyl)-[2'-hydroxy-14C])[carbonyl-14C]acetamidobenzoic acid. Journal of Labelled Compounds and Radiopharmaceuticals, 46(2): 159-165, 2003.

Donnahoo, "Review Article: The Role of Tumor Necrosis Factor in Renal Ischemia-Reperfusion Injury," J. Urol., 1999, 162(1), 196-203.

Ershler, et. al., "Immunologic Aspects of Osteoporosis," Development and Comparative Immunol., 1997, 21, 487-499.

Escher, et. al., "Treatment of Inflammatory Bowel Disease in Childhood: Best Available Evidence," Inflamm. Bowel. Dis., 2003, Jan. 9(1), 34-58.

Evans, et. al., "Nitric Oxide and Bone," J. Bone Miner. Res., 1996, 11, 300-305.

Feldman, et. al., "The Role of Tumor Necrosis Factor in the Pathophysiology of Heart Failure," J. Amer. College of Cardiology, 2000, 35(3), 537-544.

Felix, "Cleavage of Protecting Groups with Boron Tribromide," J. Org. Chem., 1974, 39(10), 1427-1429.

Galadari, et. al., "Newly available treatments for psoriatic arthritis and their impact on skin psoriasis," Int. J. Dermatol., 2003, 42, 231-237.

Geng, "Regulation of programmed cell death or apoptosis in atherosclerosis," Heart Vessels, 1997, Suppl 12, 76-80.

Grammas, "Inflammatory factors are elevated in brain microvessels in Alzheimer's disease," Neurobiol. Aging, 2001, 22(6), 837-842.

Griffiths, "Novel therapeutic approaches to psoriasis," Hospital Medicine, 1998, vol. 59(7), 539-542.

Groul, et. al., "Physiological and Pathological Roles of Interleukin-6 in the Central Nervous System," Molecular Neurobiology, 1997, 15, 307-339.

Hayden, et. al., "Local and Systemic Cytokine Responses during Experimental Human Influenza A Virus Infection," J. Clin. Invest., 1998, 101, 643-649.

Heath, et. al., "Improved deprotection of cysteine-containing peptides in HF," J. Pept. Protein Res., 1986, 28, 498-507.

Henry, et. al., "p38 mitogen-activated protein kinase as a target for drug discovery," Drugs Fut., 1999, 24, 1345-1354.

Higham, et. al., "Tumour necrosis factor-α gene promoter polymorphism in chronic obstructive pulmonary disease," Eur. Respiratory J., 2000, 15, 281-284.

Holden, et. al., "The Role of Tumor Necrosis Factor-α in the Pathogenesis of Anorexia and Bulimia Nervosa, Cancer Cachexia and Obesity," Med. Hypotheses., 1996, 47, 423-438.

Horowitz, "Control of osteoclastogenesis and bone resorption by members of the TNF family of receptors and ligands," Cytokine Growth Factor Rev., 2001, 12(1), 9-18.

Hüttel, et. al., "Die Bromierung der Pyrazole," Justis Liebigs Ann. Chem., 1955, 593, 179-199.

Jaffray, et. al., J. Surg. Res., 2000, 90(2), 95-101.

Jewell, Discussion of paper by Sartor, Aliment Pharmacol. Ther., 1996, 10(Supp. 2), 43-44.

Karkar, et. al., "Prevention and treatment of experimental crescentic glomerulonephritis by blocking tumour necrosis factor—α," Nephrol. Dial. Transplant, 2001, 16(3), 518-524.

Kilboum, et. al., "Nitric Oxide and Shock," Dis. Mon., 1997, 43, 279-348.

Kluger, et. al., "The Use of Knockout Mice To Understand The Role of Cytokines in Fever," Clin. Exp. Pharmacol. Physiol., 1998, 25, 141-144.

Kruezer, et. al., "The IL-1 system in HIV infection: peripheral concentrations of IL-1β, IL-1 receptor antagonist and soluble IL-1 receptor type II," Clin. Exp. Immunol., 1997, 109(1), 54-58.

Krishnadasan, "The role of proinflammatory cytokines in lung ischemia-reperfusion injury," J. Thorac. Cardiovasc. Surg., 2003, 125(2), 261-72.

Lavine, et. al., Circulating Antibody Against Tumor Necrosis Factor-Alpha Protects Rat Brain from Reperfusion Injury, J. Cereb. Blood Flow Metab., 1998, 18(1), 52-58.

Lee, "Cytokine networks in the pathogenesis of bronchial asthma: implications for therapy," J. R. Coll. Physicians Lond., 1998, 32(1), 56-64.

Lemay, et. al., "Prominent and Sustained up-Regulation of GP130-Signaling Cytokines and of the Chemokine MIP-2 In Murine Renal Ischemia-Reperfusion Injury," Transplantation, 2000, 69, 959-963.

Li, et. al., Facile Regio- and Stereoselective Total Synthesis of Racemic Aklavione,: J. Am. Chem. Soc., 1981, 103, 7007-7009.

Linton et al, Oxamyl dipeptide caspase inhibitors developed for the treatment of strokes. Bioorg. Med. Chem. Lett., 14:2685-91, 2004.

Loffreda, et. al., "Leptin regulates proinflammatory immune responses," FASEB J., 1998, 12, 57-.

Manaev, et. al., "Nucleophilic Substitution Reactions in 4-Halonitropyrazolecarboxylic Acids," Chem. Heterocycl. Compd., 1986, 22(3), 265-267.

Martino, et. al., "Proinflammatory Cytokines Regulate Antigen-Independent T-Cell Activation by Two Separate Calcium-Signaling Pathways in Multiple Sclerosis Patients," Ann. Neurol., 1998, 43, 340-349.

Masucci, "New clinical applications of granulocyte-macrophage colony-stimulating factor," Medical Oncology, 1996, 13, 149-154.

McDaniel, et. al., "Cytokines and Nitric Oxide in Islet Inflammation and Diabetes," Proc. Soc. Exp. Biol. Med., 1996, 211, 24-32.

McTiernan, et. al., "The Role of Tumor Necrosis Factor Alpha in the Pathophysiology of Congestive Heart Failure," Curr. Cardiol. Rep., 2000, 2(3), 189-197.

Mills, et. al., "Cytokines Expressed in Multinucleated Cells: Paget's Disease and Giant Cell tumors versus Normal Bone," Calcif. Tissue Int., 1997, 61, 16-21.

Mitsui, et. al., "The expression of proinflammatory cytokine mRNA in the sciatic—tibial nerve of ischemia—reperfusion injury," Brain Res., 1999, 844, 192-195.

Mizia-Stec, et. al., "Hyperlipidaemias and serum cytokines in patients with coronary artery disease," Acta. Cardiol., 2003, 58(1), 9-15.

Moreland, et. al., "Etanercept Therapy in Rheumatoid Arthritis: A Randomized, Controlled Trail," Ann. Intern. Med., 1999, 130, 478-486.

Moskaleuko and Shumelyak, Action of phosphorus pentasulfide on 5-acetamidothiohydantoins and 4-bromo-5-acetamidopyrazoles. Chemistry of Heterocyclic Compounds, 10(7): 813-815, 1974.

Muller, et. al., "Basic Science Answers To Questions In Clinical Contact Dermatitis," Am. J. Contact Dernat., 1996, 7, 177-184.

Newton, et. al., "Cyclic Meso-ionic Compounds. Part 21.[1] The Examination of Nitro-derivatives of Meso-ionic Heterocycles as Potential Pharmaceuticals," J. Chem. Soc. Perkin Trans. 1984, 1, 63-67.

Notari, "Theory and Practice of Prodrug Kinetics," Methods in Enzymology, 1985, 112, 309-323.

O'Banion, et. al., "cDNA cloning and functional activity of a glucocorticoid-regulated inflammatory cyclooxygenase," Proc. Natl. Acad. Sci. USA, 1992, 89, 4888-4892.

Orfanos, "Treatment of Psoriasis with Retinoids: Present Status," Cutis, 1999, 64(5), 347-353.

Parkman, "Chronic graft-versus-host disease," Curr. Opin. Hematol., 1998, 5, 22-25.

Patel et al., Enanthioselective microbial reduction of 2-oxo-2-(1',2',3',4'-tetrahydro-1',1',4',4'-tetramethyl-6'-naphthalenyl)acatic acid and its ether ester. Tetrahedron: Asymmetry, 13(4): 349-355, 2002.

Peeters, et. al., "Pro-inflammatory cytokines in patients with essential hypertension," Eur. J. Clin. Invest., 2001, 31, 31-36.

Plate, et. al., "Synthesis and Muscarinic Activities of 3-(Pyrazolyl)-1,2,5,6-tetrahydropyridine Derivatives," Bioorg. Med. Chem., 1996, 4(2), 227-237.

Qi, "BMP4 supports self-renewal of embryonic stem cells by inhibiting mitogen-activated protein kinase pathways," Proc. Natl. Acad. Sci. USA, 2004, 101, 6027-6032.

Rankin, et. al., "The Therapeutic Effects of An Engineered Human Anti-Tumour Necrosis Factor Alpha Antibody (CDP571) In Rheumatoid Arthritis," Br. J. Rheumatol., 1995, 34, 334-342.

Reimold, New Indications for Treatment of Chronic Inflammation by TNF-α Blockade, Am. J. Med. Sci., 2003, 352(2), 75-92.

Rempel, et. al., "Interleukin-1β up-regulates expression of neurofilament light in human neuronal cells," J. Neurochem., 2001, 78(3), 640-645.

Sakakibara, et. al., "Use of Anhydrous Hydrogen Fluoride in Peptide Synthesis. I. Behavior of Various Protective Groups in Anhydrous Hydrogen Fluoride," Bull. Chem. Soc. Jpn., 1967, 40, 2164-2167.

Salim, et. al., "Targeting interleukin-2 as a treatment for psoriasis," Current Opinion in Investigational Drugs, 2001, 2(11), 1546-1548.

Salituro, et. al., "Inhibitors of p38 MAP Kinase: Therapeutic Intervention in Cytokine-Mediated Diseases," Curr. Med. Chem., 1999, 6, 807-823.

Sandborn, et. al., "Strategies for targeting tumour necrosis factor in IBD," Best Pract. Res. Clin. Gastroenterol., 2003, 17(1), 105-117.

Saurat, "Retinoids and psoriasis: Novel issues in retinoid pharmacology and implications for psoriasis treatment," J. Am. Acad. Derm., 1999, 41(3)Pt.2, S2-S6.

Scholz, et. al., "Inhibition of FcεRI-Medicated Activation of Mast Cells by 2,3,4-Trihydropyrimidinol[2,1-α]isoquinolines," J. Med. Chem., 1998, 41, 1050-1059.

Schon, Animal models of Psoriasis—What can we learn from them, The Society for Investigative Dermatology—Reviews, 1999, 112(4), 405-410.

Shohami, et. al., "Cytokine production in the brain following closed head injury dexanabinol (HU-211) is a novel TNF-α inhibitor and an effective neuroprotectant," J. Neuroimmunol., 1997, 72, 169-177.

Simpson, et. al., "Interleukin-6: Structure-function relationships," Protein Sci., 1997, 6, 929-955.

Singh, et. al., "Inducible Nitric Oxide Synthase in Vascular Smooth Muscle Cells From Prehypertensive Spontaneously Hypertensive Rats," Am. J. Hypertens., 1996, 9, 867-877.

Sirisoma, et. al., "Fipronil-based Phtoaffinity Probe for Drosophila and Human β3 GABA Receptors," Bioorg. Med. Chem. Lett., 2001, 11(22), 2979-2981.

Strassman, et. al., "Inhibition of experimental cancer cachexia by anti-cytokine and anti-cytokine-receptor therapy," Cytokins. Mol. Ther., 1995, 1, 107-113.

Szepietowski, et. al., "Atopic and non-atopic individuals react to nickel challenge in a similar way. A study of the cytokine profile in nickel-induced contact dermatitis," Br. J. Dermatol., 1997, 137, 195-200.

Takabatake, et. al., The Relationship between Chronic Hypoxemia and Activation of the Tumor Necrosis Factor-α System in Patients with Chronic Obstructive Pulmonary Disease, Amer. J. Resp. & Crit. Care Med., 2000, 161(4)Pt.1, 1179-1184.

Teramoto, et. al., Serum IgE level is negatively correlated with the ability of peripheral mononuclear cells to produce interferon gamma (IFNγ): evidence of reduced expression of IFNγ mRNA in atopic patients.

Terregino, et. al., "Endogenous Mediators in Emergency Department Patients With Presumed Sepsis: Are Levels Associated With Progression to Severe Sepsis and Death?," Ann. Emerg. Med., 2000, 35(1), 26-34.

Treon, et. al., "Interleukin-6 in multiple myeloma and related plasma cell dyscrasias," Current Opinion in Hematology, 1998, 5, 42-48.

Thiruvikraman, et. al., "Synthesis of Pyrazolo[3,4]thiazoles," Chem. Soc., Jpn., 1985, 58, 785-786.

Tutrone, "Biologic Therapy for Psoriasis, A Brief History, I," Biologic Therapy for Psoriasis, 2001, 68, 331-336.

Udomsangpetch, et. al., "Involvement of Cytokines in the Histopathology of Cerebral Malaria," Am. J. Trop. Med. Hyg., 1997, 57, 501-506.

van de Kerkhof, "Combinations and Comparisons," Clinics in Dermatology, 1997, 15, 831-834.

Van't Hof, "Nitric oxide and bone," Immunology, 2001, 103(3), 255-261.

Winther, et. al., Viral-induced rhinitis. Am. J. Rhinol., 1998, 12:17-20.

Wooley, "Animal Models of Arthritis," Rheumatoid Arthritis: Animal Models of Arthritis, in Klippel J. H., Dieppe, P. A., (eds.), 1998, 5, 8.1-8.6.

Xuan, et. al., Effective Treatment of Experimental Uveitis with Interleukin-1 Blockers, CK 123 and CK 124, J. Ocular. Pharmacol. And Ther., 1998, 14, 31-44.

Yang, et. al., "The Physiologic Consequences of Macrophage Pacification During Severe Acute Pancreatitis," Shock, 1998, 10(3), 169-175.

International Search Report for PCT Application PCT/US2004/29372 filed Sep. 10, 2004.

Regan et al., Structure-activity relationships of the p38α MAP kinase inhibitor 1-(5-*tert*-Butyl-2-*p*-tolyl-2*H*-pyrazol-3-yl)-3-[4-(2-morpholin-4-yl-ethoxy)naph-thalen-1-yl]urea (BIRD 796). J. Med. Chem., 46: 4676-4686, 2003.

Hamajima et al., Studies on the compounds related to azulene. II. Synthesis and antiallergic activity of p-(3-gualazulenyl azo) benzenesulfonamides. Yakugaku Zasshi, 98(8): 1108-13, 1978. Abstract.

Hamajima et al., Studies on the compounds related to azulene. II. Synthesis and antiallergic activity of gualazulenylglyoxylamides, gualazulenylglyoxylic acid eaters and acylaminoguaiazulenes. Yakugaku Zasshi, 98(8): 1101-7, 1978. Abstract.

Fries, Zur Kenntnis des Oxindigos. Ann. 442:254-305, 1925. (German language).

Bartens and Pusch, Oxindigo, Dibenzo-4,5,4',5' and dibenzo-6,7,6',7,-oxindigo. Ann. 442:254-305, 1925. (English Abstract of a Section of Reference A1 above).

Fries, Oxindigo.II. Ann. 442:254-305, 1925. (English Abstract of a Section of Reference A1 above).

Hamajima et al., Studies on the compounds related to Azulene.I. Synthesis and antiallergic activity of guaiazulenylglyoxylamides, guaiazulenylglyoxylic acid esters and acylaminoguaiazulenes. Yakugaku Zasshi, 98(8): 1101-7, 1978.

Hamajima et al., Studies on the compounds related to Azulene.II. Synthesis and antiallergic activity of p-(3-Guaiazulenyl Azo) benzenesulfonamides. Yakugaku Zasshi, 98(8): 1108-13, 1978.

Daniel R. Goldberg et al., "Discovery and Optimization of p38 Inhibitors via Computer-Assisted Drug Design", *Journal of Medicinal Chemistry*, 2007, A-K.

Mitsui, et. al., "The expression of proinflammatory cytokine mRNA in the sciatic—tibial nerve of ischemia—reperfusion injury," Brain Res., 1999, 844, 192-195.

Mizia-Stec, et. al., "Hyperlipidaemias and serum cytokines in patients with coronary artery disease," Acta. Cardiol., 2003, 58(1), 9-15.

Moreland, et. al., "Etanercept Therapy in Rheumatoid Arthritis: A Randomized, Controlled Trail," Ann. Intern. Med., 1999, 130, 478-486.

Moskaleuko and Shumelyak, Action of phosphorus pentasulfide on 5-acetamidothiohydantoins and 4-bromo-5-acetamidopyrazoles. Chemistry of Heterocyclic Compounds, 10(7): 813-815, 1974.

Muller, et. al., "Basic Science Answers To Questions in Clinical Contact Dermatitis," Am. J. Contact Dernat., 1996, 7, 177-184.

Newton, et. al., "Cyclic Meso-ionic Compounds. Part 21. The Examination of Nitro-derivatives of Meso-ionic Heterocycles as Potential Pharmaceuticals," J. Chem. Soc. Perkin Trans. 1984, 1, 63-67.

Notari, "Theory and Practice of Prodrug Kinetics," Methods in Enzymology, 1985, 112, 309-323.

O'Banion, et. at., "cDNA cloning and functional activity of a glucocorticoid-regulated inflammatory cyclooxygenase," Proc. Natl. Acad. Sci. USA, 1992, 89, 4888-4892.

Orfanos, "Treatment of Psoriasis with Retinoids: Present Status," Cutis, 1999, 64(5), 347-353.

Parkman, "Chronic graft-versus-host disease," Curr. Opin. Hematol., 1998, 5, 22-25.

Patel et al., Enanthioselective microbial reduction of 2-oxo-2-(1',2',3',4'-tetrahydro-1',1',4',4'-tetramethyl-6'-naphthalenyl)acatic acid and its ether ester. Tetrahedron: Asymmetry, 13(4): 349-355, 2002.

Peeters, et. al., "Pro-inflammatory cytokines in patients with essential hypertension," Eur. J. Clin. Invest., 2001, 31, 31-36.

Database CA [Online] Chemical Abstracts Service Abstract for Ehrhardt, Heinz et al: "Amides and thioamides of squaric acid: syntheses and reactions" and Abstract for Chemische Berichte, 110(7), 2506-23, ISSN: 0009-2940, 1977. XP-002519129.

Giua, Michele. New method for manufacturing picryl sulfide. Gazzetta Chimica Italiana, vol. 54, (1924), pp. 509-516.

Giua and de Franciscis, Azione del cloruro di ossalile sui naftoli. Gazzetta Chimica Italiana, 54:509-516, 1924. ISSN: 0016-5603, Full English translation is being provided herewith: Giua and de Franciscis, The action of oxalyl chloride on the naphthols. Italian Chemical Gazette, 54:509-516, 1924.

Fries and Pusch, Zur Kenntnis des Oxindigos. Justus Liebigs Annalen fer Chemie, 442:255-305, 1925. ISSN 0075-4617, Partial English translation is being provided herewith: pp. 259 (starting with last paragraph of the page) -261 (ending with section entitled Versuche) and pp. 272 (starting at the middle of the page beginning with Uber Dibenzo . . . ) -277 (ending with 4$^{th}$ line from the bottom of the page).

* cited by examiner

ALPHA-KETOAMIDES AND DERIVATIVES THEREOF

CROSS-REFERENCES TO RELATED APPLICATIONS

This application claims priority to U.S. Provisional Application No. 60/502,569, filed Sep. 11, 2003, U.S. Provisional Application No. 60/531,234, filed Dec. 18, 2003, U.S. Provisional Application No. 60/575,704, filed May 28, 2004, and U.S. Provisional Application 60/585,012, filed Jul. 2, 2004, the entire contents of which are herein incorporated by reference.

FIELD OF THE INVENTION

The present invention relates to low molecular weight compounds and compositions thereof, useful as cytokine inhibitors, and their preparation. The invention further relates to methods of prevention and treatment of cytokine mediated diseases.

BACKGROUND OF THE INVENTION

Tumor necrosis factor-α (TNF-α) and interleukin-1 (IL-1) are proinflammatory cytokines that mediate inflammatory responses associated with infectious agents and other cellular stresses. Overproduction of cytokines such as IL-1 and TNF-α is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others (Dinarello, C. A. et al., Rev. Infect. Diseases 1984, 6:51; Salituro et al., Curr. Med. Chem. 1999, 6:807-823; Henry et al., Drugs Fut. 1999, 24:1345-1354). An accepted therapeutic approach for potential drug intervention in these conditions is the reduction of proinflammatory cytokines such as TNF-α (also referred to as TNFa) and interleukin-1β (IL-1b).

Recent data from clinical trials support the use of protein antagonists of cytokines, for example soluble TNFa receptor fusion protein (etanercept) (Moreland et al., Ann. Intern. Med. 1999, 130:478-486) or the monoclonal TNFa antibody (Enbrel) for the treatment of rheumatoid arthritis, Crohn's disease, juvenile chronic arthritis and psoriatic arthritis (Rankin et al., Br. J. Rheumatol. 1995, 34:334-342; Galadari et al. Int J Dermatol. 2003, 42:231-7; Reimold, Am J Med Sci. 2003 325(2):75-92). Thus, small molecules that inhibit or antagonize the effects of cytokines such as, for example, TNFa and or IL-1b are expected to be beneficial for the treatment rheumatoid arthritis, Crohn's disease, juvenile chronic arthritis and psoriatic arthritis.

Il-1 is detected in synovial fluid and in cartilage matrix joints of patients with osteoarthritis. IL-1 antagonists have been shown to diminish the degradation of cartilage matrix components in a variety of experimental models of arthritis (Chevalier, Biomed Pharmacother. 1997, 51:58).

Il-1 receptor antagonists have been evaluated in humans (Bresnihan et al., Arthritis Rheum. 1998, 41:2196-2204). Efficacy has been demonstrated for the treatment of rheumatoid arthritis (Antril, Amgen). Il-1 receptor antagonist also demonstrated reduced mortality in a group of patients with septic shock syndrome (Dinarello, Nutrition 1995, 11:492).

Cytokines such as IL-1 and TNFa are potent stimulators of nitric oxide (NO) production. NO is a mediator of cardiovascular homeostasis, neurotransmission, immune function and a modulator of bone remodeling with effects on osteoblasts and osteoclasts (van't Hof, Immunology 2001, 103(3):255-61 Evans, et al., J. Bone Miner. Res. 1996, 11:300).

IL-1 has also been linked to beta-cell destruction which is one of the hallmarks of insulin dependent diabetes mellitus. Although other factors can also mediate beta-cell damage, Il-1 is linked to this process through its effect on cyclooxygenase II (COX-2) and inducible NO synthase (McDaniel et al., Proc Soc Exp Biol Med. 1996, 211:24).

IL-1 has also been shown to induce uveitis in rats which could be inhibited with IL-1 blockers. (Xuan et al., J. Ocular Pharmacol. and Ther. 1998, 14: 31). Cytokines including IL-1, TNFa and GM-CSF have been shown to stimulate proliferation of acute myelogenous leukemia blasts (Bruserud, Leukemia Res. 1996, 20: 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., Am J Contact Demat. 1996, 7: 177). Data obtained from IL-1 knock out mice indicates the critical involvement in fever for this cytokine (Kluger et al., Clin Exp Pharmacol Physiol. 1998, 25: 141). A variety of cytokines including TNFa, IL-1, IL-6 and IL-8 initiate the acute-phase reaction which is stereotyped in fever, malaise, myalgia, headaches, cellular hypermetabolism and multiple endocrine and enzyme responses (Beisel, Am J Clin Nutr. 1995, 62: 813). The production of these inflammatory cytokines rapidly follows trauma or pathogenic organism invasion.

Rhinovirus triggers the production of various proinflammatory cytokines, predominantly IL-8, which results in symptomatic illnesses such as acute rhinitis (Winther et al., Am J Rhinol. 1998, 12: 17).

Cytokine inhibitors are also expected to block inducible COX-2, an enzyme involved in inflammation (M. K. O'Banion et al., Proc. Natl. Acad. Sci. USA 1992, 89:4888). Cytokine inhibitors such as, for example, IL-1 receptor antagonist (IL-1ra) would be expected to show efficacy against disorders where COX-2 inhibitors (such as the NSAIDs) would be used. These disorders include but are not limited to inflammatory diseases, chronic pain and cardiovascular disease.

Several cytokines are known to be elevated in inflammatory bowel disease (IBD) conditions. An imbalance of IL-1 and IL-1ra has been described in patients with IBD. Insufficient production of IL-1ra could at least partially contribute to the pathogenesis of IBD (Cominelli, et al. Aliment Pharmacol. Ther. 1996, 10:49).

Beta-amyloid protein deposits, neurofibrillary tangles and cholinergic dysfunction throughout the hippocampal region have been observed in Alzheimer's disease patients. Sustained levels of cytokines, such as, for example IL-1 and/or TNFa could be at least partially responsible for the damage in the brains of Alzheimer's disease patients (Grammas, Neurobiol. Aging 2001, 22(6):837-42; Rempel, J. Neurochem. 2001, 78(3):640-645).

Cytokines such as TNFa and Il-1 have been also implicated in the pathogenesis of human immunodeficiency virus (HIV) infection and acute inflammatory events (Kreuzer, Clin. Exp. Immunol. 1997, 109(1):54-58; Baqui, Immunopharmacol Immunotoxicol 2000, 22(3):401-421). The concentrations of cytokines and receptors are elevated in bone marrow supernatant of HIV-infected patients with hematologic abnormalities, and these concentrations were shown to correlate with clinical parameters in these patients (Dallalio, J. Investig. Med. 1999, 47(9):477-483).

Proinflammatory cytokines such as TNFa and IL-1b and interleukin-6 (IL-6) are important mediators of septic shock, cardiopulmonary dysfunction, acute respiratory distress syndrome (ARDS) and multiple organ failure. Patients admitted with presumed sepsis have elevated cytokine levels compared with patients with sepsis who are discharged and with those patients with presumed noninfectious systemic inflammatory response syndrome (SIRS) suggesting an association between cytokines and subsequent septic complications in these patients (Terregino, Ann. Emerg. Med. 2000, 35(1):26-34).

Cytokine imbalance is also implicated in cachexia and muscle degradation associated with HIV infection. The serum concentrations of inflammatory (IL-1b, TNFa, IL-6) and regulatory cytokines (Interleukin twelve) have been studied in ten AIDS cachectic patients and compared to a control group. A cytokine imbalance and a significant increase in proinflammatory cytokines (IL-1, IL-6, TNFa) was observed in the patient group (Baronzio, In Vivo 1999, 13(6):499-502).

Obesity is associated with an increase incidence of infection, diabetes and cardiovascular disease. Abnormalities in TNFa expression have been noted for each of the above conditions (Loffreda, et al., FASEB J. 1998, 12: 57). It has been proposed that elevated levels of TNFa are involved in other eating related disorders such as anorexia and bulimia nervosa. Pathophysiological parallels are drawn between anorexia nervosa and cancer cachexia (Holden, et al., Med Hypotheses 1996, 47: 423). An inhibitor of TNFa production, HU-211, was shown to improve the outcome of closed brain injury in an experimental model (Shohami, et al., J Neuroimmunol. 1997, 72: 169).

There is mounting evidence that inflammation plays a role in the development of coronary heart disease (CHD) and coronary artery disease (CAD). Elevated concentrations of acute phase reactants, such as C-reactive protein (CRP), are found in patients with acute coronary syndromes, and predict future risk in apparently healthy subjects. Cytokines such as TNFa, Il-1 and Il-6 have been suggested to promote atherosclerosis and heart disease. Coronary disease patients are characterized by increased serum concentrations of TNFa. It seems likely that immune activation (TNFa, soluble TNF receptors 1 and 2 (sTNFR 1, sTNFR 2), and interleukin-10 (IL-10)) in coronary patients is related to serum lipid levels (Mizia-Stec, Acta Cardiol. 2003, 58(1):9-15).

A large percentage of acute coronary syndrome is the consequence of unstable plaque rupturing, followed by thrombus formation. A characteristic of these unstable plaque is an increase in inflammatory cells (macrophages and T lymphocytes). The serum concentration of CRP (C-reactive protein) might reflect the amount of inflammation within atherosclerotic plaque and thus might provide a measurement of the instability of the plaque. CRP is believed therefore to have a predictive value for the occurrence of plaque rupture. Furthermore, there are indications that CRP itself is active in the inflammatory process. Studies have shown that so-called high-sensitivity CRP (hsCRP) measurements could be used as a tool for determining the risk for acute coronary syndromes. Antiinflammatory agents, capable of reducing the levels of hsCRP might contribute to reducing the risk of plaque rupture (Abjil, Ned Tijdschr Geneeskd 2003, 147(1): 15-20; Branger, J. Immunol. 2002, 168(8):4070-7).

Elevated TNFa levels have also been found to be associated with congestive heart failure, and levels of cytokines have been correlated with the severity of the disease. Serum levels of TNFa are elevated in patients with heart failure, and both cardiac and infiltrating cells of the myocardium can produce this proinflammatory cytokine. Studies in both animal models and clinical investigations suggest that anti-TNFa therapies may limit the pathophysiologic consequences of congestive heart failure (McTiernan, Curr. Cardiol. Rep. 2000, 2(3): 189-97). Furthermore, treatment with etanercept (a soluble TNF receptor) led to a significant dose-dependent improvement in left ventricular ejection fraction and remodeling, and there was a trend toward improvement in patient functional status, as determined by clinical composite score (Bozkurt, Circulation 2001 Feb. 27;103(8):1044-7).

TNFa levels are elevated in airways of patients with chronic obstructive pulmonary disease and it may contribute to the pathogenesis of this disease (M. A. Higham et al., Eur. Respiratory J. 2000, 15: 281). Circulating TNFa may also contribute to weight loss associated with this disease (N. Takabatake et al., Amer. J. Resp. & Crit. Care Med. 2000, 161 (4 Pt 1): 1179). Elevated TNFa levels have also been found to be associated with congestive heart failure and the level has been correlated with severity of the disease (A. M. Feldman et al., J. Amer. College of Cardiology 2000, 35: 537). In addition, TNFa has been implicated in reperfusion injury in lung (Borjesson et al., Amer. J. Physiol. 2000, 278: L3-12), kidney (Lemay et al., Transplantation 2000, 69: 959), and the nervous system (Mitsui et al., Brain Res. 1999, 844: 192). Proinflammatory cytokines are also known to play roles in ischemia-reperfusion injury of the heart, kidney, small bowel, skin, and liver. For example, TNFa and IL-1 beta were shown to help regulate the development of lung ischemia-reperfusion injury. They appear to promote injury by altering expression of proinflammatory and anti-inflammatory cytokines. Neutrophil recruitment and lung neutrophil accumulation was markedly reduced among animals receiving anti-TNFa and anti-IL-1beta and combination blockade afforded even greater protection (Krishnadasan, J. Thorac. Cardiovasc. Surg. 2003, 125(2):261-72). In brain injury, pretreatment with intravenous anti-TNFa antibody reduced cortical and subcortical injury, enhanced cerebral blood flow during reperfusion, and improved the neurologic outcome. This supports the contention that TNFa is a deleterious cytokine in stroke, whereas circulating antibody against TNF-alpha may protect brain from reperfusion injury (Lavine, J. Cereb. Blood Flow Metab. 1998, 18(1):52-8; Mitsui, Brain Res. 1999, 844 (1-2):192-5). TNFa is also believed to be released from the kidney in response to, and has been implicated in the pathogenesis of, renal ischemia-reperfusion injury (Donnahoo, J. Urol. 1999, 162(1):196-203).

Skeletal mass is maintained by a balance between cells which resorb bone (osteoclasts) and cells which form bone (osteoblasts). Recent observations have identified members of the TNF family of ligands and receptors as critical regulators of osteoclastogenesis (Horowitz, Cytokine Growth Factor Rev 2001, 12(1):9-18) and it was suggested that cytokines such as TNFa and IL-1 alpha may play an important role in pathological bone resorption. Data support the concept that TNFa is involved critically in osteoclastogenesis and bone resorption during periprosthetic osteolysis and suggest that TNFa inhibitors may be useful as therapeutic agents for the treatment of diseases involving bone resorption (Childs, J. Bone Miner. Res. 2001, 16(2):338-47; Abu-Amer, J. Biol. Chem. 2000, 275(35):27307-10).

Periodontal disease is a significant cause of tooth loss among adults and is characterized by the alteration and permanent destruction of the deeper periodontal tissues. Studies showed that IL-1 and TNF antagonists significantly reduced the loss of connective tissue attachment and the loss of alveolar bone height. This suggests that the loss of connective tissue attachment and progression of periodontal disease can be retarded by antagonists to cytokines such as IL-1 (Delima, J. Clin. Periodontol. 2001, 28(3):233-40).

TNFa plays a role in many aspects of glomerulonephritis progression. Studies showed that neutralization of endogenous TNFa is effective in preventing acute glomerular inflammation and crescent formation (Karkar, Nephrol. Dial. Transplant 2001, 16(3):518-24).

Ulcerative colitis (UC) and Crohn's disease (CD) comprise a series of inflammatory bowel diseases (IBD) resulting from chronic upregulation of the mucosal immune system and elevated levels of cytokines such as, for example, TNFa, IL1-b and IL-6. Strategies aimed at reducing cytokine levels, such as TNFa in patients with inflammatory bowel disease include the mouse/human chimeric monoclonal antibody infliximab, the humanized monoclonal antibody CDP571, the human soluble TNF p55 receptor onercept, the human monoclonal antibody D2E7 (adalimumab), the anti-TNF human antibody Fab' fragment-polyethelene glycol (PEG) conjugate CDP870, and the small molecules thalidomide and CNI-1493 MAP-kinase inhibitor (Escher et al., Inflamm. Bowel. Dis. 2003 January; 9(1):34-58; Sandbor et al., Best Pract. Res. Clin. Gastroenterol. 2003, 17(1):105-17).

Abnormalities in the immune response are believed to play a role in the pathogenesis of hypertension. Studies showed that hypertensive patients had an increased IL-1 and IL-6 production capacity when whole blood was stimulated ex vivo with lipopolysaccharide (Peeters, Eur. J. Clin. Invest. 2001, (1):31-6). Inducible nitric oxide synthase (iNOS) present in vascular smooth muscle cells (VSMC) were suggested to play a role in the generation of nitric oxide (NO) in the vascular wall, regulating blood vessel tone in normotension and hypertension. IL-1 beta was shown to control iNOS gene expression at the transcriptional level (Singh, Am. J. Hypertens. 1996, (9):867-77) suggesting that agents inhibiting cytokines such as IL-1 inhibitors could be useful for the treatment of hypertension.

Diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., Current Opinion in Hematology 1998, 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., Molecular Neurobiology 1997, 15: 307). IL-6 also plays a significant role in osteoporosis. In murine models it has been shown to effect bone resorption and to induce osteoclast activity (Ershler et al., Development and Comparative Immunol. 1997, 21: 487). Marked cytokine differences, such as IL-6 levels, exist in vivo between osteoclasts of normal bone and bone from patients with Paget's disease (Mills, et al., Calcif Tissue Int. 1997, 61: 16). A number of cytokines have been shown to be involved in cancer cachexia. The severity of key parameters of cachexia can be reduced by treatment with anti IL-6 antibodies or with IL-6 receptor antagonists (Strassmann, et al., Cytokins Mol Ther. 1995, 1: 107). Several infectious diseases, such as influenza, indicate IL-6 and IFN alpha as key factors in both symptom formation and in host defense (Hayden, et al., J Clin Invest. 1998, 101: 643). Overexpression of IL-6 has been implicated in the pathology of a number of diseases including multiple myeloma, rheumatoid arthritis, Castleman's disease, psoriasis and post-menopausal osteoporosis (Simpson, et al., Protein Sci. 1997, 6: 929). Compounds that interfered with the production of cytokines including IL-6, and TNFa were effective in blocking a passive cutaneous anaphylaxis in mice (Scholz et al., J. Med. Chem. 1998, 41: 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, Medical Oncology 1996, 13: 149). GM-CSF also appears to play a role in the replication of human immunodeficiency virus (HIV) in cells of macrophage lineage with relevance to AIDS therapy (Crowe et al., Journal of Leukocyte Biology 1997, 62: 41). Bronchial asthma is characterized by an inflammatory process in lungs. Involved cytokines include GM-CSF amongst others (Lee, J R Coll Physicians Lond 1998, 32: 56).

Interferon-gamma (IFN-gamma) has been implicated in a number of diseases. It has been associated with increased collagen deposition that is a central histopathological feature of graft-versus-host disease (Parkman, Curr Opin Hematol. 1998, 5: 22). Following kidney transplantation, a patient was diagnosed with acute myelogenous leukemia. Retrospective analysis of peripheral blood cytokines revealed elevated levels of GM-CSF and IFN-gamma. These elevated levels coincided with a rise in peripheral blood white cell count (Burke, et al., Leuk Lymphoma. 1995, 19: 173). The development of insulin-dependent diabetes (Type 1) can be correlated with the accumulation in pancreatic islet cells of T-cells producing IFN-gamma (Ablumunits, et al., J Autoimmun. 1998, 11: 73). IFN-gamma along with TNFa, IL-2 and IL-6 lead to the activation of most peripheral T-cells prior to the development of lesions in the central nervous system for diseases such as multiple sclerosis (MS) and AIDS dementia complex (Martino et al., Ann Neurol. 1998, 43: 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNFa, IL-1 and IFN-gamma. These cytokines are thought to be involved in promoting apoptosis or programmed cell death of the surrounding vascular smooth muscle cells resulting in the atherosclerotic lesions (Geng, Heart Vessels 1997, Suppl 12: 76). Allergic subjects produce mRNA specific for IFN-gamma following challenge with Vespula venom (Bonay, et al., Clin Exp Immunol. 1997, 109: 342). The expression of a number of cytokines, including IFN-gamma has been shown to increase following a delayed type hypersensitivity reaction thus indicating a role for IFN-gamma in atopic dermatitis (Szepietowski, et al., Br J Dermatol. 1997, 137: 195). Histopathologic and immunohistologic studies were performed in cases of fatal cerebral malaria. Evidence for elevated IFN-gamma amongst other cytokines was observed indicating a role in this disease (Udomsangpetch et al., Am J Trop Med Hyg. 1997, 57: 501). The importance of free radical species in the pathogenesis of various infectious diseases has been established. The nitric oxide synthesis pathway is activated in response to infection with certain viruses via the induction of proinflammatory cytokines such as IFN-gamma. (Akaike, et al., Proc Soc Exp Biol Med. 1998, 217: 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN-gamma, TNFa and IL-2 (Chisari, et al., Springer Semin Immunopathol. 1995, 17: 261). IFN-gamma can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., J Bone Miner Res. 1996, 11: 300). Studies with gene deficient mice have demonstrated that the IL-12 dependent production of IFN-gamma is critical in the control of early parasitic growth. Although this process is independent of nitric oxide the control of chronic infection does appear to be NO dependent (Alexander et al., Philos Trans R Soc Lond B Biol Sci 1997, 352: 1355). NO is an important vasodilator and convincing evidence exists for its role in cardiovascular shock (Kilboum, et al., Dis Mon. 1997, 43: 277). IFN-gamma is required for progression of chronic intestinal inflammation in such diseases as Crohn's disease and inflammatory bowel disease (IBD) presumably through the intermediacy of CD4+lymphocytes probably of the THI phenotype (Sartor, Aliment Pharmacol Ther. 1996, 10 Suppl 2: 43). An elevated level of serum IgE is associated with various atopic diseases such as bronchial asthma and atopic dermatitis. The level of IFN-gamma was negatively correlated with serum IgE suggesting a role for IFN-gamma in atopic patients (Teramoto et al., Clin Exp Allergy 1998, 28: 74).

Recently it was shown that cytokine pathways play a role in the derivation and maintenance of embryonic stem cells (ES cells) (Proc Natl Acad Sci USA. 2004, 101: 6027), suggesting the potential application of cytokine inhibitors in conjunction with stem cell therapy.

WO 01/01986 discloses particular compounds alleged to having the ability to inhibit TNFa. The specific inhibitors disclosed are structurally distinct from the novel compounds disclosed in the present application disclosed herein below. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivop-ontocerebellar atrophy, neuropathic pain syndromes, diabetic neuropathy, HIV-related neuropathy, MERRF and MELAS syndromes, Leber's disease, Wemicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFa are allegedly useful for treating acute and chronic inflammation in the lung caused by inhalation of smoke such as cigarette smoke. TNFa antagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production (J Surg Res 2000, 90(2): 95-101; Shock 1998, 10(3): 160-75.)

It is known in the art that anti-inflammatory compounds such as cytokine inhibitors can be used in combination with other active ingredients in the treatment of diseases and pathological conditions. For example, cytokine inhibitors have been combined with anti-cholinergics for the purpose of treating respiratory tract diseases (see WO03/084539 and corresponding U.S. application 2003/0225089, and WO2004/004725 and corresponding U.S. application 2004/0044020). Combination therapy with cytokine inhibitors and a variety of other active ingredients is disclosed in U.S. patent application 2004/0110755.

The need for new therapies is especially important in the case of arthritic diseases. The primary disabling effect of osteoarthritis, rheumatoid arthritis and septic arthritis is the progressive loss of articular cartilage and thereby normal joint function.

TNFa plays an important role in many cell types in mediating responses to an external stimulus, such as, for example, an infection, trauma or a mitogen.

Thus, a need exists for therapeutics useful in the treatment of cytokine mediated diseases. While some protein therapeutics have been developed, they suffer from bioavailability and stability problems. In particular, there is a need for low molecular weight compounds that inhibit TNFa and/or IL-1b production.

SUMMARY OF THE INVENTION

The present invention provides low molecular weight compounds and pharmaceutical compositions thereof. In particular, compounds of the invention are useful as cytokine release inhibitory agents. There are further provided methods for the preparation of such compounds and their use in the prevention and treatment of various diseases mediated by cytokines.

Thus, there are provided in accordance with one aspect of the invention cytokine inhibitors comprising:

a targeting moiety, TM, comprising at least an amide group having an amide NH, the targeting moiety capable of forming one or more hydrogen bonds with a target protein, and wherein the targeting moiety is not a urea group;

a pocket-expanding moiety, PEM, directly attached to the targeting moiety, the pocket-expanding moiety comprising a planar moiety attached to a bulky non-planar hydrophobic moiety, wherein the non-planar moiety can form hydrophobic interactions with a target protein;

an orienting moiety, OM, comprising a planar hydrophobic moiety and attached to a different atom of the targeting moiety than the pocket-expanding moiety, wherein the orienting moiety is capable of forming a $\pi$-$\pi$ or edge-to-face aromatic interaction with a target protein.

In this aspect of the invention, cytokine inhibitors have the structure PEM-TM-OM. At a concentration of 10 μM such compounds typically inhibit induced TNFa-release from a cell by about 50% or greater than 50%.

The targeting moiety can hydrogen bond to residues at the binding site of the target protein and may further include additional hydrogen bond donor or acceptor groups that also form hydrogen bonds to the target protein. Targeting moieties include amide and thioamide groups, methyl amide and thioamide groups, carbamates, hydroxymethyl amides, alpha-ketoamides, diamides, and the like. Cyclic targeting moieties are also contemplated such as imidazolinone, imidazoline dione and trione.

The pocket-expanding moiety is of sufficient size to force a conformational change in the target protein, resulting in an expanded binding pocket therein. Such moieties include, for example, pyrazolyl, oxazolyl, phenyl or the like, each substituted by bulky moieties. Bulky moieties fill a large volume of space in comparison to, for example, a methyl group and include groups such as t-butyl, norbornyl, and the like.

The orienting moiety, by binding to a hydrophobic pocket on the target protein, provides the proper orientation of the targeting moiety and pocket-expanding moiety for binding of the cytokine inhibitor to its target protein. The planar hydrophobic moieties which make up the orienting moiety have either few or no polar groups. Such moieties include, for example, phenyl, naphthyl, indazolyl, and the like.

In other embodiments, the cytokine inhibitors further comprise a hydrophilic moiety having at least one finctionality selected from the group consisting of a hydrogen-bond donor, hydrogen-bond acceptor, basic heteroatom, or acidic heteroatom, wherein the hydrophilic moiety is indirectly attached to the hydrophobic orienting moiety and is capable of forming a hydrogen bond with the backbone of the protein. Typically the hydrophilic moiety is attached to the orienting moiety by a linker chain of atoms of from about 2 to about 10 angstroms in length. The hydrophilic moiety binds in or near an ATP-binding pocket on the target protein, forming at least one hydrogen bond with a residue of the ATP-binding pocket. Hydrophilic moieties include morpholinyl, piperazinyl, and pyrimidinyl groups, among others. Such moieties may be attached to the orienting moiety by, for example, oxy, ethylene, methyleneoxy and ethyleneoxy chains.

In certain embodiments of the cytokine inhibitors of the invention, the pocket-expanding moiety is not a substituted 5-member heterocyclyl ring if the cytokine inhibitor is PEM-CHR"C(O)NH—OM, wherein R" is H or $C_{1-6}$ alkyl, optionally partially or fully halogenated. In other embodiments, the targeting moiety is not a substituted tricyclic heterocyclyl ring having a nitrogen atom ring member bonded to the amide carbonyl of the targeting moiety.

There is provided in accordance with another aspect of the invention, a first group of compounds having Formula IA,

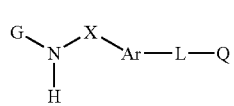

IA stereoisomers thereof, tautomers thereof, solvates thereof, prodrugs thereof, and pharmaceutically acceptable salts thereof, wherein:

X is C(O), C(S) or $CH_2$;

G is a $C_{3-10}$ carbocyclyl, 5-8 membered monocyclic heterocyclyl, or 8-11 membered bicyclic heterocyclyl containing 1 or more heteroatoms selected from O, N or S; wherein G is substituted by one or more $R^1$, $R^2$ or $R^3$;

Ar is indazolyl, indolyl, isoindolyl, imidazolyl, benzimidazolyl, pyrazolyl, pyrazolinyl, pyrrolyl, pyrrolinyl, pyridinyl, pyridazinyl, quinolinyl, isoquinolinyl, phthalazinyl, dihydroindolyl, benzoisoxazolyl, dihydrobenzoisoxazolyl, dihydroisoindolyl, benzoisothiazolyl, benzoisothiazolyl dioxide, $C_{6-10}$ aryl, —($C_{1-3}$ alkyl)-($C_{6-10}$ aryl), —(Y)—($C_{0-3}$ alkyl)-($C_{6-10}$ aryl), or —(Y)—($C_{0-3}$ alkyl)-(5-10 member heteroaryl), each of which is optionally substituted with one or more $R^4$ or $R^5$;

each Y is independently —CHZ-, —$CZ_2$-, —CHR—, —O—, —C(=CHR)—, —C(=C—$CO_2R$)—;

each Z is independently F, Cl, —OR, —$NR_2$, —SR, —NH-CONHR, or —NHCOR;

L is a covalent bond or a saturated or unsaturated branched or unbranched $C_{1-10}$ carbon chain, wherein one or more methylene groups are optionally independently replaced by heteroatoms chosen from O, NR and $S(O)_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ alkyl-$S(O)_m$, or phenyl-$S(O)_m$, wherein the cycloalkyl, aryl, heterocyclyl, $C_{1-6}$ alkoxy, $C_{1-6}$ alkyl-$S(O)_m$, or phenyl-$S(O)_m$ is each optionally substituted with one or more $R^{27}$;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —$C(O)NR_2$, —C(O)OR, —OR, —NR'R', —$SiR_3$, —$S(O)_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, $S(O)_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —$OR^6$, —C(O)R', —C(O)OR', —C(O)$NR'_2$, —$NR'_2$, —$NO_2$, —$S(O)_m$R", —NR'$SO_2$R", —NR'C(O)NR'R', —NR'C(S)NR'R', —NR'C(O)OR' or —$SO_2NR'_2$;

each R" is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, $S(O)_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or $S(O)_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or $NR'_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)NR'$_2$, —C(O)OR', —OR', —NR'R', —SiR'$_3$, —S(O)$_m$R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, S(O)$_m$;

provided however that when Ar is —(Y)—($C_{6-10}$ aryl) and G is N-(substituted or unsubstituted phenyl)-pyrazolyl, the pyrazolyl is additionally substituted with one or more $R^1$, $R^2$ or $R^3$; and IA is not N-(5-tert-butyl-2-phenyl-2H-pyrazol-3-yl)-2-(4-chloro-phenyl)-acetamide.

In certain embodiments of the first group of compounds of Formula IA, the compound at a concentration of 10 µM inhibits induced TNFa-release from a cell by about 50% or greater than 50%.

In some embodiments of the first group of compounds of Formula IA, G is phenyl, naphthyl, benzocyclobutanyl, dihydronaphthyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-only, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In other embodiments of the first group of compounds of Formula IA, G is phenyl, naphthyl, benzocyclobutanyl, dihydronaphthyl, tetrahydronaphthyl, benzocycloheptanyl, benzocycloheptenyl, indanyl, indenyl, or benzofuran-3-one. In yet others, G is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl. Alternatively, G is pyrrolidinyl, tetrahydrofuiranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, isoxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl. In other embodiments, G is phenyl, naphthyl, pyrazolyl, pyrrolyl, pyrrolidinyl, imidazolyl, imidazolonyl, thiazolyl, oxazolyl, isoxazolyl, furanyl, thienyl, or pyridinyl.

In certain embodiments of the first group of compounds of Formula IA, Ar is indazolyl, indolyl, isoindolyl, imidazolyl, benzimidazolyl, pyrazolyl, pyrazolinyl, pyrrolyl, pyrrolinyl, pyridinyl, pyridazinyl, quinolinyl, isoquinolinyl, phthalazinyl, dihydroindolyl, benzoisoxazolyl, dihydrobenzoisoxazolyl, dihydroisoindolyl, benzoisothiazolyl, benzoisothiazolyl dioxide, or $C_{6-10}$ aryl. In some such embodiments, Ar is substituted with at least one $R^4$ or $R^5$. Alternatively, Ar is indazolyl, isoindolyl, pyrazolyl, pyrrolinyl, phenyl, naphthyl, dihydronaphthyl, tetrahydronaphthyl, indanyl, indenyl or imidazolyl. In still other such embodiments, Ar is indazolyl, phenyl, tetrahydronapthyl or naphthyl.

In certain embodiments of compounds having Formula IA, Ar is —($C_{1-3}$ alkyl)-($C_{6-10}$ aryl), —(Y)—($C_{0-3}$ alkyl)-($C_{6-10}$ aryl), or —(Y)—($C_{0-3}$ alkyl)-(5-10 member heteroaryl). In some such embodiments, Ar is substituted with at least one $R^4$ or $R^5$. In some such embodiments, Y is —$CZ_2$- and each Z is independently F, —OR or —CHR. For example, Y is —$CF_2$—. In others, Y is —CHR or —CHZ- and Z is —OR. Thus, for example, Y is —CHOH—. Alternatively, Y is —O— or —CH$_2$—. In still other such embodiments, the $C_{6-10}$ aryl is phenyl or naphthyl, and/or the 5-10 member heteroaryl is quinolinyl, isoquinolinyl, phthalazinyl, or quinazolinyl. In yet other such embodiments Ar is —($C_{1-3}$ alkyl)-($C_{6-10}$ aryl).

In some embodiments of the first group of compounds of Formula IA, one or more methylene groups of L are independently replaced by hetero atoms selected from O, N or S(O)$_m$. In others, L is a covalent bond, a $C_1$-$C_9$ alkoxy, —C(O)O—, —NH— or —O—.

As noted above, Q, other than —H or —NR'R', is optionally substituted with $R^{27}$. In certain embodiments of the first group of compounds of Formula IA Q is phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl, tetrahydropyranyl, tetrahydrofuranyl, 1,3-dioxolanone, 1,3-dioxanone, 1,4-dioxanyl, morpholino, thiomorpholino sulfoxide, thiomorpholino sulfone, piperazinyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone, $C_{1-6}$ alkoxy, secondary or tertiary amine wherein the amino nitrogen is covalently bonded to $C_{1-3}$ alkyl or $C_{1-5}$ alkoxyalkyl, phenylamino; $C_{1-6}$ alkyl-S(O)$_m$ or phenyl-S(O)$_m$. In some such embodiments, $R^{27}$ is $C_{1-6}$ alkyl, $C_{1-6}$ alkoxy, hydroxy amino, substituted or unsubstituted 5-10 member heterocyclyl, mono- or di-($C_{1-3}$ alkyl)amino, mono- or di-(phenyl-$C_{1-3}$ alkyl)amino, $C_{1-6}$ alkyl-S(O)$_m$, phenyl-$C_{1-3}$-alkoxy or phenylamino wherein the phenyl ring is optionally substituted with one to two halogen, $C_{1-6}$ alkyl or $C_{1-6}$ alkoxy.

In some embodiments of the first group of compounds of Formula IA, G is phenyl, naphthyl, benzocyclobutanyl, dihydronaphthyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In some embodiments of the first group of compounds of Formula IA, when $R^4$ and $R^5$ are absent, -L-Q is not —H.

In some embodiments of the first group of compounds of Formula IA, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, $S(O)_m$, CHOH, C=O, C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully halogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, $C_{1-3}$ alkoxy optionally partially or fully halogenated, $NH_2C(O)$ or mono- or di-($C_{1-3}$ alkyl)aminocarboxyl; and wherein the $C_{3-10}$ branched or unbranched alkenyl is optionally interrupted by one or more O, N or $S(O)_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, or I;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-$S(O)_2$;

$C_{2-6}$ branched or unbranched alkynyl optionally partially or fully halogenated, wherein one or more methylene groups are optionally replaced by O, NH and $S(O)_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms.

In other embodiments of the first group of compounds of Formula IA, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl. For example, each $R^1$ is independently $C_{3-10}$ branched or unbranched alkyl.

In some embodiments of the first group of compounds of Formula IA, each $R^2$ is independently —OR', —$OR^6$, —C(O)R', —C(O)OR', —C(O)NR'$_2$, —NR'$_2$, —$NO_2$, —$S(O)_mR''$, —$NR'SO_2R''$, —NR'C(O)NR'R', —NR'C(S)NR'R', —NR'C(O)OR' or —$SO_2NR'_2$. Alternatively, each $R^2$ is independently —NR'$_2$, —$NO_2$, —C(O)NR'$_2$, —$NR'SO_2R''$, —NR'C(O)NR'R', —NR'C(S)NR'R', —NR'C(O)OR' or —$SO_2NR'_2$.

In some embodiments of the first group of compounds of Formula IA, each $R^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-$S(O)_2$, di-($C_{1-3}$ alkyl)amino-$S(O)_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, carboxy-mono- or di-($C_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, $C_{1-6}$ branched or unbranched alkyl which is optionally partially or fully halogenated, cyano, $C_{1-3}$ alkoxy optionally partially or fully halogenated, phenyloxy, naphthyloxy, heterocyclyloxy, heteroaryloxy, nitro, amino, mono- or di-($C_{1-3}$ alkyl)amino, phenylamino, naphthylamino, heterocyclic or heteroaryl amino, $NH_2C(O)$, a mono- or di-($C_{1-3}$ alkyl)aminocarbonyl, $C_{1-4}$ alkyl-$C(O)$, $C_{1-5}$ alkylamino-$S(O)_2$, mono- or di-($C_{1-3}$ alkyl)amino-$C_{1-5}$ alkyl, $R^{12}$—$C_{1-5}$ alkyl, $R^{13}$—$C_{1-5}$ alkoxy, $R^{14}$—$C(O)$—$C_{1-5}$ alkyl, $R^{15}$—$C_{1-5}$ alkyl($R^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S$(O)_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three $C_{1-3}$ alkyl groups;

$C_{1-4}$ alkyl or alkylene-phenyl-$C(O)$—$C_{0-4}$ alkyl or alkylene, $C_{1-4}$ alkyl or alkylene-$C(O)$—$C_{0-4}$ alkyl or alkylene, $C_{1-4}$ alkyl or alkylene-phenyl-$S(O)_m$—$C_{0-4}$ alkyl or alkylene;

$C_{1-6}$ alkyl or $C_{1-6}$ alkoxy, each optionally partially or fully halogenated or optionally substituted with $R^{17}$, amino, $OR^{18}$, or $C_{1-5}$ mono- or di-alkylamino optionally substituted with $R^{19}$;

cyclopropyloxy, cyclobutyloxy, cyclopentyloxy, cyclohexyloxy, cycloheptyloxy, which are optionally partially or fully halogenated and optionally substituted with one to three $C_{1-3}$ alkyl groups optionally partially or fully halogenated wherein one to three ring methylene groups are replaced independently by O, $S(O)_m$, CHOH, C=O, C=S or NH;

$R^{20}C(O)N(R^{21})$—, $R^{22}O$—, $R^{23}R^{24}NC(O)$—, $R^{26}(CH_2)_mC(O)N(R^{21})$— or $R^{26}C(O)(CH_2)_mN(R^{21})$—;

$C_{2-6}$ alkenyl substituted by $R^{23}R^{24}NC(O)$—;

$C_{2-6}$ alkynyl branched or unbranched carbon chain optionally partially or fully halogenated, wherein one or more methylene groups are optionally replaced by O, NH or $S(O)_m$, and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms; or benzoyl or naphthoyl; and wherein each $R^7$, $R^8$, $R^9$, $R^{10}$, $R^{12}$, $R^{13}$, $R^{14}$, $R^{15}$, $R^{17}$, $R^{19}$, and $R^{25}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

each $R^{11}$ and $R^{16}$ is independently hydrogen or $C_{1-4}$ branched or unbranched alkyl optionally partially or fully halogenated; and $R^{18}$ is independently hydrogen or $C_{1-4}$ branched or unbranched alkyl optionally independently substituted with oxo or $R^{25}$.

In some such embodiments, each $R^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-$C(O)$—$C_{1-4}$ alkyl, amino-$C_{1-5}$ alkyl, mono- or di-($C_{1-3}$ alkyl)amino-$C_{1-5}$ alkyl, amino-$S(O)_2$, di-($C_{1-3}$ alkyl)amino-$S(O)_2$, $R^7$—$C_{1-5}$ alkyl, $R^8$—$C_{1-5}$ alkoxy, $R^9$—$C(O)$—$C_{1-5}$ alkyl, $R^{10}$—$C_{1-5}$ alkyl($R^{11}$)N, or carboxy-mono- or di-($C_{1-5}$ alkyl)amino. In others, each $R^3$ is independently phenyl, pyridazinyl or pyridyl, each of which is optionally partially or fully halogenated and optionally substituted with $C_{1-6}$ branched or unbranched alkyl which is optionally partially or fully halogenated, hydroxy, oxo, cyano, $C_{1-3}$ alkoxy optionally partially or fully halogenated, nitro, amino, mono- or di-($C_{1-3}$ alkyl)amino; $C_{1-6}$ alkyl or $C_{1-6}$ alkoxy, each optionally partially or fully halogenated or optionally substituted with $R^{17}$, amino, $OR^{18}$, $C_{1-5}$ mono- or di-alkylamino optionally substituted with $R^{19}$; $R^{20}C(O)N(R^{21})$—, $R^{22}O$—, $R^{23}R^{24}NC(O)$—, $R^{26}(CH_2)_mC(O)N(R^{21})$— or $R^{26}C(O)(CH_2)_mN(R^{21})$—. For example, $R^3$ can be phenyl or tolyl.

In some embodiments of the first group of compounds of Formula IA, X is C=O.

In another aspect of the invention there are provided a first group of compounds having Formula IB:

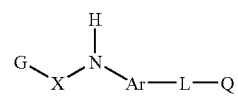

IB stereoisomers thereof, tautomers thereof, solvates thereof, prodrugs thereof, and pharmaceutically acceptable salts thereof, wherein:

X is $C(O)$, $C(S)$ or $CH_2$;

G is a $C_{3-10}$ carbocyclyl, 5-8 membered monocyclic heterocyclyl, or 8-11 membered bicyclic heterocyclyl containing 1 or more heteroatoms selected from O, N or S; wherein G is substituted by one or more $R^1$, $R^2$ or $R^3$;

Ar is indazolyl, indolyl, isoindolyl, imidazolyl, benzimidazolyl, pyrazolyl, pyrazolinyl, pyrrolyl, pyrrolinyl, pyridinyl, pyridazinyl, quinolinyl, isoquinolinyl, phthalazinyl, dihydroindolyl, benzoisoxazolyl, dihydrobenzoisoxazolyl, dihydroisoindolyl, benzoisothiazolyl, benzoisothiazolyl dioxide, $C_{6-10}$ aryl, —($C_{1-3}$ alkyl)-($C_{6-10}$ aryl), —(Y)—($C_{0-3}$ alkyl)-($C_{6-10}$ aryl), or —(Y)—($C_{0-3}$ alkyl)-(5-10 member heteroaryl), each of which is optionally substituted with one or more $R^4$ or $R^5$;

each Y is independently —CHZ-, —$CZ_2$-, —CHR—, —C(=CHR)—, —C(=C—$CO_2$R)—;

each Z is independently F, Cl, —OR, —$NR_2$, —SR, —NHCONHR, or —NHCOR;

L is a covalent bond or a saturated or unsaturated branched or unbranched $C_{1-10}$ carbon chain, wherein one or more methylene groups are optionally independently replaced by heteroatoms chosen from O, NR and $S(O)_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ alkyl-$S(O)_m$, or phenyl-$S(O)_m$, wherein the cycloalkyl, aryl, heterocyclyl, $C_{1-6}$ alkoxy, $C_{1-6}$ alkyl-$S(O)_m$, or phenyl-$S(O)_m$ is each optionally substituted with one, or more $R^{27}$; provided that if $R^4$ and $R^5$ are absent, -L-Q is not —H;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —C(O)NR$_2$, —C(O)OR, —OR, —NR'R', —SiR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, $S(O)_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$;

each R" is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, $S(O)_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or $S(O)_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or NR'$_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)NR'$_2$, —C(O)OR', —OR', —NR'R', —SiR'$_3$, —S(O)$_m$R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, $S(O)_m$.

In some embodiments of the first group of compounds of Formula IB, the compound at a concentration of 10 μM inhibits induced TNFa-release from a cell by about 50% or greater than 50%.

In certain embodiments of the first group of compounds of Formula IB, G is phenyl, naphthyl, benzocyclobutanyl, dihydronaphthyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In other embodiments of the first group of compounds of Formula IB, G is phenyl, naphthyl, benzocyclobutanyl, dihydronaphthyl, tetrahydronaphthyl, benzocycloheptanyl, benzocycloheptenyl, indanyl, indenyl, or benzofuran-3-one. Alternatively, G is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl. In others, G is pyrrolidinyl, tetrahydrofuiranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, isoxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl. In yet other embodiments, G is phenyl, naphthyl, pyrazolyl, pyrrolyl, pyrrolidinyl, imidazolyl, imidazolonyl, thiazolyl, oxazolyl, isoxazolyl, furanyl, thienyl, or pyridinyl.

In certain embodiments of the first group of compounds of Formula IB, Ar is indazolyl, indolyl, isoindolyl, imidazolyl, benzimidazolyl, pyrazolyl, pyrazolinyl, pyrrolyl, pyrrolinyl, pyridinyl, piperidinyl, pyridazinyl, quinolinyl, isoquinolinyl, phthalazinyl, dihydroindolyl, benzoisoxazolyl, dihydrobenzoisoxazolyl, dihydroisoindolyl, benzoisothiazolyl, benzoisothiazolyl dioxide, or $C_{6-10}$ aryl. In some such embodiments, Ar is substituted with at least one $R^4$ or $R^5$. In others, Ar is indazolyl, isoindolyl, pyrazolyl, pyrrolinyl, phenyl, naphthyl, dihydronaphthyl, tetrahydronapthyl, indanyl, indenyl, or imidazolyl. For example, Ar is indazolyl, phenyl, naphthyl, or tetrahydronaphthyl. In other embodiments, Ar is —$(C_{1-3}$ alkyl)-$(C_{6-10}$ aryl), —(Y)—$(C_{0-3}$ alkyl)-$(C_{6-10}$ aryl), or —(Y)—$(C_{0-3}$ alkyl)-(5-10 member heteroaryl). In some such embodiments Ar is substituted with at least one $R^4$ or $R^5$. In others, Y is —CHR or —CHZ- and Z is —OR. For example, Y is —$CH_2$—. In still other such embodiments, the $C_{6-10}$ aryl is phenyl or naphthyl or the 5-10 member heteroaryl is quinolinyl, isoquinolinyl, phthalazinyl, or quinazolinyl. Alternatively, Ar is —$(C_{1-3}$ alkyl)-$(C_{6-10}$ aryl).

In some embodiments of the first group of compounds of Formula IB, one or more methylene groups of L are independently replaced by hetero atoms selected from O, N or $S(O)_m$. Alternatively, L is a covalent bond, a $C_1$-$C_9$ alkoxy, —C(O)O—, —NH— or —O—.

As noted above, Q, other than —H or —NR'R', is optionally substituted with $R^{27}$. In certain embodiments of the first group of compounds of Formula IB Q is phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuranyl, 1,3-dioxolanone, 1,3-dioxanone, 1,4-dioxanyl, morpholino, thiomorpholino sulfoxide, thiomorpholino sulfone, piperazinyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; $C_{1-6}$ alkoxy, secondary or tertiary amine wherein the amino nitrogen is covalently bonded to $C_{1-3}$ alkyl or $C_{1-5}$ alkoxyalkyl, phenylamino; $C_{1-6}$ alkyl-$S(O)_m$ or phenyl-$S(O)_m$. In some such embodiments, $R^{27}$ is $C_{1-6}$ alkyl, $C_{1-6}$ alkoxy, hydroxy amino, substituted or unsubstituted 5-10 member heterocyclyl, mono- or di-$(C_{1-3}$ alkyl)amino, mono- or di-(phenyl-$C_{1-3}$ alkyl)amino, $C_{1-6}$ alkyl-$S(O)_m$, phenyl-$C_{1-3}$-alkoxy or phenylamino wherein the phenyl ring is optionally substituted with one to two halogen, $C_{1-6}$ alkyl or $C_{1-6}$ alkoxy. Alternatively, Q is hydrogen, phenyl, thiomorpholino sulfoxide, thiomorpholino sulfone, piperazinonyl, oxazepinyl, diazepinonyl, imidazolyl, pyridinyl or morpholino. In yet other embodiments, Q is morpholino, piperazinyl, pyrimidinyl or pyridinyl. In some such embodiments, $R^{27}$ is —C(O)OR, —NR'R', substituted or unsubstituted straight or branched $C_{1-10}$ alkyl, substituted or unsubstituted $C_{7-20}$ aralkyl, or substituted or unsubstituted saturated or unsaturated 3-11 member heterocyclyl or heterocyclylalkyl containing 1, 2, 3, or 4 heteroatoms selected independently from N, O, $S(O)_m$. Alternatively, Q is pyrimidinyl and $R^{27}$ is —NR'R'or substituted or unsubstituted saturated or unsaturated 3-11 member heterocyclyl containing 1, 2, 3, or 4 heteroatoms selected independently from N, O, $S(O)_m$. In yet other embodiments, Q is pyridinyl, and $R^{27}$ is —NR'R' or substituted or unsubstituted $C_{1-6}$ alkyl, or substituted or unsubstituted saturated or unsaturated 3-11 member heterocyclyl or heterocyclylalkyl containing 1, 2, 3, or 4 heteroatoms selected independently from N, O, $S(O)_m$.

In some embodiments of the first group of compounds of Formula IB each $R^1$ is independently:

$C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-$(C_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, S $(O)_m$, CHOH, C=O, C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully halogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, $C_{1-3}$ alkoxy optionally partially or fully halogenated, $NH_2C(O)$ or mono- or di-$(C_{1-3}$ alkyl)aminocarboxyl; and wherein the $C_{3-10}$ branched or unbranched alkenyl is optionally interrupted by one or more O, N or $S(O)_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, or I;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-$S(O)_2$;

$C_{2-6}$ branched or unbranched alkynyl optionally partially or fully halogenated, wherein one or more methylene groups are optionally replaced by O, NH and $S(O)_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms.

In other embodiments of the first group of compounds of Formula IB, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C$ (O) or mono- or di-$(C_{1-3}$ alkyl)aminocarbonyl. For example, each $R^1$ is independently $C_{3-10}$ branched or unbranched alkyl.

In certain embodiments of the first group of compounds of Formula IB, each $R^2$ is independently —OR', —$OR^6$, —C(O)

R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$. In others, R$^2$ is independently —NR'$_2$, —NO$_2$, —C(O)NR'$_2$, —NR'SO$_2$R", —NR'C(O)NR'R', —NR'C(S)NR'R', —NR'C(O)OR' or —SO$_2$NR'$_2$.

In some embodiments of the first group of compounds of Formula IB each R$^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, C$_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl C$_{1-5}$ alkyl, naphthyl C$_{1-5}$ alkyl, hydroxy, oxo, cyano, C$_{1-3}$ alkoxy optionally partially or fully halogenated, phenyloxy, naphthyloxy, heterocyclyloxy, nitro, amino, mono- or di-(C$_{1-3}$ alkyl)amino, phenylamino, naphthylamino, heterocyclylamino, NH$_2$C(O), a mono- or di-(C$_{1-3}$ alkyl)aminocarbonyl, C$_{1-5}$ alkyl-C(O)—C$_{1-4}$ alkyl, amino-C$_{1-5}$ alkyl, mono- or di-(C$_{1-3}$ alkyl)amino-C$_{1-5}$ alkyl, amino-S(O)$_2$, di-(C$_{1-3}$ alkyl)amino-S(O)$_2$, R$^7$—C$_{1-5}$ alkyl, R$^8$—C$_{1-5}$ alkoxy, R$^9$—C(O)—C$_{1-5}$ alkyl, R$^{10}$—C$_{1-5}$ alkyl(R$^{11}$)N, carboxy-mono- or di-(C$_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, C$_{1-6}$ branched or unbranched alkyl which is optionally partially or fully halogenated, cyano, C$_{1-3}$ alkoxy optionally partially or fully halogenated, phenyloxy, naphthyloxy, heterocyclyloxy, heteroaryloxy, nitro, amino, mono- or di-(C$_{1-3}$ alkyl)amino, phenylamino, naphthylamino, heterocyclic or heteroaryl amino, NH$_2$C(O), a mono- or di-(C$_{1-3}$ alkyl)aminocarbonyl, C$_{1-4}$ alkyl-C(O), C$_{1-5}$ alkylamino-S(O)$_2$, mono- or di-(C$_{1-3}$ alkyl)amino-C$_{1-5}$ alkyl, R$^{12}$—C$_{1-5}$ alkyl, R$^{13}$—C$_{1-5}$ alkoxy, R$^{14}$—C(O)—C$_{1-5}$ alkyl, R$^{15}$—C$_{1-5}$ alkyl(R$^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three C$_{1-3}$ alkyl groups optionally partially or fully halogenated, cyano, hydroxyl C$_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S(O)$_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three C$_{1-3}$ alkyl groups;

C$_{1-4}$ alkyl or alkylene-phenyl-C(O)—C$_{0-4}$ alkyl or alkylene, C$_{1-4}$ alkyl or alkylene-C(O)—C$_{0-4}$ alkyl or alkylene, C$_{1-4}$ alkyl or alkylene-phenyl-S(O)$_m$—C$_{0-4}$ alkyl or alkylene;

C$_{1-6}$ alkyl or C$_{1-6}$ alkoxy, each optionally partially or fully halogenated or optionally substituted with R$^{17}$, amino, OR$^{18}$, or C$_{1-5}$ mono- or di-alkylamino optionally substituted with R$^{19}$;

cyclopropyloxy, cyclobutyloxy, cyclopentyloxy, cyclohexyloxy, cycloheptyloxy, which are optionally partially or fully halogenated and optionally substituted with one to three C$_{1-3}$ alkyl groups optionally partially or fully halogenated wherein one to three ring methylene groups are replaced independently by O, S(O)$_m$, CHOH, C=O, C=S or NH;

R$^{20}$C(O)N(R$^{21}$)—, R$^{22}$O—, R$^{23}$R$^{24}$NC(O)—, R$^{26}$(CH$_2$)$_m$C(O)N(R$^{21}$)— or R$^{26}$C(O)(CH$_2$)$_m$N(R$^{21}$)—;

C$_{2-6}$ alkenyl substituted by R$^{23}$R$^{24}$NC(O)—;

C$_{2-6}$ alkynyl branched or unbranched carbon chain optionally partially or fully halogenated, wherein one or more methylene groups are optionally replaced by O, NH or S(O)$_m$, and wherein said alkynyl group is optionally independently substituted with 0-2 oxo groups, pyrrolidinyl, pyrrolyl, one or more C$_{1-4}$ branched or unbranched alkyl optionally substituted by one or more halogen atoms, nitrile, morpholino, piperidinyl, piperazinyl, imidazolyl, phenyl, pyridinyl, tetrazolyl, or C$_{1-4}$ branched or unbranched alkylamino optionally substituted by one or more halogen atoms; or benzoyl or naphthoyl; and wherein each R$^7$, R$^8$, R$^9$, R$^{10}$, R$^{12}$, R$^{13}$, R$^{14}$, R$^{15}$, R$^{17}$, R$^{19}$, R$^{25}$ and R$^{26}$ is independently cyano, morpholino, piperidinyl, piperazinyl, imidazolyl, phenyl, pyridinyl, tetrazolyl, or mono or di-(C$_{0-4}$ alkyl)amino optionally partially or fully halogenated;

each R$^{11}$ and R$^{16}$ is independently hydrogen or C$_{1-4}$ branched or unbranched alkyl optionally partially or fully halogenated;

R$^{18}$ is independently hydrogen or C$_{1-4}$ branched or unbranched alkyl optionally independently substituted with oxo or R$^{25}$.

In some such embodiments, each R$^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, C$_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl C$_{1-5}$ alkyl, naphthyl C$_{1-5}$ alkyl, hydroxy, oxo, cyano, C$_{1-3}$ alkoxy optionally partially or fully halogenated, phenyloxy, naphthyloxy, heterocyclyloxy, nitro, amino, mono- or di-(C$_{1-3}$ alkyl)amino, phenylamino, naphthylamino, heterocyclylamino, NH$_2$C(O), a mono- or di-(C$_{1-3}$ alkyl)aminocarbonyl, C$_{1-5}$ alkyl-C(O)—C$_{1-4}$ alkyl, amino-C$_{1-5}$ alkyl, mono- or di-(C$_{1-3}$ alkyl)amino-C$_{1-5}$ alkyl, amino-S(O)$_2$, di-(C$_{1-3}$ alkyl)amino-S(O)$_2$, R$^7$—C$_{1-5}$ alkyl, R$^8$—C$_{1-5}$ alkoxy, R$^9$—C(O)—C$_{1-5}$ alkyl, R$^{10}$—C$_{1-5}$ alkyl(R$^{11}$)N, or carboxy-mono- or di-(C$_{1-5}$ alkyl)amino. In others, each R$^3$ is independently phenyl, pyridazinyl or pyridyl, each of which is optionally partially or fully halogenated and optionally substituted with $C_{1-6}$ branched or unbranched alkyl which is optionally partially or fully halogenated, hydroxy, oxo, cyano, $C_{1-3}$ alkoxy optionally partially or fully halogenated, nitro, amino, mono- or di-($C_{1-3}$ alkyl)amino; $C_{1-6}$ alkyl or $C_{1-6}$ alkoxy, each optionally partially or fully halogenated or optionally substituted with $R^{17}$, amino, $OR^{18}$, $C_{1-5}$ mono- or di-alkylamino optionally substituted with $R^{19}$; $R^{20}C(O)N(R^{21})$—, $R^{22}O$—, $R^{23}R^{24}NC(O)$—, $R^{26}(CH_2)_mC(O)N(R^{21})$— or $R^{26}C(O)(CH_2)_mN(R^{21})$—. For example, each $R^3$ can be phenyl or tolyl.

In certain embodiments of the first group of compounds of Formula IB, X is C=O.

There is provided in accordance with another aspect of the invention, a second group of compounds having Formula IA:

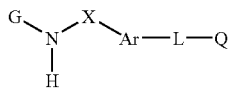

IA stereoisomers thereof, tautomers thereof, solvates thereof prodrugs thereof, and pharmaceutically acceptable salts thereof wherein:

X is C(O) or C(S);

G is a $C_{3-10}$ carbocyclyl, a 5-8 membered monocyclic heterocyclyl, or a 8-11 membered bicyclic heterocyclyl containing 1 or more heteroatoms selected from O, N or S; wherein G is substituted by one or more $R^1$, $R^2$ or $R^3$;

Ar is —(Y)—($C_{0-3}$ alkyl)-(bicyclic aryl), or —Y—($C_{0-3}$ alkyl)-(bicyclic heteroaryl), wherein the bicyclic heteroaryl is indazolyl, isoindolyl, quinolinyl, isoquinolinyl, phthalazinyl, dihydroindolyl, benzofuranyl, benzoxazolyl, benzoisoxazolyl, dihydrobenzoisoxoazolyl, dihydroisoindolyl, benzimidazolyl, benzothienyl, benzothiazolyl, benzoisothiazolyl, or benzoisothiazolyl dioxide, and wherein Ar is optionally substituted with one or more $R^4$ or $R^5$; provided however, that the bicyclic aryl is not 1,1,4,4-tetramethyl-1,2,3,4-tetrahydro-naphthyl;

Y is —C(O)—, —C(NNRC(O)OR)—, —C(NNRR)—, —C(NNHC(O)NRR)—, or —C(NOR)—;

L is a covalent bond or a saturated or unsaturated branched or unbranched $C_{1-10}$ carbon chain, wherein one or more methylene groups are optionally independently replaced by heteroatoms chosen from O, NR and $S(O)_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ alkyl-$S(O)_m$, or phenyl-$S(O)_m$, wherein the cycloalkyl, aryl, heterocyclyl, $C_{1-6}$ alkoxy, $C_{1-6}$ alkyl-$S(O)_m$, or phenyl-$S(O)_m$ is each optionally substituted with one or more $R^{27}$; and provided that if $R^4$ and $R^5$ are absent, -L-Q is not —H;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —C(O)$NR^2$, —C(O)OR, —OR, —NR'R', —$SiR^3$, —$S(O)_m$R, substituted or unsubstituted straight or branched $C_{1-10}$ alkyl $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, $S(O)_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —$OR^6$, —C(O)R', —C(O)OR', —C(O)$NR'_2$, —$NR'_2$, —$NO_2$, —$S(O)_m$R", —$NR'SO_2R"$, —NR'C(O)NR'R', —NR'C(S)NR'R', —NR'C(O)OR' or —$SO_2NR'_2$;

each R" is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently H, substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, $S(O)_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or $S(O)_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or $NR'_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)$NR'_2$, —C(O)OR', —OR', —NR'R', —$SiR'_3$, —$S(O)_m$ R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, $S(O)_m$;

provided however that when Ar is —(Y)-(bicyclic aryl) and G is N-(substituted or unsubstituted phenyl)-pyrazolyl, the pyrazolyl is additionally substituted with one or more $R^1$, $R^2$ or $R^3$; and IA is not N-(4-chloro-3-methyl-isothiazol-5-yl)-2-[2-(2,2-dimethyl-propyl)-benzooxazol-5-yl]-2-oxo-acetamide.

In certain embodiments of compounds of Formula IA, the compound at a concentration of 10 μM inhibits induced TNFa-release from a cell by about 50% or greater than 50%.

In certain embodiments of the second group of compounds of Formula IA, G is phenyl, naphthyl, benzocyclobutanyl, dihydronaphthyl, cyclopropyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In other embodiments, G is phenyl, naphthyl, cyclopropyl, benzocyclobutanyl, dihydronaphthyl, tetrahydronaphthyl, benzocycloheptanyl, benzocycloheptenyl, indanyl, indenyl, or benzofuran-3-one. Alternatively, G is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl. In others, G is pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, isoxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl. In yet other embodiments, G is phenyl, naphthyl, cyclopropyl, pyrazolyl, pyrrolyl, pyrrolidinyl, imidazolyl, imidazolonyl, thiazolyl, oxazolyl, isoxazolyl, furanyl, thienyl, or pyridinyl.

In certain embodiments of the second group of compounds of Formula IA, Ar is —(Y)—(C$_{0-3}$ alkyl)-(bicyclic aryl), and the bicyclic aryl is naphthyl, tetrahydronaphthyl, dihydronaphthyl, indenyl, indanyl or azulenyl. In some such embodiments, Ar is substituted with at least one R$^4$ or R$^5$. In others, Y is —C(O)—, —C(NNRC(O)OR)— or —C(NOR)—. Alternatively, Ar is —C(O)-(bicyclic aryl) or —C(NOR)-(bicyclic aryl) and the bicyclic aryl can be naphthyl, dihydronapthyl, tetrahydronaphthyl, indanyl, indenyl or azulenyl. In other embodiments, Ar is —(Y)—(C$_{0-3}$ alkyl)-(bicyclic heteroaryl). In some such embodiments, Ar is substituted with at least one R$^4$ or R$^5$. In others, Y is —C(O)—, —C(NNRC(O)OR)— or —C(NOR)—. In yet others, Ar is —C(O)-(bicyclic heteroaryl) or —C(NOR)-(bicyclic heteroaryl). For example, the bicyclic heteroaryl is quinolinyl, isoquinolinyl, phthalazinyl, or quinazolinyl.

In certain embodiments of the second group of compounds of Formula IA, one or more methylene groups of L are independently replaced by hetero atoms selected from O, N or S(O)$_m$. Alternatively, L is a covalent bond, a C$_1$-C$_9$ alkoxy, —C(O)O—, —NH— or —O—.

In certain embodiments of the second group of compounds of Formula IA, Q is hydrogen, phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuiranyl, 1,3-dioxolanone, 1,3-dioxanone, 1,4-dioxanyl, morpholino, thiomorpholino sulfoxide, thiomorpholino sulfone, piperazinyl, piperazinonyl, oxazepinyl, diazepanonyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; C$_{1-6}$ alkoxy, secondary or tertiary amine wherein the amino nitrogen is covalently bonded to C$_{1-3}$ alkyl or C$_{1-5}$ alkoxyalkyl, phenylamino; C$_{1-6}$ alkyl-S(O)$_m$ or phenyl-S(O)$_m$. In some such embodiments, R$^{27}$ is C$_{1-6}$ alkyl, C$_{1-6}$ alkoxy, hydroxy amino, substituted or unsubstituted 5-10 member heterocyclyl, mono- or di-(C$_{1-3}$ alkyl)amino, mono- or di-(phenyl-C$_{1-3}$ alkyl)amino, C$_{1-6}$ alkyl-S(O)$_m$, phenyl-C$_{1-3}$-alkoxy or phenylamino wherein the phenyl ring is optionally substituted with one to two halogen, C$_{1-6}$ alkyl or C$_{1-6}$ alkoxy.

In other embodiments of the second group of compounds of Formula IA, Q is hydrogen, thiomorpholino sulfoxide, thiomorpholino sulfone, piperazinonyl, oxazepinyl, diazepinonyl, imidazolyl, pyridinyl or morpholino. In yet other embodiments, Q is morpholino, piperazinyl, pyrimidinyl or pyridinyl. In some such embodiments, R$^{27}$ is —C(O)OR, —NR'R', substituted or unsubstituted straight or branched C$_{1-10}$ alkyl, substituted or unsubstituted C$_{7-20}$ aralkyl, or substituted or unsubstituted saturated or unsaturated 3-11 member heterocyclyl or heterocyclylalkyl containing 1, 2, 3, or 4 heteroatoms selected independently from N, O, S(O)$_m$. For example, Q is pyrimidinyl and R$^{27}$ is —NR'R' or substituted or unsubstituted saturated or unsaturated 3-11 member heterocyclyl containing 1, 2, 3, or 4 heteroatoms selected independently from N, O, S(O)$_m$. Alternatively, Q is pyridinyl, and R$^{27}$ is —NR'R', substituted or unsubstituted C$_{1-6}$ alkyl, or substituted or unsubstituted saturated or unsaturated 3-11 member heterocyclyl or heterocyclylalkyl containing 1, 2, 3, or 4 heteroatoms selected independently from N, O, S(O)$_m$.

In certain embodiments of the second group of compounds of Formula IA, each R$^1$ is independently:

C$_{3-10}$ branched or unbranched alkyl optionally partially or fully halogenated, and optionally substituted with one to three C$_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, C$_{1-6}$ branched or unbranched alkyl which is optionally partially or fully halogenated, C$_{3-8}$ cycloalkyl, C$_{5-8}$ cycloalkenyl, hydroxy, cyano, C$_{1-3}$ alkoxy which is optionally partially or fully halogenated and NH$_2$C(O) or mono- or di-(C$_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three C$_{1-3}$ alkyl groups optionally partially or fully halogenated, cyano, hydroxyl C$_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, S(O)$_m$, CHOH, C=O, C=S or NH;

C$_{3-10}$ branched or unbranched alkenyl optionally partially or fully halogenated, and optionally substituted with one to three C$_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully halogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, $C_{1-3}$ alkoxy optionally partially or fully halogenated, $NH_2C(O)$ or mono- or di-$(C_{1-3}$ alkyl)aminocarboxyl; and wherein the $C_{3-10}$ branched or unbranched alkenyl is optionally interrupted by one or more O, N or $S(O)_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, or I;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-S(O)$_2$;

$C_{2-6}$ branched or unbranched alkynyl optionally partially or fully halogenated, wherein one or more methylene groups are optionally replaced by O, NH and $S(O)_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms. Alternatively, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-$(C_{1-3}$ alkyl)aminocarbonyl. For example, n each $R^1$ is independently $C_{3-10}$ branched or unbranched alkyl.

In certain embodiments of the second group of compounds of Formula IA, each $R^2$ is independently —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$. Alternatively, $R^2$ is independently —NR'$_2$, —NO$_2$, —C(O)NR'$_2$, —NR'SO$_2$R", —NR'C(O)NR'R', —NR'C(S)NR'R', —NR'C(O)OR' or —SO$_2$NR'$_2$.

In certain embodiments of the second group of compounds of Formula IA, each $R^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-$(C_{1-3}$ alkyl)amino, phenylamino, naphthylamino, heterocyclylamino, $NH_2C(O)$, a mono- or di-$(C_{1-3}$ alkyl)aminocarbonyl, $C_{1-5}$ alkyl-C(O)—$C_{1-4}$ alkyl, amino-$C_{1-5}$ alkyl, mono- or di-$(C_{1-3}$ alkyl)amino-$C_{1-5}$ alkyl, amino-S(O)$_2$, di-$(C_{1-3}$ alkyl) amino-S(O)$_2$, $R^7$—$C_{1-5}$ alkyl, $R^8$—$C_{1-5}$ alkoxy, $R^9$—C(O)— $C_{1-5}$ alkyl, $R^{10}$—$C_{1-5}$ alkyl($R^{11}$)N, carboxy-mono- or di-$(C_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, $C_{1-6}$ branched or unbranched alkyl which is optionally partially or fully halogenated, cyano, $C_{1-3}$ alkoxy optionally partially or fully halogenated, phenyloxy, naphthyloxy, heterocyclyloxy, heteroaryloxy, nitro, amino, mono- or di-$(C_{1-3}$ alkyl)amino, phenylamino, naphthylamino, heterocyclic or heteroaryl amino, $NH_2C(O)$, a mono- or di-$(C_{1-3}$ alkyl)aminocarbonyl, $C_{1-4}$ alkyl-C(O), $C_{1-5}$ alkylamino-S(O)$_2$, mono- or di-$(C_{1-3}$ alkyl)amino-$C_{1-5}$ alkyl, $R^{12}$—$C_{1-5}$ alkyl, $R^{13}$—$C_{1-5}$ alkoxy, $R^{14}$—C(O)—$C_{1-5}$ alkyl, $R^{15}$—$C_{1-5}$ alkyl($R^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S $(O)_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three $C_{1-3}$ alkyl groups;

$C_{1-4}$ alkyl or alkylene-phenyl-C(O)—$C_{0-4}$ alkyl or alkylene, $C_{1-4}$ alkyl or alkylene-C(O)—$C_{0-4}$ alkyl or alkylene, $C_{1-4}$ alkyl or alkylene -phenyl-S(O)$_m$—$C_{0-4}$ alkyl or alkylene;

$C_{1-6}$ alkyl or $C_{1-6}$ alkoxy, each optionally partially or fully halogenated or optionally substituted with $R^{17}$, amino, OR$^{18}$, or $C_{1-5}$ mono- or di-alkylamino optionally substituted with $R^{19}$;

cyclopropyloxy, cyclobutyloxy, cyclopentyloxy, cyclohexyloxy, cycloheptyloxy, which are optionally partially or fully halogenated and optionally substituted with one to three $C_{1-3}$ alkyl groups optionally partially or fully halogenated wherein one to three ring methylene groups are replaced independently by O, $S(O)_m$, CHOH, C=O, C=S or NH;

$R^{20}C(O)N(R^{21})$—, $R^{22}O$—, $R^{23}R^{24}NC(O)$—, $R^{26}(CH_2)_m$ $C(O)N(R^{21})$— or $R^{26}C(O)(CH_2)_mN(R^{21})$—;

$C_{2-6}$ alkenyl substituted by $R^{23}R^{24}NC(O)$—;

$C_{2-6}$ alkynyl branched or unbranched carbon chain optionally partially or fully halogenated, wherein one or more methylene groups are optionally replaced by O, NH or S(O)$_m$, and wherein said alkynyl group is optionally independently substituted with 0-2 oxo groups, pyrrolidinyl, pyrrolyl, one or more C$_{1-4}$ branched or unbranched alkyl optionally substituted by one or more halogen atoms, nitrile, morpholino, piperidinyl, piperazinyl, imidazolyl, phenyl, pyridinyl, tetrazolyl, or C$_{1-4}$ branched or unbranched alkylamino optionally substituted by one or more halogen atoms; or benzoyl or naphthoyl; and wherein each R$^7$, R$^8$, R$^9$, R$^{10}$, R$^{12}$, R$^{13}$, R$^{14}$, R$^{15}$, R$^{17}$, R$^{19}$, and R$^{25}$ is independently cyano, morpholino, piperidinyl, piperazinyl, imidazolyl, phenyl, pyridinyl, tetrazolyl, or mono or di-(C$_{0-4}$ alkyl)amino optionally partially or fully halogenated;

each R$^{11}$ and R$^{16}$ is independently hydrogen or C$_{1-4}$ branched or unbranched alkyl optionally partially or fully halogenated; and R$^{18}$ is independently hydrogen or C$_{1-4}$ branched or unbranched alkyl optionally independently substituted with oxo or R$^{25}$.

In some such embodiments of the second group of compounds of Formula IA, each R$^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, C$_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl C$_{1-5}$ alkyl, naphthyl C$_{1-5}$ alkyl, hydroxy, oxo, cyano, C$_{1-3}$ alkoxy optionally partially or fully halogenated, phenyloxy, naphthyloxy, heterocyclyloxy, nitro, amino, mono- or di-(C$_{1-3}$ alkyl)amino, phenylamino, naphthylamino, heterocyclylamino, NH$_2$C(O), a mono- or di-(C$_{1-3}$ alkyl)aminocarbonyl, C$_{1-5}$ alkyl-C(O)—C$_{1-4}$ alkyl, amino-C$_{1-5}$ alkyl, mono- or di-(C$_{1-3}$ alkyl)amino-C$_{1-5}$ alkyl, amino-S(O)$_2$, di-(C$_{1-3}$ alkyl)amino-S(O)$_2$, R$^7$—C$_{1-5}$ alkyl, R$^8$—C$_{1-5}$ alkoxy, R$^9$—C(O)—C$_{1-5}$ alkyl, R$^{10}$—C$_{1-5}$ alkyl (R$^{11}$)N, or carboxy-mono- or di-(C$_{1-5}$ alkyl)amino. In other such embodiments, R$^3$ is phenyl, pyridazinyl or pyridyl, each of which is optionally partially or fully halogenated and optionally substituted with C$_{1-6}$ branched or unbranched alkyl which is optionally partially or fully halogenated, hydroxy, oxo, cyano, C$_{1-3}$ alkoxy optionally partially or fully halogenated, nitro, amino, or mono- or di-(C$_{1-3}$ alkyl)amino; C$_{1-6}$ alkyl or C$_{1-6}$ alkoxy, each optionally partially or fully halogenated or optionally substituted with R$^{17}$, amino, OR$^{18}$, C$_{1-5}$ mono- or di-alkylamino optionally substituted with R$^{19}$; R$^{20}$C(O)N(R$^{21}$)—, R$^{22}$O—, R$^{23}$R$^{24}$NC(O)—, R$^{26}$(CH$_2$)$_m$C(O)N(R$^{21}$)— or R$^{26}$C(O)(CH$_2$)$_m$N(R$^{21}$)—.

In some embodiments of the second group of compounds of Formula IA, X is C═O.

In certain embodiments of the second group of compounds of Formula IA, Ar is —(Y)-naphthyl-, Y is —C(O)—, or —C(═NOH)— and G is selected from phenyl, pyridinyl, pyrazolyl, pyrrolyl, imidazolyl, oxazolyl, isoxazolyl, furanyl or thienyl. In others, Ar is —(Y)-naphthyl-, Y is —C(O)—, or —C(═NOH)— and G is phenyl or pyridyl. In some such embodiments, each R$^1$ is independently a substituted or unsubstituted straight or branched C$_{1-10}$ alkyl and each R$^3$ can be independently R$^{23}$R$^{24}$N—C(O)—, R$^{20}$—C(O)—NR$^{21}$—, or OR$^{22}$. In some such embodiments, each R$^2$ is independently —NR'SO$_2$R", —Cl, —Br, —F, —C(O)—NR'$_2$, substituted or unsubstituted straight or branched C$_{1-6}$ alkyl, —NR'$_2$, or —OR'.

In other embodiments of the second group of compounds of Formula IA, Ar is —(Y)-naphthyl-, Y is —C(O)—, or —C(═NOH)—, and G is pyrazolyl, thienyl or isoxazolyl. In some such embodiments, each R$^1$ is independently a substituted or unsubstituted straight or branched C$_{1-10}$ alkyl each R$^3$ can be independently phenyl or pyridinyl, optionally substituted with one, two, or three —F, —Cl, substituted or unsubstituted C$_{1-6}$ branched or unbranched alkyl or substituted or unsubstituted C$_{1-4}$ alkoxy.

There is provided in accordance with another aspect of the invention, a second group of compounds having Formula IB:

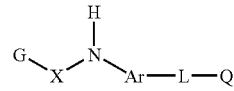

IB stereoisomers thereof, tautomers thereof, solvates thereof, prodrugs thereof, and pharmaceutically acceptable salts thereof, wherein:

X is C(O) or C(S);

G is a G'-(Y)— wherein G' is a C$_{3-10}$ carbocyclyl, 5-8 membered monocyclic heterocyclyl, or 8-11 membered bicyclic heterocyclyl other than indolyl containing 1 or more heteroatoms selected from O, N or S, wherein G' is substituted by one or more R$^1$, R$^2$ or R$^3$;

Ar is bicyclic aryl or 8-11 membered bicyclic heteroaryl containing 1 or more heteroatoms selected from O, N or S, wherein Ar is optionally substituted with one or more R$^4$ or R$^5$;

Y is independently —C(O)—, —C(NNRC(O)OR)—, —C(NNRR)—, —C(NNC(O)NRR) or —C(NOR)—;

L is a covalent bond or a saturated or unsaturated branched or unbranched C$_{1-10}$ carbon chain, wherein one or more methylene groups are optionally independently replaced by heteroatoms chosen from O, NR and S(O)$_m$; and wherein L is optionally substituted with 0-2 oxo groups and one or more C$_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, C$_{1-6}$ alkoxy, C$_{1-6}$ alkyl-S(O)$_m$, or phenyl-S(O)$_m$, wherein the cycloalkyl, aryl, heterocyclyl, C$_{1-6}$ alkoxy, C$_{1-6}$ alkyl-S(O)$_m$, or phenyl-S(O)$_m$ is each optionally substituted with one or more R$^{27}$; and provided that if R$^4$ and R$^5$ are absent, -L-Q is not —H;

each R is independently hydrogen or substituted or unsubstituted C$_{1-6}$ alkyl;

each R' is independently hydrogen, substituted or unsubstituted C$_{1-8}$ alkyl, substituted or unsubstituted (C$_{0-4}$ alkyl)-(C$_{6-10}$ aryl) or substituted or unsubstituted (C$_{0-4}$ alkyl)-(5-10 member heterocyclyl);

each R$^1$ is independently F, Cl, Br, I, cyano, —C(O)R, —C(O)NR$_2$, —C(O)OR, —OR, —NR'R', —SiR$_3$, —S(O)$_m$R, substituted or unsubstituted straight or branched C$_{1-10}$ alkyl, C$_{2-10}$ alkenyl, or C$_{2-10}$ alkynyl, substituted or unsubstituted C$_{3-10}$ cycloalkyl, substituted or unsubstituted C$_{5-8}$ cycloalkenyl, substituted or unsubstituted C$_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$;

each R" is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, S(O)$_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or S(O)$_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or NR'$_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)NR'$_2$, —C(O)OR', —OR', —NR'R', —SiR'$_3$, —S(O)$_m$ R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, S(O)$_m$;

provided however that IB is not 2-[6-(2-biphenyl-4-yl-2-oxo-acetylamino)-indol-1-ylmethyl]-benzoic acid.

In certain embodiments of the second group of compounds of Formula IB, the compound at a concentration of 10 µM inhibits induced TNFa-release from a cell by about 50% or greater than 50%.

In some embodiments of the second group of compounds of Formula IB, G' is phenyl, naphthyl, cyclopropyl, benzocyclobutanyl, dihydronaphthyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In other embodiments of the second group of compounds of Formula IB, G' is phenyl, naphthyl, cyclopropyl, benzocyclobutanyl, dihydronaphthyl, tetrahydronaphthyl, benzocycloheptanyl, benzocycloheptenyl, indanyl, indenyl, or benzofuran-3-one. In others, G' is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl. Alternatively, G' is pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, isoxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl. In yet other embodiments, G' is phenyl, naphthyl, pyrazolyl, cyclopropyl, pyrrolyl, pyrrolidinyl, imidazolyl, imidazolonyl, thiazolyl, oxazolyl, isoxazolyl, furanyl, thienyl, or pyridinyl.

In certain embodiments of the second group of compounds of Formula IB, Y is —C(O)—, —C(NNRC(O)OR)— or —C(NOR)—.

In certain embodiments of the second group of compounds of Formula IB, Ar is naphthyl, dihydronapthyl, tetrahydronaphtyl, indenyl or azulenyl. Alternatively, Ar is indazolyl, isoindolyl, quinolinyl, isoquinolinyl, phthalazinyl, indolyl, dihydroindolyl, benzofuranyl, benzoxazolyl, benzoisoxazolyl, dihydrobenzoisoxoazolyl, dihydroisoindolyl, benzimidazolyl, benzothienyl, benzothiazolyl, benzoisothiazolyl or benzoisothiazolyl dioxide.

In certain embodiments of the second group of compounds of Formula IB, one or more methylene groups of L are independently replaced by hetero atoms selected from O, N or S(O)$_m$. Alternatively, L is a covalent bond, a $C_1$-$C_9$ alkoxy, —C(O)O—, —NH— or —O—.

In certain embodiments of the second group of compounds of Formula IB, Q is hydrogen, phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuranyl, 1,3-dioxolanone, 1,3-dioxanone, 1,4-dioxanyl, morpholino, thiomorpholino sulfoxide, thiomorpholino sulfone, piperazinyl, piperazinonyl, oxazepinyl, diazepanonyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; $C_{1-6}$ alkoxy, secondary or tertiary amine wherein the amino nitrogen is covalently bonded to $C_{1-3}$ alkyl or $C_{1-5}$ alkoxyalkyl, phenylamino; $C_{1-6}$ alkyl-$S(O)_m$ or phenyl-$S(O)_m$. In some such embodiments, $R^{27}$ is $C_{1-6}$ alkyl, $C_{1-6}$ alkoxy, hydroxy amino, substituted or unsubstituted 5-10 member heterocyclyl, mono- or di-($C_{1-3}$ alkyl)amino, mono- or di-(phenyl-$C_{1-3}$ alkyl)amino, $C_{1-6}$ alkyl-$S(O)_m$, phenyl-$C_{1-3}$-alkoxy or phenylamino wherein the phenyl ring is optionally substituted with one to two halogen, $C_{1-6}$ alkyl or $C_{1-6}$ alkoxy.

In other embodiments of compounds of Formula IB, Q is hydrogen, thiomorpholino sulfoxide, thiomorpholino sulfone, piperazinonyl, oxazepinyl, diazepinonyl, imidazolyl, pyridinyl or morpholino. In yet others, Q is morpholino, piperazinyl, pyrimidinyl or pyridinyl. In some such embodiments, $R^{27}$ is —C(O)OR, —NR'R', substituted or unsubstituted straight or branched $C_{1-10}$ alkyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, $S(O)_m$. For example, Q is pyrimidinyl, and $R^{27}$ is —NR'R' or substituted or unsubstituted saturated or unsaturated 3-11 member heterocyclyl containing 1, 2, 3, or 4 heteroatoms selected independently from N, O, $S(O)_m$. Alternatively, Q is pyridinyl, and $R^{27}$ is —NR'R', substituted or unsubstituted $C_{1-6}$ alkyl, or substituted or unsubstituted saturated or unsaturated 3-11 member heterocyclyl or heterocyclylalkyl containing 1, 2, 3, or 4 heteroatoms selected independently from N, O, $S(O)_m$.

In certain embodiments of the second group of compounds of Formula IB, each $R^1$ is independently:

$C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, S $(O)_m$, CHOH, C=O, C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully haiogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, $C_{1-3}$ alkoxy optionally partially or fully halogenated, $NH_2C(O)$ or mono- or di-($C_{1-3}$ alkyl)aminocarboxyl; and wherein the $C_{3-10}$ branched or unbranched alkenyl is optionally interrupted by one or more O, N or $S(O)_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, or I;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-$S(O)_2$;

$C_{2-6}$ branched or unbranched alkynyl optionally partially or fully halogenated, wherein one or more methylene groups are optionally replaced by O, NH and $S(O)_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms.

In other embodiments, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl. For example, each $R^1$ is independently $C_{3-10}$ branched or unbranched alkyl.

In certain embodiments of the second group of compounds of Formula IB, each $R^2$ is independently —OR', —$OR^6$, —C(O)R', —C(O)OR', —C(O)NR'$_2$, —NR'$_2$, —$NO_2$, —$S(O)_mR''$, —NR'$SO_2R''$, —NR'C(O)NR'R', —NR'C(S)NR'R', —NR'C(O)OR' or —$SO_2NR'_2$. In others, each $R^2$ is independently —NR'$_2$, —$NO_2$, —C(O)NR'$_2$, —NR'$SO_2R''$, —NR'C(O)NR'R', —NR'C(S)NR'R', —NR'C(O)OR' or —$SO_2NR'_2$.

In certain embodiments of the second group of compounds of Formula IB, each $R^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-$S(O)_2$, di-($C_{1-3}$ alkyl)

amino-S(O)$_2$, R$^7$—C$_{1-5}$ alkyl, R$^8$—C$_{1-5}$ alkoxy, R$^9$—C(O)—C$_{1-5}$ alkyl, R$^{10}$—C$_{1-5}$ alkyl(R$^{11}$)N, carboxy-mono- or di-(C$_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, C$_{1-6}$ branched or unbranched alkyl which is optionally partially or fully halogenated, cyano, C$_{1-3}$ alkoxy optionally partially or fully halogenated, phenyloxy, naphthyloxy, heterocyclyloxy, heteroaryloxy, nitro, amino, mono- or di-(C$_{1-3}$ alkyl)amino, phenylamino, naphthylamino, heterocyclic or heteroaryl amino, NH$_2$C(O), a mono- or di-(C$_{1-3}$ alkyl)aminocarbonyl, C$_{1-4}$ alkyl-C(O), C$_{1-5}$ alkylamino-S(O)$_2$, mono- or di-(C$_{1-3}$ alkyl)amino-C$_{1-5}$ alkyl, R$^{12}$—C$_{1-5}$ alkyl, R$^{13}$—C$_{1-5}$ alkoxy, R$^{14}$—C(O)—C$_{1-5}$ alkyl, R$^{15}$—C$_{1-5}$ alkyl(R$^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three C$_{1-3}$ alkyl groups optionally partially or fully halogenated, cyano, hydroxyl C$_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S(O)$_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three C$_{1-3}$ alkyl groups;

C$_{1-4}$ alkyl or alkylene-phenyl-C(O)—C$_{0-4}$ alkyl or alkylene, C$_{1-4}$ alkyl or alkylene-C(O)—C$_{0-4}$ alkyl or alkylene, C$_{1-4}$ alkyl or alkylene-phenyl-S(O)$_m$—C$_{0-4}$ alkyl or alkylene;

C$_{1-6}$ alkyl or C$_{1-6}$ alkoxy, each optionally partially or fully halogenated or optionally substituted with R$^{17}$, amino, OR$^{18}$, or C$_{1-5}$ mono- or di-alkylamino optionally substituted with R$^{19}$;

cyclopropyloxy, cyclobutyloxy, cyclopentyloxy, cyclohexyloxy, cycloheptyloxy, which are optionally partially or fully halogenated and optionally substituted with one to three C$_{1-3}$ alkyl groups optionally partially or fully halogenated wherein one to three ring methylene groups are replaced independently by O, S(O)$_m$, CHOH, C=O, C=S or NH;

R$^{20}$C(O)N(R$^{21}$)—, R$^{22}$O—, R$^{23}$R$^{24}$NC(O)—, R$^{26}$(CH$_2$)$_m$C(O)N(R$^{21}$)— or R$^{26}$C(O)(CH$_2$)$_m$N(R$^{21}$)—;

C$_{2-6}$ alkenyl substituted by R$^{23}$R$^{24}$NC(O)—;

C$_{2-6}$ alkynyl branched or unbranched carbon chain optionally partially or fully halogenated, wherein one or more methylene groups are optionally replaced by O, NH or S(O)$_m$, and wherein said alkynyl group is optionally independently substituted with 0-2 oxo groups, pyrrolidinyl, pyrrolyl, one or more C$_{1-4}$ branched or unbranched alkyl optionally substituted by one or more halogen atoms, nitrile, morpholino, piperidinyl, piperazinyl, phenyl, pyridinyl, tetrazolyl, or C$_{1-4}$ branched or unbranched alkylamino optionally substituted by one or more halogen atoms; or benzoyl or naphthoyl; and wherein each R$^7$, R$^8$, R$^9$, R$^{10}$, R$^{12}$, R$^{13}$, R$^{14}$, R$^{15}$, R$^{17}$, R$^{19}$, and R$^{25}$ is independently cyano, morpholino, piperidinyl, piperazinyl, imidazolyl, phenyl, pyridinyl, tetrazolyl, or mono or di-(C$_{0-4}$ alkyl)amino optionally partially or fully halogenated;

each R$^{11}$ and R$^{16}$ is independently hydrogen or C$_{1-4}$ branched or unbranched alkyl optionally partially or fully halogenated; and R$^{18}$ is independently hydrogen or C$_{1-4}$ branched or unbranched alkyl optionally independently substituted with oxo or R$^{25}$.

In some such embodiments, each R$^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, C$_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl C$_{1-5}$ alkyl, naphthyl C$_{1-5}$ alkyl, hydroxy, oxo, cyano, C$_{1-3}$ alkoxy optionally partially or fully halogenated, phenyloxy, naphthyloxy, heterocyclyloxy, nitro, amino, mono- or di-(C$_{1-3}$ alkyl)amino, phenylamino, naphthylamino, heterocyclylamino, NH$_2$C(O), a mono- or di-(C$_{1-3}$ alkyl)aminocarbonyl, C$_{1-5}$ alkyl-C(O)—C$_{1-4}$ alkyl, amino-C$_{1-5}$ alkyl, mono- or di-(C$_{1-3}$ alkyl)amino-C$_{1-5}$ alkyl, amino-S(O)$_2$, di-(C$_{1-3}$ alkyl)amino-S(O)$_2$, R$^7$—C$_{1-5}$ alkyl, R$^8$—C$_{1-5}$ alkoxy, R$^9$—C(O)—C$_{1-5}$ alkyl, R$^{10}$—C$_{1-5}$ alkyl (R$^{11}$)N, or carboxy-mono- or di-(C$_{1-5}$ alkyl)amino. In other such embodiments, R$^3$ is phenyl, pyridazinyl or pyridyl, each of which is optionally partially or fully halogenated and optionally substituted with C$_{1-6}$ branched or unbranched alkyl which is optionally partially or fully halogenated, hydroxy, oxo, cyano, C$_{1-3}$ alkoxy optionally partially or fully halogenated, nitro, amino, or mono- or di-(C$_{1-3}$ alkyl)amino; C$_{1-6}$ alkyl or C$_{1-6}$ alkoxy, each optionally partially or fully halogenated or optionally substituted with R$^{17}$, amino, OR$^{18}$, C$_{1-5}$ mono- or di-alkylamino optionally substituted with R$^{19}$; R$^{20}$C(O)N(R$^{21}$)—, R$^{22}$O—, R$^{23}$R$^{24}$NC(O)—, R$^{26}$(CH$_2$)$_m$C(O)N(R$^{21}$)— or R$^{26}$C(O)(CH$_2$)$_m$N(R$^{21}$)—.

In some embodiments of the second group of compounds of Formula IB, X is C=O.

In certain embodiments of the second group of compounds of Formula IB, Ar is naphthyl, G is G'-(Y)—, Y is —C(O)— or —C(=NOH)— and G' is selected from phenyl, pyridinyl, pyrazolyl, pyrrolyl, imidazolyl, oxazolyl, isoxazolyl, furanyl or thienyl. In others, Ar is naphthyl, G is G'-(Y)—, Y is —C(O)— or —C(=NOH)— and G' is phenyl or pyridinyl, substituted by one or more R$^1$, R$^2$ or R$^3$. In some such embodiments, each R$^1$ is independently a substituted or unsubstituted straight or branched C$_{1-10}$ alkyl. In these, each R$^3$ can be independently R$^{23}$R$^{24}$N—C(O)—, R$^{20}$—C(O)—NR$^{21}$—, or OR$^{22}$. In others such embodiments each R$^2$ is independently —NR'SO$_2$R", —Cl, —Br, —F, —C(O)—NR'$_2$, substituted or unsubstituted straight or branched C$_{1-6}$ alkyl, —NR'$_2$, or —OR'.

In other embodiments of the second group of compounds of Formula IB, Ar is -naphthyl- and G is G'-(Y)—, wherein Y is selected from —C(O)— and —C(=NOH)— and G' is pyrazolyl, isoxazolyl or furanyl, substituted by one or more R$^1$, R$^2$ or R$^3$. In some such embodiments, each R$^1$ is independently a substituted or unsubstituted straight or branched $C_{1-10}$ alkyl. In these, each $R^3$ can be independently substituted or unsubstituted $C_{1-6}$ alkyl, pyridinyl or phenyl, optionally substituted with one to three —F, —Cl, substituted or unsubstituted $C_{1-6}$ branched or unbranched alkyl, or substituted or unsubstituted $C_{1-3}$ alkoxy.

There is provided in accordance with another aspect of the inxention, a third group of compounds having Formula IA:

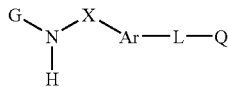

stereoisomers thereof, tautomers thereof, solvates thereof, prodrugs thereof, and pharmaceutically acceptable salts thereof, wherein:

X is C(O) or C(S);

G is a $C_{3-5}$ cycloalkyl, pyrazolyl, thiazolyl, oxazolyl, isothiazolyl, thiadiazolyl, oxadiazolyl, pyrrolinyl, pyridazinyl, pyrrolyl, imidazolyl, imidazolonyl, isoxazolyl, furanyl, thienyl, pyridonyl, naphthyl, dihydronaphthyl, tetrahydronaphthyl, indanyl, indenyl, quinolinyl, dihydroquinolinyl, tetrahydroquinoyl, isoquinolinyl, tetrahydroisoquinoyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tetrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl; wherein G is substituted by one or more $R^1$, $R^2$ or $R^3$;

Ar is —(Y)—($C_{0-3}$ alkyl)-(phenyl), or —(Y)—($C_{0-3}$ alkyl)-(monocyclic heteroaryl), wherein Ar is optionally substituted with one or more $R^4$ or $R^5$;

Y is —C(O)—, —C(NNRC(O)OR)—, —C(NNRR)—, —C(NNHC(O)NRR)— or —C(NOR)—,

L is a covalent bond or a saturated or unsaturated branched or unbranched $C_{1-10}$ carbon chain, wherein one or more methylene groups are optionally independently replaced by heteroatoms chosen from O, NR and $S(O)_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ alkyl-$S(O)_m$, or phenyl-$S(O)_m$, wherein the cycloalkyl, aryl, heterocyclyl, $C_{1-6}$ alkoxy, $C_{1-6}$ alkyl-$S(O)_m$, or phenyl-$S(O)_m$ is each optionally substituted with one or more $R^{27}$; provided that if $R^4$ and $R^5$ are absent, -L-Q is not —H;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —C(O)NR$^2$, —C(O)OR, —OR, —NR'R', —SiR$^3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, $S(O)_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R'', —NR'SO$_2$R'', —NR'C(O)NR'R', —NR'C(S)NR'R', —NR'C(O)OR' or —SO$_2$NR'$_2$;

each R'' is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, $S(O)_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl wherein one or more methylene groups of the $C_{1-8}$ alkyl, $C_{2-8}$ alkenyl, or $C_{2-8}$ alkynyl are optionally replaced by O, NH, or $S(O)_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or NR'$_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)NR'$_2$, —C(O)OR', —OR', —NR'R', —SiR'$_3$, —S(O)$_m$R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted C-$_{7-20}$ aralkyl, substituted or unsubstituted 3-11 member heterocyclyl or heterocyclylalkyl containing 1, 2, 3, or 4 heteroatoms selected independently from N, O, $S(O)_m$;

provided however that when Ar is phenyl and G is N-(substituted or unsubstituted phenyl)-pyrazolyl, the pyrazolyl is additionally substituted with one or more $R^1$, $R^2$ or $R^3$; and IA is not 2-[6-(2-biphenyl-4-yl-2-oxo-acetylamino)-indol-1-yl-methyl]-benzoic acid In certain embodiments of the third group of compounds of Formula IA, the compound at a concentration of 10 μM inhibits induced TNFa-release from a cell by about 50% or greater than 50%.

In certain embodiments of the third group of compounds of Formula IA, G is cyclopropyl, cyclobutyl or cyclopentyl. In others, G is cyclopropyl, pyrazolyl, pyrrolyl, pyrrolidinyl, imidazolyl, imidazolonyl, thiazolyl, oxazolyl, isoxazolyl, furanyl, or thienyl.

In some embodiments of the third group of compounds of Formula IA, Ar is —(Y)—(C$_{0-3}$ alkyl)-(phenyl) and Y is —C(O)—, —C(NNRC(O)OR)— or —C(NOR)—. In some such embodiments, Ar is substituted by at least one R$^4$ or R$^5$. In others, Ar is —C(O)-(phenyl). In yet other embodiments, Ar is —(Y)—(C$_{0-3}$ alkyl)-(monocyclic heteroaryl), and the monocyclic heteroaryl is pyrazolyl, imidazolyl, pyrazolinyl, pyrrolyl, pyrrolinyl, pyridinyl, pyrimidinyl or pyridazinyl. In some such embodiments, Ar is substituted by at least one R$^4$ or R$^5$. Alternatively, Y is —C(O)—, —C(NNRC(O)OR)— or —C(NOR)—. In yet others, Ar is —C(O)-(monocyclic heteroaryl) or —C(NOR)-(monocyclic heteroaryl). For example, the monocyclic heteroaryl can be pyrazolyl, imidazolyl, pyrazolinyl, pyrrolyl, pyrrolinyl, pyridinyl, pyrimidyl, or pyridazinyl.

In certain embodiments of the third group of compounds of Formula IA, one or more methylene groups of L are independently replaced by hetero atoms selected from O, N or S(O)$_m$. In others, L is a covalent bond, a C$_1$-C$_9$ alkoxy, —C(O)O—, —NH— or —O—.

In certain embodiments of the third group of compounds of Formula IA, Q is hydrogen, phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuranyl, 1,3-dioxolanone, 1,3-dioxanone, 1,4-dioxanyl, morpholino, thiomorpholino sulfoxide, thiomorpholino sulfone, piperazinyl, piperazinonyl, oxazepinyl, diazepanonyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; C$_{1-6}$ alkoxy, secondary or tertiary amine wherein the amino nitrogen is covalently bonded to C$_{1-3}$ alkyl or C$_{1-5}$ alkoxyalkyl, phenylamino; C$_{1-6}$ alkyl-S(O)$_m$ or phenyl-S(O)$_m$. In some such embodiments, R$^{27}$ is C$_{1-6}$ alkyl, C$_{1-6}$ alkoxy, hydroxy amino, substituted or unsubstituted 5-10 member heterocyclyl, mono- or di-(C$_{1-3}$ alkyl)amino, mono- or di-(phenyl-C$_{1-3}$ alkyl)amino, C$_{1-6}$ alkyl-S(O)$_m$, phenyl-C$_{1-3}$-alkoxy or phenylamino wherein the phenyl ring is optionally substituted with one to two halogen, C$_{1-6}$ alkyl or C$_{1-6}$ alkoxy.

In other embodiments, Q is hydrogen, thiomorpholino sulfoxide, thiomorpholino sulfone, piperazinonyl, oxazepinyl, diazepinonyl, imidazolyl, pyridinyl or morpholino. In yet others, Q is morpholino, piperazinyl, pyrimidinyl or pyridinyl. In some such embodiments, R$^{27}$ is —C(O)OR, —NR'R', substituted or unsubstituted straight or branched C$_{1-10}$ alkyl, substituted or unsubstituted C$_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$. For example, Q is pyrimidinyl, and R$^{27}$ is —NR'R' or substituted or unsubstituted saturated or unsaturated 3-11 member heterocyclyl containing 1, 2, 3, or 4 heteroatoms selected independently from N, O, S(O)$_m$. Alternatively, Q is pyridinyl, and R$^{27}$ is —NR'R', substituted or unsubstituted C$_{1-6}$ alkyl, or substituted or unsubstituted saturated or unsaturated 3-11 member heterocyclyl or heterocyclylalkyl containing 1, 2, 3, or 4 heteroatoms selected independently from N, O, S(O)$_m$.

In certain embodiments of the third group of compounds of Formula IA, each R$^1$ is independently:

C$_{3-10}$ branched or unbranched alkyl optionally partially or fully halogenated, and optionally substituted with one to three C$_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, C$_{1-6}$ branched or unbranched alkyl which is optionally partially or fully halogenated, C$_{3-8}$ cycloalkyl, C$_{5-8}$ cycloalkenyl, hydroxy, cyano, C$_{1-3}$ alkoxy which is optionally partially or fully halogenated and NH$_2$C(O) or mono- or di-(C$_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three C$_{1-3}$ alkyl groups optionally partially or fully halogenated, cyano, hydroxyl C$_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, S(O)$_m$, CHOH, C=O, C=S or NH;

C$_{3-10}$ branched or unbranched alkenyl optionally partially or fully halogenated, and optionally substituted with one to three C$_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully halogenated, C$_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, C$_{1-3}$ alkoxy optionally partially or fully halogenated, NH$_2$C(O) or mono- or di-(C$_{1-3}$ alkyl)aminocarboxyl; and wherein the C$_{3-10}$ branched or unbranched alkenyl is optionally interrupted by one or more O, N or S(O)$_m$;

cyclopentenyl, cyclohexenyl, cyclohexadienyl, cycloheptenyl, cycloheptadienyl, bicyclohexenyl or bicycloheptenyl, each optionally substituted with one to three C$_{1-3}$ alkyl groups;

cyano, F, Cl, Br, or I;

methoxycarbonyl, ethoxycarbonyl or propoxycarbonyl;

silyl containing three C$_{1-4}$ independently branched or unbranched alkyl groups optionally partially or fully halogenated;

C$_{2-6}$ branched or unbranched alkyl-C(O), C$_{2-6}$ branched or unbranched-S, C$_{2-6}$ branched or unbranched-S(O), C$_{2-6}$ branched or unbranched-S(O)$_2$;

C$_{2-6}$ branched or unbranched alkynyl optionally partially or fully halogenated, wherein one or more methylene groups are optionally replaced by O, NH and S(O)$_m$ and wherein said alkynyl group is optionally independently substituted with 0-2 oxo groups, pyrrolidinyl, pyrrolyl, one or more C$_{1-4}$ branched or unbranched alkyl optionally substituted by one or more halogen atoms, nitrile, morpholino, piperidinyl, piperazinyl, imidazolyl, phenyl, pyridinyl, tetrazolyl, or C$_{1-4}$ branched or unbranched alkylamino optionally substituted by one or more halogen atoms.

In some other embodiments of the third group of compounds of Formula IA, each R$^1$ is independently C$_{3-10}$ branched or unbranched alkyl optionally partially or fully halogenated, and optionally substituted with one to three C$_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl. For example, each $R^1$ is independently $C_{3-10}$ branched or unbranched alkyl.

In certain embodiments of the third group of compounds of Formula IA, each $R^2$ is independently —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$. Alternatively, each $R^2$ is independently —NR'$_2$, —NO$_2$, —C(O)NR'$_2$, —NR'SO$_2$R", —NR'C(O)NR'R', —NR'C(S)NR'R', —NR'C(O)OR' or —SO$_2$NR'$_2$.

In some embodiments of the third group of compounds of Formula IA, each $R^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-S(O)$_2$, di-($C_{1-3}$ alkyl)amino-S(O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, carboxy-mono- or di-($C_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, $C_{1-6}$ branched or unbranched alkyl which is optionally partially or fully halogenated, cyano, $C_{1-3}$ alkoxy optionally partially or fully halogenated, phenyloxy, naphthyloxy, heterocyclyloxy, heteroaryloxy, nitro, amino, mono- or di-($C_{1-3}$ alkyl)amino, phenylamino, naphthylamino, heterocyclic or heteroaryl amino, $NH_2C(O)$, a mono- or di-($C_{1-3}$ alkyl)aminocarbonyl, $C_{1-4}$ alkyl-C(O), $C_{1-5}$ alkylamino-S(O)$_2$, mono- or di-($C_{1-3}$ alkyl)amino-$C_{1-5}$ alkyl, $R^{12}$—$C_{1-5}$ alkyl, $R^{13}$—$C_{1-5}$ alkoxy, $R^{14}$—C(O)—$C_{1-5}$ alkyl, $R^{15}$—$C_{1-5}$ alkyl($R^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S(O)$_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three $C_{1-3}$ alkyl groups;

$C_{1-4}$ alkyl or alkylene-phenyl-C(O)—$C_{0-4}$ alkyl or alkylene, $C_{1-4}$ alkyl or alkylene-C(O)—$C_{0-4}$ alkyl or alkylene, $C_{1-4}$ alkyl or alkylene-phenyl-S(O)$_m$—$C_{0-4}$ alkyl or alkylene;

$C_{1-6}$ alkyl or $C_{1-6}$ alkoxy, each optionally partially or fully halogenated or optionally substituted with $R^{17}$, amino, OR$^{18}$, or $C_{1-5}$ mono- or di-alkylamino optionally substituted with $R^{19}$;

cyclopropyloxy, cyclobutyloxy, cyclopentyloxy, cyclohexyloxy, cycloheptyloxy, which are optionally partially or fully halogenated and optionally substituted with one to three $C_{1-3}$ alkyl groups optionally partially or fully halogenated wherein one to three ring methylene groups are replaced independently by O, S(O)$_m$, CHOH, C=O, C=S or NH;

$R^{20}C(O)N(R^{21})$—, $R^{22}O$—, $R^{23}R^{24}NC(O)$—, $R^{26}(CH_2)_m C(O)N(R^{21})$— or $R^{26}C(O)(CH_2)_m N(R^{21})$—;

$C_{2-6}$ alkenyl substituted by $R^{23}R^{24}NC(O)$—;

$C_{2-6}$ alkynyl branched or unbranched carbon chain optionally partially or fully halogenated, wherein one or more methylene groups are optionally replaced by O, NH or S(O)$_m$, and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms; or benzoyl or naphthoyl; and wherein each $R^7$, $R^8$, $R^9$, $R^{10}$, $R^{12}$, $R^{13}$, $R^{14}$, $R^{15}$, $R^{17}$, $R^{19}$, and $R^{25}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

each $R^{11}$ and $R^{16}$ is independently hydrogen or $C_{1-4}$ branched or unbranched alkyl optionally partially or fully halogenated; and $R^{18}$ is independently hydrogen or $C_{1-4}$ branched or unbranched alkyl optionally independently substituted with oxo or $R^{25}$.

In some such embodiments of the third group of compounds of Formula IA, each $R^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-S(O)$_2$, di-($C_{1-3}$ alkyl)amino-S(O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl ($R^{11}$)N, or carboxy-mono- or di-($C_{1-5}$ alkyl)amino. In others, $R^3$ is phenyl, pyridazinyl or pyridyl, each of which is optionally partially or fully halogenated and optionally substituted with $C_{1-6}$ branched or unbranched alkyl which is optionally partially or fully halogenated, hydroxy, QXO, cyano, $C_{1-3}$ alkoxy optionally partially or fully halogenated, nitro, amino, or mono- or di-($C_{1-3}$ alkyl)amino; $C_{1-6}$ alkyl or $C_{1-6}$ alkoxy, each optionally partially or fully halogenated or optionally substituted with $R^{17}$, amino, $OR^{18}$, $C_{1-5}$ mono- or di-alkylamino optionally substituted with $R^{19}$; $R^{20}$ C(O)N($R^{21}$)—, $R^{22}$O—, $R^{23}R^{24}$NC(O)—, $R^{26}(CH_2)_mC(O)N(R^{21})$— or $R^{26}C(O)(CH_2)_mN(R^{21})$—.

In some embodiments of the third group of compounds of Formula IA, X is C=O.

In certain embodiments of the third group of compounds of Formula IA, Ar is —(Y)-phenyl-, Y is —C(O)—, or —C(=NOH)— and G is selected from pyrazolyl, pyrrolyl, imidazolyl, oxazolyl, isoxazolyl, furanyl or thienyl. In others, Ar is —(Y)-phenyl-, Y is —C(O)—, or —C(=NOH)—, and G is pyrazolyl, thienyl or isoxazolyl. In some such embodiments, each $R^1$ is independently a substituted or unsubstituted straight or branched $C_{1-10}$ alkyl. In these embodiments, each $R^3$ can be independently phenyl or pyridinyl, optionally substituted with one, two, or three —F, —Cl, substituted or unsubstituted $C_{1-6}$ branched or unbranched alkyl or substituted or unsubstituted $C_{1-4}$ alkoxy.

There is provided in accordance with another aspect of the invention, a third group of compounds having Formula IB:

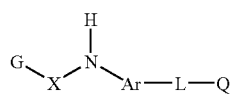

IB stereoisomers thereof, tautomers thereof, solvates thereof, prodrugs thereof, and pharmaceutically acceptable salts thereof, wherein:

X is C(O) or C(S);

G is a G'-(Y)— wherein G' is a $C_{3-10}$ cycloalkyl, phenyl, naphthyl, tetrahydronaphthyl other than 1,1,4,4-tetramethyl-1,2,3,4-tetrahydronaphthyl, pyrazolyl, thiazolyl, pyridinyl, oxazolyl, isoxazolyl, isothiazolyl, thiadiazolyl, oxadiazolyl, pyridazinyl, imidazolyl, furanyl other than furan-2-yl, thienyl other than thien-2-yl, dihydronaphthyl, indanyl, indenyl, quinolinyl, isoquinolinyl, pyrimidinyl, pyrazinyl, benzimidazolyl, benzthiazolyl, benzoxazolyl, benzpyrazolyl, or homopiperidinyl; wherein G' is substituted by one or more $R^1$, $R^2$ or $R^3$;

Ar is phenyl, pyrimidinyl, pyrazolyl, thiazolyl, thiadiazolyl, oxazolyl, isoxazolyl, oxadiazolyl, isothiazolyl, pyrrolinyl, pyridazinyl, pyrrolyl, imidazolyl, furanyl, thienyl, pyrimidinyl, pyrazinyl; wherein Ar is optionally substituted with one or more $R^4$ or $R^5$;

Y is independently —C(O)—, —C(NNRC(O)OR)—, —C(NNRR)—, —C(NNC(O)NRR)— or —C(NOR)—;

L is a covalent bond or a saturated or unsaturated branched or unbranched $C_{1-10}$ carbon chain, wherein one or more methylene groups are optionally independently replaced by heteroatoms chosen from O, NR and S(O)$_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ alkyl-S(O)$_m$, or phenyl-S(O)$_m$, wherein the cycloalkyl, aryl, heterocyclyl, $C_{1-6}$ alkoxy, $C_{1-6}$ alkyl-S(O)$_m$, or phenyl-S(O)$_m$ is each optionally substituted with one or more $R^{27}$; and provided that if $R^4$ and $R^5$ are absent, -L-Q is not —H;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —C(O)NR$_2$, —C(O)OR, —NR'R', —OR, —SiR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$;

each R" is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, S(O)$_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}$C(O)N($R^{21}$)—, $R^{22}$O—, $R^{23}R^{24}$NC(O)—, $R^{26}(CH_2)_mC(O)N(R^{21})$—, $R^{26}C(O)(CH_2)_m$ $N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or S(O)$_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or NR'$_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)NR'$_2$, —C(O)OR', —OR', —NR'R', —SiR'$_3$, —S(O)$_m$R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, S(O)$_m$;

provided however that when Ar-L-Q is —N-(substituted or unsubstituted phenyl)-pyrazolyl and Q is phenyl, naphthyl, indane or tetrahydronaphthyl, the pyrazolyl is additionally substituted with one or more $R^4$ or $R^5$; and that IB is not N-{2-chloro-4-[2-(3,5-dimethyl-1-phenyl-1H-pyrazol-4-yl)-2-oxo-acetylamino]-5-hydroxy-phenyl}-2-(3-pentadecyl-benzenesulfonyl)-butyramide or 5-(4-ethoxy-phenyl)-1-p-tolyl-4-p-tolylaminooxalyl-1H-pyrazole-3-carboxylic acid methyl ester.

In certain embodiments of the third group of compounds of Formula IB, the compound at a concentration of 10 μM inhibits induced TNFa-release from a cell by about 50% or greater than 50%.

In some embodiments of the third group of compounds of Formula IB, G' is phenyl, naphthyl, cyclopropyl, cyclobutyl, cyclopentyl, cyclohexyl, tetrahydronaphthyl, pyrazolyl, thiazolyl, pyridinyl, oxazolyl, isoxazolyl, isothiazolyl, thiadiazolyl, oxadiazolyl, pyridazinyl, imidazolyl, furanyl, thienyl, dihydronaphthyl, indanyl, indenyl, quinolinyl, isoquinolinyl, pyrimidinyl, or pyrazinyl. In others, G' is phenyl, naphthyl, pyrazolyl, cyclopropyl, imidazolyl, thiazolyl, oxazolyl, isoxazolyl, furanyl, thienyl, or pyridinyl.

In certain embodiments of the third group of compounds of Formula IB, Y is —C(O)—, —C(NNRC(O)OR)— or —C(NOR)—.

In some embodiments of the third group of compounds of Formula IB, Ar is phenyl, pyrazoly, imidazolyl, pyrazolinyl, pyrrolyl, pyrrolinyl, pyridinyl, or pyrimidinyl.

In other embodiments of the third group of compounds of Formula IB, one or more methylene groups of L are independently replaced by hetero atoms selected from O, N or S(O)$_m$. Alternatively, L is a covalent bond, a $C_1$-$C_9$ alkoxy, —C(O) O—, —NH— or —O—.

In certain embodiments of the third group of compounds of Formula IB, Q is hydrogen, phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuranyl, 1,3-dioxolanone, 1,3-dioxanone, 1,4-dioxanyl, morpholino, thiomorpholino sulfoxide, thiomorpholino sulfone, piperazinyl, piperazinonyl, oxazepinyl, diazepanonyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; $C_{1-6}$ alkoxy, secondary or tertiary amine wherein the amino nitrogen is covalently bonded to $C_{1-3}$ alkyl or $C_{1-5}$ alkoxyalkyl, phenylamino; $C_{1-6}$ alkyl-S(O)$_m$ or phenyl-S(O)$_m$. In some such embodiments, $R^{27}$ is $C_{1-6}$ alkyl, $C_{1-6}$ alkoxy, hydroxy amino, substituted or unsubstituted 5-10 member heterocyclyl, mono- or di-($C_{1-3}$ alkyl)amino, mono- or di-(phenyl-$C_{1-3}$ alkyl)amino, $C_{1-6}$ alkyl-S(O)$_m$, phenyl-$C_{1-3}$-alkoxy or phenylamino wherein the phenyl ring is optionally substituted with one to two halogen, $C_{1-6}$ alkyl or $C_{1-6}$ alkoxy.

In other embodiments of the third group of compounds of Formula IB, Q is hydrogen, thiomorpholino sulfoxide, thiomorpholino sulfone, piperazinonyl, oxazepinyl, diazepinonyl, imidazolyl, pyridinyl or morpholino. In yet others, Q is morpholino, piperazinyl, pyrimidinyl or pyridinyl. In some such embodiments, $R^{27}$ is —C(O)OR, —NR'R', substituted or unsubstituted straight or branched $C_{1-10}$ alkyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$. For example, Q is pyrimidinyl, and $R^{27}$ is —NR'R' or substituted or unsubstituted saturated or unsaturated 3-11 member heterocyclyl containing 1, 2, 3, or 4 heteroatoms selected independently from N, O, S(O)$_m$. Alternatively, Q is pyridinyl, and $R^{27}$ is —NR'R', substituted or unsubstituted $C_{1-6}$ alkyl, or substituted or unsubstituted saturated or unsaturated 3-11 member heterocyclyl or heterocyclylalkyl containing 1, 2, 3, or 4 heteroatoms selected independently from N, O, S(O)$_m$.

In certain embodiments of the third group of compounds of Formula IB, each $R^1$ is independently:

$C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and NH$_2$C(O) or mono- or di-($C_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, S(O)$_m$, CHOH, C=O, C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully halogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, $C_{1-3}$ alkoxy optionally partially or fully halogenated, NH$_2$C(O) or mono- or di-($C_{1-3}$ alkyl)aminocarboxyl; and wherein the $C_{3-10}$ branched or unbranched alkenyl is optionally interrupted by one or more O, N or S(O)$_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, or I;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-S(O)$_2$;

$C_{2-6}$ branched or unbranched alkynyl optionally partially or fully halogenated, wherein one or more methylene groups are optionally replaced by O, NH and S(O)$_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms.

In other embodiments of the third group of compounds of Formula IB, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and NH$_2$C(O) or mono- or di-($C_{1-3}$ alkyl)aminocarbonyl. For example, each $R^1$ is independently $C_{3-10}$ branched or unbranched alkyl.

In certain embodiments of the third group of compounds of Formula IB, each $R^2$ is independently —OR', —OR$^6$, —C(O)R', —C(O)OR', —C(O)NR'$_2$, —NR'$_2$, —NO$_2$, —S(O)$_m$R'', —NR'SO$_2$R'', —NR'C(O)NR'R', —NR'C(S)NR'R', —NR'C(O)OR' or —SO$_2$NR'$_2$. alternatively, each $R^2$ is independently —NR'$_2$, —NO$_2$, —C(O)NR'$_2$, —NR'SO$_2$R'', —NR'C(O)NR'R', —NR'C(S)NR'R', —NR'C(O)OR' or —SO$_2$NR'$_2$.

In certain embodiments of the third group of compounds of Formula IB, $R^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, NH$_2$C(O), a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-S(O)$_2$, di-($C_{1-3}$ alkyl)amino-S(O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, carboxy-mono- or di-($C_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, $C_{1-6}$ branched or unbranched alkyl which is optionally partially or fully halogenated, cyano, $C_{1-3}$ alkoxy optionally partially or fully halogenated, phenyloxy, naphthyloxy, heterocyclyloxy, heteroaryloxy, nitro, amino, mono- or di-($C_{1-3}$ alkyl)amino, phenylamino, naphthylamino, heterocyclic or heteroaryl amino, NH$_2$C(O), a mono- or di-($C_{1-3}$ alkyl)aminocarbonyl, $C_{1-4}$ alkyl-C(O), $C_{1-5}$ alkylamino-S(O)$_2$, mono- or di-($C_{1-3}$ alkyl)amino-$C_{1-5}$ alkyl, $R^{12}$—$C_{1-5}$ alkyl, $R^{13}$—$C_{1-5}$ alkoxy, $R^{14}$-C(O)—$C_{1-5}$ alkyl, $R^{15}$—$C_{1-5}$ alkyl($R^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S(O)$_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three $C_{1-3}$ alkyl groups;

$C_{1-4}$ alkyl or alkylene-phenyl-C(O)—$C_{0-4}$ alkyl or alkylene, $C_{1-4}$ alkyl or alkylene-C(O)—$C_{0-4}$ alkyl or alkylene, $C_{1-4}$ alkyl or alkylene -phenyl-S(O)$_m$—$C_{0-4}$ alkyl or alkylene;

$C_{1-6}$ alkyl or $C_{1-6}$ alkoxy, each optionally partially or fully halogenated or optionally substituted with $R^{17}$, amino, OR$^{18}$, or $C_{1-5}$ mono- or di-alkylamino optionally substituted with $R^{19}$;

cyclopropyloxy, cyclobutyloxy, cyclopentyloxy, cyclohexyloxy, cycloheptyloxy, which are optionally partially or fully halogenated and optionally substituted with one to three $C_{1-3}$ alkyl groups optionally partially or fully halogenated wherein one to three ring methylene groups are replaced independently by O, S(O)$_m$, CHOH, C=O, C=S or NH;

$R^{20}$C(O)N(R$^{21}$)—, R$^{22}$O—, R$^{23}$R$^{24}$NC(O)—, R$^{26}$(CH$_2$)$_m$C(O)N(R$^{21}$)— or R$^{26}$C(O)(CH$_2$)$_m$N(R$^{21}$)—;

$C_{2-6}$ alkenyl substituted by $R^{23}R^{24}$NC(O)—;

$C_{2-6}$ alkynyl branched or unbranched carbon chain optionally partially or fully halogenated, wherein one or more methylene groups are optionally replaced by O, NH or S(O)$_m$, and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms; or benzoyl or naphthoyl; and wherein each $R^7$, $R^8$, $R^9$, $R^{10}$, $R^{12}$, $R^{13}$, $R^{14}$, $R^{15}$, $R^{17}$, $R^{19}$, and $R^{25}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

each $R^{11}$ and $R^{16}$ is independently hydrogen or $C_{1-4}$ branched or unbranched alkyl optionally partially or fully halogenated; and $R^{18}$ is independently hydrogen or $C_{1-4}$ branched or unbranched alkyl optionally independently substituted with oxo or $R^{25}$.

In some such embodiments of the third group of compounds of Formula IB, each $R^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-$S(O)_2$, di-($C_{1-3}$ alkyl)amino-$S(O)_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl ($R^{11}$)N, or carboxy-mono- or di-($C_{1-5}$ alkyl)amino. In other such embodiments, $R^3$ is phenyl, pyridazinyl or pyridyl, each of which is optionally partially or fully halogenated and optionally substituted with $C_{1-6}$ branched or unbranched alkyl which is optionally partially or fully halogenated, hydroxy, oxo, cyano, $C_{1-3}$ alkoxy optionally partially or fully halogenated, nitro, amino, or mono- or di-($C_{1-3}$ alkyl)amino; $C_{1-6}$ alkyl or $C_{1-6}$ alkoxy, each optionally partially or fully halogenated or optionally substituted with $R^{17}$, amino, $OR^{18}$, $C_{1-5}$ mono- or di-alkylamino optionally substituted with $R^{19}$; $R^{20}C(O)N(R^{21})$—, $R^{22}O$—, $R^{23}R^{24}NC(O)$—, $R^{26}(CH_2)_mC(O)N(R^{21})$— or $R^{26}C(O)(CH_2)_mN(R^{21})$—.

In certain embodiments of the third group of compounds of Formula IB, X is C=O.

In some embodiments of the third group of compounds of Formula IB, Ar is phenyl, G is G'-(Y)—, Y is —C(O)— or —C(=NOH)— and G' is selected from phenyl, pyridinyl, pyrazolyl, imidazolyl, oxazolyl, isoxazolyl, furanyl or thienyl. In others, Ar is phenyl, G is G'-(Y)—, Y is —C(O)— or —C(=NOH)— and G' is phenyl or pyridinyl, substituted by one or more $R^1$, $R^2$ or $R^3$. In some such embodiments, each $R^1$ is independently a substituted or unsubstituted straight or branched $C_{1-10}$ alkyl. In these, each $R^3$ can be independently $R^{23}R^{24}N$—C(O)—, $R^{20}$—C(O)—$NR^{21}$—, or $OR^{22}$. Alternatively, each $R^2$ is independently —NR'$SO_2R''$, —Cl, —Br, —F, —C(O)—$NR'_2$, substituted or unsubstituted straight or branched $C_{1-6}$ alkyl, —$NR'_2$, or —OR'.

In other embodiments of the third group of compounds of Formula IB, Ar is phenyl and G is G'-(Y)—, wherein Y is selected from —C(O)— and —C(=NOH)— and G' is pyrazolyl, isoxazolyl or furanyl, substituted by one or more $R^1$, $R^2$ or $R^3$. In some such embodiments, each $R^1$ is independently a substituted or unsubstituted straight or branched $C_{1-10}$ alkyl. In these, each $R^3$ can be independently substituted or unsubstituted $C_{1-6}$ alkyl, pyridinyl or phenyl, optionally substituted with one to three —F, —Cl, substituted or unsubstituted $C_{1-6}$ branched or unbranched alkyl, or substituted or unsubstituted $C_{1-3}$ alkoxy.

There is provided in accordance with another aspect of the invention, compounds having Formula IC:

G-Ring-Ar-L-Q      IC stereoisomers thereof, tautomers thereof, solvates thereof, prodrugs thereof, and pharmaceutically acceptable salts thereof, wherein:

Ring is maleimide, succinimide, imidazolidinone, imidazolidine-dione, imidazolidine-trione, triazolidin-dione, or triazine-dione;

G is a $C_{3-10}$ carbocyclyl, $C_{4-12}$ carbocyclylalkyl, 5-8 membered monocyclic heterocyclyl or heterocyclylalkyl, 8-11 membered bicyclic heterocyclyl or heterocyclylalkyl, wherein the heterocyclyl rings contain 1 or more heteroatoms selected from O, N or S; and G is substituted by one or more $R^1$, $R^2$ or $R^3$;

Ar is indazolyl, indolyl, isoindolyl, imidazolyl, benzimidazolyl, pyrazolyl, pyrazolinyl, pyrrolyl, pyrrolinyl, pyridinyl, pyridazinyl, quinolinyl, isoquinolinyl, phthalazinyl, dihydroindolyl, benzofuranyl, benzoxazolyl, benzoisoxazolyl, dihydrobenzoisoxazolyl, dihydroisoindolyl, benzothiazolyl, benzoisothiazolyl, benzoisothiazolyl dioxide, $C_{6-10}$ aryl, or —($C_{1-3}$ alkyl)-($C_{6-10}$ aryl), wherein Ar is optionally substituted with one or more $R^4$ or $R^5$;

L is a covalent bond or a saturated or unsaturated branched or unbranched $C_{1-10}$ carbon chain, wherein one or more methylene groups are optionally independently replaced by heteroatoms chosen from O, NR and $S(O)_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ alkyl-$S(O)_m$, or phenyl-$S(O)_m$, wherein the cycloalkyl, aryl, heterocyclyl, $C_{1-6}$ alkoxy, $C_{1-6}$ alkyl-$S(O)_m$, or phenyl-$S(O)_m$ is each optionally substituted with one or more $R^{27}$; and provided that if $R^4$ and $R^5$ are absent, -L-Q is not —H;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —$C(O)NR_2$, —C(O)OR, —OR, —NR'R', —$SiR_3$, —$S(O)_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, $S(O)_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —$OR^6$, —C(O)R', —C(O)OR', —$C(O)NR'_2$, —$NR'_2$, —$NO_2$, —$S(O)_mR''$, —NR'$SO_2R''$, —NR'C(O)NR'R', —NR'C(S)NR'R', —NR'C(O)OR' or —$SO_2NR'_2$;

each R'' is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, $S(O)_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or $S(O)_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or $NR'_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring; and each $R^{27}$ is independently F, Cl, Br, I, cyano, —C(O)R', —C(O)NR'$_2$, —C(O)OR', —OR', —NR'R', —SiR'$_3$, —S(O)$_m$ R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, $S(O)_m$.

In certain embodiments of compounds of Formula IC, the compound at a concentration of 10 μM inhibits induced TNFa-release from a cell by about 50% or greater than 50%.

In certain embodiments of compounds of Formula IC, G is phenyl, naphthyl, benzocyclobutanyl, dihydronaphthyl, cyclopropyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In other embodiments of compounds of Formula IC, G is phenyl, naphthyl, cyclopropyl, benzocyclobutanyl, dihydronaphthyl, tetrahydronaphthyl, benzocycloheptanyl, benzocycloheptenyl, indanyl, indenyl, or benzofuran-3-one. In yet others, G is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl. In still others, G is pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, isoxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl. For example, G is phenyl, naphthyl, cyclopropyl, pyrazolyl, pyrrolyl, pyrrolidinyl, imidazolyl, imidazolonyl, thiazolyl, oxazolyl, isoxazolyl, furanyl, thienyl, or pyridinyl.

In certain embodiments of compounds of Formula IC, Ar is indazolyl, indolyl, isoindolyl, imidazolyl, benzimidazolyl, pyrazolyl, pyrazolinyl, pyrrolyl, pyrrolinyl, pyridinyl, pyridazinyl, quinolinyl, isoquinolinyl, phthalazinyl, dihydroindolyl, benzoisoxazolyl, dihydrobenzoisoxazolyl, dihydroisoindolyl, benzoisothiazolyl, benzoisothiazolyl dioxide, $C_{6-10}$ aryl. In some such embodiments, Ar is substituted with at least one $R^4$ or $R^5$. Alternatively, Ar is indazolyl, isoindolyl, pyrazolyl, pyrrolinyl, phenyl, naphthyl, tetrahydronaphthyl, dihydronaphthyl, indanyl, indenyl or imidazolyl. For example, Ar is indazolyl, phenyl, naphthyl, or tetrahydronaphthyl.

In some embodiments of compounds of Formula IC, one or more methylene groups of L are independently replaced by hetero atoms selected from O, N or $S(O)_m$. Alternatively, L is a covalent bond, a $C_1$-$C_9$ alkoxy, —C(O)O—, —NH— or —O—.

In certain embodiments of compounds of Formula IC, Q is hydrogen, phenyl, naphthyl, pyridinyl, pyrimidinyl, pyridazinyl, imidazolyl, pyrrolyl, pyrrolidinyl, benzimidazolyl, furanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuranyl, 1,3-dioxolanone, 1,3-dioxanone, 1,4-dioxanyl, morpholino, thiomorpholino sulfoxide, thiomorpholino sulfone, piperazinyl, piperazinonyl, oxazepinyl, diazepanonyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; $C_{1-6}$ alkoxy, secondary or tertiary amine wherein the amino nitrogen is covalently bonded to $C_{1-3}$ alkyl or $C_{1-5}$ alkoxyalkyl, phenylamino; $C_{1-6}$ alkyl-S(O)$_m$ or phenyl-S(O)$_m$. In some such embodiments, $R^{27}$ is $C_{1-6}$ alkyl, $C_{1-6}$ alkoxy, hydroxy amino, substituted or unsubstituted 5-10 member heterocyclyl, mono- or di-($C_{1-3}$ alkyl)amino, mono- or di-(phenyl-$C_{1-3}$ alkyl)amino, $C_{1-6}$ alkyl-S(O)$_m$, phenyl-$C_{1-3}$-alkoxy or phenylamino wherein the phenyl ring is optionally substituted with one to two halogen, $C_{1-6}$ alkyl or $C_{1-6}$ alkoxy.

In other embodiments of compounds of Formula IC, Q is hydrogen, thiomorpholino sulfoxide, thiomorpholino sulfone, piperazinonyl, oxazepinyl, diazepinonyl, imidazolyl, pyridinyl or morpholino. In yet others, Q is morpholino, piperazinyl, pyrimidinyl or pyridinyl. In some such embodiments, $R^{27}$ is —C(O)OR, —NR'R', substituted or unsubstituted straight or branched $C_{1-10}$ alkyl, substituted or unsubstituted $C_{7-20}$ aralkyl, or substituted or unsubstituted saturated or unsaturated 3-11 member heterocyclyl or heterocyclylalkyl containing 1, 2, 3, or 4 heteroatoms selected independently from N, O, $S(O)_m$. For example, Q is pyrimidinyl, and $R^{27}$ is —NR'R' or substituted or unsubstituted saturated or unsaturated 3-11 member heterocyclyl containing 1, 2, 3, or 4 heteroatoms selected independently from N, O, S(O)$_m$. Alternatively, Q is pyridinyl, and $R^{27}$ is —NR'R', substituted or unsubstituted $C_{1-6}$ alkyl, or substituted or unsubstituted saturated or unsaturated 3-11 member heterocyclyl or heterocyclylalkyl containing 1, 2, 3, or 4 heteroatoms selected independently from N, O, S(O)$_m$.

In certain embodiments of compounds of Formula IC, each $R^1$ is independently:

$C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-13}$ alkoxy which is optionally partially or fully halogenated and NH$_2$C(O) or mono- or di-($C_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl, or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by O, S (O)$_m$, CHOH, C=O, C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl; each of the aforementioned being optionally, partially or fully halogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxy, cyano, $C_{1-3}$ alkoxy optionally partially or fully halogenated, NH$_2$C(O) or mono- or di-($C_{1-3}$ alkyl)aminocarboxyl; and wherein the $C_{3-10}$ branched or unbranched alkenyl is optionally interrupted by one or more O, N or S(O)$_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, I;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-S(O)$_2$;

$C_{2-6}$ branched or unbranched alkynyl optionally partially or fully halogenated, wherein one or more methylene groups are optionally replaced by O, NH and S(O)$_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms.

In other embodiments of compounds of Formula IC, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially Qr fully halogenated and NH$_2$C(O) or mono- or di-($C_{1-3}$ alkyl)aminocarbonyl. For example, each $R^1$ is independently $C_{3-10}$ branched or unbranched alkyl.

In certain embodiments of compounds of Formula IC, each $R^2$ is independently —OR', —OR$^6$, —C(O)R', —C(O)OR', —C(O)NR'$_2$, —NR'$_2$, —NO$_2$, —S(O)$_m$R'', —NR'SO$_2$R'', —NR'C(O)NR'R', —NR'C(S)NR'R', —NR'C(O)OR' or —SO$_2$NR'$_2$. Alternatively, each $R^2$ is independently —NR'$_2$, —NO$_2$, —C(O)NR'$_2$, —NR'SO$_2$R'', —NR'C(O)NR'R', —NR'C(S)NR'R', —NR'C(O)OR' or —SO$_2$NR'$_2$.

In certain embodiments of compounds of Formula IC, each $R^3$ is independently hydrogen, phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl) amino, phenylamino, naphthylamino, heterocyclylamino, NH$_2$C(O), a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-S(O)$_2$, di-($C_{1-3}$ alkyl)amino-S (O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, carboxy-mono- or di-($C_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, $C_{1-6}$ branched or unbranched alkyl which is optionally partially or fully halogenated, cyano, $C_{1-3}$ alkoxy optionally partially or fully halogenated, phenyloxy, naphthyloxy, heterocyclyloxy, heteroaryloxy, nitro, amino, mono- or di-($C_{1-3}$ alkyl)amino, phenylamino, naphthylamino, heterocyclic or heteroaryl amino, NH$_2$C(O), a mono- or di-($C_{1-3}$ alkyl)aminocarbonyl, $C_{1-4}$ alkyl-C(O), $C_{1-5}$ alkylamino-S(O)$_2$, mono- or di-($C_{1-3}$ alkyl)amino-$C_{1-5}$ alkyl, $R^{12}$—$C_{1-5}$ alkyl, $R^{13}$—$C_{1-5}$ alkoxy, $R^{14}$—C(O)—$C_{1-5}$ alkyl, $R^{15}$—$C_{1-5}$ alkyl($R^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are independently replaced by O, S(O)$_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three $C_{1-3}$ alkyl groups;

$C_{1-4}$ alkyl or alkylene-phenyl-C(O)—$C_{0-4}$ alkyl or alkylene, $C_{1-4}$ alkyl or alkylene-C(O)—$C_{0-4}$ alkyl or alkylene, $C_{1-4}$ alkyl or alkylene-phenyl-S(O)$_m$—$C_{0-4}$ alkyl or alkylene;

$C_{1-6}$ alkyl or $C_{1-6}$ alkoxy, each optionally partially or fully halogenated or optionally substituted with $R^{17}$, amino, OR$^{18}$, or $C_{1-5}$ mono- or di-alkylamino optionally substituted with $R^{19}$;

cyclopropyloxy, cyclobutyloxy, cyclopentyloxy, cyclohexyloxy, cycloheptyloxy, which are optionally partially or fully halogenated and optionally substituted with one to three $C_{1-3}$ alkyl groups optionally partially or fully halogenated wherein one to three ring methylene groups are replaced independently by O, S(O)$_m$, CHOH, C=O, C=S or NH;

$R^{20}$C(O)N($R^{21}$)—, $R^{22}$O—, $R^{23}R^{24}$NC(O)—, $R^{26}$(CH$_2$)$_m$C(O)N($R^{21}$)— or $R^{26}$C(O)(CH$_2$)$_m$N($R^{21}$)—;

$C_{2-6}$ alkenyl substituted by $R^{23}R^{24}$NC(O)—;

$C_{2-6}$ alkynyl branched or unbranched carbon chain optionally partially or fully halogenated, wherein one or more methylene groups are optionally replaced by O, NH or S(O)$_m$, and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms; or benzoyl or naphthoyl; and wherein
each $R^7$, $R^8$, $R^9$, $R^{10}$, $R^{12}$, $R^{13}$, $R^{14}$, $R^{15}$, $R^{17}$, $R^{19}$, and $R^{25}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

each $R^{11}$ and $R^{16}$ is independently hydrogen or $C_{1-4}$ branched or unbranched alkyl optionally partially or fully halogenated; and $R^{18}$ is independently hydrogen or $C_{1-4}$ branched or unbranched alkyl optionally independently substituted with oxo or $R^{25}$.

In some such embodiments of compounds of Formula IC, each $R^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, NH$_2$C(O), a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-S(O)$_2$, di-($C_{1-3}$ alkyl)amino-S(O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, or carboxy-mono- or di-($C_{1-5}$ alkyl)amino. In other such embodiments $R^3$ is phenyl, pyridazinyl or pyridyl, each of which is optionally partially or fully halogenated and optionally substituted with $C_{1-6}$ branched or unbranched alkyl which is optionally partially or fully halogenated, hydroxy, oxo, cyano, $C_{1-3}$ alkoxy optionally partially or fully halogenated, nitro, amino, or mono- or di-($C_{1-3}$ alkyl)amino; $C_{1-6}$ alkyl or $C_{1-6}$ alkoxy, each optionally partially or fully halogenated or optionally substituted with $R^{17}$, amino, OR$^{18}$, $C_{1-5}$ mono- or di-alkylamino optionally substituted with $R^{19}$; $R^{20}$C(O)N($R^{21}$)—, $R^{22}$O—, $R^{23}R^{24}$NC(O)—, $R^{26}$(CH$_2$)$_m$C(O)N($R^{21}$)— or $R^{26}$C(O)(CH$_2$)$_m$N($R^{21}$)—.

In certain embodiments of compounds of Formula IC, Ring is maleimide, succinimide or triazine-dione. In others, Ring is succinimid-1,4-diyl, maleimide-1,4-diyl, imidazolidin-2-one-1,3-diyl, imidazolidine-2,4,5-trione-1,3-diyl, [1,2,4]triazolidine-3,5-dione-1,4-diyl, or 2H-[1,2,4]triazine-3,5-dione-4,6-diyl.

In another aspect of the invention there are provided compounds having Formula II:

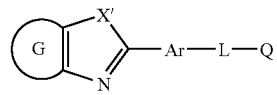

II stereoisomers thereof, tautomers thereof, solvates thereof, and pharmaceutically acceptable salts thereof, wherein:

G is a $C_{3-10}$ carbocyclyl, 5-8 membered monocyclic heterocyclyl, or 8-11 membered bicyclic heterocyclyl containing 1 or more heteroatoms selected from O, N or S; wherein G is substituted by one or more $R^1$, $R^2$ or $R^3$;

X' is CR'=CR', CR'=N, NR', CR'$_2$, O or S;

Ar is phenyl, naphthyl, quinoline, isoquinoline, tetrahydronaphthyl, pyridinyl, pyridazinyl, quinolinyl, isoquinolinyl, phthalazinyl, tetrahydroquinoline, tetrahydroisoquinoline, benzimidazole, benzofuran, indanyl, indenyl, indole, or the structure —(Y')-($C_{0-3}$ alkyl)-($C_{6-10}$ aryl), each being optionally substituted with one or more $R^4$ groups;

Y' is absent or is —O— or —NH—;

L is a covalent bond or saturated or unsaturated branched or unbranched $C_{1-10}$ carbon chain, wherein one or more methylene groups are optionally independently replaced by heteroatoms chosen from O, NR and S(O)$_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is hydrogen, —NR'R', cycloalkyl, aryl, heterocyclyl, $C_{1-6}$ alkoxy, $C_{1-6}$ Alkyl-S(O)$_m$, or phenyl-S(O)$_m$, wherein the cycloalkyl, aryl, heterocyclyl, $C_{1-6}$ alkoxy, $C_{1-6}$ Alkyl-S(O)$_m$, or phenyl-S(O)$_m$ is each optionally substituted with one or more $R^{27}$;

each R is independently hydrogen or substituted or unsubstituted $C_{1-6}$ alkyl;

each R' is independently hydrogen, substituted or unsubstituted $C_{1-8}$ alkyl or substituted or unsubstituted -($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —C(O)NR$_2$, —C(O)OR, —NR'R', —OR, —SiR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$;

each $R^2$ and $R^4$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR' R', —NR'C(S)NR'R', —NR'C(O)OR' or —SO$_2$NR'$_2$;

each R" is independently substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^3$ is independently H, substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, S(O)$_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or S(O)$_m$;

$R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is $C_{1-10}$ branched or unbranched alkyl optionally partially or fully halogenated, phenyl, pyridinyl, OR' or NR'$_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, $C_{1-6}$ branched or unbranched alkyl optionally substituted by carbonylamino- mono- or di-$C_{1-3}$ alkyl or amino-mono or di-$C_{1-3}$ alkyl or wherein said $C_{1-6}$ alkyl is optionally partially or fully halogenated and optionally interrupted by one or more O, N or S, phenyl, pyridine, mono- or di-$C_{0-4}$ branched or unbranched alkyl optionally partially or fully halogenated and alkylamino; or $R^{23}$ and $R^{24}$ taken together optionally form a heterocyclic or heteroaryl ring; and each $R^{27}$ is independently F, Cl, Br, I, cyano, —C(O)R', —C(O)NR'$_2$, —C(O)OR', —OR', —NR'R', —SiR'$_3$, —S(O)$_m$R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, S(O)$_m$.

In certain embodiments of compounds of Formula II, the compound at a concentration of 10 μM inhibits induced TNFa-release from a cell by about 50% or greater than 50%.

In certain embodiments of compounds of Formula II, G is phenyl, naphthyl, benzocyclobutanyl, dihydronaphthyl, tetrahydronaphthyl, benzocycloheptanyl, benzocycloheptenyl, indanyl, indenyl, benzofuran-3-one;

pyrazolyl, pyrrolyl, imidazolyl, imidazolonyl, thiazolyl, oxazolyl, isoxazolyl, furanyl, thienyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, 4H-benzo[1,4]oxazine-3-onyl, benzodioxolyl, benzo[1,3]dioxol-2-onyl, tetrahydrobenzopyranyl, indolyl, indolinyl, indolonyl, indolinonyl, phthalimidyl;

pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl.

In other embodiments of compounds of Formula II, G is phenyl, naphthyl, benzocyclobutanyl, dihydronaphthyl, tetrahydronaphthyl, benzocycloheptanyl, benzocycloheptenyl, indanyl, indenyl, benzofuran-3-one, or 4H-benzo[1,4]oxazine-3-one. In yet others, G is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl. In still others, G is pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl. In certain embodiments, G is phenyl, pyrazolyl, pyrrolyl, pyrrolidinyl, imidazolyl, imidazolonyl, thiazolyl, oxazolyl, isoxazolyl, furanyl, thienyl, or pyridinyl.

In certain embodiments of compounds of Formula II, Ar is indazolyl, isoindolyl, pyrazolyl, imidazolyl, or imidazolonyl. In some such embodiments, Ar is substituted with at least one $R^4$. Alternatively, Ar is indazolyl, optionally substituted with one or more $R^4$. In yet other embodiments, Ar is phenyl or naphthyl. In some such embodiments, Ar is substituted with at least one $R^4$.

In yet other embodiments of compounds of Formula II, Ar is —(Y')-($C_{0-3}$ alkyl)-($C_{6-10}$ aryl). In some such embodiments, Ar is substituted with at least one $R^4$. In others, the $C_{6-10}$ aryl is phenyl or naphthyl. Alternatively, Y' is —NH—.

In certain embodiments of compounds of Formula II, one or more methylene groups of L are independently replaced by hetero atoms selected from O, N or S(O)$_m$. In others, L is a bond, a $C_1$-$C_9$ alkoxy, —C(O)O—, —NH— or —O—.

In some embodiments of compounds of Formula II, Q is hydrogen, phenyl, naphthyl, pyridinyl, pyrimidinyl, pyridazinyl, imidazolyl, pyrrolyl, pyrrolidinyl, benzimidazolyl, firanyl, thienyl, pyranyl, naphthylpyridinyl, pyrazinyl, pyrazolyl, thiazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, or imidazo[4,5-b]pyridinyl; tetrahydropyranyl, tetrahydrofuranyl, 1,3-dioxianone, 1,3-dioxanone, 1,4-dioxanyl, morpholino, thiomorpholino sulfoxide, thiomorpholino sulfone, piperazinyl, piperidinyl, piperidinonyl, tetrahydropyrimidonyl, cyclohexanone, cyclohexanolol, pentamethylene sulfide, pentamethylene sulfoxide, pentamethylene sulfone, tetramethylene sulfide, tetramethylene sulfoxide or tetramethylene sulfone; $C_{1-6}$ alkoxy, secondary or tertiary amine wherein the amino nitrogen is covalently bonded to $C_{1-3}$ alkyl or $C_{1-5}$ alkoxyalkyl, phenylamino; $C_{1-6}$ alkyl-S(O)$_m$ or phenyl-S(O)$_m$. In some such embodiments, $R^{27}$ is $C_{1-6}$ alkyl, $C_{1-6}$ alkoxy, hydroxy amino, substituted or unsubstituted 5-10 member heterocyclyl, mono- or di-($C_{1-3}$ alkyl)amino, mono- or di-(phenyl-$C_{1-3}$ alkyl)amino, $C_{1-6}$ alkyl-S(O)$_m$, phenyl-$C_{1-3}$-alkoxy or phenylamino wherein the phenyl ring is optionally substituted with one to two halogen, $C_{1-6}$ alkyl or $C_{1-6}$ alkoxy.

In other embodiments of compounds of Formula II, Q is hydrogen, thiomorpholino sulfoxide, thiomorpholino sulfone, piperazinonyl, oxazepinyl, diazepinonyl, imidazolyl, pyridinyl or or morpholino. In yet others, Q is morpholino, piperazinyl, pyrimidinyl or pyridinyl. In some such embodiments, $R^{27}$ is —C(O)OR, —NR'R', substituted or unsubstituted straight or branched $C_{1-10}$ alkyl, substituted or unsubstituted $C_{7-20}$ aralkyl, or substituted or unsubstituted saturated or unsaturated 3-11 member heterocyclyl or heterocyclylalkyl containing 1, 2, 3, or 4 heteroatoms selected independently from N, O, S(O)$_m$. For example, Q is pyrimidinyl, and $R^{27}$ is —NR'R', or substituted or unsubstituted saturated or unsaturated 3-11 member heterocyclyl containing 1, 2, 3, or 4 heteroatoms selected independently from N, O, S(O)$_m$. Alternatively, Q is pyridinyl, and $R^{27}$ is —NR'R', substituted or unsubstituted $C_{1-6}$ alkyl, or substituted or unsubstituted saturated or unsaturated 3-11 member heterocyclyl or heterocyclylalkyl containing 1, 2, 3, or 4 heteroatoms selected independently from N, O, S(O)$_m$.

In certain embodiments of compounds of Formula II, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl;

cyclopropyl, cyclobutyl, cyclopentanyl, cyclohexanyl, cycloheptanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclopentanyl, bicyclohexanyl or bicycloheptanyl wherein one to three ring methylene groups are replaced independently by Q, S(O)$_m$, CHOH, C=O, C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, thienyl, furyl, isoxazolyl, isothiazolyl; each of the aforementioned being optionally, partially or fully halogenated, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclopentanyl, bicyclohexanyl or bicycloheptanyl, hydroxyl, cyano, $C_{1-3}$ alkoxy optionally partially or fully halogenated, $NH_2C(O)$ or mono- or di-($C_{1-3}$ alkyl)aminocarboxyl; the $C_{3-10}$ branched or unbranched alkenyl is optionally interrupted by one or more O, N or S(O)$_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, F, Cl, Br, or I;

methoxycarbonyl, ethoxycarbonyl or propoxycarbonyl;

silyl containing $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched o unbranched-S(O), $C_{2-6}$ branched or unbranched-S(O)$_2$ $C_{2-6}$ alkynyl branched or unbranched carbon chain optionally partially or fully halogenated, wherein one or more methylene groups are optionally partially or fully halogenated, wherein one or more methylene groups are optionally replaced by O, NH and S(O)$_m$ and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms.

In other embodiments of compounds of Formula II, each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-($C_{1-3}$ alkyl)aminocarbonyl. For example, each $R^1$ is independently $C_{3-10}$ branched or unbranched alkyl.

In certain embodiments of compounds of Formula II, each $R^3$ is independently hydrogen or phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterihdinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, $NH_2C(O)$, a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, Amino-S(O)$_2$, di-($C_{1-3}$ alkyl)amino-S(O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, carboxy-mono- or di-($C_{1-5}$ alkyl)amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclopentanoindole, cyclohexanoindole, cyclobenzimidazole, cyclopentanoimidazole, cyclohexanoimidazole, cyclopentanothiophene and cyclohexanothiophene; wherein the fused aryl or fused heterocyclic ring is optionally, independently substituted with 1 to 3 groups selected from phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, isothiazolyl, $C_{1-6}$ branched or unbranched alkyl which is optionally partially or fully halogenated, cyano, $C_{1-3}$ alkoxy optionally partially or fully halogenated, phenyloxy, naphthyloxy, heterocyclyloxy, heteroaryloxy, nitro, amino, mono- or di-($C_{1-3}$ alkyl)amino, phenylamino, naphthylamino, heterocyclic or heteroaryl amino, NH$_2$C(O), a mono- or di-($C_{1-3}$ alkyl)aminocarbonyl, $C_{1-4}$ alkyl-C(O), $C_{1-5}$ alkylamino-S(O)$_2$, mono- or di-($C_{1-3}$ alkyl)amino-$C_{1-5}$ alkyl, $R^{12}$—$C_{1-5}$ alkyl, $R^{13}$—$C_{1-5}$ alkoxy, $R^{14}$—C(O)—$C_{1-5}$ alkyl, $R^{15}$—$C_{1-5}$ alkyl($R^{16}$)N;

cyclopropyl, cyclobutyl, cyclopentanyl, cyclohexanyl, cycloheptanyl, bicyclopentanyl, bicyclohexanyl, or bicycloheptanyl, which are optionally partially or fully halogenated and optionally substituted with one to three $C_{1-3}$ alkyl groups optionally partially or fully halogenated, cyano, hydroxyl $C_{1-3}$ alkyl or aryl; or an analogue of cyclopropyl, cyclobutyl, cyclopentanyl, cyclohexanyl, cycloheptanyl, bicyclopentanyl, bicyclohexanyl or bicycloheptanyl wherein one to three ring methylene groups are replaced independently by O, S(O)$_m$, CHOH, C=O, C=S or NH;

cyclopentenyl, cyclohexenyl, cyclohexadienyl, cycloheptenyl, cycloheptadienyl, bicyclohexenyl, bicycloheptenyl, each optionally substituted with one to three $C_{1-3}$ alkyl groups;

$C_{1-4}$ branched or unbranched alkyl-phenyl-C(O)—$C_{0-4}$ branched or unbranched alkyl, $C_{1-4}$ branched or unbranched alkyl-C(O)—$C_{0-4}$ branched or unbranched alkyl, $C_{1-4}$ branched or unbranched alkyl-phenyl-S(O)$_m$—$C_{0-4}$ branched or unbranched alkyl;

$C_{1-6}$ branched or unbranched alkyl or $C_{1-6}$ branched or unbranched alkoxy each is optionally partially or fully halogenated or optionally substituted with $R^{17}$;

$C_{1-6}$ branched or unbranched alkyl optionally substituted with OR$^{18}$; amino or $C_{1-5}$ branched or unbranched mono- or di-alkylamino optionally substituted with $R^{19}$;

cyclopropyloxy, cyclobutyloxy, cyclopentyloxy, cyclohexyloxy, cycloheptyloxy, which are optionally partially or fully halogenated and optionally substituted with one to three $C_{1-3}$ alkyl groups optionally partially or fully halogenated wherein one to three ring methylene groups are replaced independently by O, S(O)$_m$, CHOH, C=O, C=S or NH;

$R^{20}$OC(O)N($R^{21}$)—, $R^{22}$—, $R^{23}R^{24}$NC(O)—, $R^{26}$(CH$_2$)$_m$C(O)N($R^{21}$)— or $R^{26}$C(O)(CH$_2$)$_m$N($R^{21}$)—;

$C_{2-6}$ alkenyl substituted by $R^{23}R^{24}$NC(O)—;

$C_{2-6}$ alkynyl branched or unbranched carbon chain optionally partially or fully halogenated, wherein one or more methylene groups are optionally partially or fully halogenated, wherein one or more methylene groups are optionally replaced by O, NH and S(O)$_m$ or S and wherein said alkynyl group is optionally independently substituted with 0-2 oxo groups, pyrrolidinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms; or benzoyl or naphthoyl; and wherein each $R^7$, $R^8$, $R^9$, $R^{10}$, $R^{12}$, $R^{13}$, $R^{14}$, $R^{15}$, $R^{17}$, $R^{19}$, and $R^{25}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

each $R^{11}$ and $R^{16}$ is independently hydrogen or $C_{1-4}$ branched or unbranched alkyl optionally partially or fully halogenated; and $R^{18}$ is independently hydrogen or $C_{1-4}$ branched or unbranched alkyl optionally independently substituted with oxo or $R^{25}$.

In some such embodiments of compounds of Formula II, each $R^3$ is independently phenyl, naphthyl, or heterocyclyl, each of which is optionally partially or fully halogenated and optionally substituted with 1-3 of phenyl, naphthyl, pyridinyl, pyrimidinyl, pyrazinyl, pyridazinyl, pyrrolyl, pyrrolidinyl, 2,5-pyrrolidin-dione, imidazolyl, pyrazolyl, thienyl, furyl, tetrahydrofuryl, isoxazolyl, thiazolyl, oxazolyl, triazolyl, tetrazolyl, isothiazolyl, quinolyl, isoquinolyl, indolyl, benzimidazolyl, benzofuranyl, benzoxazolyl, benzoisooxazolyl, benzpyrazolyl, benzothiofuranyl, cinnolinyl, pterindinyl, phthalazinyl, naphthylpyridinyl, quinoxalinyl, quinazolinyl, purinyl, indazolyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, hydroxy, oxo, cyano, $C_{1-3}$ alkoxy optionally partially or fully halogenated, phenyloxy, naphthyloxy, heterocyclyloxy, nitro, amino, mono- or di-($C_{1-3}$ alkyl)amino, phenylamino, naphthylamino, heterocyclylamino, NH$_2$C(O), a mono- or di-($C_{1-3}$ alkyl)aminocarbonyl, $C_{1-5}$ alkyl-C(O)—$C_{1-4}$ alkyl, amino-$C_{1-5}$ alkyl, mono- or di-($C_{1-3}$ alkyl)amino-$C_{1-5}$ alkyl, amino-S(O)$_2$, di-($C_{1-3}$ alkyl)amino-S(O)$_2$, $R^7$—$C_{1-5}$ alkyl, $R^8$—$C_{1-5}$ alkoxy, $R^9$—C(O)—$C_{1-5}$ alkyl, $R^{10}$—$C_{1-5}$ alkyl($R^{11}$)N, or carboxy-mono- or di-($C_{1-5}$ alkyl)amino. In others, $R^3$ is phenyl, pyridazinyl or pyridyl, each of which is optionally partially or fully halogenated and optionally substituted with $C_{1-6}$ branched or unbranched alkyl which is optionally partially or fully halogenated, hydroxy, oxo, cyano, $C_{1-3}$ alkoxy optionally partially or fully halogenated, nitro, amino, or mono- or di-($C_{1-3}$ alkyl)amino; $C_{1-6}$ alkyl or $C_{1-6}$ alkoxy, each optionally partially or fully halogenated or optionally substituted with $R^{17}$, amino, OR$^{18}$, $C_{1-5}$ mono- or di-alkylamino optionally substituted with $R^{19}$; $R^{20}$OC(O)N($R^{21}$)—, $R^{22}$O—, $R^{23}R^{24}$NC(O)—, $R^{26}$(CH$_2$)$_m$C(O)N($R^{21}$)— or $R^{26}$C(O)(CH$_2$)$_m$N($R^{21}$)—. For example, $R^3$ is phenyl or tolyl.

In certain embodiments of compounds of Formula II, X' is NR', CR'=N or CR'=CR'.

In accordance with yet another aspect of the invention, there are provided the following compounds, including representative examples of the compounds of Formula IA, IB, IC and II:

1H-Indazole-3-carboxylic acid (5-tert-butyl-2-p-tolyl-2H-pyrazol-3-yl)-amide;

3-tert-Butyl-5-phenyl-1-p-tolyl-1,6-dihydro-imidazo[4,5-c]pyrazole;

N-(5-tert-Butyl-2-p-tolyl-2H-pyrazol-3-yl)-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-[4-(2-morpholin-4-yl-pyrimidin-4-yloxy)-naphthalen-1-yl]-2-oxo-acetamide;

N-(5 -tert-Butyl-2-hydroxy-3-morpholin-4-ylmethyl-phenyl)-2-[4-(2-morpholin-4-yl-ethoxy)-naphthalen-1-yl]-2-oxo-acetamide;

N-(5-tert-Butyl-2-hydroxy-3-methyl-phenyl)-2-[4-(2-morpholin-4-yl-ethoxy)-naphthalen-1-yl]-2-oxo-acetamide;

N-(5-tert-Butyl-2-methoxy-3-methyl-phenyl)-2-[4-(2-morpholin-4-yl-ethoxy)-naphthalen-1-yl]-2-oxo-acetamide;

N-(5-tert-Butyl-3-chloro-2-methoxy-phenyl)-2-[4-(2-morpholin-4-yl-ethoxy)-naphthalen-1-yl]-2-oxo-acetamide;

N-(5-tert-Butyl-2-methoxy-3-trifluoromethyl-phenyl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[7-chloro-4-(2-morpholin-4-yl-ethoxy)-naphthalen-1-yl]-2-oxo-acetamide;

5-tert-Butyl-N-cyclopropyl-2-methoxy-3-{2-[4-(2-morpholin-4-yl-ethoxy)-naphthalen-1-yl]-2-oxo-acetylamino}-benzamide;

N-[5-tert-Butyl-2-methoxy-3-(piperidine-1-carbonyl)-phenyl]-2-[4-(2-morpholin-4-yl-ethoxy)-naphthalen-1-yl]-2-oxo-acetamide;

5-tert-Butyl-2-hydroxy-3-{2-[4-(2-morpholin-4-yl-ethoxy)-naphthalen-1-yl]-2-oxo-acetylamino}-benzoic acid;

N-(2-Benzenesulfonyl-5-tert-butyl-2H-pyrazol-3-yl)-2-[4-(2-morpholin-4-yl-ethoxy)-naphthalen-1-yl]-2-oxo-acetamide;

2-(5-tert-Butyl-2-p-tolyl-2H-pyrazol-3-yl)-N-[4-(2-morpholin-4-yl-ethoxy)-naphthalen-1-yl]-2-oxo-acetamide;

1-Bicyclo[2.2.1]hept-2-yl-5-phenylamino-3-p-tolyl-1,3-dihydro-imidazo[4,5 -b]pyridin-2-one;

3-p-Tolyl-5-p-tolylamino-1,3-dihydro-imidazo[4,5 -b]pyridin-2-one;

1-Bicyclo[2.2.1]hept-2-yl-3-p-tolyl-5 -p-tolylamino-1,3-dihydro-imidazo[4,5-b]pyridin-2-one;

N-(5-tert-Butyl-2-p-tolyl-2H-pyrazol-3-yl)-2,2-difluoro-2-[4-(2-morpholin-4-yl-ethoxy)-naphthalen-1-yl]-acetamide;

N-(5-tert-Butyl-2-p-tolyl-2H-pyrazol-3-yl)-N'-naphthalen-1-yl-oxalamide;

N-(5-tert-Butyl-2-p-tolyl-2H-pyrazol-3-yl)-2-[(Z)-hydroxyimino]-2-[4-(2-morpholin-4-yl-ethoxy)-naphthalen-1-yl]-acetamide;

N-(5-tert-Butyl-2-p-tolyl-2H-pyrazol-3-yl)-2-[(Z)-methoxyimino]-2-[4-(2-morpholin-4-yl-ethoxy)-naphthalen-1-yl]-acetamide;

2-(5-tert-Butyl-2-p-tolyl-2H-pyrazol-3-ylamino)-1-[4-(2-morpholin-4-yl-ethoxy)-naphthalen-1-yl]-ethanol;

1-(3-tert-Butyl-phenyl)-4-[4-(2-morpholin-4-yl-ethoxy)-naphthalen-1-yl]-[1,2,4]triazolidine-3,5-dione;

4-(3-tert-Butyl-phenyl)-1-[4-(2-morpholin-4-yl-ethoxy)-naphthalen-1-yl]-[1,2,4]triazolidine-3,5-dione;

(E)-3-(5-tert-Butyl-3-methanesulfonylamino-2-methoxyphenylcarbamoyl)-3-[4-(2-morpholin-4-yl-ethoxy)-naphthalen-1-yl]-acrylic acid methyl ester;

N-(5-tert-Butyl-2-methoxy-3-{3-[4-(2-morpholin-4-yl-ethoxy)-naphthalen-1-yl]-2,5-dioxo-2,5-dihydro-pyrrol-1-yl}-phenyl)-methanesulfonamide;

N-(5-tert-Butyl-2-methoxy-3-{3-[4-(2-morpholin-4-yl-ethoxy)-naphthalen-1-yl]-2,5-dioxo-pyrrolidin-1-yl}-phenyl)-methanesulfonamide;

N-(5-tert-Butyl-3-methanesulfonylamino-2-methoxy-phenyl)-2-[4-(2-morpholin-4-yl-ethoxy)-naphthalen-1-yl]-acetamide;

N-(5 -tert-Butyl-3-methanesulfonylamino-2-methoxy-phenyl)-2-oxo-2-[4-(2-piperidin-1-yl-pyrimidin-4-yloxy)-naphthalen-1-yl]-acetamide;

3-tert-Butyl-1-p-tolyl-5-(3-trifluoromethyl-phenyl)-1,6-dihydro-imidazo[4,5 -c]pyrazole;

1-(2-Morpholin-4-yl-ethyl)-1H-indazole-3-carboxylic acid (5-tert-butyl-3-methanesulfonylamino-2-methoxy-phenyl)-amide;

N-[4-(2-Morpholin-4-yl-ethoxy)-naphthalen-1-yl]-2-oxo-2-(2,4,6-trimethyl-phenyl)-acetamide;

1-Phenyl-cyclopropanecarboxylic acid (5-tert-butyl-2-p-tolyl-2H-pyrazol-3-yl)-amide;

N-[5-tert-Butyl-2-(2,5-difluoro-phenyl)-2H-pyrazol-3-yl]-2-[4-(2-morpholin-4-yl-ethoxy)-naphthalen-1-yl]-2-oxo-acetamide;

N-(5-tert-Butyl-2-methoxy-phenyl)-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-(4-methoxy-naphthalen-1-yl)-2-oxo-acetamide;

N-[5-tert-Butyl-2-(3-chloro-benzoyl)-2H-pyrazol-3-yl]-2-[4-(2-morpholin-4-yl-ethoxy)-naphthalen-1-yl]-2-oxo-acetamide;

N-[5-tert-Butyl-2-(3-methanesulfonyl-phenyl)-2H-pyrazol-3-yl]-2-[4-(2-morpholin-4-yl-ethoxy)-naphthalen-1-yl]-2-oxo-acetamide;

4-[(5-tert-Butyl-2-p-tolyl-2H-pyrazol-3-ylcarbamoyl)-methyl]-piperidine-1-carboxylic acid tert-butyl ester;

N-[3-(Benzenesulfonyl-carbamoylmethyl-amino)-5-tert-butyl-2-methoxy-phenyl]-2-naphthalen-1-yl-2-oxo-acetamide;

N-(3-tert-Butyl-isoxazol-5-yl)-2-[4-(2-morpholin-4-yl-ethoxy)-naphthalen-1-yl]-2-oxo-acetamide;

N-(5-tert-Butyl-3-ethanesulfonylamino-2-methoxy-phenyl)-3-[4-(2-morpholin-4-yl-ethoxy)-naphthalen-1-yl]-succinamic acid methyl ester;

2-(2-Benzyl-5-tert-butyl-2H-pyrazol-3-yl)-N-[4-(2-morpholin-4-yl-ethoxy)-naphthalen-1-yl]-2-oxo-acetamide;

N-(5-tert-Butyl-2-p-tolyl-2H-pyrazol-3-yl)-2-[4-(2-morpholin-4-yl-pyrimidin-4-ylamino)-naphthalen-1-yl]-2-oxo-acetamide;

5-tert-Butyl-2-(3-chloro-phenyl)-2H-pyrazole-3-carboxylic acid [4-(2-morpholin-4-yl-ethoxy)-naphthalen-1-yl]-amide;

2-(3-Bromo-4-methoxy-phenyl)-N-(5-tert-butyl-2-p-tolyl-2H-pyrazol-3-yl)-acetamide;

N-(5-tert-Butyl-2-p-tolyl-2H-pyrazol-3-yl)-2-[3-fluoro-4-(2-morpholin-4-yl-ethoxy)-phenyl]-acetamide;

(5-tert-Butyl-2-p-tolyl-2H-pyrazol-3-yl)-(2,2-dimethyl-propyl)-amine;

2-(4-Benzyloxy-phenyl)-N-(5-tert-butyl-2-p-tolyl-2H-pyrazol-3-yl)-acetamide;

N-(5-tert-Butyl-2-p-tolyl-2H-pyrazol-3-yl)-2-hydroxy-2-[4-(2-morpholin-4-yl-ethoxy)-naphthalen-1-yl]-acetamide;

N-[5-tert-Butyl-2-(4-sulfamoyl-phenyl)-2H-pyrazol-3-yl]-2-[4-(2-morpholin-4-yl-ethoxy)-naphthalen-1-yl]-2-oxo-acetamide;

5-tert-Butyl-2-methoxy-3-(1-naphthalen-1-yl-3,5-dioxo-[1,2,4]triazolidin-4-yl)-benzamide;

2-(4-Bromo-naphthalen-1-yl)-N-(5-tert-butyl-2-methyl-2H-pyrazol-3-yl)-2-oxo-acetamide;

5-tert-Butyl-2-hydroxy-3-{2-[4-(2-morpholin-4-yl-ethoxy)-naphthalen-1-yl]-2-oxo-acetylamino}-benzamide;

N-(5-tert-Butyl-2-p-tolyl-2H-pyrazol-3-yl)-2-hydroxy-2-(4-methoxy-naphthalen-1-yl)-acetamide;

N-(5-tert-Butyl-3-methanesulfonylamino-2-methoxy-phenyl)-2-[4-(6-morpholin-4-ylmethyl-pyridin-3-yl)-naphthalen-1-yl]-2-oxo-acetamide;

N-(5-tert-Butyl-2-methoxy-phenyl)-2-[4-(2-methylamino-pyrimidin-4-ylamino)-naphthalen-1-yl]-2-oxo-acetamide;

N-(5-tert-Butyl-2-methoxy-phenyl)-2-[4-(2-dimethylamino-pyrimidin-4-ylamino)-naphthalen-1-yl]-2-oxo-acetamide;

N-(5-tert-Butyl-2-p-tolyl-2H-pyrazol-3-yl)-2-oxo-2-{4-[2-(1-oxo-1$\lambda^4$-thiomorpholin-4-yl)-ethoxy]-naphthalen-1-yl}-acetamide;

5-tert-Butyl-3-{2-[(Z)-hydroxyimino]-2-[4-(2-morpholin-4-yl-ethoxy)-naphthalen-1-yl]-acetylamino}-thiophene-2-carboxylic acid methyl ester;

N-[5-tert-Butyl-2-(3-methanesulfonyl-phenyl)-2H-pyrazol-3-yl]-2-hydroxy-2-[4-(2-morpholin-4-yl-ethoxy)-naphthalen-1-yl]-acetamide;

N-(5-tert-Butyl-2-p-tolyl-2H-pyrazol-3-yl)-2-{4-[2-((2R,6R)-2,6-dimethyl-morpholin-4-yl)-ethoxy]-naphthalen-1-yl}-2-oxo-acetamide;

N-(5-tert-Butyl-2-methyl-2H-pyrazol-3-yl)-2-[4-(6-morpholin-4-ylmethyl-pyridin-3-yl)-naphthalen-1-yl]-2-oxo-acetamide;

N-(5-tert-Butyl-3-methanesulfonylamino-2-methoxy-phenyl)-2-[7-chloro-4-(2-morpholin-4-yl-ethoxy)-naphthalen-1-yl]-2-oxo-acetamide;

N-(5-tert-Butyl-3-methanesulfonylamino-2-methoxy-phenyl)-2-[(Z)-hydroxyimino]-2-[4-(2-morpholin-4-yl-ethoxy)-naphthalen-1-yl]-acetamide;

N-(5-tert-Butyl-2-methoxy-phenyl)-2-[4-(6-morpholin-4-ylmethyl-pyridin-3-yl)-naphthalen-1-yl]-2-oxo-acetamide;

5-tert-Butyl-N-cyclopropyl-2-methoxy-3-[2-(4-methoxy-naphthalen-1-yl)-2-oxo-acetylamino]-benzamide;

4-tert-Butyl-N-[4-(2-piperidin-1-yl-ethoxy)-naphthalen-1-yl]-benzamide;

N-(2-Acetyl-5-tert-butyl-2H-pyrazol-3-yl)-2-[4-(2-morpholin-4-yl-ethoxy)-naphthalen-1-yl]-2-oxo-acetamide;

5-tert-Butyl-N-cyclopropyl-3-{2-hydrazono-2-[4-(2-morpholin-4-yl-ethoxy)-naphthalen-1-yl]-acetylamino}-2-methoxy-benzamide;

N-(5-tert-Butyl-2-methoxy-phenyl)-2-hydroxy-2-(4-methoxy-naphthalen-1-yl)-propionamide;

N-(5-tert-Butyl-2-p-tolyl-2H-pyrazol-3-yl)-2-oxo-2-phenyl-acetamide;

N-(5-tert-Butyl-3-methanesulfonylamino-2-methoxy-phenyl)-2-hydrazono-2-[4-(2-morpholin-4-yl-ethoxy)-naphthalen-1-yl]-acetamide;

2,3-Dihydro-indole-1-carboxylic acid (5-tert-butyl-2-p-tolyl-2H-pyrazol-3-yl)-amide;

N-(3,4-Dimethyl-phenyl)-2-[4-(2-morpholin-4-yl-ethoxy)-naphthalen-1-yl]-2-oxo-acetamide;

N-(5-tert-Butyl-2-cyclohexyl-2H-pyrazol-3-yl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-(3,5-difluorophenyl)-acetamide;

N-(5-tert-Butyl-2-methoxy-phenyl)-2-oxo-2-(4-pyridin-3-yl-naphthalen-1-yl)-acetamide;

N-(5-tert-Butyl-isoxazol-3-yl)-2-[(Z)-hydroxyimino]-2-[4-(2-morpholin-4-yl-ethoxy)-naphthalen-1-yl]-acetamide;

N-(5-tert-Butyl-3-methanesulfonylamino-2-methoxy-phenyl)-2-[4-(2-diethylamino-ethoxy)-naphthalen-1-yl]-2-oxo-acetamide;

N-(5-tert-Butyl-2-p-tolyl-2H-pyrazol-3-yl)-2-oxo-2-{4-[2-(3-oxo-[1,4]diazepan-1-yl)-ethyl]-naphthalen-1-yl}-acetamide;

5-tert-Butyl-N-ethyl-2-methoxy-3-[2-(4-methoxy-naphthalen-1-yl)-2-oxo-acetylamino]-benzamide;

N-(5-tert-Butyl-2-methoxy-phenyl)-2-oxo-2-{4-[6-(tetrahydro-pyran-4-ylamino)-pyridin-3-yl]-naphthalen-1-yl}-acetamide;

5-tert-Butyl-3-ethanesulfonylamino-2-methoxy-N-[4-(2-morpholin-4-yl-ethoxy)-naphthalen-1-yl]-benzamide;

2-(5-tert-Butyl-2-methyl-2H-pyrazol-3-yl)-2-oxo-N-m-tolyl-acetamide;

N-(2,5-Dimethyl-phenyl)-2-[4-(2-morpholin-4-yl-ethoxy)-naphthalen-1-yl]-2-oxo-acetamide;

Pyrrolidine-1-carboxylic acid (5-tert-butyl-2-methoxy-3-{2-[4-(2-morpholin-4-yl-ethoxy)-naphthalen-1-yl]-2-oxo-acetylamino}-phenyl)-amide;

2-(4-Bromo-phenyl)-N-(5-tert-butyl-2-methoxy-phenyl)-acetamide;

N-(3-Amino-5-tert-butyl-2-methoxy-phenyl)-2-oxo-2-{4-[2-((S)-1-phenyl-ethylamino)-pyrimidin-4-ylamino]-naphthalen-1-yl}-acetamide;

5-tert-Butyl-3-[1-(2,3-dimethyl-phenyl)-3,5-dioxo-[1,2,4]triazolidin-4-yl]-2-methoxy-benzamide;

N-(5-tert-Butyl-2-p-tolyl-2H-pyrazol-3-yl)-2-naphthalen-2-yl-acetamide;

5-tert-Butyl-2-methoxy-3-{2-[4-(2-morpholin-4-yl-ethoxy)-naphthalen-1-yl]-2-oxo-acetylamino}-benzamide;

N-(5-tert-Butyl-2-p-tolyl-2H-pyrazol-3-yl)-2-methoxy-2-(4-methoxy-naphthalen-1-yl)-propionamide;

5-tert-Butyl-2-methoxy-N-[4-(2-morpholin-4-yl-ethoxy)-naphthalen-1-ylmethyl]-3-nitro-benzamide;

N-(5-tert-Butyl-2-methoxy-3-{2-[4-(2-morpholin-4-yl-ethoxy)-naphthalen-1-yl]-2-oxo-acetylamino}-phenyl)-benzamide;

N-(5-tert-Butyl-2-p-tolyl-2H-pyrazol-3-yl)-2-(2,5-difluoro-phenyl)-acetamide;

N-(3,5-Di-tert-butyl-2-methoxy-phenyl)-2-[(Z)-hydroxyimino]-2-[4-(2-morpholin-4-yl-ethoxy)-naphthalen-1-yl]-acetamide;

N'-[1-(5-tert-Butyl-2-methyl-2H-pyrazol-3-ylcarbamoyl)-1-[4-(2-morpholin-4-yl-ethoxy)-naphthalen-1-yl]-meth-(E)-ylidene]-hydrazinecarboxamide;

N-[2-(4-Amino-phenyl)-5-tert-butyl-2H-pyrazol-3-yl]-2-hydroxy-2-[4-(2-morpholin-4-yl-ethoxy)-naphthalen-1-yl]-acetamide;

5-tert-Butyl-3-{2-[(Z)-methoxyimino]-2-[4-(2-morpholin-4-yl-ethoxy)-naphthalen-1-yl]-acetylamino}-thiophene-2-carboxylic acid amide;

Ethanesulfonic acid (5-tert-butyl-2-methoxy-3-{3-[4-(2-morpholin-4-yl-ethoxy)-naphthalen-1-yl]-2,5-dioxo-2,5-dihydro-pyrrol-1-yl}-phenyl)-amide;

5-tert-Butyl-N-cyclopropylmethyl-2-methoxy-3-{2-[4-(2-morpholin-4-yl-ethoxy)-naphthalen-1-yl]-2-oxo-acetylamino}-benzamide;

5-Fluoro-1H-indazole-3-carboxylic acid (5-tert-butyl-2-p-tolyl-2H-pyrazol-3-yl)-amide;

N-[5-tert-Butyl-2-methoxy-3-(2-methoxy-acetylamino)-phenyl]-2-[4-(2-morpholin-4-yl-ethoxy)-naphthalen-1-yl]-2-oxo-acetamide;

7-Bicyclo[2.2.1]hept-2-yl-9-p-tolyl-2-p-tolylamino-7,9-dihydro-purin-8-one;

N-(5-tert-Butyl-2-isopropoxy-3-methanesulfonylamino-phenyl)-2-[4-(2-morpholin-4-yl-ethoxy)-naphthalen-1-yl]-2-oxo-acetamide;

N-[5-tert-Butyl-2-(3,4-dimethyl-phenyl)-2H-pyrazol-3-yl]-2-[4-(2-morpholin-4-yl-ethoxy)-naphthalen-1-yl]-2-oxo-acetamide;

3-tert-Butyl-1-(3,4-dichloro-phenyl)-5-phenyl-1,6-dihydro-imidazo[4,5-c]pyrazole;

N-(5-tert-Butyl-2-p-tolyl-2H-pyrazol-3-yl)-2-oxo-2-[4-(2-thiomorpholin-4-yl-ethoxy)-naphthalen-1-yl]-acetamide;

5-Nitro-1H-pyrazole-3-carboxylic acid (5-tert-butyl-2-p-tolyl-2H-pyrazol-3-yl)-amide;

N-(5-tert-Butyl-3-methanesulfonylamino-2-methoxy-phenyl)-2-[4-(2-dimethylamino-pyrimidin-4-ylamino)-naphthalen-1-yl]-2-oxo-acetamide;

1-(2-Amino-4-tert-butyl-6-{2-[4-(2-morpholin-4-yl-ethoxy)-naphthalen-1-yl]-2-oxo-acetylamino}-phenyl)-pyridinium;

N-(5-tert-Butyl-2-isopropoxy-phenyl)-2-[4-(2-morpholin-4-yl-ethoxy)-naphthalen-1-yl]-2-oxo-acetamide;

N-[4-(2-Morpholin-4-yl-ethoxy)-naphthalen-1-yl]-2,5-bis-trifluoromethyl-benzamide;

2-(tert-Butyl-dimethyl-silanyloxy)-N-(5-tert-butyl-2-p-tolyl-2H-pyrazol-3-yl)-2-(4-methoxy-phenyl)-acetamide;

N-(5-tert-Butyl-2-m-tolyl-2H-pyrazol-3-yl)-2-[(Z)-hydroxyimino]-2-[4-(2-morpholin-4-yl-ethoxy)-naphthalen-1-yl]-acetamide;

5-tert-Butyl-2-methoxy-3-[2-(4-methoxy-naphthalen-1-yl)-2-oxo-acetylamino]-benzamide;

N-(5-tert-Butyl-2-p-tolyl-2H-pyrazol-3-yl)-2-oxo-2-phenyl-acetamide;

5-tert-Butyl-2-methoxy-N-(2-methoxy-ethyl)-3-{2-[4-(2-morpholin-4-yl-ethoxy)-naphthalen-1-yl]-2-oxo-acetylamino}-benzamide;

(E)-3-(5-tert-Butyl-3-ethanesulfonylamino-2-methoxy-phenylcarbamoyl)-3-[4-(2-morpholin-4-yl-ethoxy)-naphthalen-1-yl]-acrylic acid methyl ester;

1-Isopropyl-3-phenyl-5-phenylamino-1,3-dihydro-imidazo[4,5-b]pyridin-2-one;

N-(5-tert-Butyl-isoxazol-3-yl)-2-[4-(2-morpholin-4-yl-pyrimidin-4-ylamino)-naphthalen-1-yl]-2-oxo-acetamide;

2-(2-Benzyl-5-tert-butyl-2H-pyrazol-3-yl)-2-[(Z)-hydroxyimino]-N-[4-(2-morpholin-4-yl-ethoxy)-naphthalen-1-yl]-acetamide;

2-(5-tert-Butyl-2-methoxy-phenyl)-N-[4-(2-morpholin-4-yl-ethoxy)-naphthalen-1-yl]-2-oxo-acetamide;

N-(5-tert-Butyl-2-p-tolyl-2H-pyrazol-3-yl)-2-(2,4-dimethoxy-phenyl)-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid methyl ester;

3-tert-Butyl-5-{2-[4-(2-morpholin-4-yl-ethoxy)-naphthalen-1-yl]-2-oxo-acetylamino}-pyrazole-1-carboxylic acid adamantan-1-ylamide;

3-tert-Butyl-5-phenyl-1-(4-trifluoromethyl-phenyl)-1,6-dihydro-imidazo[4,5-c]pyrazole;

N-(5-tert-Butyl-2-methoxy-3-{3-[4-(2-morpholin-4-yl-ethoxy)-naphthalen-1-yl]-2,4,5-trioxo-imidazolidin-1-yl}-phenyl)-methanesulfonamide;

3-tert-Butyl-1-(3-chloro-phenyl)-5-phenyl-1,6-dihydro-imidazo[4,5-c]pyrazole;

5-tert-Butyl-3-{2-[4-(2-morpholin-4-yl-ethoxy)-naphthalen-1-yl]-2-oxo-acetylamino}-thiophene-2-carboxylic acid amide;

2-(5-tert-Butyl-2-p-tolyl-2H-pyrazol-3-yl)-2-hydroxy-N-[4-(2-morpholin-4-yl-ethoxy)-naphthalen-1-yl]-acetamide;

N-(5-tert-Butyl-2-p-tolyl-2H-pyrazol-3-yl)-2-{4-[2-(2,6-dimethyl-morpholin-4-yl)-ethyl]-naphthalen-1-yl}-2-oxo-acetamide;

N-(5-tert-Butyl-2H-pyrazol-3-yl)-2-[4-(2-morpholin-4-yl-ethoxy)-naphthalen-1-yl]-2-oxo-acetamide;

N-[5-tert-Butyl-2-methoxy-3-(propane-1-sulfonylamino)-phenyl]-2-[4-(2-morpholin-4-yl-ethoxy)-naphthalen-1-yl]-acetamide;

3-tert-Butyl-5-{2-[4-(2-morpholin-4-yl-ethoxy)-naphthalen-1-yl]-2-oxo-acetylamino}-pyrazole-1-carboxylic acid tert-butylamide;

1-(5-tert-Butyl-2-methyl-2H-pyrazol-3-yl)-3-(2,3-dichlorophenyl)-3'-(carbamic acid ethyl ester)-urea;

2-(3,5-Difluoro-phenyl)-N-[4-(2-morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid amide;

N-Allyl-5-tert-butyl-2-methoxy-3-{2-[4-(2-morpholin-4-yl-ethoxy)-naphthalen-1-yl]-2-oxo-acetylamino}-benzamide;

N-(5-tert-Butyl-isoxazol-3-yl)-2-[(Z)-methoxyimino]-2-[4-(2-morpholin-4-yl-ethoxy)-naphthalen-1-yl]-acetamide;

3-(5-tert-Butyl-2-methyl-2H-pyrazol-3-yl)-1-[4-(2-morpholin-4-yl-ethoxy)-naphthalen-1-yl]-pyrrole-2,5-dione;

2-(5-tert-Butyl-2-methyl-2H-pyrazol-3-yl)-2-[(Z)-hydroxyimino]-N-[4-(2-morpholin-4-yl-ethoxy)-naphthalen-1-yl]-acetamide;

3-tert-Butyl-5-o-tolyl-1-p-tolyl-1,6-dihydro-imidazo[4,5-c]pyrazole;

N-(5-tert-Butyl-2-p-tolyl-2H-pyrazol-3-yl)-2-[(E)-hydroxyimino]-2-phenyl-acetamide;

N-(5-tert-Butyl-2-methoxy-phenyl)-2-hydroxy-2-phenyl-acetamide;

N-(3-Acetylamino-5-tert-butyl-2-methoxy-phenyl)-2-[4-(2-morpholin-4-yl-ethoxy)-naphthalen-1-yl]-2-oxo-acetamide;

1H-Indazole-3-carboxylic acid (5-tert-butyl-3-methanesulfonylamino-2-methoxy-phenyl)-amide;

5-tert-Butyl-2-methoxy-N-[4-(2-morpholin-4-yl-ethoxy)-naphthalen-1-yl]-3-nitro-benzamide;

5-tert-Butyl-3-{2-[(Z)-hydroxyimino]-2-[4-(2-morpholin-4-yl-pyrimidin-4-yloxy)-naphthalen-1-yl]-acetylamino}-thiophene-2-carboxylic acid amide;

N-[3-(4-Acetyl-piperazine-1-carbonyl)-5-tert-butyl-2-methoxy-phenyl]-2-[4-(2-morpholin-4-yl-ethoxy)-naphthalen-1-yl]-2-oxo-acetamide;

2-(5-tert-Butyl-2-methyl-2H-pyrazol-3-yl)-N-[4-(2-morpholin-4-yl-pyrimidin-4-yloxy)-naphthalen-1-yl]-2-oxo-acetamide;

N-(5-tert-Butyl-4-methyl-2-p-tolyl-2H-pyrazol-3-yl)-2-[(Z)-hydroxyimino]-2-[4-(2-morpholin-4-yl-ethoxy)-naphthalen-1-yl]-acetamide;

2-[4-(2-Morpholin-4-yl-ethoxy)-naphthalen-1-yl]-2-oxo-N-(2-phenyl-cyclopropyl)-acetamide;

N-(5-tert-Butyl-isoxazol-3-yl)-2-[4-(6-morpholin-4-ylmethyl-pyridin-3-yl)-naphthalen-1-yl]-2-oxo-acetamide;

N-(5-tert-Butyl-2,3-dimethoxy-phenyl)-2-[(Z)-hydroxyimino]-2-[4-(2-morpholin-4-yl-ethoxy)-naphthalen-1-yl]-acetamide;

N-(5-tert-Butyl-2-p-tolyl-2H-pyrazol-3-yl)-2-(2-chlorophenyl)-acetamide;

N-(5-tert-Butyl-2-p-tolyl-2H-pyrazol-3-yl)-2-{4-[2-(4-methyl-piperazin-1-yl)-ethyl]-naphthalen-1-yl}-2-oxo-acetamide;

N-(5-tert-Butyl-3-methanesulfonylamino-2-methoxy-phenyl)-2-(1H-indol-3-yl)-2-oxo-acetamide;

N-(5-tert-Butyl-2-methoxy-phenyl)-2-[4-(2-morpholin-4-yl-pyridin-4-ylamino)-naphthalen-1-yl]-2-oxo-acetamide;

N-(4-tert-Butyl-6-trifluoromethyl-pyrimidin-2-yl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-o-tolyl-acetamide;

5-tert-Butyl-3-{2-[(Z)-hydroxyimino]-2-[4-(2-morpholin-4-yl-ethoxy)-naphthalen-1-yl]-acetylamino}-thiophene-2-carboxylic acid methylamide;

N-[5-tert-Butyl-2-(3,5-dichloro-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-{4-[2-((2R,6S)-2,6-dimethyl-morpholin-4-yl)-ethoxy]-naphthalen-1-yl}-2-oxo-acetamide;

3-tert-Butyl-1,5-diphenyl-1,6-dihydro-imidazo[4,5-c]pyrazole;

N-(5-tert-Butyl-2-p-tolyl-2H-pyrazol-3-yl)-2-[4-(2-imidazol-1-yl-ethyl)-naphthalen-1-yl]-2-oxo-acetamide;

3-tert-Butyl-5-(3-chloro-phenyl)-1-p-tolyl-1,6-dihydro-imidazo[4,5-c]pyrazole;

N-(5-tert-Butyl-2-methoxy-3-phenylmethanesulfonylamino-phenyl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-oxo-2-[4-(2-pyridin-4-yl-ethoxy)-naphthalen-1-yl]-acetamide;

1-(5-tert-Butyl-2-methoxy-phenyl)-3-(4-{2-[(pyridin-2-ylmethyl)-amino]-pyrimidin-4-yloxy}-naphthalen-1-yl)-imidazolidine-2,4,5-trione;

N-[5-tert-Butyl-2-(3-chloro-phenyl)-2H-pyrazol-3-yl]-2-[4-(2-morpholin-4-yl-ethoxy)-naphthalen-1-yl]-2-oxo-acetamide;

5-Methoxy-1H-indazole-3-carboxylic acid (5-tert-butyl-2-p-tolyl-2H-pyrazol-3-yl)-amide;

N-[5-tert-Butyl-2-(6-chloro-pyridazin-3-yl)-2H-pyrazol-3-yl]-2-[4-(2-morpholin-4-yl-ethoxy)-naphthalen-1-yl]-2-oxo-acetamide;

N-(5-tert-Butyl-2-m-tolyl-2H-pyrazol-3-yl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-(2-methoxyphenyl)-acetamide;

5-tert-Butyl-N-cyclopropyl-2-methoxy-3-{2-[4-(2-morpholin-4-yl-pyrimidin-4-ylamino)-naphthalen-1-yl]-2-oxo-acetylamino}-benzamide;

[(5-tert-Butyl-2-methoxy-3-{2-[4-(2-morpholin-4-yl-ethoxy)-naphthalen-1-yl]-2-oxo-acetylamino}-phenyl)-methanesulfonyl-amino]-acetic acid ethyl ester;

N-(5-tert-Butyl-4-methyl-2-m-tolyl-2H-pyrazol-3-yl)-2-[(Z)-hydroxyimino]-2-[4-(2-morpholin-4-yl-ethoxy)-naphthalen-1-yl]-acetamide;

N-[5-tert-Butyl-2-(2,5-dichloro-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[4-(2-[1,4]oxazepan-4-yl-ethoxy)-naphthalen-1-yl]-2-oxo-acetamide;

1-(5-tert-Butyl-2-methoxy-3-benzamide)-3-(4-methoxyphenyl)-3'-(carbamic acid ethyl ester)-urea;

N-[5-tert-Butyl-2-(4-methoxy-phenyl)-2H-pyrazol-3-yl]-2-(4-methoxy-naphthalen-1-yl)-acetamide;

N-(5-tert-Butyl-2-p-tolyl-2H-pyrazol-3-yl)-4-chloro-benzamide;

N-(2-Bromo-5-trifluoromethyl-phenyl)-2-[4-(2-morpholin-4-yl-ethoxy)-naphthalen-1-yl]-2-oxo-acetamide;

3-Isopropyl-5-phenyl-1-p-tolyl-1,6-dihydro-imidazo[4,5-c]pyrazole;

3,5-Di-tert-butyl-1-p-tolyl-1,6-dihydro-imidazo[4,5-c]pyrazole;

5-tert-Butyl-N-cyclopentyl-2-methoxy-3-{2-[4-(2-morpholin-4-yl-ethoxy)-naphthalen-1-yl]-2-oxo-acetylamino}-benzamide;

2-[5-tert-Butyl-2-(3-fluoro-4-methyl-phenyl)-2H-pyrazol-3-yl]-N-[4-(2-morpholin-4-yl-ethoxy)-naphthalen-1-yl]-2-oxo-acetamide;

N-(5-tert-Butyl-2-p-tolyl-2H-pyrazol-3-yl)-2-(4-methoxyphenyl)-2-oxo-acetamide;

1,3-Di-tert-butyl-5-phenyl-1,6-dihydro-imidazo[4,5-c]pyrazole;

4-(4-Bromo-naphthalen-1-yl)-1-(3-tert-butyl-phenyl)-[1,2,4]triazolidine-3,5-dione;

N-[5-tert-Butyl-2-(morpholine-4-carbonyl)-thiophen-3-yl]-2-[4-(2-morpholin-4-yl-ethoxy)-naphthalen-1-yl]-2-oxo-acetamide;

3-tert-Butyl-5-(3-methoxy-phenyl)-1-p-tolyl-1,6-dihydro-imidazo[4,5-c]pyrazole;

N-(5-tert-Butyl-2-methoxy-phenyl)-2-[4-(2-morpholin-4-yl-pyrimidin-4-yloxy)-naphthalen-1-yl]-2-oxo-acetamide;

1-tert-Butyl-5-[4-(2-morpholin-4-yl-ethoxy)-naphthalen-1-ylamino]-3-p-tolyl-1,3-dihydro-imidazo[4,5-b]pyridin-2-one;

2-[5-tert-Butyl-2-(3-fluoro-phenyl)-2H-pyrazol-3-yl]-2-[(Z)-hydroxyimino]-N-[4-(2-morpholin-4-yl-ethoxy)-naphthalen-1-yl]-acetamide;

5-tert-Butyl-2-p-tolyl-2H-pyrazole-3-carboxylic acid [4-(2-morpholin-4-yl-ethoxy)-naphthalen-1-ylmethyl]-amide;

2-[5-tert-Butyl-2-(3-fluoro-phenyl)-2H-pyrazol-3-yl]-N-[4-(2-morpholin-4-yl-ethoxy)-naphthalen-1-yl]-2-oxo-acetamide;

5-tert-Butyl-N-cyclopropylmethyl-2-methoxy-3-[2-(4-methoxy-naphthalen-1-yl)-2-oxo-acetylamino]-benzamide;

N-[5-tert-Butyl-3-(3,3-diethyl-ureido)-2-methoxy-phenyl]-2-[4-(2-morpholin-4-yl-ethoxy)-naphthalen-1-yl]-2-oxo-acetamide;

N-[5-tert-Butyl-2-(4-fluoro-phenyl)-2H-pyrazol-3-yl]-2-[4-(2-morpholin-4-yl-ethoxy)-naphthalen-1-yl]-2-oxo-acetamide;

N-(2-Benzyl-5-tert-butyl-2H-pyrazol-3-yl)-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-oxo-2-[4-(2-piperazin-1-yl-ethoxy)-naphthalen-1-yl]-acetamide;

N-(5-tert-Butyl-3-methanesulfonylamino-2-methoxy-phenyl)-2-[4-(2-morpholin-4-yl-pyridin-4-ylamino)-naphthalen-1-yl]-2-oxo-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid isopropyl ester;

1-(5-tert-Butyl-2-methoxy-phenyl)-3-[4-(2-dimethylamino-pyrimidin-4-yloxy)-naphthalen-1-yl]-imidazolidine-2,4,5-trione;

N-(5-tert-Butyl-3-methanesulfonylamino-2-methoxy-phenyl)-2-[4-(2-morpholin-4-yl-pyrimidin-4-ylamino)-naphthalen-1-yl]-2-oxo-acetamide;

4-(3-tert-Butyl-1-p-tolyl-1,6-dihydro-imidazo[4,5-c]pyrazol-5-yl)-2-methoxy-phenol;

N-(5-tert-Butyl-2-p-tolyl-2H-pyrazol-3-yl)-2-(3,4-dichlorophenyl)-acetamide;

N-[3-(3-Allyl-ureido)-5-tert-butyl-2-methoxy-phenyl]-2-[4-(2-morpholin-4-yl-ethoxy)-naphthalen-1-yl]-2-oxo-acetamide;

5-tert-Butyl-N,N-diethyl-2-methoxy-3-{2-[4-(2-morpholin-4-yl-ethoxy)-naphthalen-1-yl]-2-oxo-acetylamino}-benzamide;

N-(5-tert-Butyl-3-methanesulfonylamino-2-methoxy-phenyl)-2-[4-(2-[1,4]oxazepan-4-yl-ethoxy)-naphthalen-1-yl]-2-oxo-acetamide;

N-(3-tert-Butyl-phenyl)-2-[4-(2-morpholin-4-yl-ethoxy)-naphthalen-1-yl]-2-oxo-acetamide;

5-tert-Butyl-N-ethyl-2-methoxy-3-{2-[4-(2-morpholin-4-yl-ethoxy)-naphthalen-1-yl]-acetylamino}-benzamide;

N-[5-tert-Butyl-2-(6-methyl-pyridin-3-yl)-2H-pyrazol-3-yl]-2-[4-(2-morpholin-4-yl-ethoxy)-naphthalen-1-yl]-2-oxo-acetamide;

N-[5-tert-Butyl-2-(4-ureido-phenyl)-2H-pyrazol-3-yl]-2-[4-(2-morpholin-4-yl-ethoxy)-naphthalen-1-yl]-2-oxo-acetamide;

N-(5-tert-Butyl-2-m-tolyl-2H-pyrazol-3-yl)-2-[4-(2-dimethylamino-ethoxy)-naphthalen-1-yl]-2-oxo-acetamide;

N-(5-tert-Butyl-2-methoxy-phenyl)-2-oxo-2-[4-(2-piperidin-1-yl-pyrimidin-4-yloxy)-naphthalen-1-yl]-acetamide;

N-[5-tert-Butyl-2-(3-fluoro-4-methyl-phenyl)-2H-pyrazol-3-yl]-2-[4-(2-morpholin-4-yl-ethoxy)-naphthalen-1-yl]-2-oxo-acetamide;

Indazole-1-carboxylic acid (5-tert-butyl-2-p-tolyl-2H-pyrazol-3-yl)-amide;

N-[3,5-Bis-(1,1-dimethyl-propyl)-2-methoxy-phenyl]-2-[4-(2-morpholin-4-yl-ethoxy)-naphthalen-1-yl]-2-oxo-acetamide;

1-Benzyl-3-tert-butyl-5-phenyl-1,6-dihydro-imidazo[4,5-c]pyrazole;

2-(5-tert-Butyl-2-methoxy-3-nitro-phenyl)-N-[4-(2-morpholin-4-yl-ethoxy)-naphthalen-1-yl]-2-oxo-acetamide;

4-{2-[4-(5-tert-Butyl-3-methanesulfonylamino-2-methoxy-phenylaminooxalyl)-naphthalen-1-yloxy]-ethyl}-piperazine-1-carboxylic acid ethyl ester;

2-Hydroxy-N-(5-isopropyl-2-p-tolyl-2H-pyrazol-3-yl)-2-[4-(2-morpholin-4-yl-ethoxy)-naphthalen-1-yl]-acetamide;

1-Bicyclo[2.2.1]hept-2-yl-3-phenyl-5-phenylamino-1,3-dihydro-imidazo[4,5-b]pyridin-2-one;

N-(3-Amino-5-tert-butyl-2-methoxy-phenyl)-2-[4-(2-morpholin-4-yl-pyrimidin-4-ylamino)-naphthalen-1-yl]-2-oxo-acetamide;

N-[5-tert-Butyl-3-(2-dimethylamino-acetylamino)-2-methoxy-phenyl]-2-[4-(2-morpholin-4-yl-ethoxy)-naphthalen-1-yl]-2-oxo-acetamide;

N-(5-tert-Butyl-2-methoxy-3-{6-[4-(2-morpholin-4-yl-ethoxy)-naphthalen-1-yl]-3,5-dioxo-2,5-dihydro-3H-[1,2,4]triazin-4-yl}-phenyl)-methanesulfonamide;

N-(5-tert-Butyl-2-methyl-2H-pyrazol-3-yl)-2-[4-(2-morpholin-4-yl-ethoxy)-naphthalen-1-yl]-2-oxo-acetamide;

(R)—N-(5-tert-Butyl-2-p-tolyl-2H-pyrazol-3-yl)-2-hydroxy-2-phenyl-acetamide;

N-(5-tert-Butyl-3-methanesulfonylamino-2-methoxy-phenyl)-2-[4-(2-dimethylamino-ethoxy)-naphthalen-1-yl]-2-oxo-acetamide;

2-(5-tert-Butyl-2-methyl-2H-pyrazol-3-yl)-N-[4-(2-morpholin-4-yl-ethoxy)-naphthalen-1-yl]-2-oxo-acetamide;

N-[2-(3-Amino-phenyl)-5-tert-butyl-2H-pyrazol-3-yl]-2-hydroxy-2-[4-(2-morpholin-4-yl-ethoxy)-naphthalen-1-yl]-acetamide;

2-[5-tert-Butyl-2-(3-chloro-phenyl)-2H-pyrazol-3-yl]-N-[4-(2-morpholin-4-yl-ethoxy)-naphthalen-1-yl]-2-oxo-acetamide;

1,5-Diphenyl-1,6-dihydro-imidazo[4,5-c]pyrazole;

N-(5-tert-Butyl-[1,3,4]thiadiazol-2-yl)-2-[(Z)-hydroxy-imino]-2-[4-(2-morpholin-4-yl-ethoxy)-naphthalen-1-yl]-acetamide;

N-(5-tert-Butyl-3-{2-hydroxy-2-[4-(2-morpholin-4-yl-pyrimidin-4-yloxy)-naphthalen-1-yl]-ethylamino}-2-methoxy-phenyl)-methanesulfonarnide;

N-(5-tert-Butyl-2-p-tolyl-2H-pyrazol-3-yl)-4-chloro-benzamide;

N-(5-tert-Butyl-2-ethoxy-phenyl)-2-[4-(2-morpholin-4-yl-ethoxy)-naphthalen-1-yl]-2-oxo-acetamide;

(5-tert-Butyl-2-methoxy-3-{2-[4-(2-morpholin-4-yl-ethoxy)-naphthalen-1-yl]-²-oxo-acetylamino}-phenyl)-carbamic acid 2-methoxy-ethyl ester;

(R)—N-(5-tert-Butyl-2-p-tolyl-2H-pyrazol-3-yl)-2-methoxy-2-phenyl-acetamide;

2-(5-tert-Butyl-2-m-tolyl-2H-pyrazol-3-yl)-2-hydroxy-N-[4-(2-morpholin-4-yl-ethoxy)-naphthalen-1-yl]-acetamide;

2-Amino-N-(5-tert-butyl-2-p-tolyl-2H-pyrazol-3-yl)-2-naphthalen-1-yl-acetamide;

N-(5-tert-Butyl-3-methanesulfonylamino-2-methoxy-phenyl)-2-[4-(2-morpholin-4-yl-ethoxy)-naphthalen-1-yl]-acrylamide;

N-(5-tert-Butyl-2-p-tolyl-2H-pyrazol-3-yl)-2-[4-(2-imidazol-1-yl-ethoxy)-naphthalen-1-yl]-2-oxo-acetamide;

N-(4-Bromo-3-trifluoromethyl-phenyl)-2-[4-(2-morpholin-4-yl-ethoxy)-naphthalen-1-yl]-2-oxo-acetamide;

4-(4-Benzyloxy-phenyl)-1-(3-tert-butyl-phenyl)-[1,2,4]triazolidine-3,5-dione;

N-(5-tert-Butyl-3-methanesulfonylamino-2-methoxy-phenyl)-2-[8-chloro-4-(2-morpholin-4-yl-ethoxy)-naphthalen-1-yl]-2-oxo-acetamide;

N-(5-tert-Butyl-3-methanesulfonylamino-2-methoxy-phenyl)-2-[4-(2-chloro-ethoxy)-naphthalen-1-yl]-2-oxo-acetamide;

5-tert-Butyl-3-{2-[4-(2-morpholin-4-yl-ethoxy)-naphthalen-1-yl]-2-oxo-acetylamino}-thiophene-2-carboxylic acid dimethylamide;

1-(5-tert-Butyl-isoxazol-3-yl)-3-[4-(2-morpholin-4-yl-ethoxy)-naphthalen-1-yl]-imidazolidine-2,4,5-trione;

N-(4—Chloro-3-trifluoromethyl-phenyl)-2-[4-(2-morpholin-4-yl-ethoxy)-naphthalen-1-yl]-2-oxo-acetamide;

1-Benzoyl-3-(5-tert-butyl-2-methoxy-phenyl)-urea;

N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(Z)-ylidene]-hydrazinecarboxylic acid ethyl ester;

3-tert-Butyl-5-(3-fluoro-phenyl)-1-p-tolyl-1,6-dihydro-imidazo[4,5-c]pyrazole;

2-[3-Bromo-4-(2-morpholin-4-yl-ethoxy)-phenyl]-N-(5-tert-butyl-2-p-tolyl-2H-pyrazol-3-yl)-acetamide;

2-(2-Chloro-5-trifluoromethyl-phenyl)-N-[4-(2-morpholin-4-yl-ethoxy)-naphthalen-1-yl]-2-oxo-acetamide;

N-[5-tert-Butyl-2-(3-chloro-benzenesulfonyl)-2H-pyrazol-3-yl]-2-[4-(2-morpholin-4-yl-ethoxy)-naphthalen-1-yl]-2-oxo-acetamide;

(5-tert-Butyl-2-p-tolyl-2H-pyrazol-3-yl)-carbarnic acid p-tolyl ester;

N-(5-tert-Butyl-2-diethylamino-3-methanesulfonylamino-phenyl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[4-(2-morpholin-4-yl-ethoxy)-naphthalen-1-yl]-acetamide;

N-[5-tert-Butyl-2-methoxy-3-(propane-1-sulfonylamino)-phenyl]-2-(4-methoxy-naphthalen-1-yl)-2-oxo-acetamide;

Propane-1-sulfonic acid (5-tert-butyl-2-methoxy-3-{4-[4-(2-morpholin-4-yl-ethoxy)-naphthalen-1-yl]-3,5-dioxo-[1,2,4]triazolidin-1-yl}-phenyl)-amide;

3-Amino-5-tert-butyl-2-methoxy-N-[4-(2-morpholin-4-yl-ethoxy)-naphthalen-1-ylmethyl]-benzamide;

2-[4-(2-Morpholin-4-yl-ethoxy)-naphthalen-1-yl]-2-oxo-N-(3-trifluoromethyl-phenyl)-acetamide;

4-(5-tert-Butyl-2-methyl-2H-pyrazol-3-yl)-6-[4-(2-morpholin-4-yl-ethoxy)-naphthalen-1-yl]-2H-[1,2,4]triazine-3,5-dione;

N-[5-tert-Butyl-2-(4-trifluoromethyl-phenyl)-2H-pyrazol-3-yl]-2-[4-(2-morpholin-4-yl-ethoxy)-naphthalen-1-yl]-2-oxo-acetamide;

N-[5-tert-Butyl-2-methoxy-3-(propane-1-sulfonylamino)-phenyl]-2-[4-(2-dimethylamino-pyrimidin-4-ylamino)-naphthalen-1-yl]-2-oxo-acetamide;

N-(5-tert-Butyl-2-p-tolyl-2H-pyrazol-3-yl)-2-phenyl-acetamide;

N-[5-tert-Butyl-2-methoxy-3-(propane-1-sulfonylamino)-phenyl]-2-[4-(2-morpholin-4-yl-pyrimidin-4-yloxy)-naphthalen-1-yl]-2-oxo-acetamide;

N-(5-tert-Butyl-3-methanesulfonylamino-2-methoxy-phenyl)-2-{4-[2-(2,6-dimethyl-morpholin-4-yl)-ethoxy]-naphthalen-1-yl}-2-oxo-acetamide;

N-(5-tert-Butyl-2-p-tolyl-2H-pyrazol-3-yl)-2-(4-methoxy-naphthalen-1-yl)-acetamide;

3-tert-Butyl-1-cyclohexyl-5-phenyl-1,6-dihydro-imidazo[4,5-c]pyrazole;

3-tert-Butyl-5-(4-fluoro-phenyl)-1-p-tolyl-1,6-dihydro-imidazo[4,5-c]pyrazole;

N-(5-tert-Butyl-2-methoxy-3-{4-[4-(2-morpholin-4-yl-ethoxy)-naphthalen-1-yl]-3,5-dioxo-[1,2,4]triazolidin-1-yl}-phenyl)-methanesulfonamide;

N-(5-tert-Butyl-2-p-tolyl-2H-pyrazol-3-yl)-2-oxo-2-{4-[2-(3-oxo-piperazin-1-yl)-ethyl]-naphthalen-1-yl}-acetamide;

N-(5-tert-Butyl-2-p-tolyl-2H-pyrazol-3-yl)-2-oxo-2-[4-(3-pyridin-4-yl-propoxy)-naphthalen-1-yl]-acetamide;

N-(5-tert-Butyl-3-methanesulfonylamino-2-methoxy-phenyl)-2-[(Z)-hydroxyimino]-2-[4-(2-morpholin-4-yl-ethoxy)-5,6,7,8-tetrahydro-naphthalen-1-yl]-acetamide;

N-[5-tert-Butyl-2-(4-methanesulfonyl-phenyl)-2H-pyrazol-3-yl]-2-[4-(2-morpholin-4-yl-ethoxy)-naphthalen-1-yl]-2-oxo-acetamide;

2-(5-tert-Butyl-2-p-tolyl-2H-pyrazol-3-ylcarbamoyl)-2,5-dihydro-pyrrole-1-carboxylic acid tert-butyl ester;

N-(5-tert-Butyl-3-methanesulfonylamino-2-methoxy-phenyl)-2-[4-(2-imidazol-1-yl-ethoxy)-naphthalen-1-yl]-2-oxo-acetamide;

N-[5-tert-Butyl-2-(3,5-dimethyl-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[4-(2-morpholin-4-yl-pyridin-4-ylamino)-naphthalen-1-yl]-2-oxo-acetamide;

N-{5-tert-Butyl-3-[carbamoylmethyl-(propane-1-sulfonyl)-amino]-2-methoxy-phenyl}-2-naphthalen-1-yl-2-oxo-acetamide;

N'-[1-(5-tert-Butyl-2-methyl-2H-pyrazol-3-ylcarbamoyl)-1-[4-(2-morpholin-4-yl-ethoxy)-naphthalen-1-yl]-meth-(Z)-ylidene]-hydrazinecarboxylic acid ethyl ester;

5-tert-Butyl-N-cyclopropyl-2-methoxy-3-{2-[4-(2-morpholin-4-yl-ethoxy)-naphthalen-1-yl]-acetylamino}-benzamide;

N-[5-tert-Butyl-2-(3-nitro-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[3-chloro-4-(2-morpholin-4-yl-ethoxy)-phenyl]-2-oxo-acetamide;

N-(3-Benzenesulfonylamino-5-tert-butyl-2-methoxy-phenyl)-2-[4-(2-morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid cyclohexylarnide;

N-[5-tert-Butyl-2-methoxy-3-(2,2,2-trifluoro-ethanesulfonylamino)-phenyl]-2-[4-(2-morpholin-4-yl-ethoxy)-naphthalen-1-yl]-2-oxo-acetamide;

N'-[1-(5-tert-Butyl-3-carbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;

5-tert-Butyl-2-methoxy-N-[4-(2-morpholin-4-yl-ethoxy)-naphthalen-1-yl]-3-(propane-1-sulfonylamino)-benzamide;

N-(5-tert-Butyl-2-methoxy-phenyl)-2-hydroxy-2-(4-methoxy-naphthalen-1-yl)-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid 2-dimethylamino-ethyl ester;

N-(5-tert-Butyl-3-methanesulfonylamino-2-methoxy-phenyl)-2-[7-fluoro-4-(2-morpholin-4-yl-ethoxy)-naphthalen-1-yl]-2-oxo-acetamide;

N-(5-tert-Butyl-isoxazol-3-yl)-2-[4-(2-morpholin-4-yl-pyridin-4-ylamino)-naphthalen-1-yl]-2-oxo-acetamide;

3-tert-Butyl-1-(4-chloro-phenyl)-5-phenyl-1,6-dihydro-imidazo[4,5-c]pyrazole;

N-(5-tert-Butyl-2-methyl-2H-pyrazol-3-yl)-2-(4-methoxy-naphthalen-1-yl)-2-oxo-acetamide;

2-[5-tert-Butyl-2-(3,4-dimethyl-phenyl)-2H-pyrazol-3-yl]-2-[(Z)-hydroxyimino]-N-[4-(2-morpholin-4-yl-ethoxy)-naphthalen-1-yl]-acetamide;

N-(5-tert-Butyl-isoxazol-3-yl)-2-(4-methoxy-naphthalen-1-yl)-2-oxo-acetamide;

N-[5-(1,1-Dimethyl-propyl)-2-p-tolyl-2H-pyrazol-3-yl]-2-hydroxy-2-[4-(2-morpholin-4-yl-ethoxy)-naphthalen-1-yl]-acetamide;

N-[5-tert-Butyl-2-(3-methoxy-phenyl)-2H-pyrazol-3-yl]-2-[4-(2-dimethylamino-pyrimidin-4-ylamino)-naphthalen-1-yl]-2-oxo-acetamide;

N-(2—Chloro-5-trifluoromethyl-phenyl)-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-[2,3-dichloro-4-(2-morpholin-4-yl-ethoxy)-phenyl]-2-oxo-acetamide;

N-(3-Methanesulfonylamino-2-methoxy-5-methyl-phenyl)-2-[4-(2-morpholin-4-yl-ethoxy)-naphthalen-1-yl]-2-oxo-acetamide;

4-{2-[4-(5-tert-Butyl-2-p-tolyl-2H-pyrazol-3-ylaminooxalyl)-naphthalen-1-yl]-ethyl}-piperazine-1-carboxylic acid ethyl ester;

(1-Benzyl-1H-benzoimidazol-2-yl)-(5-tert-butyl-2-p-tolyl-2H-pyrazol-3-yl)-amine;

N-(3,5-Di-tert-butyl-2-hydroxy-phenyl)-2-[4-(2-morpholin-4-yl-ethoxy)-naphthalen-1-yl]-2-oxo-acetamide;

N-(5-tert-Butyl-2-naphthalen-1-yl-2H-pyrazol-3-yl)-2-[4-(2-morpholin-4-yl-ethoxy)-naphthalen-1-yl]-2-oxo-acetamide;

N-(5-tert-Butyl-2-methoxy-phenyl)-2-[4-(2-morpholin-4-yl-pyrimidin-4-ylamino)-naphthalen-1-yl]-2-oxo-acetamide;

4-{2-[4-(5-tert-Butyl-2-p-tolyl-2H-pyrazol-3-ylaminooxalyl)-naphthalen-1-yloxy]-ethyl}-piperazine-1-carboxylic acid ethyl ester;

5-tert-Butyl-2-methoxy-3-{2-[4-(2-morpholin-4-yl-pyrimidin-4-ylamino)-naphthalen-1-yl]-2-oxo-acetylamino}-benzamide;

N-(5-tert-Butyl-3-methanesulfonylamino-2-methoxy-phenyl)-2-(1-methyl-1H-indol-3-yl)-2-oxo-acetamide;
4-Phenyl-piperidine-4-carboxylic acid (5-tert-butyl-2-methoxy-phenyl)-amide;
5-tert-Butyl-2-methoxy-3-{2-[4-(2-morpholin-4-yl-ethoxy)-naphthalen-1-yl]-acetylamino}-benzamide;
N-[2-(4-Acetyl-phenyl)-5-tert-butyl-2H-pyrazol-3-yl]-2-[4-(2-morpholin-4-yl-ethoxy)-naphthalen-1-yl]-2-oxo-acetamide;
1-(5-tert-Butyl-2-p-tolyl-2H-pyrazol-3-yl)-3-[4-(2-morpholin-4-yl-ethoxy)-naphthalen-1-yl]-imidazolidine-2,4,5-trione;
N-(5-tert-Butyl-2-p-tolyl-2H-pyrazol-3-yl)-2-(2,3-difluoro-phenyl)-acetamide;
N-[5-tert-Butyl-3-(carbamoylmethyl-methanesulfonyl-amino)-2-methoxy-phenyl]-2-naphthalen-1-yl-2-oxo-acetamide;
N-(5-tert-Butyl-2-methyl-2H-pyrazol-3-yl)-2-[2-methyl-4-(2-morpholin-4-yl-ethoxy)-phenyl]-2-oxo-acetamide;
N-[2-(4-Amino-phenyl)-5-tert-butyl-2H-pyrazol-3-yl]-2-[4-(2-morpholin-4-yl-ethoxy)-naphthalen-1-yl]-2-oxo-acetamide;
(5-tert-Butyl-2-methoxy-3-{2-[4-(2-morpholin-4-yl-ethoxy)-naphthalen-1-yl]-2-oxo-acetylamino}-phenyl)-carbamic acid phenyl ester;
N-(5-tert-Butyl-2-methyl-2H-pyrazol-3-yl)-2-[4-(2-morpholin-4-yl-ethoxy)-naphthalen-1-yl]-acetamide;
N-(5-tert-Butyl-2-isobutoxy-phenyl)-2-[4-(2-morpholin-4-yl-ethoxy)-naphthalen-1-yl]-2-oxo-acetamide;
N-(4-tert-Butyl-phenyl)-2-[4-(2-morpholin-4-yl-ethoxy)-naphthalen-1-yl]-2-oxo-acetamide;
N-[5-tert-Butyl-2-(3-methyl-benzoyl)-2H-pyrazol-3-yl]-2-[4-(2-morpholin-4-yl-ethoxy)-naphthalen-1-yl]-2-oxo-acetamide;
5-tert-Butyl-3-{2-[(Z)-hydroxyimino]-2-[4-(2-morpholin-4-yl-ethoxy)-naphthalen-1-yl]-acetylamino}-thiophene-2-carboxylic acid amide;
1-(5-tert-Butyl-2-methoxy-phenyl)-3-[4-(2-chloro-pyrimidin-4-yloxy)-naphthalen-1-yl]-imidazolidine-2,4,5-trione;
(S)—N-(5-tert-Butyl-2-p-tolyl-2H-pyrazol-3-yl)-2-hydroxy-2-phenyl-acetamide;
N-[5-tert-Butyl-2-(2,3-dimethyl-phenyl)-2H-pyrazol-3-yl]-2-[4-(2-morpholin-4-yl-ethoxy)-naphthalen-1-yl]-2-oxo-acetamide;
N-[5-tert-Butyl-2-(4-nitro-phenyl)-2H-pyrazol-3-yl]-2-[4-(2-morpholin-4-yl-ethoxy)-naphthalen-1-yl]-2-oxo-acetamide;
2-(5-tert-Butyl-2-m-tolyl-2H-pyrazol-3-yl)-N-[4-(2-morpholin-4-yl-ethoxy)-naphthalen-1-yl]-2-oxo-acetamide;
2-[(Z)-Hydroxyimino]-N-(3-methanesulfonylamino-2-methoxy-5-methyl-phenyl)-2-[4-(2-morpholin-4-yl-ethoxy)-naphthalen-1-yl]-acetamide;
N-[5-tert-Butyl-2-(morpholine-4-carbonyl)-thiophen-3-yl]-2-[(Z)-hydroxyimino]-2-[4-(2-morpholin-4-yl-ethoxy)-naphthalen-1-yl]-acetamide;
N-(5-tert-Butyl-2-phenyl-2H-pyrazol-3-yl)-2-[4-(2-morpholin-4-yl-ethoxy)-naphthalen-1-yl]-2-oxo-acetamide;
N'-[1-(5-tert-Butyl-2-methyl-2H-pyrazol-3-ylcarbarnoyl)-1-[4-(2-morpholin-4-yl-ethoxy)-naphthalen-1-yl]-meth-(E)-ylidene]-hydrazinecarboxylic acid ethyl ester;
N'-[1-(5-tert-Butyl-2-methyl-2H-pyrazol-3-ylcarbamoyl)-1-[4-(2-morpholin-4-yl-ethoxy)-naphthalen-1-yl]-meth-(Z)-ylidene]-hydrazinecarboxamide;
N-[5-tert-Butyl-2-(3-methoxy-phenyl)-2H-pyrazol-3-yl]-2-[4-(2-morpholin-4-yl-ethoxy)-naphthalen-1-yl]-2-oxo-acetamide;
5-tert-Butyl-2-methoxy-3-{2-[4-(2-morpholin-4-yl-ethoxy)-naphthalen-1-yl]-2-oxo-acetylamnino}-N-pyridin-2-yl-benzamide;
N-[5-tert-Butyl-3-(3,3-dimethyl-ureido)-2-methoxy-phenyl]-2-[4-(2-morpholin-4-yl-ethoxy)-naphthalen-1-yl]-2-oxo-acetamide;
5-tert-Butyl-3-{2-[7-chloro-4-(2-morpholin-4-yl-ethoxy)-naphthalen-1-yl]-2-oxo-acetylamnino}-2-methoxy-benzamide;
N-(5-tert-Butyl-2-p-tolyl-2H-pyrazol-3-yl)-2-m-tolyl-acetamide;
1-(5-tert-Butyl-2-methoxy-phenyl)-3-[4-(2-pyrrolidin-1-yl-pyrimidin-4-yloxy)-naphthalen-1-yl]-imidazolidine-2,4,5-trione;
N-(5-tert-Butyl-2-p-tolyl-2H-pyrazol-3-yl)-2-hydroxy-2-phenyl-propionamide;
2-[4-(2-Morpholin-4-yl-ethoxy)-naphthalen-1-yl]-2-oxo-N-quinolin-3-yl-acetamide;
1-(5-tert-Butyl-2-m-tolyl-2H-pyrazol-3-yl)-3-[4-(2-morpholin-4-yl-ethoxy)-naphthalen-1-yl]-imidazolidine-2,4,5-trione;
(5-tert-Butyl-2-p-tolyl-2H-pyrazol-3-yl)-(3-trifluoromethyl-benzyl)-amine;
N-[5-tert-Butyl-2-methoxy-3-(morpholine-4-carbonyl)-phenyl]-2-[4-(2-morpholin-4-yl-ethoxy)-naphthalen-1-yl]-2-oxo-acetamide;
N-[5-tert-Butyl-3-(3-isopropyl-ureido)-2-methoxy-phenyl]-2-[4-(2-morpholin-4-yl-ethoxy)-naphthalen-1-yl]-2-oxo-acetamide;
N-(5-tert-Butyl-2-p-tolyl-2H-pyrazol-3-yl)-2-methoxy-2-(4-methoxy-naphthalen-1-yl)-acetamide;
N-(3-Amino-5-trifluoromethyl-phenyl)-2-[4-(2-morpholin-4-yl-ethoxy)-naphthalen-1-yl]-2-oxo-acetamide;
N-(5-tert-Butyl-2-methyl-2H-pyrazol-3-yl)-2-[4-(2-morpholin-4-yl-pyrimidin-4-yloxy)-naphthalen-1-yl]-2-oxo-acetamide;
3-Methyl-1,5-diphenyl-1,6-dihydro-imidazo[4,5-c]pyrazole;
N-(5-tert-Butyl-isoxazol-3-yl)-2-hydroxy-2-[4-(2-morpholin-4-yl-ethoxy)-naphthalen-1-yl]-acetamide;
N-[4-(2-Morpholin-4-yl-ethoxy)-naphthalen-1-yl]-2-oxo-2-(2-phenyl-cyclopropyl)-acetamide;
2-{4-[2-(4-Acetyl-piperazin-1-yl)-ethoxy]-naphthalen-1-yl}-N-(5-tert-butyl-3-methanesulfonylamino-2-methoxy-phenyl)-2-oxo-acetamide;
2-(1H-Indol-3-yl)-N-[4-(2-morpholin-4-yl-ethoxy)-naphthalen-1-yl]-2-oxo-acetamide;
N-[5-tert-Butyl-2-(3-fluoro-phenyl)-2H-pyrazol-3-yl]-2-[4-(2-morpholin-4-yl-ethoxy)-naphthalen-1-yl]-2-oxo-acetamide;
2-(3-Amino-5-tert-butyl-2-methoxy-phenyl)-N-[4-(2-morpholin-4-yl-ethoxy)-naphthalen-1-yl]-2-oxo-acetamiide;
N-[5-tert-Butyl-2-(3,4-dichloro-phenyl)-2H-pyrazol-3-yl]-2-[4-(2-morpholin-4-yl-ethoxy)-naphthalen-1-yl]-2-oxo-acetamide;
N-(5-tert-Butyl-isoxazol-3-yl)-2-[4-(2-morpholin-4-yl-pyrimidin-4-yloxy)-naphthalen-1-yl]-2-oxo-acetamide;
N-[5-tert-Butyl-2-(2,5-dimethyl-phenyl)-2H-pyrazol-3-yl]-2-[4-(2-morpholin-4-yl-ethoxy)-naphthalen-1-yl]-2-oxo-acetamide;
N-(5-tert-Butyl-3-methanesulfonylamino-2-methoxy-phenyl)-2-[4-(2-morpholin-4-yl-ethoxy)-5,6,7,8-tetrahydro-naphthalen-1-yl]-2-oxo-acetamide;
1H-Indazole-3-carboxylic acid (5-tert-butyl-2-pyridin-2-yl-2H-pyrazol-3-yl)-amide;
N-(4—Chloro-3-trifluoromethyl-phenyl)-2-(4-methoxy-naphthalen-1-yl)-2-oxo-acetamide;

N-[5-(1,1-Dimethyl-butyl)-2-p-tolyl-2H-pyrazol-3-yl]-2-[4-(2-morpholin-4-yl-ethoxy)-naphthalen-1-yl]-2-oxo-acetamide;

1H-Indazole-3-carboxylic acid [5-tert-butyl-2-(4-methoxy-phenyl)-2H-pyrazol-3-yl]-amide;

1H-Indazole-3-carboxylic acid [5-tert-butyl-2-(4-hydroxy-phenyl)-2H-pyrazol-3-yl]-amide;

N'-[1-(5-tert-Butyl-3-methanesulfonylamino-2-methoxy-phenylcarbamoyl)-1-[4-(2-morpholin-4-yl-ethoxy)-naphthalen-1-yl]-meth-(E)-ylidene]-hydrazinecarboxamide;

N-(5-tert-Butyl-2-p-tolyl-2H-pyrazol-3-yl)-N'-[4-(2-morpholin-4-yl-ethoxy)-naphthalen-1-yl]-oxalamide;

N-(5-tert-Butyl-3-methanesulfonylamino-2-methoxy-phenyl)-2-[4-(2-methylamino-pyrimidin-4-ylamino)-naphthalen-1-yl]-2-oxo-acetamide;

N-(5-tert-Butyl-2-m-tolyl-2H-pyrazol-3-yl)-2-[(Z)-methoxyimino]-2-[4-(2-morpholin-4-yl-ethoxy)-naphthalen-1-yl]-acetamide;

5-tert-Butyl-N-cyclopropyl-3-[2-[(E)-hydroxyimino]-2-(4-methoxy-naphthalen-1-yl)-acetylamino]-2-methoxy-benzamide;

N-(5-tert-Butyl-2-p-tolyl-2H-pyrazol-3-yl)-2-{4-[2-(2,6-dimethyl-morpholin-4-yl)-ethoxy]-naphthalen-1-yl}-2-oxo-acetamide;

N-(5-tert-Butyl-3-methanesulfonylamino-2-methoxy-phenyl)-2-[8-fluoro-4-(2-morpholin-4-yl-ethoxy)-naphthalen-1-yl]-2-oxo-acetamide;

N-(5-tert-Butyl-2-p-tolyl-2H-pyrazol-3-yl)-2-(3-fluoro-phenyl)-acetamide;

5-tert-Butyl-N-furan-2-ylmethyl-2-methoxy-3-{2-[4-(2-morpholin-4-yl-ethoxy)-naphthalen-1-yl]-2-oxo-acetylamino}-benzamide;

N-[5-tert-Butyl-2-(3-trifluoromethyl-benzoyl)-2H-pyrazol-3-yl]-2-[4-(2-morpholin-4-yl-ethoxy)-naphthalen-1-yl]-2-oxo-acetamide;

N-[5-tert-Butyl-2-3-methoxy-3-(propane-1-sulfonylamino)-phenyl]-2-[4-(2-morpholin-4-yl-pyrimidin-4-ylamino)-naphthalen-1-yl]-2-oxo-acetamide;

1-(5-tert-Butyl-isoxazol-3-yl)-3-[4-(2-morpholin-4-yl-pyrimidin-4-yloxy)-naphthalen-1-yl]-imidazolidine-2,4,5-trione;

1-(5-tert-Butyl-2-methyl-2H-pyrazol-3-yl)-3-[4-(2-morpholin-4-yl-ethoxy)-naphthalen-1-yl]-3'-(carbamic acid ethyl ester)-urea;

N-(5-tert-Butyl-3-methanesulfonylamino-2-methoxy-phenyl)-2-oxo-2-{4-[2-(3-oxo-piperazin-1-yl)-ethoxy]-naphthalen-1-yl}-acetamide;

2-{4-[2-(4-Acetyl-piperazin-1-yl)-ethyl]-naphthalen-1-yl}-N-(5-tert-butyl-2-p-tolyl-2H-pyrazol-3-yl)-2-oxo-acetamide;

N-(5-tert-Butyl-2-phenylacetyl-2H-pyrazol-3-yl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-oxo-2-{4-[2-(3-oxo-piperazin-1-yl)-ethoxy]-naphthalen-1-yl}-acetamide;

2-(5-tert-Butyl-2-m-tolyl-2H-pyrazol-3-yl)-2-[(Z)-hydroxyimino]-N-[4-(2-morpholin-4-yl-ethoxy)-naphthalen-1-yl]-acetamide;

N-[5-tert-Butyl-2-(3-ureido-phenyl)-2H-pyrazol-3-yl]-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-[(Z)-methoxyimino]-2-[4-(2-morpholin-4-yl-pyrimidin-4-yloxy)-naphthalen-1-yl]-acetamide;

N-[5-tert-Butyl-2-methoxy-3-(3-oxo-piperazine-1-carbonyl)-phenyl]-2-[4-(2-morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid propylamide;

5-tert-Butyl-N-cyclopropyl-2-methoxy-3-{2-[4-(2-morpholin-4-yl-pyrimidin-4-yloxy)-naphthalen-1-yl]-2-oxo-acetylamino}-benzamide;

N-(5-tert-Butyl-2-p-tolyl-2H-pyrazol-3-yl)-2-{4-[2-(4-methyl-piperazin-1-yl)-ethoxy]-naphthalen-1-yl}-2-oxo-acetamide;

N-(3-Amino-5-tert-butyl-2-methoxy-phenyl)-2-[4-(2-morpholin-4-yl-pyrimidin-4-yloxy)-naphthalen-1-yl]-2-oxo-acetamide;

5-tert-Butyl-2-methoxy-3-{2-[4-(2-morpholin-4-yl-ethoxy)-naphthalen-1-yl]-2-oxo-acetylamino}-N-propyl-benzamide;

N-(5-tert-Butyl-2-p-tolyl-2H-pyrazol-3-yl)-2-hydroxy-2-(4-methoxy-phenyl)-acetamide;

N-(5-tert-Butyl-2-methyl-2H-pyrazol-3-yl)-2-[(Z)-hydroxyimino]-2-[4-(2-morpholin-4-yl-ethoxy)-naphthalen-1-yl]-acetamide;

N-(5-tert-Butyl-2-p-tolyl-2H-pyrazol-3-yl)-2-(3-phenoxy-phenyl)-acetamide;

N-(5-Isopropyl-2-methyl-phenyl)-2-[4-(2-morpholin-4-yl-ethoxy)-naphthalen-1-yl]-2-oxo-acetamide;

7-Isopropyl-9-phenyl-2-phenylamino-7,9-dihydro-purin-8-one;

(5-tert-Butyl-2-methoxy-3-{2-[4-(2-morpholin-4-yl-ethoxy)-naphthalen-1-yl]-2-oxo-acetylamino}-phenyl)-carbamic acid pyridin-3-ylmethyl ester;

N-(5-tert-Butyl-3-methanesulfonylamino-2-methoxy-phenyl)-2-[4-(2-ethylamino-ethoxy)-naphthalen-1-yl]-2-oxo-acetamide;

N-(3,5-Di-tert-butyl-phenyl)-2-[4-(2-morpholin-4-yl-ethoxy)-naphthalen-1-yl]-2-oxo-acetamide;

2-Amino-N-(5-tert-butyl-2-p-tolyl-2H-pyrazol-3-yl)-2-naphthalen-2-yl-acetamide;

N-[5-tert-Butyl-2-(3-fluoro-4-methyl-phenyl)-2H-pyrazol-3-yl]-2-hydroxy-2-[4-(2-morpholin-4-yl-ethoxy)-naphthalen-1-yl]-acetamide;

2-[5-tert-Butyl-2-(3,4-difluoro-phenyl)-2H-pyrazol-3-yl]-N-[4-(2-morpholin-4-yl-ethoxy)-naphthalen-1-yl]-2-oxo-acetamide;

N-(3-Amino-5-tert-butyl-2-methoxy-phenyl)-2-[4-(2-methylamino-pyrimidin-4-ylamino)-naphthalen-1-yl]-2-oxo-acetamide;

N-(5-tert-Butyl-2-p-tolyl-2H-pyrazol-3-yl)-2-[4-(2-morpholin-4-yl-pyrimidin-4-yloxy)-naphthalen-1-yl]-2-oxo-acetamide;

N-[5-tert-Butyl-2-(2,3-dichloro-phenyl)-2H-pyrazol-3-yl]-2-[4-(2-morpholin-4-yl-ethoxy)-naphthalen-1-yl]-2-oxo-acetamide;

N-[3,5-Bis-(1,1-dimethyl-propyl)-2-hydroxy-phenyl]-2-[4-(2-morpholin-4-yl-ethoxy)-naphthalen-1-yl]-2-oxo-acetamide;

4-{2-[4-(5-tert-Butyl-3-methanesulfonylamino-2-methoxy-phenylaminooxalyl)-naphthalen-1-yloxy]-ethyl}-piperazine-1-carboxylic acid tert-butyl ester;

3-tert-Butyl-1-naphthalen-2-yl-5-phenyl-1,6-dihydro-imidazo[4,5-c]pyrazole;

2-Biphenyl-4-yl-N-(5-tert-butyl-2-p-tolyl-2H-pyrazol-3-yl)-acetamide;

5-tert-Butyl-N-isopropyl-2-methoxy-3-{2-[4-(2-morpholin-4-yl-ethoxy)-naphthalen-1-yl]-2-oxo-acetylamino}-benzamide;

N-(5-tert-Butyl-3-diethylaminomethyl-2-hydroxy-phenyl)-2-[4-(2-morpholin-4-yl-ethoxy)-naphthalen-1-yl]-2-oxo-acetamide;

6-Hydroxy-nicotinic acid 3-[5-tert-butyl-2-methoxy-3-(propane-1-sulfonylamino)-phenylcarbamoyl]-1H-indazol-5-yl ester;

N-(5-tert-Butyl-2-m-tolyl-2H-pyrazol-3-yl)-2-[4-(2-morpholin-4-yl-pyrimidin-4-ylamino)-naphthalen-1-yl]-2-oxo-acetamide;

N-(5-tert-Butyl-2-methyl-2H-pyrazol-3-yl)-2-[4-(2-morpholin-4-yl-pyrimidin-4-ylamino)-naphthalen-1-yl]-2-oxo-acetamide;

N-(5-tert-Butyl-3-methanesulfonylamino-2-methoxy-phenyl)-2-[4-(4-morpholin-4-yl-pyrimidin-2-ylamino)-naphthalen-1-yl]-2-oxo-acetamide;

N-(3-Amino-5-tert-butyl-2-methoxy-phenyl)-2-[4-(2-morpholin-4-yl-ethoxy)-naphthalen-1-yl]-2-oxo-acetamide;

1,3,5-Triphenyl-1,6-dihydro-imidazo[4,5-c]pyrazole;

N-(5-tert-Butyl-2-p-tolyl-2H-pyrazol-3-yl)-2-cyclohexyl-acetamide;

2-[5-tert-Butyl-2-(2-chloro-phenyl)-2H-pyrazol-3-yl]-N-[4-(2-morpholin-4-yl-ethoxy)-naphthalen-1-yl]-2-oxo-acetamide;

7-Cyclohexylmethyl-9-phenyl-2-phenylamino-7,9-dihydro-purin-8-one;

5-tert-Butyl-3-{2-[4-(2-morpholin-4-yl-ethoxy)-naphthalen-1-yl]-2-oxo-acetylamino}-thiophene-2-carboxylic acid methylamide;

5-tert-Butyl-N-cyclopropylmethyl-2-methoxy-3-{2-[4-(2-morpholin-4-yl-ethoxy)-naphthalen-1-yl]-acetylamino}-benzamide;

N-[5-tert-Butyl-2-(3-methoxy-phenyl)-2H-pyrazol-3-yl]-2-[4-(2-morpholin-4-yl-pyrimidin-4-ylamino)-naphthalen-1-yl]-2-oxo-acetamide;

N'-[-(5-tert-Butyl-3-carbamoyl-2-methoxy-phenylcarbamoyl) 1-[4-(2-morpholin-4-yl-ethoxy)-naphthalen-1-yl]-meth-(Z)-ylidene]-hydrazinecarboxylic acid ethyl ester;

4-(5-tert-Butyl-2-methyl-2H-pyrazol-3-yl)-1-(2,3-dimethyl-phenyl)-[1,2,4]triazolidine-3,5-dione;

N-(4-Fluoro-3-trifluoromethyl-phenyl)-2-[4-(2-morpholin-4-yl-ethoxy)-naphthalen-1-yl]-2-oxo-acetamide;

1-Benzyl-3-phenyl-5-phenylamino-1,3-dihydro-imidazo[4,5-b]pyridin-2-one;

N-(5-tert-Butyl-2-methoxy-phenyl)-2-naphthalen-2-yl-acetamide;

2-[4-(2-Morpholin-4-yl-ethoxy)-naphthalen-1-ylcarbamoyl]-pyrrole-1-carboxylic acid tert-butyl ester;

N-(2,5-Di-tert-butyl-phenyl)-2-[4-(2-morpholin-4-yl-ethoxy)-naphthalen-1-yl]-2-oxo-acetamide;

2-[4-(2-Morpholin-4-yl-ethoxy)-naphthalen-1-yl]-2-oxo-N-((1S,2R)-2-phenyl-cyclopropyl)-acetamide;

2—Oxo-2,3-dihydro-benzoimidazole-1-carboxylic acid (5-tert-butyl-2-p-tolyl-2H-pyrazol-3-yl)-amide;

N-(2-Methoxy-5-trifluoromethyl-phenyl)-2-[4-(2-morpholin-4-yl-ethoxy)-naphthalen-1-yl]-2-oxo-acetamide;

N-[2-(4-Bromo-phenyl)-5-tert-butyl-2H-pyrazol-3-yl]-2-[4-(2-morpholin-4-yl-ethoxy)-naphthalen-1-yl]-2-oxo-acetamide;

1-(5-tert-Butyl-2-methoxy-phenyl)-3-[4-(2-morpholin-4-yl-pyrimidin-4-yloxy)-naphthalen-1-yl]-imidazolidine-2,4,5-trione;

5-tert-Butyl-2-methoxy-N-methyl-3-{2-[4-(2-morpholin-4-yl-ethoxy)-naphthalen-1-yl]-2-oxo-acetylamino}-benzamide;

N-(5-tert-Butyl-2-methoxy-3-piperidin-1-ylmethyl-phenyl)-2-[4-(2-morpholin-4-yl-ethoxy)-naphthalen-1-yl]-2-oxo-acetamide;

N-(5-tert-Butyl-2-methoxy-phenyl)-2-naphthalen-1-yl-2-oxo-acetamide;

N-(2,5-Di-tert-butyl-2H-pyrazol-3-yl)-2-[4-(2-morpholin-4-yl-ethoxy)-naphthalen-1-yl]-2-oxo-acetamide;

(5-tert-Butyl-2-p-tolyl-2H-pyrazol-3-yl)-carbamic acid 4-methoxy-phenyl ester;

N-(3-Amino-5-tert-butyl-2-methoxy-phenyl)-2-naphthalen-1-yl-2-oxo-acetamide;

5-tert-Butyl-N-ethyl-3-{2-[(Z)-hydroxyimino]-2-[4-(2-morpholin-4-yl-ethoxy)-naphthalen-1-yl]-acetylamino}-2-methoxy-benzamide;

4-{2-[4-(5-tert-Butyl-2-p-tolyl-2H-pyrazol-3-ylaminooxalyl)-naphthalen-1-yl]-ethyl }-piperazine-1-carboxylic acid tert-butyl ester;

5-tert-Butyl-N-ethyl-2-hydroxy-3-{2-[4-(2-morpholin-4-yl-ethoxy)-naphthalen-1-yl]-2-oxo-acetylamino}-benzamide;

N-(5-tert-Butyl-2-p-tolyl-2H-pyrazol-3-yl)-2-naphthalen-1-yl-acetamide;

N-(5-tert-Butyl-2-ethoxy-3-methanesulfonylamino-phenyl)-2-[4-(2-morpholin-4-yl-ethoxy)-naphthalen-1-yl]-2-oxo-acetamide;

N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(E)-ylidene]-hydrazinecarboxamide;

2-{4-[2-(4-Acetyl-piperazin-1-yl)-ethoxy]-naphthalen-1-yl}-N-(5-tert-butyl-2-p-tolyl-2H-pyrazol-3-yl)-2-oxo-acetamide;

5-tert-Butyl-N-ethyl-2-methoxy-3-{2-[4-(2-morpholin-4-yl-ethoxy)-naphthalen-1-yl]-2-oxo-acetylamino}-benzamide;

5-tert-Butyl-2-methoxy-3-{2-[4-(2-morpholin-4-yl-ethoxy)-naphthalen-1-yl]-2-oxo-acetylamino}-benzoic acid;

N-(5-tert-Butyl-3-methanesulfonylamino-2-methoxy-phenyl)-2-hydroxy-2-[4-(2-morpholin-4-yl-ethoxy)-5,6,7,8-tetrahydro-naphthalen-1-yl]-acetamide;

N-(5-tert-Butyl-isoxazol-3-yl)-2-[4-(2-dimethylamino-pyrimidin-4-ylamino)-naphthalen-1-yl]-2-oxo-acetamide;

5-tert-Butyl-3-{2-[4-(2-morpholin-4-yl-pyridin-4-ylamino)-naphthalen-1-yl]-2-oxo-acetylamino}-thiophene-2-carboxylic acid amide;

2-[4-(2-Morpholin-4-yl-ethoxy)-naphthalen-1-yl]-2-oxo-N-m-tolyl-acetamide;

5-tert-Butyl-3-{2-[4-(2-morpholin-4-yl-ethoxy)-naphthalen-1-yl]-2-oxo-acetylamino}-thiophene-2-carboxylic acid methyl ester;

N'-[1-(5-tert-Butyl-3-methanesulfonylamino-2-methoxy-phenylcarbamoyl)-1-[4-(2-morpholin-4-yl-ethoxy)-naphthalen-1-yl]-meth-(Z)-ylidene]-hydrazinecarboxamide;

N-[5-tert-Butyl-2-(3-methoxy-phenyl)-2H-pyrazol-3-yl]-2-[4-(2-morpholin-4-yl-pyridin-4-ylamino)-naphthalen-1-yl]-2-oxo-acetamide;

N-(5-Isopropyl-2-p-tolyl-2H-pyrazol-3-yl)-2-[4-(2-morpholin-4-yl-ethoxy)-naphthalen-1-yl]-2-oxo-acetamide;

N-(5-tert-Butyl-isoxazol-3-yl)-2-[4-(2-morpholin-4-yl-ethoxy)-naphthalen-1-yl]-2-oxo-acetamide;

N-(2-Benzoyl-5-tert-butyl-2H-pyrazol-3-yl)-2-[4-(2-morpholin-4-yl-ethoxy)-naphthalen-1-yl]-2-oxo-acetamide;

6-Bromo-1H-indazole-3-carboxylic acid (5-tert-butyl-2-p-tolyl-2H-pyrazol-3-yl)-amide;

5-tert-Butyl-N-ethyl-3-{2-hydrazono-2-[4-(2-morpholin-4-yl-ethoxy)-naphthalen-1-yl]-acetylamino}-2-methoxy-benzamide;

N-(5-tert-Butyl-3-ethanesulfonylamino-2-methoxy-phenyl)-2-[(Z)-hydroxyimino]-2-[4-(2-morpholin-4-yl-ethoxy)-naphthalen-1-yl]-acetamide;

N-(3-Amino-5-tert-butyl-2-methoxy-phenyl)-2-[4-(2-dimethylamino-pyrimidin-4-ylamino)-naphthalen-1-yl]-2-oxo-acetamide;

N-(5-tert-Butyl-thiophen-3-yl)-2-[4-(2-morpholin-4-yl-ethoxy)-naphthalen-1-yl]-2-oxo-acetamide;

N-[5-tert-Butyl-2-(4-chloro-phenyl)-2H-pyrazol-3-yl]-2-[4-(2-morpholin-4-yl-ethoxy)-naphthalen-1-yl]-2-oxo-acetamide;

N'-[1-(5-tert-Butyl-3-carbamoyl-2-methoxy-phenylcarbamoyl)-1-[4-(2-morpholin-4-yl-ethoxy)-naphthalen-1-yl]-meth-(E)-ylidene]-hydrazinecarboxamide;

N-[5-tert-Butyl-2-(4-methoxy-phenyl)-2H-pyrazol-3-yl]-2-[4-(2-morpholin-4-yl-ethoxy)-naphthalen-1-yl]-2-oxo-acetamide;

5-tert-Butyl-3-{2-[7-chloro-4-(2-morpholin-4-yl-ethoxy)-naphthalen-1-yl]-2-oxo-acetylamino}-N-cyclopropyl-2-methoxy-benzamide;

N-(5-tert-Butyl-3-methanesulfonylamino-2-methoxy-phenyl)-2-{4-[2-(4-methyl-piperazin-1-yl)-ethoxy]-naphthalen-1-yl}-2-oxo-acetamide;

1-(5-tert-Butyl-2-p-tolyl-2H-pyrazol-3-yl)-3-[4-(2-morpholin-4-yl-ethoxy)-naphthalen-1-yl]-imidazolidin-2-one;

N-(5-tert-Butyl-thiophen-3-yl)-2-[(Z)-hydroxyimino]-2-[4-(2-morpholin-4-yl-ethoxy)-naphthalen-1-yl]-acetamide;

5-tert-Butyl-N-cyclopropyl-3-[2-[(Z)-hydroxyimino]-2-(4-methoxy-naphthalen-1-yl)-acetylamino]-2-methoxy-benzamide;

N-(5-tert-Butyl-2-methyl-2H-pyrazol-3-yl)-2-[4-(4-morpholin-4-yl-pyrimidin-2-ylamino)-naphthalen-1-yl]-2-oxo-acetamide;

N-[5-tert-Butyl-2-(3-methoxy-phenyl)-2H-pyrazol-3-yl]-2-[(Z)-hydroxyimino]-2-[4-(2-morpholin-4-yl-ethoxy)-naphthalen-1-yl]-acetamide;

N-[2-Methoxy-5-(1-methyl-1-phenyl-ethyl)-phenyl]-2-[4-(2-morpholin-4-yl-ethoxy)-naphthalen-1-yl]-2-oxo-acetamide;

2-[5-tert-Butyl-2-(3,4-dimethyl-phenyl)-2H-pyrazol-3-yl]-N-[4-(2-morpholin-4-yl-ethoxy)-naphthalen-1-yl]-2-oxo-acetamide;

5-tert-Butyl-3-{2-[4-(2-morpholin-4-yl-pyrimidin-4-ylamino)-naphthalen-1-yl]-2-oxo-acetylamino}-thiophene-2-carboxylic acid amide;

5-tert-Butyl-N-isobutyl-2-methoxy-3-{2-[4-(2-morpholin-4-yl-ethoxy)-naphthalen-1-yl]-2-oxo-acetylamino}-benzamide;

2-(5-tert-Butyl-2-p-tolyl-2H-pyrazol-3-yl)-2-[(Z)-hydroxyimino]-N-[4-(2-morpholin-4-yl-ethoxy)-naphthalen-1-yl]-acetamide;

3-tert-Butyl-1-(2,3-dichloro-phenyl)-5-phenyl-1,6-dihydro-imidazo[4,5-c]pyrazole;

N-(3,5-Di-tert-butyl-2-methoxy-phenyl)-2-[4-(2-morpholin-4-yl-ethoxy)-naphthalen-1-yl]-2-oxo-acetamide;

5-tert-Butyl-3-{2-[(Z)-hydroxyimino]-2-[4-(2-morpholin-4-yl-ethoxy)-naphthalen-1-yl]-acetylamino}-thiophene-2-carboxylic acid dimethylamide;

N-(5-tert-Butyl-2-methoxy-3-methyl-phenyl)-2-[(Z)-hydroxyimino]-2-[4-(2-morpholin-4-yl-ethoxy)-naphthalen-1-yl]-acetamide;

N'-[1-(5-tert-Butyl-3-cyclopropylcarbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;

N-Indan-5-yl-2-[4-(2-morpholin-4-yl-ethoxy)-naphthalen-1-yl]-2-oxo-acetamide;

N-[5-tert-Butyl-2-(3-chloro-4-fluoro-phenyl)-2H-pyrazol-3-yl]-2-[4-(2-morpholin-4-yl-ethoxy)-naphthalen-1-yl]-2-oxo-acetamide;

N-[5-tert-Butyl-3-(imidazole-1-carbonyl)-2-methoxy-phenyl]-2-[4-(2-morpholin-4-yl-ethoxy)-naphthalen-1-yl]-2-oxo-acetamide;

2-(2,5-Bis-trifluoromethyl-phenyl)-N-[4-(2-morpholin-4-yl-ethoxy)-naphthalen-1-yl]-2-oxo-acetamide;

N-[5-tert-Butyl-2-(2,4-difluoro-phenyl)-2H-pyrazol-3-yl]-2-[4-(2-morpholin-4-yl-ethoxy)-naphthalen-1-yl]-2-oxo-acetamide;

1H-Indazole-3-carboxylic acid (5-tert-butyl-2-methoxy-phenyl)-amide;

N-(5-tert-Butyl-2-p-tolyl-2H-pyrazol-3-yl)-2-oxo-2-{4-[2-(5-oxo-[1,4]diazepan-1-yl)-ethoxy]-naphthalen-1-yl}-acetamide;

3-tert-Butyl-1-p-tolyl-5-(4-trifluoromethyl-phenyl)-1,6-dihydro-imidazo[4,5-c]pyrazole;

N-(5-tert-Butyl-3-ethanesulfonylamino-2-methoxy-phenyl)-2-[4-(2-morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid isopropylamide;

N-(5-tert-Butyl-[1,3,4]thiadiazol-2-yl)-2-hydroxy-2-[4-(2-morpholin-4-yl-ethoxy)-naphthalen-1-yl]-acetamide;

N-(5-tert-Butyl-3-methanesulfonylamino-2-methoxy-phenyl)-2-[(Z)-hydroxyimino]-2-[4-(2-morpholin-4-yl-pyrimidin-4-yloxy)-naphthalen-1-yl]-acetamide;

N-[2-(3-Amino-phenyl)-5-tert-butyl-2H-pyrazol-3-yl]-2-[4-(2-morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid phenylamide;

2-(5-tert-Butyl-2-methyl-furan-3-yl)-N-[4-(2-morpholin-4-yl-ethoxy)-naphthalen-1-yl]-2-oxo-acetamide;

N-(5-tert-Butyl-2-o-tolyl-2H-pyrazol-3-yl)-2-[4-(2-morpholin-4-yl-ethoxy)-naphthalen-1-yl]-2-oxo-acetamide;

N-(5-tert-Butyl-isoxazol-3-yl)-2-[4-(2-morpholin-4-yl-ethoxy)-naphthalen-1-yl]-acetamide;

N-(5-tert-Butyl-2-methoxy-phenyl)-2-(3-methoxy-phenyl)-acetamide;

5-tert-Butyl-3-{2-[4-(2-morpholin-4-yl-pyrimidin-4-yloxy)-naphthalen-1-yl]-2-oxo-acetylamino}-thiophene-2-carboxylic acid amide;

N-(5-tert-Butyl-3-methanesulfonylamino-2-methoxy-phenyl)-2-hydroxy-2-[4-(2-morpholin-4-yl-ethoxy)-naphthalen-1-yl]-acetamide;

N-[5-tert-Butyl-2-(2,4-dichloro-phenyl)-2H-pyrazol-3-yl]-2-[4-(2-morpholin-4-yl-ethoxy)-naphthalen-1-yl]-2-oxo-acetamide;

N-(5-tert-Butyl-isoxazol-3-yl)-2-[4-(3-hydroxy-propoxy)-naphthalen-1-yl]-2-oxo-acetamide;

N-(3-tert-Butyl-isoxazol-5-yl)-2-[(Z)-hydroxyimino]-2-[4-(2-morpholin-4-yl-ethoxy)-naphthalen-1-yl]-acetamide;

1H-Indole-3-carboxylic acid (5-tert-butyl-2-methoxy-phenyl)-amide;

N-[5-tert-Butyl-2-methoxy-3-(propane-1-sulfonylamino)-phenyl]-2-[4-(2-morpholin-4-yl-ethoxy)-naphthalen-1-yl)-2-oxo-acetamide;

7-Bicyclo[2.2.1]hept-2-yl-9-phenyl-2-phenylamino-7,9-dihydro-purin-8-one;

N-(5-tert-Butyl-2-p-tolyl-2H-pyrazol-3-yl)-2-(2,4-dichloro-phenyl)-acetamide;

5-tert-Butyl-2-methoxy-N-[4-(2-morpholin-4-yl-ethoxy)-naphthalen-1-yl]-benzamide;

N-(5-tert-Butyl-2-methyl-2H-pyrazol-3-yl)-2-[2,3-dimethyl-4-(2-morpholin-4-yl-ethoxy)-phenyl]-2-oxo-acetamide;

N-(5-tert-Butyl-2-methoxy-phenyl)-2-(3-fluoro-phenyl)-acetamide;
1-(5-tert-Butyl-2-methoxy-3-benzamide)-3-(2,3-dimethylphenyl)-3'-(carbamic acid ethyl ester)-urea;
2-(5-tert-Butyl-2-methyl-2H-pyrazol-3-yl)-2-oxo-N-(3-trifluoromethyl-phenyl)-acetamide;
7-Benzyl-9-phenyl-2-phenylamino-7,9-dihydro-purin-8-one;
2,5-Dihydro-1H-pyrrole-2-carboxylic acid (5-tert-butyl-2-p-tolyl-2H-pyrazol-3-yl)-amide;
N-(5-tert-Butyl-3-methanesulfonylamino-2-methoxy-phenyl)-2-oxo-2-{4-[2-(5-oxo-[1,4]diazepan-1-yl)-ethoxy]-naphthalen-1-yl}-acetamide;
N-[5-tert-Butyl-2-(3-cyano-phenyl)-2H-pyrazol-3-yl]-2-[4-(2-morpholin-4-yl-ethoxy)-naphthalen-1-yl]-2-oxo-acetamide;
N-(5-tert-Butyl-2-methoxy-3-phenylacetylamino-phenyl)-2-[4-(2-morpholin-4-yl-ethoxy)-naphthalen-1-yl]-2-oxo-acetamide;
2-(2-Chloro-5-trifluoromethyl-phenyl)-N-[4-(2-morpholin-4-yl-pyrimidin-4-yloxy)-naphthalen-1-yl]-2-oxo-acetamide;
1-(5-tert-Butyl-2-methoxy-phenyl)-3-[4-(2-piperidin-1-yl-pyrimidin-4-yloxy)-naphthalen-1-yl]-imidazolidine-2,4,5-trione;
2-(2-Benzyl-5-tert-butyl-2H-pyrazol-3-yl)-2-hydroxy-N-[4-(2-morpholin-4-yl-ethoxy)-naphthalen-1-yl]-acetamide;
5-tert-Butyl-3-{2-[4-(2-dimethylamino-pyrimidin-4-ylamino)-naphthalen-1-yl]-2-oxo-acetylamino}-thiophene-2-carboxylic acid amide;
N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;
N-(3-Methanesulfonylamino-5-trifluoromethyl-phenyl)-2-[4-(2-morpholin-4-yl-ethoxy)-naphthalen-1-yl]-2-oxo-acetamide;
N-(5-tert-Butyl-2-hydroxy-3-piperidin-1-ylmethyl-phenyl)-2-[4-(2-morpholin-4-yl-ethoxy)-naphthalen-1-yl]-2-oxo-acetamide;
2-(1-Methyl-1H-indol-3-yl)-N-[4-(2-morpholin-4-yl-ethoxy)-naphthalen-1-yl]-2-oxo-acetamide;
N-(5-tert-Butyl-2-methoxy-phenyl)-2-oxo-2-{4-[2-((S)-1-phenyl-ethylamino)-pyrimidin-4-ylamino]-naphthalen-1-yl}-acetamide;
N-[5-tert-Butyl-2-(4-cyano-phenyl)-2H-pyrazol-3-yl]-2-[4-(2-morpholin-4-yl-ethoxy)-naphthalen-1-yl]-2-oxo-acetamide;
N'-[1-(5-tert-Butyl-3-methanesulfonylamino-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;
N-[5-tert-Butyl-2-(3-methoxy-phenyl)-2H-pyrazol-3-yl]-2-hydroxy-2-[4-(2-morpholin-4-yl-ethoxy)-naphthalen-1-yl]-acetamide;
N-(5-tert-Butyl-2-methoxy-3-{2-[4-(2-morpholin-4-yl-ethoxy)-naphthalen-1-yl]-2-oxo-acetylamino}-phenyl)-isobutyramide;
N-[5-tert-Butyl-2-(4-methyl-benzoyl)-2H-pyrazol-3-yl]-2-[4-(2-morpholin-4-yl-ethoxy)-naphthalen-1-yl]-2-oxo-acetamide;
N-[5-tert-Butyl-2-(2-chloro-phenyl)-2H-pyrazol-3-yl]-2-[4-(2-morpholin-4-yl-ethoxy)-naphthalen-1-yl]-2-oxo-acetanide;
N-[5-tert-Butyl-2-(3-chloro-4-methyl-phenyl)-2H-pyrazol-3-yl]-2-[4-(2-morpholin-4-yl-ethoxy)-naphthalen-1-yl]-2-oxo-acetamide;
2-(4-Bromo-phenyl)-N-(5-tert-butyl-2-p-tolyl-2H-pyrazol-3-yl)-acetamide;
2-(5-tert-Butyl-2-methyl-furan-3-yl)-N-[4-(6-morpholin-4-ylmethyl-pyridin-3-yl)-naphthalen-1-yl]-2-oxo-acetamide;
4-(4-{4-[2-(5-tert-Butyl-2-methyl-furan-3-yl)-2-oxo-acetylamino]-naphthalen-1-ylamino}-phenoxy)-pyridine-2-carboxylic acid methylamide;
N-[5-tert-Butyl-2-methoxy-3-(propane-1-sulfonylamino)-phenyl]-2-[4-(2-morpholin-4-yl-pyridin-4-ylamino)-naphthalen-1-yl]-2-oxo-acetamide;
5-tert-Butyl-N-cyclopropyl-2-methoxy-3-{2-[4-(2-morpholin-4-yl-pyridin-4-ylamino)-naphthalen-1-yl]-2-oxo-acetylamino}-benzamide;
N-(5-tert-Butyl-3-methanesulfonylamino-2-methoxy-phenyl)-2-oxo-2-{4-[6-(tetrahydro-pyran-4-ylamino)-pyridin-3-yl]-naphthalen-1-yl}-acetamide;
3-[2-(4-Bromo-naphthalen-1-yl)-2-oxo-acetylamino]-5-tert-butyl-N-cyclopropyl-2-methoxy-benzamide;
N-(5-tert-Butyl-3-methanesulfonylamino-2-methoxy-phenyl)-2-[4-(6-morpholin-4-yl-pyridin-3-yl)-naphthalen-1-yl]-2-oxo-acetamide;
N-(5-tert-Butyl-2-p-tolyl-2H-pyrazol-3-yl)-2-[4-(6-morpholin-4-ylmethyl-pyridin-3-yl)-naphthalen-1-yl]-2-oxo-acetamide;
N-(5-tert-Butyl-3-methanesulfonylamino-2-methoxy-phenyl)-2-oxo-2-(4-pyridin-3-yl-naphthalen-1-yl)-acetamide;
N-(5-tert-Butyl-2-methyl-2H-pyrazol-3-yl)-2-oxo-2-(4-pyridin-3-yl-naphthalen-1-yl)-acetamide;
2-(4—Chloro-3-trifluoromethyl-phenyl)-N-[4-(2-morpholin-4-yl-ethoxy)-naphthalen-1-yl]-2-oxo-acetamide; or
4-{4-[2-(4—Chloro-3-trifluoromethyl-phenyl)-2-oxo-acetylamino]-phenoxy}-pyridine-2-carboxylic acid methylamide.

In yet another aspect, the invention provides pharmaceutical compositions comprising a compound as described herein (e.g., a compound of Formula IA, IB, IC or II) and a pharmaceutically acceptable carrier.

In accordance with a further aspect of the invention, there are provided methods for preparing cytokine inhibitors of the present invention. For example, methods for preparing compounds of Formula IA comprise reacting G-NH$_2$ with Q-L-Ar—X—OH in the presence of a coupling agent and a base, or reacting G-NH$_2$ with Q-L-Ar—X—X" in the presence of a base, to yield a compound of Formula IA, wherein the variables G, Q, L are defined as in any of the compounds described herein, X is C(O) or C(S), and X" is an activating moiety. Compounds of IB may be similarly prepared using G-X—X" and Q-L-Ar—NH$_2$.

In yet another aspect of the invention, there are provided methods for preparing compounds of Formula II where X' is NH, comprising heating G(NO)—NH—CH$_2$—Ar-L-Q with a suitable organoamine to yield a compound of Formula II, wherein G, Ar, L, and Q are as defined as in Formula II.

In another aspect of the invention, there are provided compounds of Formula III, suitable for preparing compounds of the invention such as compounds of Formula IB.

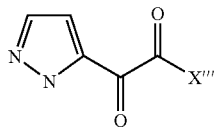

In compounds of Formula III, the pyrazole moiety is substituted at the 1-position, 3-position, or at both by one or more $R^1$, $R^2$ or $R^3$;

$X'''$ is $OR^x$ or an activating moiety;

$R^x$ is H, substituted or unsubstituted $C_{1-4}$ alkyl, or substituted or unsubstituted aralkyl;

each $R^1$ is independently F, Cl, Br, I, cyano, —C(O)R, —C(O)NR$_2$, —C(O)OR, —OR, —SiR$_3$, —NR'R',—S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$;

each $R^2$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$; and each $R^3$ is independently H, substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, S(O)$_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}C(O)N(R^{21})$—, $R^{22}O$—, $R^{23}R^{24}NC(O)$—, $R^{26}(CH_2)_mC(O)N(R^{21})$—, $R^{26}C(O)(CH_2)_m N(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or S(O)$_m$; and R, R', R", $R^{20}$, $R^{21}$, $R^{23}$, $R^{24}$, $R^{26}$, and m are as defined in any of the compounds described herein.

In another aspect, the invention provides methods of preventing or treating diseases mediated by cytokines which comprise administering to a subject in need of such treatment a therapeutically effective amount of a compound as described herein, e.g., a compound according to Formula IA, IB, IC and/or II. Such cytokine-mediated diseases include rheumatoid arthritis, osteoarthritis, Crohn's disease, ulcerative colitis, psoriatic arthritis, traumatic arthritis, rubella arthritis, inflammatory bowel disease, multiple sclerosis, psoriasis, graft versus host disease, systemic lupus erythematosus, toxic shock syndrome, irritable bowel syndrome, muscle degeneration, allograft rejections, pancreatitis, insulinitis, glomerulonephritis, diabetic nephropathy, renal fibrosis, chronic renal failure, gout, leprosy, acute synovitis, Reiter's syndrome, gouty arthritis, Behcet's disease, spondylitis, endometriosis, non-articular inflammatory conditions, such as intervertbral disk syndrome conditions, bursitis, tendonitis, tenosynovitis or fibromyalgic syndrome; and acute or chronic pain, including but not limited to neurological pain, neuropathies, polyneuropathies, diabetes-related polyneuropathies, trauma, migraine, tension and cluster headache, Horton's disease, varicose ulcers, neuralgias, musculo-skeletal pain, osteo-traumatic pain, fractures, algodystrophy, spondylarthritis, fibromyalgia, phantom limb pain, back pain, vertebral pain, post-surgery pain, herniated intervertebral disc-induced sciatica, cancer-related pain, vascular pain, visceral pain, childbirth, or HIV-related pain. Other cytokine mediated diseases are stroke, chronic heart failure, endotoxemia, reperfusion injury, ischemia reperfusion, myocardial ischemia, restenosis, thrombosis, angiogenesis, Coronary Heart Disease, Coronary Artery Disease, acute coronary syndrome, Takayasu arteritis, cardiac failure such as heart failure, cardiomyopathy, myocarditis, vasculitis, vascular restenosis, valvular disease or coronary artery bypass; hypercholesteremia, diseases or conditions related to blood coagulation or fibrinolysis, such as for example, acute venous thrombosis, pulmonary embolism, thrombosis during pregancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia or thrombocytopenia; or atherosclerosis. Yet others are allergic conjunctivitis, uveitis, glaucoma, optic neuritis, retinal ischemia, diabetic retinopathy, laser induced optic damage, or surgery or trauma-induced proliferative vitreoretinopathy. Cytokine mediated diseases further include allergic rhinitis, asthma, adult respiratory distress syndrome, chronic pulmonary inflammation, chronic obstructive pulmonary disease, emphysema, bronchitis, mucus hypersecretion, silicosis, SARS infection and respiratory tract inflammation. Also included are psoriasis, eczema, atopic dermatitis, contact dermatitis, or acne. Yet other cytokine mediated diseases are Guillain-Barre syndrome, Parkinson's disease, Huntington's disease, Alzheimer's disease, amyotrophic lateral sclerosis, multiple sclerosis and other demyelinating diseases, viral and bacterial meningitis, CNS trauma, spinal cord injury, seizures, convulsions, olivopontocerebellar atrophy, AIDS dementia complex, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia, aneurism, or epilepsy. In another aspect of the invention, the cytokine mediated diseases include bone resorption diseases, osteopetrosis, osteoporosis, or osteoarthritis. Also included are diabetes, systemic cachexia, cachexia secondary to infection or malignancy, cachexia secondary to acquired immune deficiency syndrome (AIDS), obesity, anorexia or bulimia nervosa. Additonally, the cytokine mediated disease can be sepsis, HIV, HCV, malaria, infectious arthritis, leishmaniasis, Lyme disease, cancer, including but not limited to breast cancer, colon cancer, lung cancer, prostatic cancer, multiple myeloma, acute myelogenous leukemia, myelodysplastic syndrome, non-Hodgkins lymphoma, or follicular lymphoma, Castleman's disease, or drug resistance.

In another aspect, the invention provides methods of treating neutrophil-mediated diseases which comprise administering to a subject in need of such treatment a therapeutically effective amount of a compound as described herein, including a compound according to Formula IA, IB, IC and/or II, wherein the neutrophil-mediated disease is bronchial asthma, rhinitis, influenza, stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukopheresis, granulocyte transfusion associated syndromes, or necrotizing enterocolitis.

Combination therapy with cytokine inhibitors provides a beneficial therapeutic effect, particularly an additive or over-additive effect or an overall reduction of side effects of therapy. Such a beneficial therapeutic effect is desirable in the treatment of cytokine mediated diseases as described herein, and in particular in the treatment of rheumatoid arthritis, Crohn's disease and psoriasis. Thus, in another aspect the invention provides methods of treating a cytokine mediated disease including administering one or more, typically one, of the active ingredients (hereafter referred to as A) described herein together with one or more, typically one, cytokine inhibitor of the invention. An additive or over-additive effect of the pharmaceutical combinations according to the invention provides for dose reduction, side-effect reduction and/or interval extension when compared to the individual compounds and A and the cytokine inhibitor used in monotherapy in the usual way. The effects mentioned above are observed both when the two active substances are administered simultaneously in a single active substance formulation and when they are administered successively in separate formulations. In the case of A being an injectable, especially a biological agent, other benefits of adding the cytokine inhibitor may be seen. For example, cost reduction by way of interval and/or dose reduction.

A variety of active ingredients A are contemplated for use in the combinations of the invention. For example, non-steroid anti-inflammatory drugs (NSAIDs), which are widely used for the treatment of inflammation, pain and fever, may be used. Such NSAIDS include acetaminophen, aspirin, ibuprofen, choline magnesium salicylate, choline salicylate, diclofenac, diflunisal, etodolac, fenoprofen calcium, flurbiprofen, indomethacin, ketoprofen, carprofen, indoprofen, ketorolac tromethamine, magnesium salicylate, meclofenamate sodium, mefenamic acid, oxaprozin, piroxicam, sodium salicylate, sulindac, tolmetin, meloxicam, rofecoxib, celecoxib, etoricoxib, valdecoxib, nabumetone, naproxen, lomoxicam, nimesulide, indoprofen, remifenzone, salsalate, tiaprofenic acid, flosulide, and the like.

Angiogenesis inhibitors may serve as A, such as compounds directed against VEGF, taxol, pentoxyfylline and thalidomide.

Biological agents shall be understood to mean any natural or artificial/synthetic biological molecule or fragment thereof as known in the art, such as antibodies, proteins, fusion proteins, receptors, nucleic acids, lipids, carbohydrates and the like. Therefore, active ingredient A includes biological agents, such as etanercept, infliximab, alefacept, adalimumab, efalizumab, anakinra, IL-1RA, alpha-interferon, interferon beta 1-B, CTLA-4, and other antibodies or receptor constructs directed against TNF-alpha, IL1-6, LFA-1, and C5.

Also within the scope of the invention for active ingredient A are steroids, such as glucocorticoids, and vitamin D3 and analogs thereof (cholecalciferols), alone (the latter being used mostly for psoriasis) or in combination. Steroids include budesonide, dexamethasone, fluocinonide, hydrocortisone, betamethasone, halobetasol (ulobetasol), methylprednisolone, prednisolone, clobetasone, deflazacort, fluocinolone acetonide, fluticasone, triamcinolone acetonide, mometasone and diflucortolone. Among vitamin D3 derivatives are calcipotriol, tacalcitol, maxacalcitol, and tacalitol, the calciotropic hormones, 1α,2,5-dihydroxyvitamin D3, and parathyroid hormone-related peptide.

Many types of immunomodulatory, immunosuppressive or cytostatic drugs can be used in combination with cytokine inhibitors. Exemplary agents include hydroxychloroquine, D-penicillamine, sulfasalazine, auranofin, gold sodium thiomalate, minocycline, dapsone, chlorambucil, mercaptopurine, tacrolimus, sirolimus, pimecrolimus, mycophenolate mofetil, cyclosporine, leflunomide, methotrexate, azathioprine, cyclophosphamide, macrolid, ascomycin, hydroxyurea, 6-thioguanine, (Orfanos C E., 1999, Cutis 64(5):347-53); alefacept, leflunomide, infliximab, etanercept, efalizumab, anti-CD4, anti-CD25, peptide T, LFA3TIP, ICAM-1 ISIS 2302, $DAB_{389}$, CTLA-4Ig, anti—CD80, for example IDEC-114 or ABX-IL8, DAB-IL-2, IL-10, anti-TAC, basiliximab and daclizumab. In addition, agents or therapies which act on other targets or immune mediated products are suitable as the active ingredient A. These include, for example, inhibitors of protein tyrosine kinases (PTKs) such as epidermal growth factor receptor (EGFR), E-selectin inhibitors, and therapies widely used for psoriasis such as anthralin, coal tar, phototherapies including ultraviolet B (UVB) or psoralen ultraviolet A (PUVA), photodynamic therapy and laser therapy.

Retinoids therapy can also be used as active ingredient A. Thus, for example, bexarotene, acitretin, etretinate and tazarotene, and hydroxyurea, 6-thioguanine and phototherapies are suitable active ingredients. (Orfanos C E., 1999, Cutis 64(5):347-53; see also Saurat J H., 1999, J.Am.Acad.Derm. 41(3 Pt 2):S2-6).

Active ingredients A useful in the invention further include small molecule inhibitors directed against enzymes involved in signal transduction pathways or to cell adhesion molecules like LFA-1 or ICAM-1.

In another aspect, there are provided the above-mentioned pharmaceutical combinations comprising A and the cytokine inhibitor, typically in therapeutically effective amounts, for use as pharmaceutical compositions with an anti-cytokine activity. Moreover, combinations comprising A and a cytokine inhibitor can be used for preparing a pharmaceutical composition for the treatment and/or prevention of a cytokine mediated disease or condition. The pharmaceutical preparations, containing as active substance one or more compound combinations comprising A and the cytokine inhibitor further include the pharmaceutically acceptable derivatives thereof, and may be optionally combined with conventional excipients and/or carriers.

For therapeutic use, the pharmaceutical combinations of A and the cytokine inhibitor according to the invention may be administered in any conventional dosage form in any conventional manner, including any of the routes described herein. Accordingly, routes of administration include, but are not limited to, intravenous, intramuscular, subcutaneous, intrasynovial, by infusion, sublingual, transdermal, oral, topical and by inhalation. Typical modes of administration are oral, topical or intravenous.

The pharmaceutical combinations of A and the cytokine inhibitor according to the invention may be administered separately, or in a combination formulation with other active ingredients or adjuvants that enhance stability of the inhibitors, facilitate administration of pharmaceutical compositions containing them, provide increased dissolution or dispersion, increase inhibitory activity, provide adjunct therapy, or provide like advantages. Such combination therapies typically utilize lower dosages of the conventional therapeutics, and avoid the possible toxicity and adverse side effects incurred when those agents are used as monotherapies. Pharmaceutical combinations of A and the cytokine inhibitor may therefore be physically combined with the conventional therapeutics or other adjuvants into a single pharmaceutical composition. The active ingredient A and/or the cytokine inhibitor may be used in the combination as a salt, solvate, tautomer and/or prodrug and as a single stereroisomer or mixtures of stereoisomers, including racemates.

The proportions in which the two active substances, A and the cytokine inhibitor, may be used in the combinations according to the invention are variable. Active substances A and the cytokine inhibitor are optionally present in the form of their solvates or hydrates. Depending on the choice of the compounds A and the cytokine inhibitor, the weight ratios which may be used within the scope of the present invention vary on the basis of the different molecular weights of the various compounds and their different potencies. Determination of ratios by weight is dependent on particular active ingredients of A and the cytokine inhibitor, and within the skill in the art.

In psoriasis, known combination treatments have been effective and are used as rotation therapy for maintenance of remission or as combination treatments if refractory to usual systemic products. Most of the combinations are with different modes of action either to improve efficacy or to reduce side effects by reduction of the dosage. See Van de Kerkhof, P. 1997 Clinics in Dermatology, 15:831-834, which showed the interest of topical steroids or Vitamin D with systemic agents. Two combinations which are widely accepted include ultraviolet B (UVB) or psoralens ultraviolet A (PUVA) plus retinoids; methotrexate, or the combination of cyclosporin and retinoids.

A typical combination for treating psoriasis is the cytokine inhibitor compound with immunotherapy drugs which include cyclosporin, pimecrolimus, tacrolimus, ascomycine, anti-CD4, anti-CD25, peptide T, LFA3TIP, $DAB_{389}$, CTLA-4Ig, E-selectin inhibitors, alefacept, infliximab, etanercept, efalizumab, and those disclosed in Griffiths, Christopher E. M., 1998 Hospital Medicine, Vol 59 No 7, and the obvious variants thereof. Another typical combination for treating psoriasis is the cytokine inhibitor compound with methotrexate (MTX). It is expected this combination will be effective because of the good tolerability of MTX in the short term and because of the acceptability if maintenance of remission is obtained with good quality of life. Another typical combination for treating psoriasis is the cytokine inhibitor compound with cyclosporine, especially because of cyclosporine's efficiency for induction of remission. Another embodiment of the invention comprises administration in the following sequence: induction with cytokine inhibitor and cyclosporine, followed by continuation with cytokine inhibitor after decrease of dosing and discontinuation of cyclosporine. Another typical combination for treating psoriasis is the cytokine inhibitor compound in combination with retinoids. Retinoids provide minimal efficacy with potential Cyt P450 interactions and risk of teratogenicity, and this would be alleviated by continuation therapy with the cytokine inhibitor. Yet another typical combination for treating psoriasis is the cytokine inhibitor compound, in combination with topical active ingredients A chosen from glucocorticoids, vitamin D derivatives, topical retinoids and dithianol. A more typical combination for treating psoriasis is a cytokine inhibitor compound with vitamin D derivatives, most typically calcipotriol or tacalcitol. Another typical combination for treating psoriasis is the cytokine inhibitor compound in combination with macrolids, most typically with ascomycin analogues topically, and even more typically with those available orally such as pimecrolimus. Another typical combination for treating psoriasis is the cytokine inhibitor compound in combination with cell adhesion molecules inhibitors, such as anti LFA3, anti LFA1. This includes adhesion molecule blockage by recombinant fusion proteins like alefacept, anti LFA3-IgCl, or by anti-CD11 monoclonal antibodies, efalizumab, and the obvious variants thereof. Cell adhesion molecules inhibitors appear to provide an acceptable response rate with limited tolerability problems. Combination with a cytokine inhibitor could avoid the disadvantage of their injectable form, with CAM inhibitors being used intermittently. Another embodiment of the invention comprises administration in the following sequence: induction with cytokine inhibitor and CAM inhibitors, followed by maintenance treatment with the cytokine inhibitor alone and retreatment with CAM inhibitors in case of significant relapse.

Another typical combination for treating psoriasis is the cytokine inhibitor compound with another anti-TNF-alpha active ingredient. A typical embodiment is one wherein the other anti-TNF-alpha active ingredient is chosen from infliximab or etanercept, typically infliximab. Infliximab is believed to have a higher rate of response for induction of remission, which recently was suggested to be maintained on the long term. Within the scope of the invention is the use of topical or general antisense inhibitors of TNF alpha, such as ICAM-1 ISIS 2302 in combination with a cytokine inhibitor compound. Another typical combination for treating psoriasis is the cytokine inhibitor compound with anti-CD4, anti CD80 (IDEC-114 or ABX-IL8), DAB IL-2, $DAB_{389}$ IL-2, CTLA4-Ig, IL10, the IL2 receptor inhibitors such as daclizumab (anti-TAC), basiliximab. (See Tutrone, W. D., 2001, Biologic Therapy for Psoriasis vol 68; Tutrone, W. D., 2001, Biologic Therapy for Psoriasis vol 68; Ben-Bassat, H. 2001 Current Opinion in Investigational Drugs Vol 2 No 11; Salim, A. et al, 2001 Current Opinion in Investigational Drugs Vol 2 No 11).

Any of the above mentioned combinations within the scope of the invention may be tested by animal models known in the art. Reference in this regard may be made to: Schon, Michael P. 1999 Animal models of Psoriasis—What can we learn from them, The Society for Investigative Dermatology—Reviews, Vol 112. No. 4, 405-410.

In Rheumatoid Arthritis, combination of immunosuppressive or immunomodulatory agents is a long and well established therapeutic paradigm. Combination partners recruit from various therapeutic entities. Their identification is either based on empirical data supported by evolving knowledge about the underlying mechanisms or based on a well defined mode of action. These agents are generally referred to as Disease Modifying Antirheumatic Drugs (DMARDs) or Slow Acting Antirheumatic Drugs (SAARDs). Apart from the combinations listed below, combination of the cytokine inhibitor, with one or more agents classified as DMARD/SAARD or NSAID and/or corticosteroid, are contemplated in this invention.

A typical combination for treating rheumatoid arthritis is the cytokine inhibitor compound combined with one or more of the following immunosuppressive, immunomodulatory, or cytostatic drugs, such as, for example, hydroxychloroquine, D-penicillamine, sulfasalazine, auranofin, gold sodium thiomalate, minocycline, dapsone, chlorambucil, mercaptopurine, tacrolimus, sirolimus, mycophenolate mofetil, cyclosporine, leflunomide, methotrexate, azathioprine and cyclophosphamide. Another typical combination for treating rheumatoid arthritis is the cytokine inhibitor compound combined with angiogenesis inhibitors, such as compounds directed against VEGF, taxol, pentoxyfylline, thalidomide, interferon beta-1B and alpha-interferon. Yet another typical combination for treating rheumatoid arthritis is the cytokine inhibitor compound in combination with inhibitors of cell adhesion, such as inhibitors of LFA-1 or ICAM-1.

A more typical combination for treating rheumatoid arthritis is the cytokine inhibitor compound combined with anti-TNF antibodies or TNF-receptor antagonists such as Etanercept, Infliximab, Adalimumab (D2E7), or biological agents such as CTLA-4, or biological agents directed against targets like CD-4, LFA-1, IL-6, ICAM-1, and C5. In another embodiment the cytokine inhibitor is combined with Infliximab and methotrexate. Another typical combination for treating rheumatoid arthritis is the cytokine inhibitor compound in combination with IL-1 receptor antagonists, such as Kineret. Yet another typical combination for treating rheumatoid arthritis is the cytokine inhibitor compound combined with non-steroid anti-inflammatory drugs (NSAIDs), including acetaminophen, aspirin, ibuprofen, choline magnesium salicylate, choline salicylate, diclofenac, diflunisal, etodolac, fenoprofen calcium, flurbiprofen, indomethacin, ketoprofen, carprofen, indoprofen, ketorolac tromethamine, magnesium salicylate, meclofenamate sodium, mefenamic acid, oxaprozin, piroxicam, sodium salicylate, sulindac, tolmetin, meloxicam, rofecoxib, celecoxib, etoricoxib, valdecoxib, nabumetone, naproxen, lomoxicam, nimesulide, indoprofen, remifenzone, salsalate, tiaprofenic acid, flosulide, and the like. Another typical combination for treating rheumatoid arthritis is the cytokine inhibitor compound combined with glucocorticosteroids, such as betamethasone, dexamethasone, methylprednisolone, prednisolone, and deflazacort.

Any of the above mentioned combinations within the scope of the invention may be tested by animal models known in the art. (See Wooley, P. H. 1998, Animal models of arthritis, in Klippel J. H., Dieppe, P. A., (eds.) Rheumatology, second edition, 5.8.1-5.8.6. Mosby, London, Philadelphia, St. Louis, Sydney, Tokio).

In Crohn's disease, the following groups of drugs combined with the cytokine inhibitor may be effective: steroids such as budesonide, 5-ASA drugs like mesalamine, immunosuppressants, biological agents and adhesion molecule inhibitors. A typical combination for treating Crohn's disease is the cytokine inhibitor compound with one or more of the following: steroids including all those listed herein, 5-ASA, methotrexate and azathioprine. Another typical combination for treating Crohn's disease is the cytokine inhibitor compound combined with IL-1 receptor antagonists, such as Kineret. Yet another typical combination for treating Crohn's disease is the cytokine inhibitor compound with anti-TNF antibodies or TNF-receptor antagonists, such as Etanercept, Infliximab, Adalimumab (D2E7), or biological agents such as CTLA-4, or biological agents directed against targets like CD-4, LFA-1, IL-6, ICAM-1, and C5. In another embodiment the cytokine inhibitor is combined with Infliximab and methotrexate. More typically, the cytokine inhibitor is combined with Infliximab. Another typical combination for treating Crohn's disease is the cytokine inhibitor compound combined with IL-10, ISIS 2302 (anti ICAM 1), or Antegren (VCAM receptor antagonist).

It has been found that cytokine inhibitors possess inhibitory effects on the procoagulant and profibrinolytic responses during human endotoxemia. The invention therefore also provides for a method of anticoagulant and fibrinolytic therapy for a disease or condition relating to blood coagulation or fibrinolysis, comprising administering to a patient in need thereof a pharmaceutically effective a amount of the cytokine inhibitor. This administration may be of benefit given either prophylactically to patients at risk or therapeutically for patients who have developed complications related to these pathways.

Also with the scope of the invention is combination therapy of the cytokine inhibitor and one or more other anticoagulant or fibrinolytic agents. These include recombinant tissue plasminogen activator (rtPA), streptokinase (SK), urokinase (UK), proUK, heparin, enoxoparin, dalteparin, coumarin anticoagulants, aspirin, dipyrimidamole, aggrennox, ticlopidine, clopidogrel (Plavix), abciximab, RheoPro, integrilin, aggrestat and the like. Particular dosages, formulations and methods of administration either alone or combined is within the skill in the art.

DETAILED DESCRIPTION OF THE INVENTION

The following terms are used throughout as defined below.

Generally, reference to a certain element such as hydrogen or H is meant to include all isotopes of that element. For example, if an R group is defined to include hydrogen or H, it also includes deuterium and tritium. Hence, isotopically labeled compounds are within the scope of the invention.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl, norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Typical unsubstituted alkyl groups include straight and branched chain alkyl groups and cyclic alkyl groups having 1 to 20 carbon atoms, and more typical such groups have from 1 to 10 carbon atoms. Even more typical such groups, also known as unsubstituted lower alkyl groups, have from 1 to 5 carbon atoms. Typically, unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in groups such as carbonyls, carboxyls, and esters; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The term "alkylene" refers to saturated, divalent straight or branched chain hydrocarbyl groups typically having in the range of about 2 up to about 20 carbon atoms, and "substituted alkylene" refers to alkylene groups further bearing one or more substituents as set forth above.

The phrase "unsubstituted aryl" refers to aryl groups that do not contain heteroatoms. Thus the phrase includes, but is not limited to, groups such as phenyl, biphenyl, anthracenyl, naphthyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A typical unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl (including cycloalkyl), alkenyl, alkynyl, aralkyl, heterocyclyl or heterocyclylalkyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Moreover, substituted aryl groups include aryl groups in which one or more aromatic carbons of the aryl group is bonded to an unsubstituted aryl or an aryl substituted with any of the groups described above except another aryl. Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. Typically unsubstituted alkenyl groups have form 2 to 20 carbons, and in some embodiments such groups have from 2 to 10 carbons.

The term "alkenylene" refers to divalent straight or branched chain hydrocarbyl groups having at least one carbon—carbon double bond, and typically having in the range of about 2 up to 20 carbon atoms, and "substituted alkenylene" refers to alkenylene groups further bearing one or more substituents as set forth above.

The phrase "unsubstituted alkynyl" refers to straight and branched chain groups such as those described with respect to unsubstituted alkyl groups as defined above, except that at least one triple bond exists between two carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others. Typically, unsubstituted alkynyl groups have form 2 to 20 carbons, and in some embodiments such groups have from 2 to 10 carbons.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus the phrase includes, but is not limited to, groups such as benzyl, diphenylmethyl, and 1-phenylethyl (—CH(C$_6$H$_5$)(CH$_3$)) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH$_2$C(=O)(C$_6$H$_5$), and —CH$_2$(2-methylphenyl) among others.

The phrase "unsubstituted heterocyclyl" refers to both aromatic and nonaromatic ring compounds including monocyclic, bicyclic, and polycyclic ring compounds containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. lH-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g., 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide and tetrahydrothiophene 1,1-dioxide. Typical heterocyclyl groups contain 5 or 6 ring members. Exemplary heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one or more of the ring members is bonded to a non-hydrogen atom such as described above with respect to substituted alkyl groups and substituted aryl groups. Examples include, but are not limited to, 2-methylbenzimidazolyl, 5-methylbenzimidazolyl, 5-chlorobenzthiazolyl, 1-methyl piperazinyl, 2-phenoxy-thiophene, and 2-chloropyridinyl among others. In addition, substituted heterocyclyl groups also include heterocyclyl groups in which the bond to the non-hydrogen atom is a bond to a carbon atom that is part of a substituted and unsubstituted aryl, substituted and unsubstituted aralkyl, unsubstituted heterocyclyl, or substituted heterocyclyl in which the substituents include any of those described above except another heterocyclyl group. Examples include but are not limited to 1-benzylpiperdinyl, 3-phenythiomorpholinyl, 3-(pyrrolidin-1-yl)-pyrrolidinyl, and 4-(piperidin-1-yl)-piperidinyl.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—$CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted aralkyl group. Examples include but are not limited to phenyl-(piperidin-1-yl)-methyl and phenyl-(morpholin-4-yl)-methyl.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylfonnate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; carbamates such as t-butyl carbamate (Boc), fluorenylmethyl carbamate (Fmoc), and benzyl carbamate (Cbz); and others. Examples of protected sulfhydryl groups include, but are not limited to, thioethers such as S-t-butyl thioether, S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Certain compounds within the scope of Formulas IA, IB, IC and II are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology* 112: 309-323 (1985); Bodor, N., "Novel Approaches in Prodrug Design," *Drugs of the Future* 6:165-182 (1981); and Bundgaard, H., "Design of Prodrugs: Bioreversible-Derivatives for Various Functional Groups and Chemical Entities," in *Design of Prodrugs* (H. Bundgaard, ed.), Elsevier, New York (1985), Goodman and Gilmans, *The Pharmacological Basis of Therapeutics*, 8th ed., McGraw-Hill, Int. Ed. 1992. The preceding references and all references listed herein are hereby incorporated in their entirety by reference.

Tautomers refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, ketones are typically in equilibrium with their enol forms. Thus, ketones and their enols are referred to as tautomers of each other. As readily understood by one skilled in the art, a wide variety of functional groups and other structures may exhibit tautomerism, and all tautomers of compounds having Formula IA, IB, and IC are within the scope of the present invention.

Compounds of the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

"Treating" within the context of the instant invention, means an alleviation, in whole or in part, of symptoms associated with a disorder or disease, or halt of further progression or worsening of those symptoms, or prevention or prophylaxis of the disease or disorder. Similarly, as used herein, a "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-inflammatory agents, anticancer agents and other agents described herein.

Compounds of the invention may be readily synthesized by techniques well known to those of skill in the art. For example, compounds of Formula IA wherein X is C(O) may be prepared by coupling of an amine-bearing G component with a carboxyl bearing Ar-L-Q, component. Coupling may be effected, for example, by the use of typical amide-bond-forming reagents such as EDC, PyBOP, and the like, or by formation of an acyl halide or active ester. Thus, any suitable amide-bond forming procedure may be used such as those described in Bodanszky, M. and Bodanszky, A., *The Practice of Peptide Synthesis*, Springer-Verlag (1984); or Jones, J. *Amino Acid and Peptide Synthesis* Ed. Steven G. Davies, Oxford Science (1992). Thionation of the resulting amide may be carried out, for example, using Lawesson's reagent or the like to give thioamides of Formula IA or IB (is C=S). Similarly, compounds of Formula IB wherein X is C(O) may be made, for example, starting with an amine-bearing Ar—L-Q component and a carboxyl bearing G. The ketoamides of Formula IA or IB (respectively obtained by coupling of G-NH$_2$ and HOOC—C(O)—Ar-L-Q, or by coupling of NH$_2$—Ar-L-Q and G'-C(O)—COOH by the methods described above), may be converted to the corresponding oximes (Y is C(=NOH)) by treatment with hydroxylamine.

As an example, Scheme 1 shows the synthesis of compounds of the present invention where G is a substituted pyrazole.

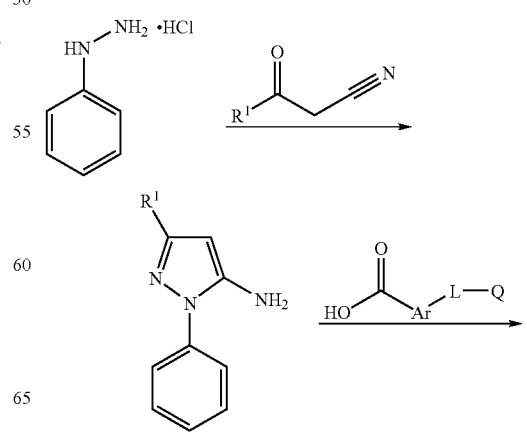

Scheme 1

-continued

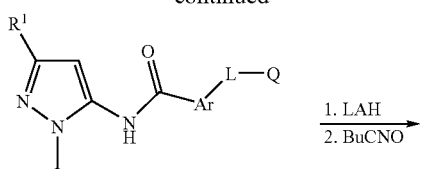

IA

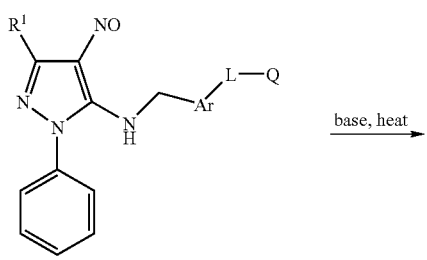

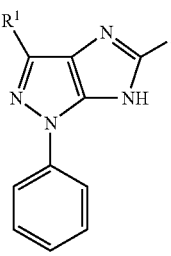

IIA

Thus, substituted phenyl hydrazine hydrochloride is heated with a beta-ketonitrile in a suitable solvent such as benzene, toluene, or the like, to give the substituted phenyl aminopyrazole as shown. The carboxyl-Ar-L-Q component is then coupled to the free amine, typically with a coupling agent such as EDC, PyBOP, and the like in the presence of a suitable base such as DIEA among others. The coupling reaction may be carried out in any suitable solvent such as methylene chloride, DMF, ethyl acetate, THF/water, and the like. Alternatively, the carboxyl component may be converted to an acid halide such as the acid chloride by exposure to oxalyl chloride, thionyl chloride, or $POCl_3$ among others. The coupled product is an example of a compound of Formula IA as shown and may be further modified to form other compounds of the invention.

Compounds of Formula II wherein X' is N may be readily prepared. The amide bond of compounds of Formula IA and IB (wherein X is C(O)) may be reduced with any suitable hydride such as LAH and the resulting compound may be converted to the nitroso derivative by exposure to BuCNO. Cyclization of the nitroso derivative gives a compound of Formula II having the structure IIA. The cyclization may be effected by heating the nitroso compound with a suitable base such as pyridine or the like.

Compounds of Formula II wherein X' is S have the following formula,

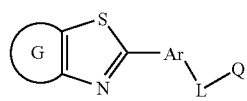

and can be prepared following procedures similar to what has been described in the literature. For instance pyrazole-amide intermediates of type A1 (synthesis described in Scheme 2, method A) can be brominated using bromine or N-bromosuccinimide according to methods described in the literature to lead to the brominated analogues of type A2 (Justus Liebigs Ann. Chem. 1955, 593:179-199; J. Chem. Soc., 1956, 4974-4977; Bioorg. Med. Chem. Lett. 11, 22, 2001, 2979-2982; J. Chem. Soc. Perkin Trans. 2, 10, 2000, 2049-2053; Bioorg. Med. Chem. 4, 2, 1996, 227-238).

Scheme 2

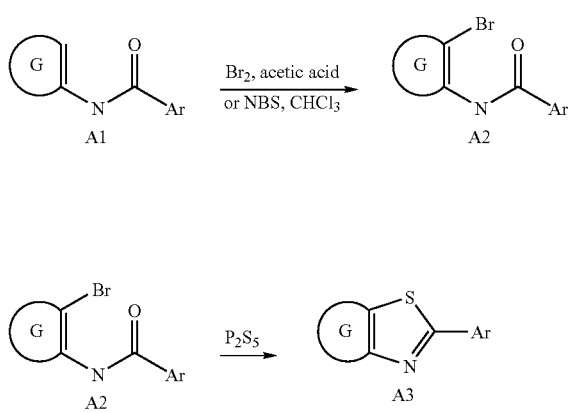

The resulting intermediates A2 can be treated with $P_2S_5$ using heat to lead to the bicyclic thiazole intermediates of type A3 following conditions similar to what has been described in the literature (Chem. Heterocycl. Compd. 10, 1974, 813-815).

Alternatively, as shown in Scheme 3, intermediate A2 can be treated with a base such as n-butyl lithium (nBuLi) followed by the addition of dibenzyl-disulfane to lead to the S-benzyl intermediate A4. Debenzylation of the thioether using HF in anisole (Bull. Chem. Soc. Jpn., 40, 1967, 2164) or using cresol-thiocresol-HF mixture (Int. J. Pept. Protein res. 28, 1986, 498) leads to the free thiol that in turn can cyclize and form a bicyclic thiazole system (Chem. Soc. Jpn., 58, 1985, 785-786).

Scheme 3

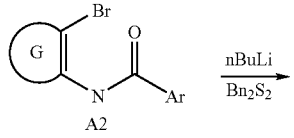

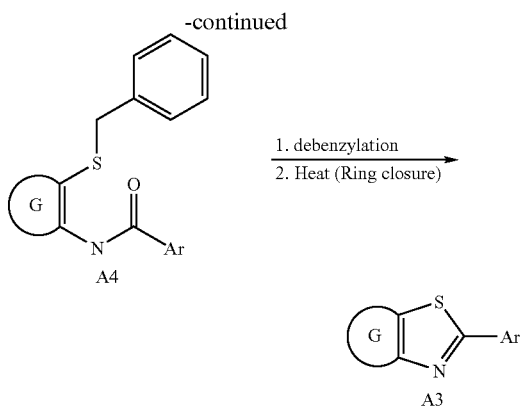

Compounds of Formula II wherein X' is O have the following formula,

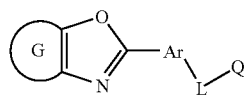

and can be prepared following procedures similar to those described in the literature. Brominated rings of type A2 described above, such as pyrazoles, can be treated with sodium methoxide in methanol to provide the methoxy intermediate A5 (J. Chem. Soc. Perkin Trans. 1, 1984, 63-67).

present invention. For example, methods for preparing compounds of Formula IA comprise reacting G-NH$_2$ with Q-L-Ar—X—OH in the presence of a coupling agent and a base, or reacting G-NH$_2$ with Q-L-Ar—X—X" in the presence of a base, to yield a compound of Formula IA, wherein the variables G, Q, and L are defined as in any of the compounds described herein, X is C(O) or C(S), and X" is an activating moiety. The activating moiety is typically F, Cl, Br, I, —N$_3$, N-hydroxysuccinimide, 1-hydroxybenzotriazole, pentafluorophenol, pentachlorophenol, para-nitrophenol, or —O—C(O)—OR$^y$, wherein R$^y$ is lower alkyl. Suitable bases include sodium bicarbonate or a suitable organoamine such as pyridine, N-methylmorpholine, diisopropylethylamine or triethylamine. In one aspect of the invention, a method is provided for preparing a compound of Formula IA, wherein Ar is —(Y)-naphthyl-, Y is —CH(OH)— or —CH$_2$— and G is selected from phenyl, pyridinyl, pyrazolyl, pyrrolyl, imidazolyl, oxazolyl, isoxazolyl or thienyl. In another, a method is provided for preparing a compound of Formula IA Ar is —C(O)-naphthyl- and G is phenyl, pyridinyl, pyrazolyl, pyrrolyl, imidazolyl, oxazolyl, isoxazolyl or thienyl. Also provided are methods for treating such a compound of Formula IA, wherein Y is —C(O)— with NH$_2$OR in the presence of a second base to provide the compound IA wherein Y is —C(NOR)—. Typically, the second base is pyridine or an acetate salt. Typically, the reaction is carried out in neat pyridine, in a pyridine/alcohol mixture, or in ethanol in the presence of sodium acetate and the reaction mixture is heated to a temperature in the range of about 40° C. to about 80° C. Hence, the invention provides a method for preparing a compound of Formula IA, wherein Ar is —C(=NOH)-naphthyl-, Scheme 4

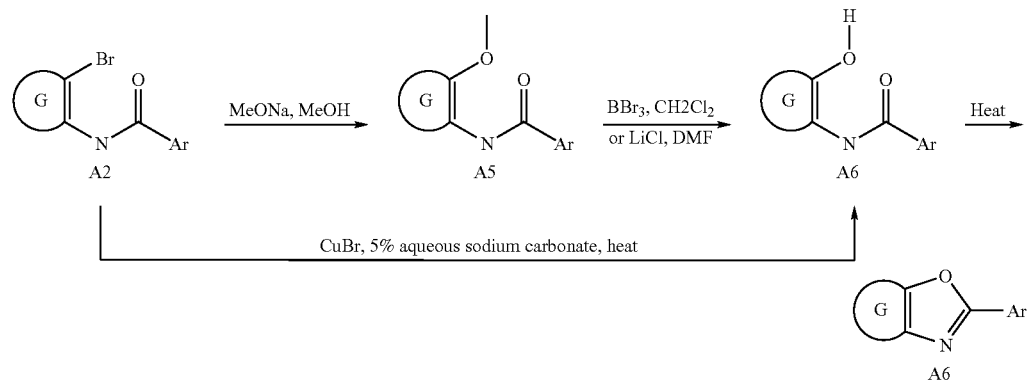

As shown in Scheme 4, the methoxy intermediate A5 can be transformed to the corresponding alcohol A6 using any of the numerous methods described in the literature (J. Org. Chem. 1974, 39, 1427; Synthesis, 1989, 287, J. Am. Chem. Soc. 1981, 103, 7007). Alternatively, the bromo intermediate A2 can be transformed directly to the alcohol A6 using copper bromide and aqueous sodium carbonate (Chem. Heterocycl. Compd. 22, 3, 1986, 265-267). The resulting alcohol type intermediates have been described to cyclize directly under heat conditions and thus may not be isolated providing directly the desired bicyclic oxazole systems (Heterocycles, 22, 10, 1984, 2309-2311).

In accordance with one aspect of the invention, there are provided methods for preparing cytokine inhibitors of the and G is selected from phenyl, pyridinyl, pyrazolyl, pyrrolyl, imidazolyl, oxazolyl, isoxazolyl or thienyl.

In yet another aspect, the invention provides a method for preparing a compound of Formula IA, wherein Ar is —(Y)-phenyl-, Y is —C(O)— and G is selected from cyclopropyl, pyrazolyl, pyrrolyl, pyrrolidiyl, imidazolyl, imidazolonyl, oxazolyl, isoxazolyl, fuiranyl or thienyl. Also provided are methods for treating such a compound, wherein Y is —C(O)— with NH$_2$OR in the presence of a second base to provide the compound IA wherein Y is —C(NOR)—, wherein the second base and reaction conditions are as described above. Hence, the invention provides methods for preparing a compound of Formula IA, wherein Ar is —C(=NOH)-phenyl-, and G is selected from pyrazolyl, pyrrolyl, imidazolyl, oxazolyl, isoxazolyl, furanyl or thienyl.

Also provided are methods for preparing a compound having Formula IB, the method comprising reacting G-X—OH with Q-L-Ar—NH$_2$ in the presence of a coupling agent and a base, or reacting Q-L-Ar—NH$_2$ with G-X—X" in the presence of a base, to yield said compound, wherein the variables Ar, G, Q, and L are as defined herein, X is C(O) or C(S) and X" is an activating moiety. In one aspect, a method is provided to prepare compounds of Formula IB, wherein Ar is —(Y)-naphthyl-, Y is —CH(OH)— or —CH$_2$— and G is selected from phenyl, pyridinyl, pyrazolyl, pyrrolyl, imidazolyl, oxazolyl, isoxazolyl or thienyl. In another aspect, a method is also provided for preparing a compound of Fomula IB, wherein Ar is -naphthyl-, G is G'-(Y)—, Y is —C(O)—, and G' is selected from phenyl, pyridinyl, pyrazolyl, pyrrolyl, imidazolyl, oxazolyl, isoxazolyl, furanyl or thienyl. Also provided are methods for treating such a compound of Formula IB, wherein Y is —C(O)— with NH$_2$OR in the presence of a second base to provide the compound IB wherein Y is —C(NOR)—, wherein the second base and reaction conditions are as described above. Hence a method is provided for preparing a compound of Formula IB, wherein Ar is -naphthyl-, G is G'-C(=NOH)—, and G' is selected from phenyl, pyridinyl, pyrazolyl, pyrrolyl, imidazolyl, oxazolyl, isoxazolyl, furanyl or thienyl.

In yet another aspect, the invention provides a method for preparing a compound of Formula IB, wherein Ar is -phenyl-, G is G'-(Y)—, Y is —C(O)—, and G' is selected from pyrazolyl, isoxazolyl or furanyl. Also provided are methods for treating such a compound of Formula IB, wherein Y is —C(O)— with NH$_2$OR in the presence of a second base to provide the compound IB wherein Y is —C(NOR)—, wherein the second base and reaction conditions are as described above. Hence, a method is provided for preparing a compound of Formula IB, wherein Ar is -phenyl-, G is G'-C(=NOH)—, and G' is selected from pyrazolyl, isoxazolyl or furanyl.

In another aspect, the invention provides a method for preparing a compound of Formula IC, wherein Ring is triazolidine dione, the method comprising reacting G-NHNHC(O)O- Et with Q-L-Ar—NCO in an aprotic solvent and cyclizing the resulting intermediate in the presence of a base to yield said compound, wherein G, Ar, L and Q are as defined previously. Typically, the aprotic solvent is DCM, chloroform, or THF and the base is an inorganic base chosen from NaOH, LiOH and K$_2$CO$_3$ or an organic base chosen from DBU, DIEA and TEA. Typically, the reaction mixture is maintained at a temperature in the range of about 0° C. to 60° C.

In another aspect, the invention provides a method for preparing a compound of Formula II, wherein X' is NH, comprising heating G(NO)—NH—CH$_2$—Ar—L-Q with an organoamine to yield said compound, wherein G, Ar, L, and Q are as defined previously. Suitable organoamines include pyridine and the like. Typically, the reaction mixture is heated to a temperature in the range of about 80° C. to about 160° C., and more typically to about 100° C. to about 140° C.

In another aspect of the invention, there are provided compounds of Formula III

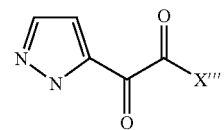

III wherein the pyrazole moiety is substituted at the 1-position, 3-position, or at both by one or more R$^1$, R$^2$ or R$^3$;

X''' is ORX or an activating moiety;

R$^x$ is H, substituted or unsubstituted C$_{1-4}$ alkyl, or substituted or unsubstituted aralkyl;

each R$^1$ is independently F, Cl, Br, I, cyano, —C(O)R, —C(O)NR$_2$, —C(O)OR, —OR, —SiR$_3$, —NR'R', —S(O)$_m$R, substituted or unsubstituted straight or branched C$_{1-10}$ alkyl, C$_{2-10}$ alkenyl, or C$_{2-10}$ alkynyl, substituted or unsubstituted C$_{3-10}$ cycloalkyl, substituted or unsubstituted C$_{5-8}$ cycloalkenyl, substituted or unsubstituted C$_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$;

each R$^2$ is independently F, Cl, Br, I, cyano, substituted or unsubstituted straight or branched C$_{1-6}$ alkyl, substituted or unsubstituted C$_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$; and each R$^3$ is independently H, substituted or unsubstituted C$_{6-10}$ aryl, substituted or unsubstituted saturated or unsaturated 3-11 member heterocyclyl or heterocyclylalkyl containing 1, 2, 3, or 4 heteroatoms selected independently from N, O, S(O)$_m$, substituted or unsubstituted C$_{3-12}$ cycloalkyl, substituted or unsubstituted C$_{5-12}$ cycloalkenyl, substituted or unsubstituted C$_{7-20}$ aralkyl, substituted or unsubstituted straight or branched C$_{1-8}$ alkyl, R$^{20}$C(O)N(R$^{21}$)—, R$^{22}$O—, R$^{23}$R$^{24}$NC(O)—, R$^{26}$(CH$_2$)$_m$C(O)N(R$^{21}$)—, R$^{26}$C(O)(CH$_2$)$_m$N(R$^{21}$)—, substituted or unsubstituted C$_{2-8}$ alkenyl, or substituted or unsubstituted C$_{2-8}$ alkynyl, wherein one or more methylene groups of the C$_{1-8}$ alkyl, C$_{2-8}$ alkenyl, or C$_{2-8}$ alkynyl are optionally replaced by O, NH, or S(O)$_m$;

R, R', R", R$^{20}$, R$^{21}$, R$^{23}$, R$^{24}$, R$^{26}$, and m are as defined in any of the compounds described herein.

The activating moiety is a group which activates the adjacent carbonyl for addition by a nucleophile such as an amine, thiol, alcohol or the like. Exemplary activating moieties include but are not limited to, F, Cl, Br, or I, substituted or unsubstituted aryloxy groups, substituted or unsubstituted heterocycloxy groups, and oxyacylalkoxy groups which form the mixed anhydride. Typically, the activating moiety is F, Cl, Br, I, —N$_3$, N-hydroxysuccinimide, 1-hydroxybenzotriazole, pentafluorophenol, pentachlorophenol, para-nitrophenol, or —O—C(O)—OR$^y$, wherein R$^y$ is lower alkyl.

The instant invention also provides for pharmaceutical compositions which may be prepared by mixing one or more compounds of Formula IA, IB, and IC or II, prodrugs thereof, pharmaceutically acceptable salts thereof, stereoisomers thereof, tautomers thereof, or solvates thereof, with pharmaceutically acceptable carriers, excipients, binders, diluents or the like to prevent and treat disorders associated with excess cytokine production. The compositions of the invention may be used to create formulations and prevent or a variety of disorders associated with excess cytokine production, e.g., diseases and pathological conditions involving inflammation. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneally, intramuscular, intra-articular, intrasynovial, intrasternal, intrathecal, intralesional and intracranial injections. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Compounds of the invention may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaquous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizes vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the invention.

Aerosols containing compounds for use according to the present invention are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present invention using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Dosage forms for the topical (including buccal and sublingual) or transdermal administration of compounds of the invention include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of the invention to the body. Such dosage forms can be made by dissolving or dispersing the agent in the proper medium. Absorption enhancers can also be used to increase the flux of the inventive compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. The compounds of this invention can be incorporated into various types of ophthalmic formulations for delivery to the eye (e.g., topically, intracamerally, or via an implant). The compounds are typically incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations. Preservatives and tonicity agents can be incorporated.

Intrathecal administration, via bolus dosage or constant infusion, allows the local administration of a compound to a region of the spinal cord, such as the dorsal horn regions, delivering the compound directly to the subarachnoid space containing the CSF (cerebrospinal fluid).

Central delivery to the spinal cord regions can also be performed by epidural injection to a region of the spinal cord exterior to the arachnoid membrane. Enhancing permeation of the active compound through meningeal membranes may be achieved by using hypertonic dosing solutions that encrease permeability of meningeal membranes, or by addition of permeation enhancers, such as, but not limited to, liposomal encapsulation, surfactants, or ion-pairing agents.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective amount of a compound of the present invention may vary depending upon the route of administration and dosage form. Effective amounts of invention compounds typically fall in the range of about 0.001 up to 100 mg/kg/day, and more typically in the range of about 0.05 up to 10 mg/kg/day. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

The following abbreviations are used throughout the application with respect to chemical terminology:
AcOH or HOAc: acetic acid
Boc: N-tert-Butoxycarbonyl
Bn: Benzyl
Cbz: Carbobenzyloxy
dba: Dibenzylidene acetone
DIEA: Diisopropylethylamine
DCM: Dichloromethane
DMF: N,N-Dimethylformamide
EDC or EDCI: 1-(3-Dimethylaminopropyl)-3-ethylcarbodiimide hydrochloride
EtOAc: Ethyl acetate
EtOH: Ethanol
Fmoc: 9-fluorenylmethyloxycarbonyl
HPLC: High Pressure Liquid Chromatography
$IC_{50}$ value: The concentration of an inhibitor that causes a 50% reduction in a measured activity.
LAH: Lithium aluminum hydride
MeCN or AcN: Acetonitrile
MeOH: Methanol
mL: Milliliter(s)
μL: Microliter(s)
PyBOP: Benzotriazol-1-yl-oxytripyrrolidinophosphonium hexafluorophosphate
rt: room temperature
THF: Tetrahydrofuran

Example 1

Synthesis of Indazole Carboxamide Derivatives

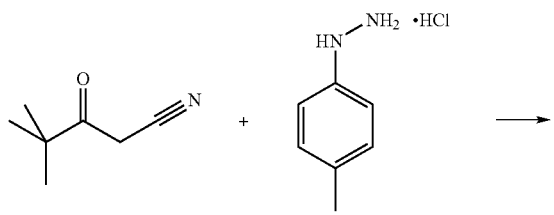

3-Amino-5-tert-butyl-2-tolyl-2H-pyrazole (1). A solution of tolyl hydrazine hydrochloride (8.0 g, 50 mmol) and 4,4-dimethyl-3-oxo-pentanenitrile (6.3 g, 50 mmol) in toluene (30 mL) was heated to reflux overnight. Removal of the volatiles in vacuo provided a residue, which was purified by silica gel chromatography using 30% ethyl acetate in hexanes as the eluent. Concentration in vacuo provided 3-amino-5-tert-butyl-2-tolyl-2H-pyrazole as a brown solid (10.5 g, 92%). LC-MS analysis of the compound indicates the desired product is present with a purity >99%. Calculated mass=229. Observed mass=230.

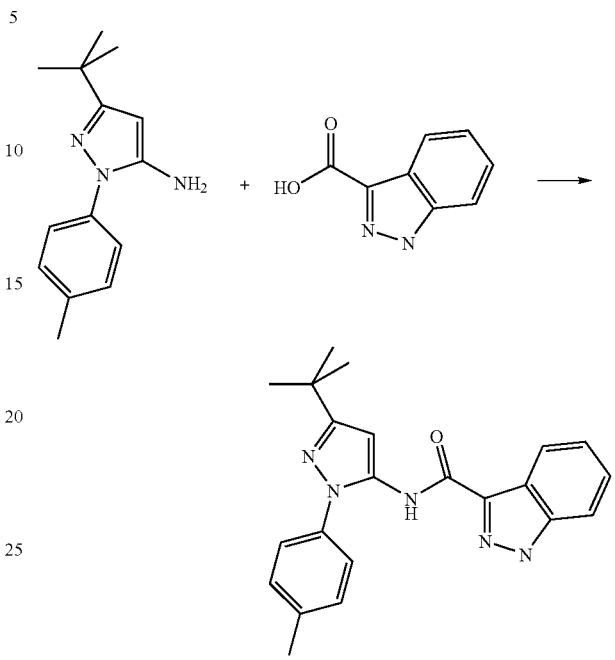

1H-Indazole-3-carboxylic acid (5-tert-butyl-2-p-tolyl-2H-pyrazol-3-yl)-amide (2). To a solution of indazole-3-carboxylic acid (28 mg, 0.17 mmol), EDC (50 mg, 0.26 mmol), and diisopropylethylamine (61 μL, 0.35 mmol) in $CH_2Cl_2$ (3.5 mL) was added 3-amino-5-tert-butyl-2-tolyl-2H-pyrazole (46 mg, 0.20 mmol). After being stirred for 14 h at room temperature, the mixture was diluted with water (10 mL) and extracted with $CH_2Cl_2$ (2×10 mL). The combined organic layer was washed with brine, dried ($MgSO_4$), and concentrated in vacuo. Purification by preparative HPLC (MeCN/$H_2O$) provided 25 mg of the indazolopyrazole (40%). LC-MS: Calculated mass=373. Observed mass=374.

General Procedure for Preparation of indazole-3-carboxylic acids

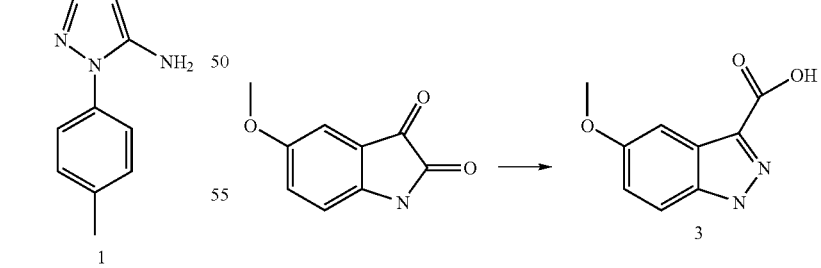

5-Methoxy-1H-indazole-3-carboxylic acid (3). In a 1L round bottom three neck-flask equipped with a mechanical stirrer, a thermometer and a funnel were added 110 mL of water, 6 mL of concentrated sulfuric acid at −5° C. To the cooled solution was added a solution of 10 g of 5-methoxy isatin, 3.9 g of sodium nitrite, 2.6 g of sodium hydroxide in 65 mL of water. After stirring for 15 min, the reaction mixture was allowed to warm up to 0° C. and a solution of $SnCl_2$ (35 g in 50 mL of concentrated HCl) was added drop wise. Stirring was continued for 1 hour at room temperature then the precipitate was collected and crystallized in EtOH providing 3 g of product ready to use for the next step. LC-MS: Calculated mass=192. Observed mass=193.

Example 2

Synthesis of Imidazolopyrazole Derivatives

2-Alkyl(aryl)imidazolopyrazoles were prepared from 5-tert-butyl-2-p-tolyl-2H-pyrazol-3-ylamine (compound 1 above).

finally with water again. The organic phase was dried over Na$_2$SO$_4$, concentration gave 115 mg NMR pure product (yield: 69%). LC-MS: Calculated mass=333. Observed mass=334.

Acylation of aminopvrazole in pyridine: A solution of the 2-aminopyrazole (115 mg, 0.5 mmol), benzoyl chloride (63.3 µL, 0.55 mmol) and DMAP (3 mg, 0.025 mmol, 5 mol %) in 2 mL pyridine was shaken at 85° C. over night (15 h). After evaporation and co-evaporation with toluene, the solid residue was dissolved in 2 mL DCM, subjected to sequential ISCO purification (4 g column, 0-40% B; A=PCM, B=10%

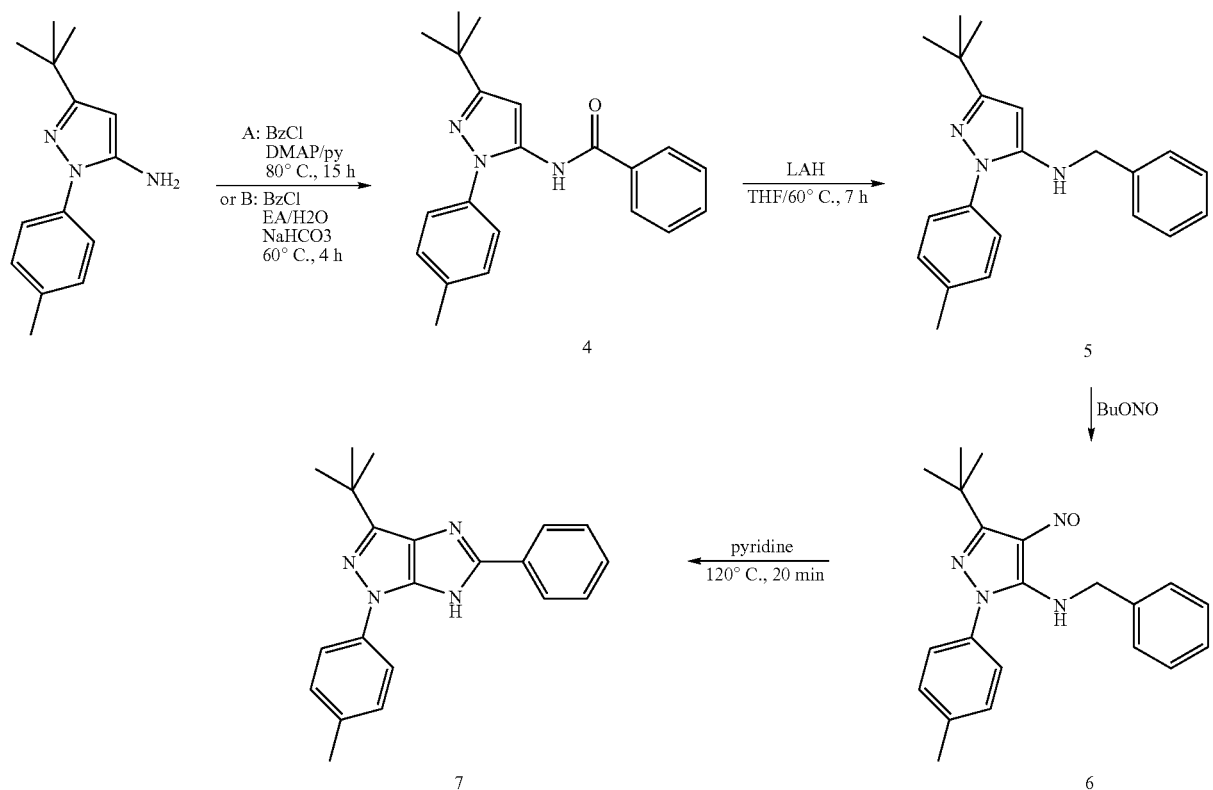

Scheme 5

Method A

General Procedure for N-acylation of Aminopyrazole

Two different procedures were used to acylate aminopyrazole, as shown in Scheme 5 and described below.

N-(5-tert-butyl-2-p-tolyl-2H-pyrazol-3-yl)-benzamide (4)

Acylation of aminopvrazole in ethyl acetate/water. 2-Aminopyrazole (115 mg, 0.5 mmol) was dissolved in 2.5 mL EtOAc and a solution of NaHCO$_3$ (46 mg, 0.55 mmol) in 1 mL of water was added. To this vigorously stirred mixture was added a solution of benzoyl chloride (57.5 µL, 0.5 mmol) in 1.5 mL of ethyl acetate at room temperature. The resulting mixture was stirred at 60° C. for 4h. After cooling down to room temperature, ethyl acetate was added. The organic phase was washed with 5% Na$_2$CO$_3$, water, 1 N HCl and MeOH in DCM). Evaporation of the fractions containing product gave 134 mg pure material. Yield: 80%. Calculated mass=333. Observed mass=334.

General Procedure for Reduction of the Amide with Lithium Aluminum Hydride

Benzyl-(5-tert-butyl-2-p-tolyl-2H-pyrazol-3-yl)-amine (5). The starting amide (167 mg, 0.5 mmol) was dissolved in 0.5 mL anhydrous THF. To this solution was added 1.5 mL IM LAH in THF (1.5 mmol) at 4° C. The resulting solution was shaken at 60° C. for 7 h. After cooling down with ice-water, the reaction mixture was basified with aqueous KOH (pH 9-10). The suspension was filtered with Celite and washed with THF. The filtrate was concentrated and the residue was dissolved in ethyl acetate and washed with water. The organic phase was dried over Na$_2$SO4, filtered and evaporated to dryness to give 156 mg brown oil. The compound was analyzed by LC-MS and NMR. Yield: 89%. Calculated mass=319. Observed mass=320.

General Procedure for Nitrosylation of N-alkylaminopyrazole

Benzyl-(3-nitroso-5-tert-butyl-2-p-tolyl-2H-pyrazol-3-yl)-amine (6). Two drops of concentrated HCl and 2 drops of H$_2$O were added to 1 mL ethanol followed by addition of BuONO (270 μL, 2.3 mmol, 5 eq). This solution was added dropwise to a solution of N-alkylaminopyrazole (148 mg, 0.46 mmol) in 1 mL ethanol at 4° C. The reaction mixture was stirred at 4° C. for 30 min then at room temperature for 2 h. After concentration, the solid residue was dissolved in 2 mL of DCM and subjected to sequential column purification (12g column, 0-40% B; A=DCM; B=10% MeOH in DCM). Yield: 48%, 76.9 mg. LC-MS: Calculated mass=348. Observed mass=349.

General Procedure for Cyclization 3-tert-Butyl-5-phenyl-1-p-tolyl-1,6-dihydro-imidazo[4,5-c]pyrazole (7). A solution of the nitroso compound (76 mg, 0.21 mmol) in 3 mL pyridine was heated in a microwave at 120° C. for 20 min. The reaction mixture was cooled down to room temperature and the solvent was co-evaporated with toluene. The residue was dissolved in 3 mL dichloromethane and subjected to column purification to give 46.9 mg of product. Yield=68%. LC-MS: Calculated mass=330. Observed mass=331.

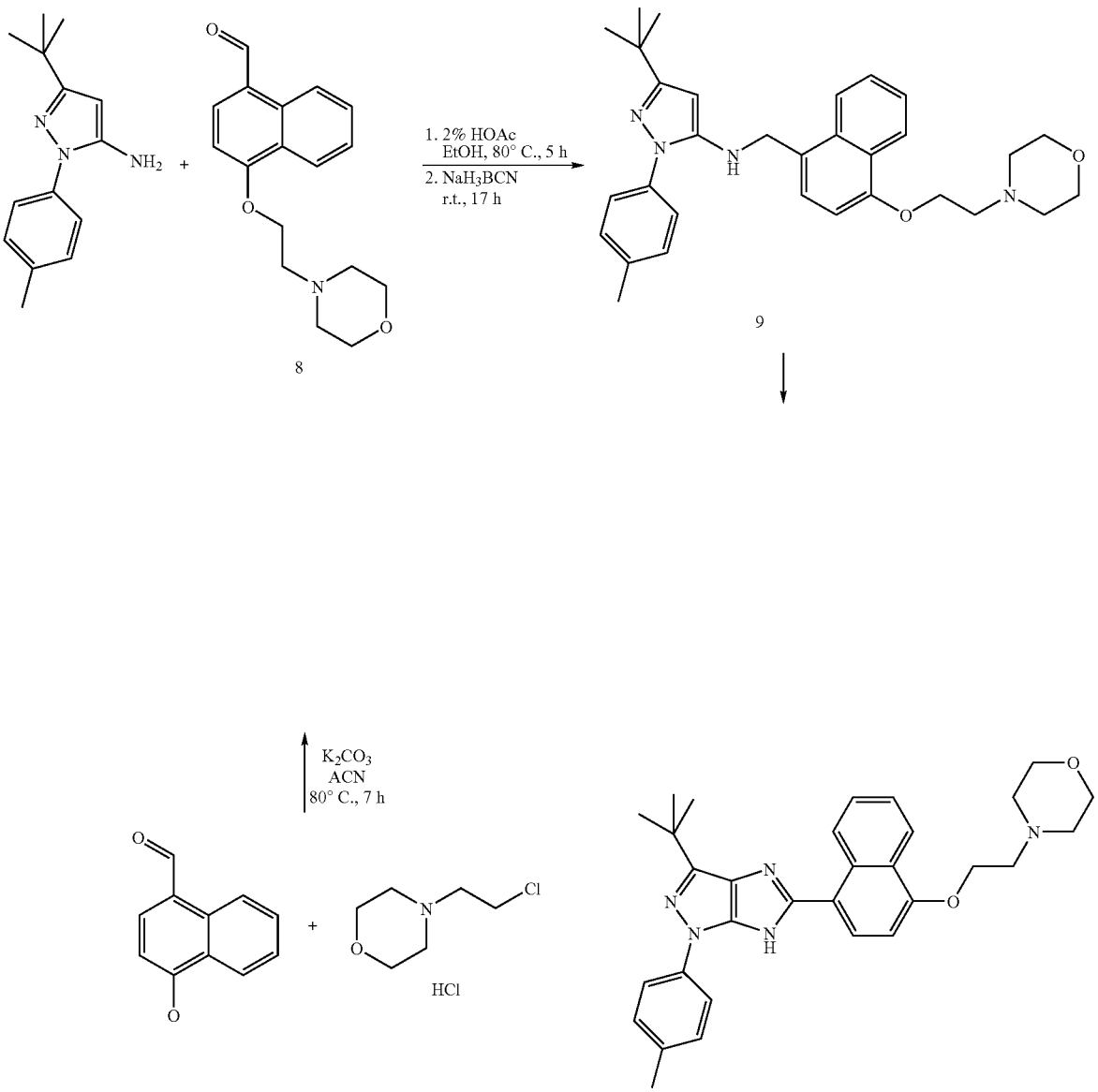

Method B

General Procedure for O-Alkylation of 4-hydroxy-1-arylaldehydes 4-(Morpholin-4-yl-ethyloxy)-1-naphthylaldehyde (8). A mixture of 4-hydroxy-1-naphthaldehyde (258 mg, 1.5 mmol), N-(2-chloroethyl)morpholine hydrochloride (307 mg, 1.65 mmol, 1.1 eq) and $K_2CO_3$ (915 mg, 6.6 mmol, 4 eq) in 12 mL acetonitrile was stirred vigorously at 80° C. for 7 h. After filtration, the deep blue filtrate was concentrated to give deep green oil, which crystallized slowly. TLC:(silica) $R_f$=0.18 in ethyl acetate. The compound was analyzed by LC-MS. This crude product was carried directly to next step reaction. Calculated mass=285. Observed mass=286.

General Procedure for Reductive Amination of Aminopyrazole (5-tert-Butyl-2-p-tolyl-2H-pyrazol-3-yl)-[4-(2-morpholin-4-yl-ethoxy)-naphthalen-1-ylmethyl]-amine (9). Aminopyrazole (344 mg, 1.5 mmol) and the aldehyde from the previous step (1.5 mmol, 1 eq) were dissolved in 4 mL EtOH, 80 µL HOAc was added. The resulting solution was shaken at 80° C. for 5 h. After cooling down to room temperature, sodium cyanoborohydride (282 mg, 3 eq) was added. The resulting solution was shaken at room temperature overnight (15 h). After evaporation, the residue was dissolved in ethyl acetate, washed with aqueous $NaHCO_3$ then with water. The organic phase was concentrated and the residue was dissolved in DCM and subjected to column purification to give 540 mg of a foam. Yield: 72.3%. LC-MS: Calculated mass=498. Observed mass=499.

3-tert-Butyl-5-[4-(2-morpholin-4-yl-ethoxy)-naphthalen-1-yl]-1-p-tolyl-1,6-dihydro-imidazo[4,5-c]pyrazole (10). The title compound was prepared using the general procedure for cyclization as described above. Calculated mass=509. Observed mass=510.

Example 3

Synthesis of Alpha-Ketoamides

Method A: Via naphthalene-1-yl-oxo-acetic acid

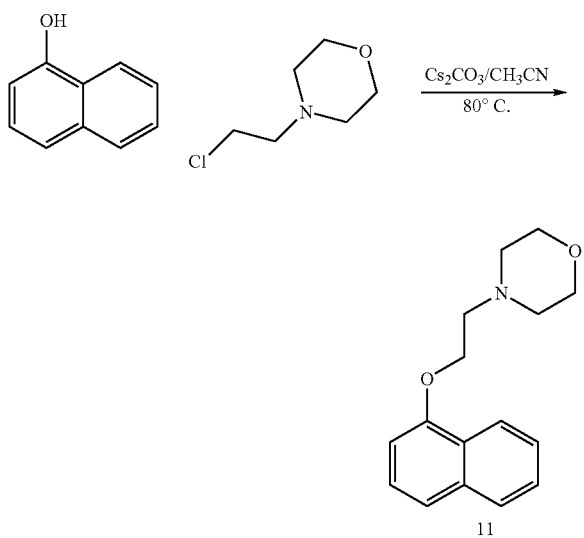

4-[2-(Naphthalen-1-yloxy)-ethyl]-morpholine (11). 2-Hydroxy-naphthylene (1.0 g, 5.37 mmol) was dissolved in acetonitrile (50 mL). To this solution was added cesium carbonate (4.0 g, 12.3 mmol) or potassium carbonate (2.97 g, 21.5 mmol) followed by addition of 2-chloroethylmorpholine (0.774 g, 5.37 mmol). The mixture was allowed to stir at 80° C. overnight and then cooled to room temperature. The resulting mixture was filtered, diluted with EtOAc and extracted with saturated $NaHCO_3$ three times, with 0.1 M NaOH one time, washed with brine, dried over $MgSO_4$, filtered, and the solvent removed under reduced pressure to give a crude brown oil. The oil was purified by column chromatography providing the desired compound 11 as a light yellow oil with a 64% to 83% yield. Calculated mass=257. Observed mass=258.

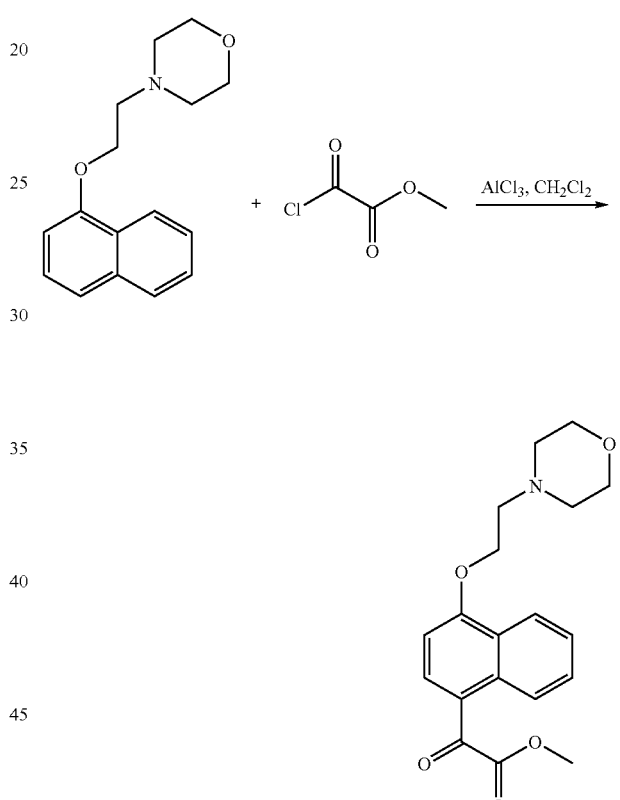

[4-(2-Morpholin-4-yl-ethoxy)-naphthalen-1-yl]-oxo-acetic acid methyl ester (12). To a round bottom flask was added $CH_2Cl_2$ (100 mL) followed by the addition of $AlCl_3$ (2.2 g, 16.3 mmol). The suspension was stirred 5 min at room temperature, methylchloroglyoxylate (1.66 mL, 17.88 mmol) was added and stirred an additional 5 min, followed by the addition of 11 (0.841 g, 3.27 mmol). The mixture was stirred at room temperature overnight, quenched with water, neutralized with $NaHCO_3$ and extracted with EtOAc three times. The combined organic extracts were washed with brine, dried over $MgSO_4$, filtered and the solvent removed leaving a brown oil. The material was purified by column chromatography (0-5% MeOH/$CH_2Cl_2$) providing 1.08 g of 12 (97%) as a yellow solid. LC-MS: Calculated mass=343. Observed mass=344.

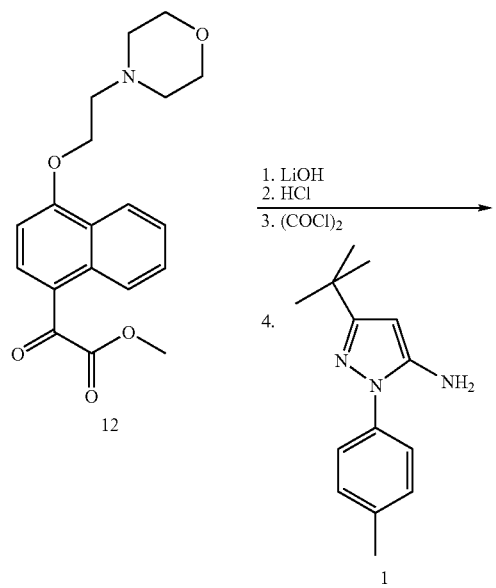

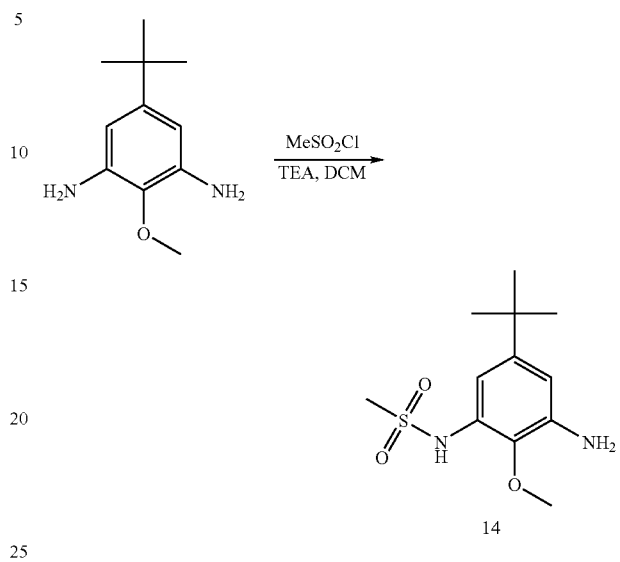

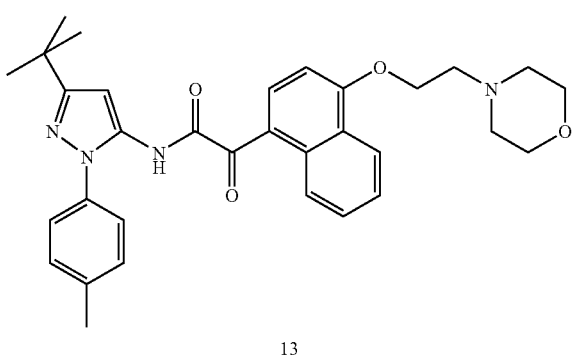

N-(5-tert-Butyl-2-p-tolyl-2H-pyrazol-3-yl)-2-[4-(2-morpholin-4-yl-ethoxy)-naphthalen-1-yl]-2-oxo-acetamide, (13). Compound 12 (0.224 g, 0.653 mmol) was dissolved in THF (20 mL). To this solution was added 1 N LiOH (3 eq, 1.96 mmol). The solution was allowed to stir for 2 hours then neutralized with 4 N HCl in dioxane and the solvent was evaporated providing a white solid. The residue was dried under high vacuum at 80° C. for 30 minutes and then suspended in CH$_2$Cl$_2$ (50 mL). To the suspension was added oxalyl chloride (0.56 mL, 6.53 mmol) and few drops of DMF. The suspension was stirred at room temperature for 2 hrs then the solvent evaporated. The resulting solid was suspended in ethyl acetate (20 mL) and added to 5-amino-3-t-butyl-1-(4-methylphenyl)pyrazole (1) (0.159 g, 0.663 mmol) dissolved in ethyl acetate (20 mL) and a 50% NaHCO$_3$ solution (10 mL) and stirred overnight at 60° C. The mixture was diluted with ethyl acetate and extracted with NaHCO$_3$. The combined organic layers were washed with brine, dried over MgSO$_4$, filtered and the solvent removed leaving a brown oil. The material was purified by column chromatography (50-100% EtOAc/Hexanes) or (0-5% methanol/DCM) providing 0.346 g (98%) of the desired compound as a yellow solid. LC-MS: Calculated mass=540. Observed mass=541.

Preparation of Additional Building Blocks and General Methods for Their Incorporation N-(3-Amino-5-tert-butyl-2-methoxy-phenyl)-methane-sulfonamide (14). To an oven dried 250 mL round bottom flask containing 5.0 g (25.73 mmol) 5-tert-butyl-2-methoxy-benzene-1,3-diamine, 150 mL DCM was added. The reaction mixture was cooled to 0° C. after which triethylamine (5.0 mL, 36.0 mmol) was added followed by the drop wise addition of methylsulfonyl chloride (1.99 mL, 25.7 mmol). The reaction was allowed to stir at 0° C. for 30 min. then warmed to room temperature stirring for an additional 2 h. The reaction mixture was poured over saturated solution of sodium bicarbonate (100 mL) and the layers separated. The aqueous layer was washed twice more with 50 mL dichloromethane and the combined organic layers were dried over magnesium sulfate and concentrated under vacuum to afford a crude oil that was purified by flash chromatography (silica gel, 1:1 EtOAc:Hex) to yield 6.1 g of the desired product (87%). Calculated mass=272. Observed mass=273

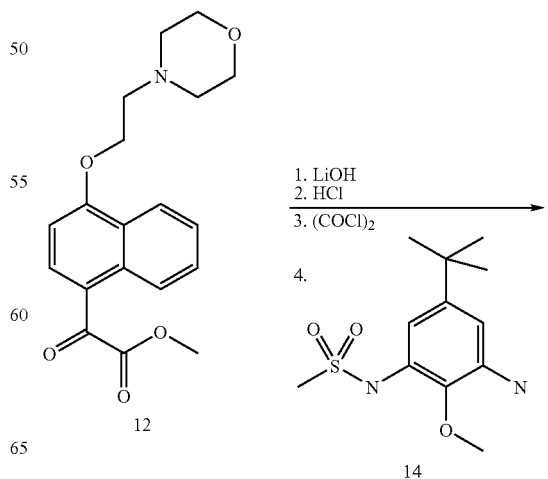

-continued

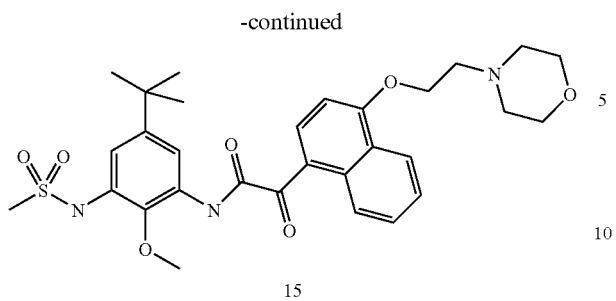

15

N-(5-tert-Butyl-3-methanesulfonylamino-2-methoxy-phenyl)-2-[4-(2-morpholin-4-yl-ethoxy)-naphthalen-1-yl]-2-oxo-acetamide (15). The title compound was prepared by the same method described for compound 13 starting from compound 12 and compound 14. Calculated mass=583. Observed mass=584.

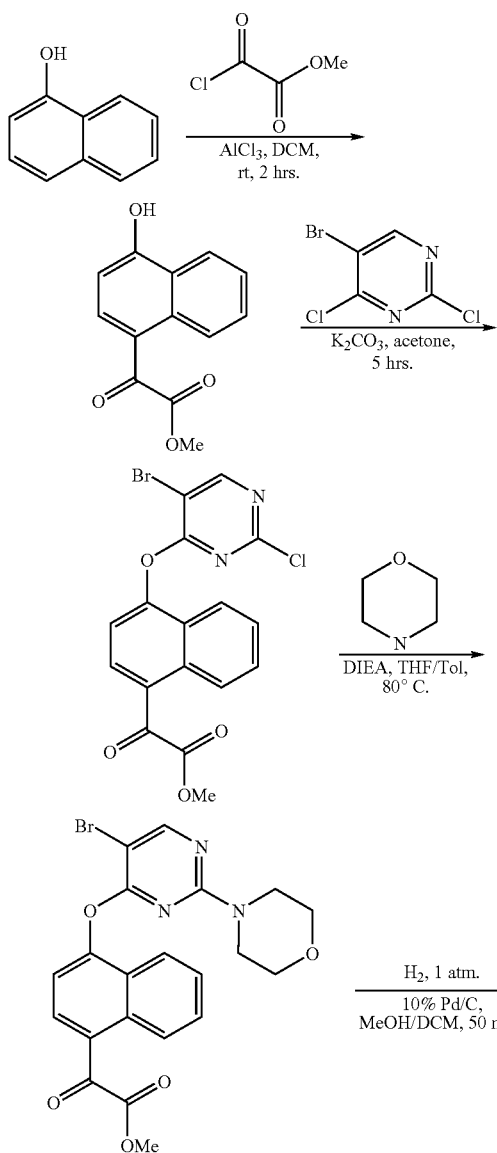

-continued

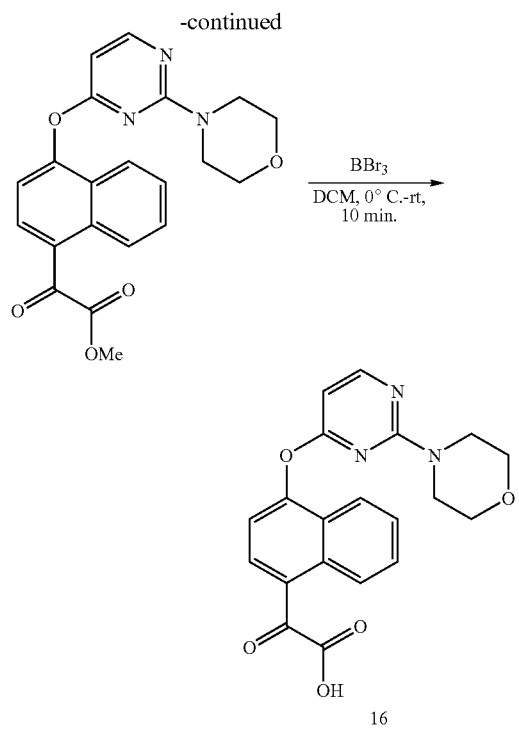

(4-Hydroxy-naphthalen-1-yl)-oxo-acetic acid methyl ester. To a suspension of AlCl$_3$ (1.11 g, 8.3 mmol) in 50 mL DCM, methylchloroglyoxylate (1.02 g, 8.3 mmol) was added. The resulting solution was stirred for 5 min., after which naphthalen-1-ol (1 g, 6.9 mmol) was added. After stirring for 2 hrs at room temperature, water was added and the phases were separated, after which the organic layer was washed with water and dried over MgSO$_4$. The residue obtained after evaporation of the organic solvent was purified by column chromatography (10-30% EtOAc/Hex), to afford the target compound in 38% yield. Calculated mass=230. Observed mass=231.

[4-(5-Bromo-2-chloro-pyrimidin-4-yl-oxy)-naphthalen-1-yl]-oxo-acetic acid methyl ester. The compound obtained in the previous reaction (1.37 g, 6 mmol) was dissolved in 30 mL acetone. 5-Bromo-2,4-dichloro-pyrimidine (1.36 g, 6 mmol) and K$_2$CO$_3$ (2.05 g, 14.8 mmol) was added and the reaction was stirred at 60° C. for 5 hrs. The acetone Was evaporated, the residue was taken up in DCM and the solution was run through a bed of silica gel. A white solid in 75% yield was obtained after evaporation of the solvent. Calculated mass=421. Observed mass=422.

[4-(5-Bromo-2-morpholin-4-yl-pyrimidin-4-yloxy)-naphthalen-1-yl]-oxo-acetic acid methyl ester. The compound obtained as described above (0.50 g, 1.19 mmol) was dissolved in THF/Toluene 8/2. Morpholine (0.124 mL, 2.97 mmol) and DIEA (0.5 mL, 2.97 mmol) were added and the solution was stirred at 80° C. overnight. The acetone was evaporated and the residue was purified by column chromatography (10-30% EtOAc/Hex) to yield 80% of the target compound. Calculated mass=472. Observed mass=473.

[4-(2-Morpholin-4-yl-pyrimidin-4-yl-oxy)-naphthalen-1-yl]-oxo-acetic acid methyl ester. The compound obtained above (108 mg, 0.228 mmol) was dissolved in MeOH/DCM 3/1, 10% Pd/C (30 mg) was added and the compound was hydrogenated for 50 min. at 1 atm H$_2$. The reaction mixture was filtered and concentrated in vacuo. The resulting residue was dissolved in DCM and purified by column chromatography (10-30% EtOAc/Hex) to yield 67% of the target product. Calculated mass=393. Observed mass=394.

[4-(2-Morpholin-4-yl-pyrimidin-4-yl-oxy)-naphthalen-1-yl]-oxo-acetic acid (16). The product from the previous reaction (66 mg, 0.168 mmol) was dissolved in DCM and cooled to 0° C. A 1M solution of BBr₃ in DCM (0.2 mL, 0.202 mmol) was added and the reaction was allowed to warm up to rt over 10 min. Water was added to the mixture and the product was extracted into EtOAc. The organic layer was dried over MgSO₄, evaporated and the residue was triturated with hexanes to afford the target product quantitatively. Calculated mass=379. Observed mass=380.

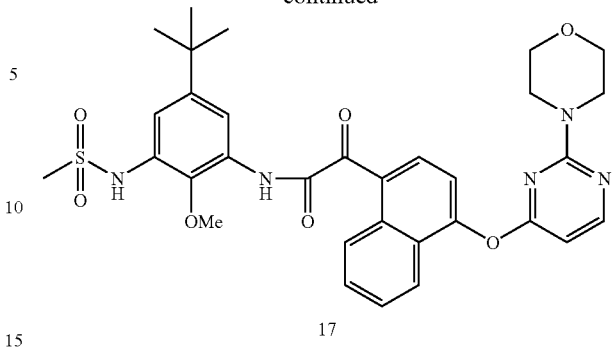

N-(5-tert-Butyl-3-methanesulfonylamino-2-methoxy-phenyl)-2-[4-(2-morpholin-4-yl-pyrimidin-4-yloxy)-naphthalen-1-yl]-2-oxo-acetamide (17). [4-(2-Morpholin-4-yl-pyrimidin-4-yl-oxy)-naphthalen-1-yl]-oxo-acetic acid (16) obtained above (36 mg, 0.095 mmol) was dissolved in 2 mL DCM and oxalyl chloride (0.08 mL, 0.949 mmol) was added, followed by catalytic DMF. The reaction mixture was stirred at rt, after which N-(3-amino-5-tert-butyl-2-methoxy-phenyl)-methanesulfonamide (14) (26 mg, 0.096 mmol) and DIEA (0.05 mL, 0.284 mmol) were added, and stirring was continued for 12 hr. The reaction mixture was concentrated in vacuo and the residue was purified by LC/MS (10-100% AcN/H₂O over 8.5 min.) Calculated mass=444. Observed mass=444.

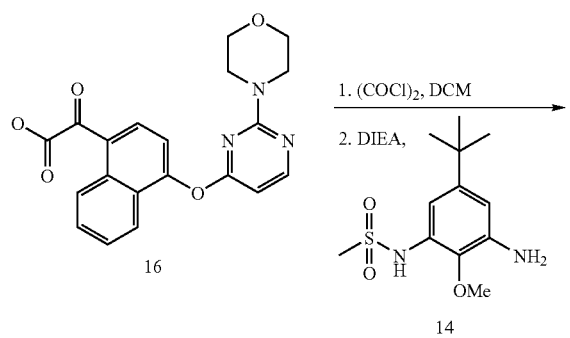

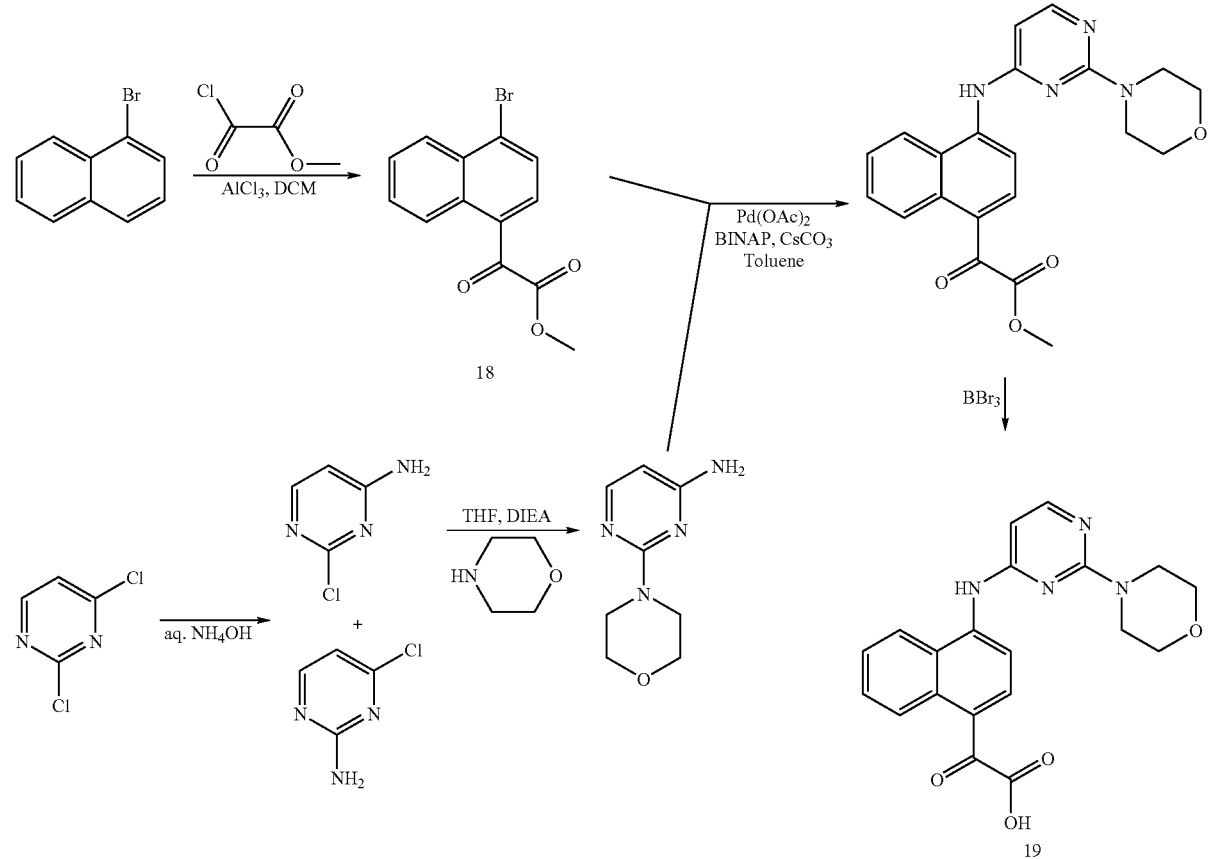

(4-Bromo-naphthalen-1-yl)-oxo-acetic acid methyl ester (18). To a suspension of AlCl$_3$ (3.20 g, 24 mmol) in 100 mL DCM at 0° C., methylchloroglyoxylate (2.2 mL, 24 mmol) was added. The resulting solution was stirred for 5 min., after which 1-bromo-naphthalene (5 g, 24 mmol) was added. After stirring for 2 hrs at room temperature, water was added and the phases were separated, after which the organic layer was washed with water and dried over MgSO$_4$. The residue obtained after evaporation of the organic solvent was purified by column chromatography (0-30% EtOAc/Hex), to afford 2.6 g of the target compound. $^1$H NMR (CDCl$_3$): 8.92 (1H, d, J=9.3 Hz, H-arom); 8.31 (1H, d, J=9.3 Hz, H-arom); 7.82 (1H, d, J=8.8 Hz, H-arom); 7.72 (1H, d, J=8.8 Hz, H-arom); 7.57-7.68 (2H, m, H-arom); 3.94 (3H, s, OMe).

2-Chloro-pyrimidyl-4-yl-amine. 2,4-Dichloro-pyrimidine (7.45 g, 50 mmol) was stirred in 150 mL aqueous NH$_4$OH overnight. Chloroform was added to the mixture and the organic and aqueous solvents were separated. The organic layer was washed with water and dried over MgSO$_4$. The residue obtained after evaporation of the organic solvent was purified by column chromatography (0-100% EtOAc/Hex), to afford 1.5 g of the target compound and 2 g of the regioisomer. Calculated mass=129. Observed mass=130.

2-Morpholin-4-yl-pyrimidin-4-ylamine. The compound obtained in the previous reaction (166 mg, 1.286 mmol) was dissolved in 2 mL THF. DIEA (0.1 mL and morpholine (134 mg, 1.5 mmol) were added and the reaction was stirred at 75° C. overnight. The solvents were removed under reduced pressure, the residue was dissolved in DCM and purified by column chromatography (50-100%EtOAc/Hex) to yield the target product in 88% yield. Calculated mass=180. Observed mass=181.

[4-(2-Morpholin-4-yl-pyrimidin-4-ylamino)-naphthalen-1-yl]-oxo-acetic acid methyl ester. 2-Morpholin-4-yl-pyrimidin-4-ylamine (140 mg, 0.77 mmol) and (4-bromo-naphthalen-1-yl)-oxo-acetic acid methyl ester (18) (228 mg, 0.77 mmol) were suspended in 5 mL toluene and Pd(OAc)$_2$ (5 mg, 3 mol %), BINAP (24 mg, 5 mol5) and CS$_2$CO$_3$ (753 mg, 2031 mmol) were added. The reaction mixture was stirred at 100° C. for 24hrs. The cooled mixture was purified by column chromatography (0-100% EtOAc/Hex) to yield 169 mg of target product.

[4-(2-Morpholin-4-yl-pyrimidin-4-ylamino)-naphthalen-1-yl]-oxo-acetic acid. The product from the previous reaction (170 mg, 0.433 mmol) was dissolved in DCM and cooled to 0° C. A 1M solution of BBr$_3$ in DCM (0.52 mL, 0.52 mmol) was added and the reaction was allowed to stir for 35 min. Water was added to the mixture and the solvents were evaporated to yield 160 mg of the crude target product, which was used as such in the coupling reaction.

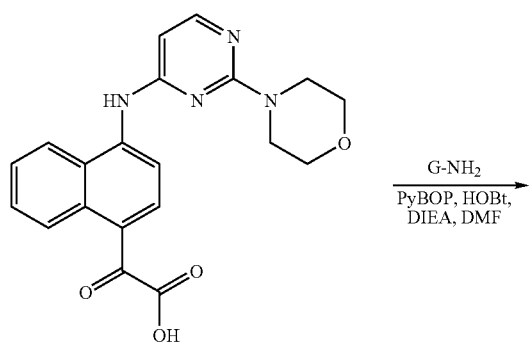

General procedure for coupling of G-NH$_2$ and [4-(2-morpholin-4-yl-pyrimidin-4-ylamino)-naphthalen-1-yl]-oxo-acetic acid. The product from the previous reaction (17 mg, 0.044 mmol) was dissolved in 1.5 mL DMF and the amine component G-NH$_2$ was added (2 eq., 0.88 mmol), followed by the addition of PyBOP (46 mg, 0.088 mmol), HOBt (14 mg, 0.088 mmol), and DIEA (0.02 mL, 0.088 mmol). The reaction was stirred overnight and the crude mixtures were purified by LC/MS (10-100% AcN), affording final compounds. The described method was applied to yield compounds as exemplified in Table 1.

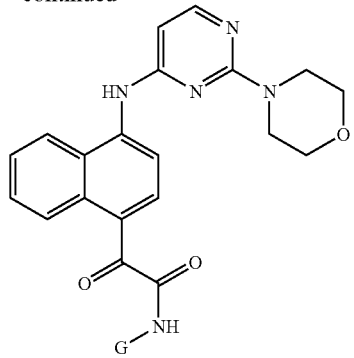

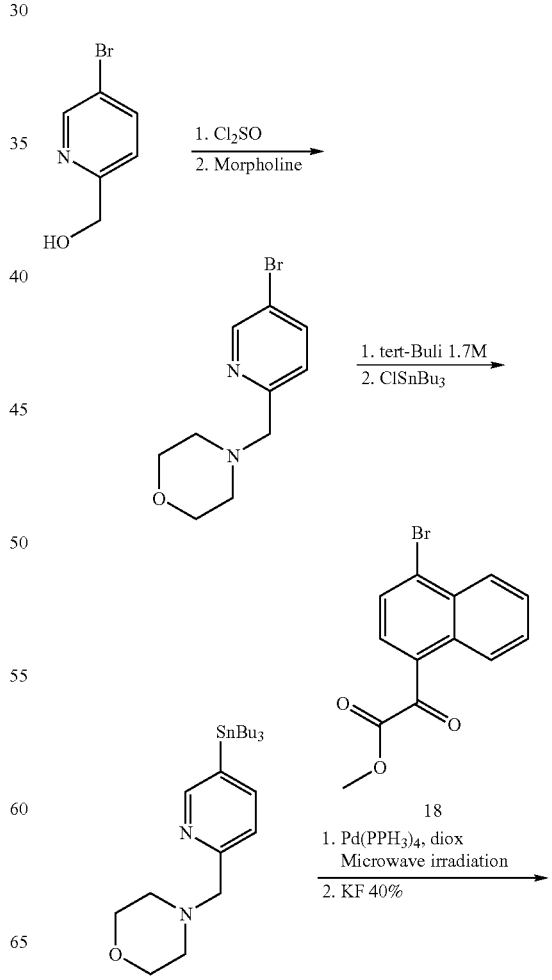

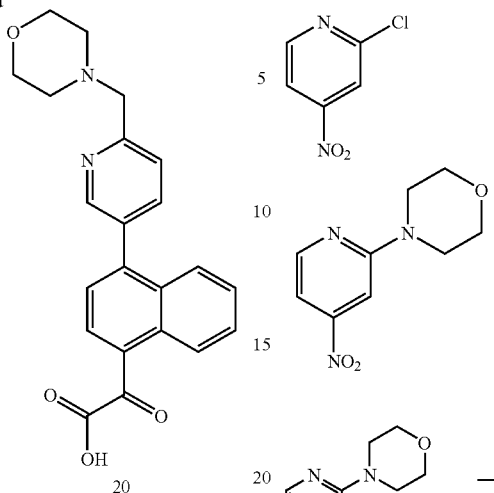

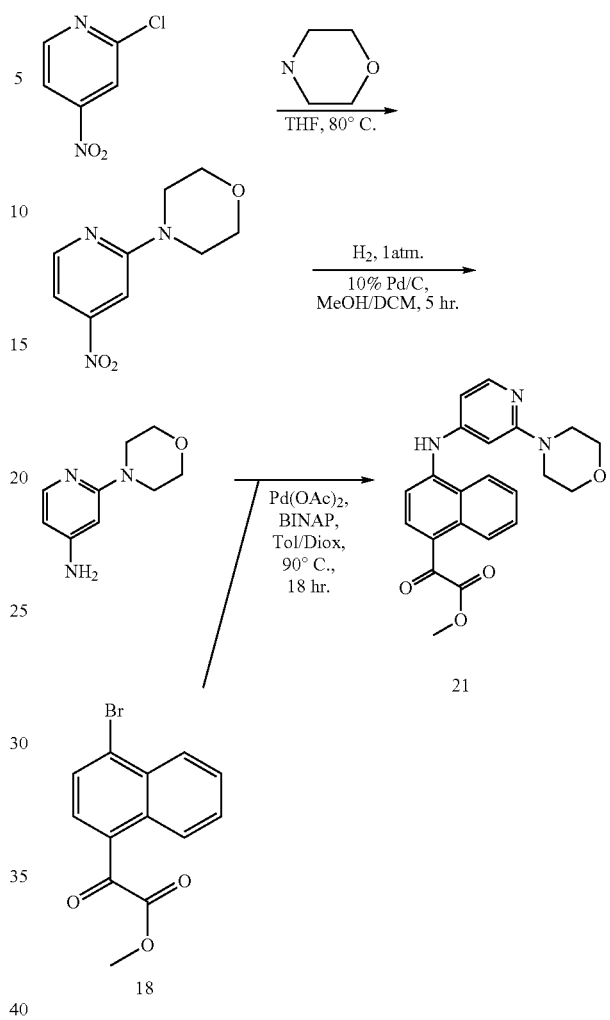

4-(5-Bromo-pyridin-2-ylmethyl)-morpholine. Thionyl chloride (0.57 g, 5 mmol) in DCM (2 mL) was added dropwise to a stirred solution of (5-bromo-pyridin-2-yl)-methanol (0.3 g, 1.59 mmol) in DCM (5 mL) while cooling to 0° C. The mixture was allowed to warm to room temperature and, after 1 h, evaporated to low volume in vacuo. The residue was dissolved in CHCl$_3$, and a solution of morpholine (0.41 g, 5 mmol) in CHCl$_3$ was added at 0° C. After 3 h, the reaction was completed. The solvent was evaporated and addition of ether afforded the target compound (85%) as a white solid. Calculated mass=257. Observed mass=258

4-(5-Tri-butylstannanyl-pyridin-2-ylmethyl)-morpholine. To a solution of the compound obtained above (0.35 g, 1.3 mmol) in dry THF, a solution of tert-Buli 1.7 M (1.7 mL, 2.2 eq) was added while cooling to −78° C. After 10 minutes and at the same temperature ClSnBu$_3$ (2.2 eq, 1.2 g) was added and the reaction mixture was stirred for 15 minutes. Then a pH 7 K$_2$HPO$_4$/KH$_2$PO$_4$ buffer was added and the residue was extracted with EtOAc and dried over MgSO$_4$ to give the target compound in 81% yield. Calculated mass=467. Observed mass=469.

[4-(6-Morpholin-4-ylmethyl-pyridin-3-yl)-naphthalen-1-yl]-oxo-acetic acid (20). 4-(5-Tri-butylstannanyl-pyridin-2-ylmethyl)-morpholine (0.47 g, 1.59 mmol) and (4-Bromo-naphthalen-1-yl)-oxo-acetic acid methyl ester (18) (0.6 g, 1.3 mmol) and catalytic tetrakis(triphenylphosphine)palladium (O) were dissolved in 2 mL anhydrous 2,4-dioxane under nitrogen atmosphere. The tube was heated under microwave irradiation for 10 minutes at 150° C. After cooling to room temperature the mixture was diluted with EtOAc, and a solution of KF 40% was added. The organic phase was separated and the aqueous layer was evaporated and purified by LC-MS to afford the target product in 54% yield. Calculated mass=376. Observed mass=376.

N-(5-tert-Butyl-3-methanesulfonylamino-2-methoxyphenyl)-2-[4-(6-morpholin-4-ylmethyl-pyridin-3-yl)-naphthalen-1-yl]-2-oxo-acetamide (302). The target compound 302 was obtained via acid chloride formation and coupling with (1b) as described above. Calculated mass=631. Observed mass=631.

4-(4-Nitro-pyridin-2-yl)-morpholine. To a solution of 2-chloro, 4-nitropyridine (0.2 g, 1.27 mmol) in THF (3 mL) was added morpholine (328 mg, 38.1 mmol). The reaction was heated to 80C and stirred overnight. The solvent was evaporated and the residue purified by column chromatography (2/1 Hex/EtOAc) to yield 150 mg of the target compound.

2-Morpholin-4-yl-pyridin-4-ylamine. The compound obtained above (40 mg, 0.86 mmol) was dissolved in MeOH/DCM 5/2, 10% Pd/C (40 mg) was added and the compound was hydrogenated for 5 hr. at 1 atm H$_2$. The reaction mixture was filtered and concentrated in vacuo. The resulting residue was purified by column chromatography (½ EtOAc/Hex) to yield 157 mg of the target product.

[4-(2-Morpholin-4-yl-pyridin-4-ylamino)-naphthalen-1-yl]-oxo-acetic acid methyl ester (21). 2-Morpholin-4-yl-pyridin-4-ylamine (159 mg, 0.88 mmol) and (4-Bromo-naphthalen-1-yl)-oxo-acetic acid methyl ester (18) (260 mg, 0.89 mmol) were suspended in 6 mL toluene/Dioxane 1/1 and Pd(OAc)$_2$ (6 mg, 3 mol %), BINAP (27 mg, 5 mol %) and CS$_2$CO$_3$ (858 mg, 2.64 mmol) were added. The reaction mixture was stirred from 80° C. to 80° C. over 18 hrs. The cooled mixture was purified by column chromatography (0-100% EtOAc/Hex) to yield 140 mg of product. This product was subjected to the methods described previously to obtain the final compounds of interest.

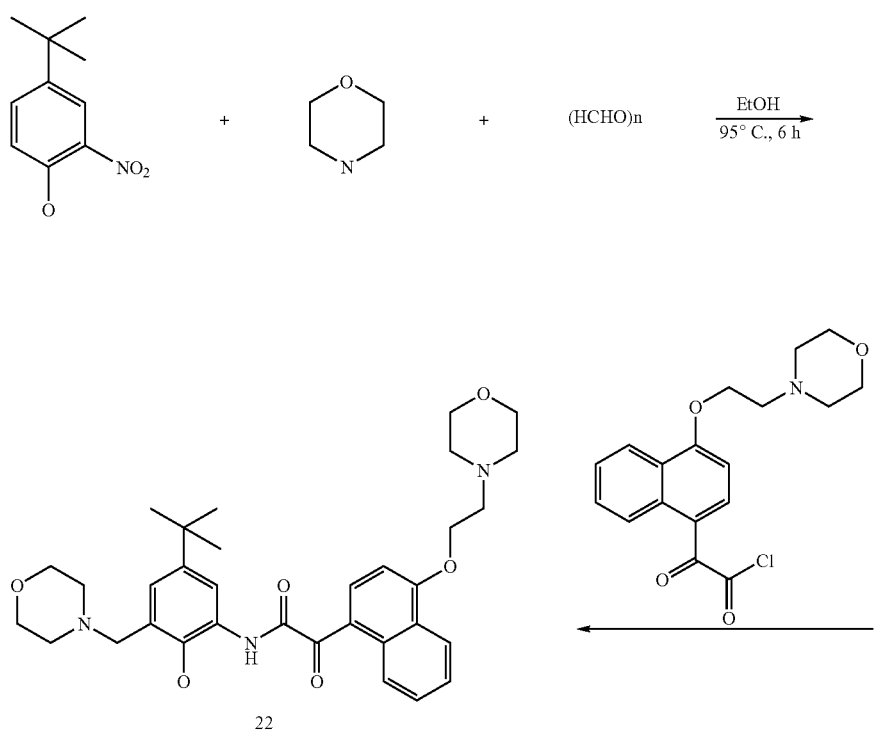

4-tert-Butyl-2-morpholin-4-ylmethyl-6-nitro-phenol. A solution of 4-t-butyl-2-nitro-phenol (980 mg, 5 mmol), morpholine (50 mmol) and paraformaldehyde (1.5 g, 50 mmol) in 20 mL ethanol was heated in a sealed vial at 95° C. for 6 hr. After removal of the solvent and morpholine, the residue was purified via silica gel column chromatography to afford 1.75 g target compound as a yellow solid.

2-Amino-4-tert-butyl-6-morpholin-4-ylmethyl-phenol. The compound obtained as described above (294 mg, 1 mmol) was heated with tin(II) chloride dihydrate (1.36 g, 6 mmol) in 2 mL conc. HCl at 90° C. for 2 hr. After cooling down, the reaction mixture was diluted with water, and diethyl ether was added. The reaction mixture was neutralized by addition of solid $K_2CO_3$ to pH=9. Extraction was done with diethyl ether and the combined organic phases were dried over sodium sulfate. Evaporation afforded 222 mg pure product as a white solid.

N-(5-tert-Butyl-2-hydroxy-3-morpholin-4-ylmethyl-phenyl)-2-[4-(2-morpholin-4-yl-ethoxy)-naphthalen-1-yl]-2-oxo-acetamide (22). To a solution of the product obtained (66 mg, 0.25 mmol) and DIEA (87μl, 0.5 mmol) in 5 mL DCM, the acid chloride (obtained as described above) (0.5 mmol) was added. The resulting mixture was stirred at rt overnight. After aq. sodium bicarbonate work-up and following silica gel column purification the final product was obtained in 59.8 mg yield. Calculated mass=575.7. Observed mass=575.7

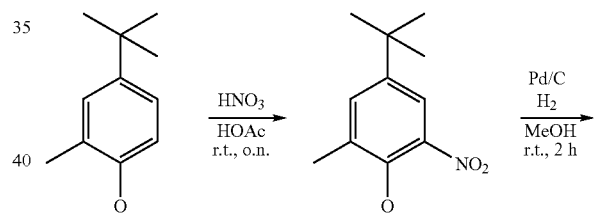

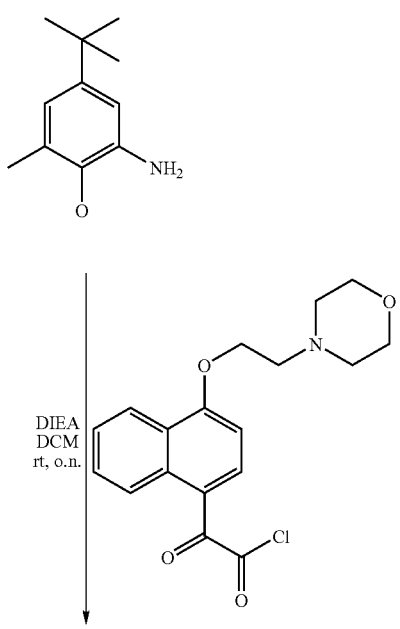

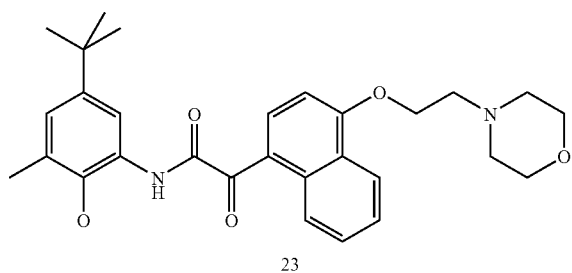

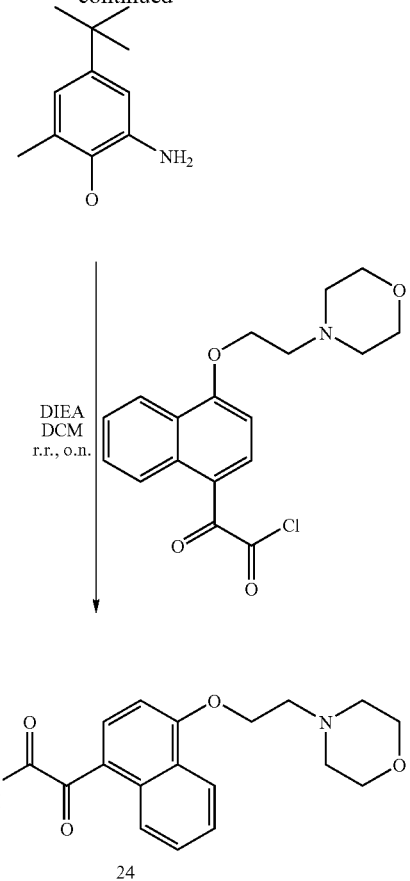

4-tert-Butyl-2-methyl-6-nitro-phenol. 4-tert-Butyl-2-methyl-phenol (1.64 g, 10 mmol) was dissolved in 15 mL acetic acid, fuming nitric acid (0.47 mL, 10 mmol) was added and the resulting solution was stirred at rt overnight. The reaction mixture was then poured onto crushed ice, and extracted with chloroform. The organic phase was washed with water, and dried over sodium sulfate. Evaporation gave 2.02 g the nitration product as a red oil.

N-(5-tert-Butyl-2-hydroxy-3-methyl-phenyl)-2-[4-(2-morpholin-4-yl-ethoxy)-naphthalen-1-yl]-2-oxo-acetamide (23). The nitro-compound obtained (31 mg) was reduced with Pd/C and $H_2$ in 3 mL MeOH at rt for 2 hr. After filtration and removal of the solvent the residue was dissolved in 2 mL DCM, DIEA (0.25 mmol) was added followed by addition of [4-(2-Morpholin-4-yl-ethoxy)-naphthalen-1-yl]-oxo-acetyl chloride (0.1 mmol). Stirring was continued at rt overnight. Purification of the residue obtained after evaporation of the solvent by LC-MS afforded 9.5 mg final product. Calculated mass=491. Observed mass=491

5-tert-Butyl-2-methoxy-1-methyl-3-nitro-benzene. 4-tert-Butyl-2-methyl-6-nitro-phenol (209 mg, 1 mmol) was dissolved in 3 mL acetone. 552 mg $K_2CO_3$ (4 eq) was added, followed by addition of MeI (0.33 mL, 5 mmol). The reaction mixture was stirred vigorously at 60° C. overnight. After removal of the acetone, the residue was shaken with DCM. Filtration and evaporation of the solution yielded 221 mg product which was used as such.

N-(5-tert-Butyl-2-methoxy-3-methyl-phenyl)-2-[4-(2-morpholin-4-yl-ethoxy)-naphthalen-1-yl]-2-oxo-acetamide (24). The product obtained above (56 mg, 0.25 mmol) was reduced with Pd/C and $H_2$ in 5 mL MeOH at rt for 5 hr. After filtration and removal of solvent, the residue was dissolved in 4 mL DCM. DIEA (0.5 mmol) was added followed by addition of the acid chloride (0.2 mmol). The reaction was continued at rt overnight. After aq. sodium bicarbonate work-up and silica gel column chromatography, the final product was obtained in 46.8 mg yield. Calculated mass=505. Observed mass=505

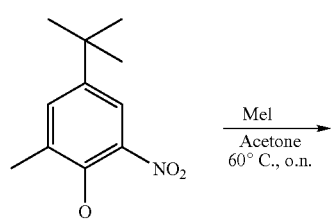

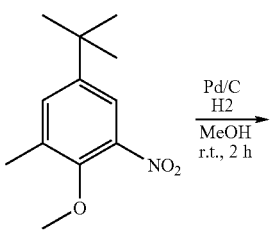

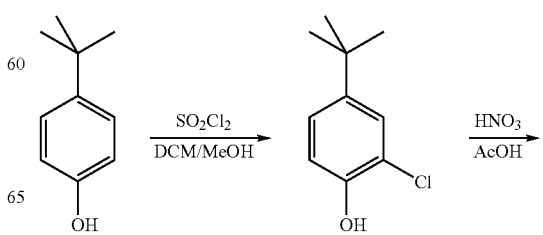

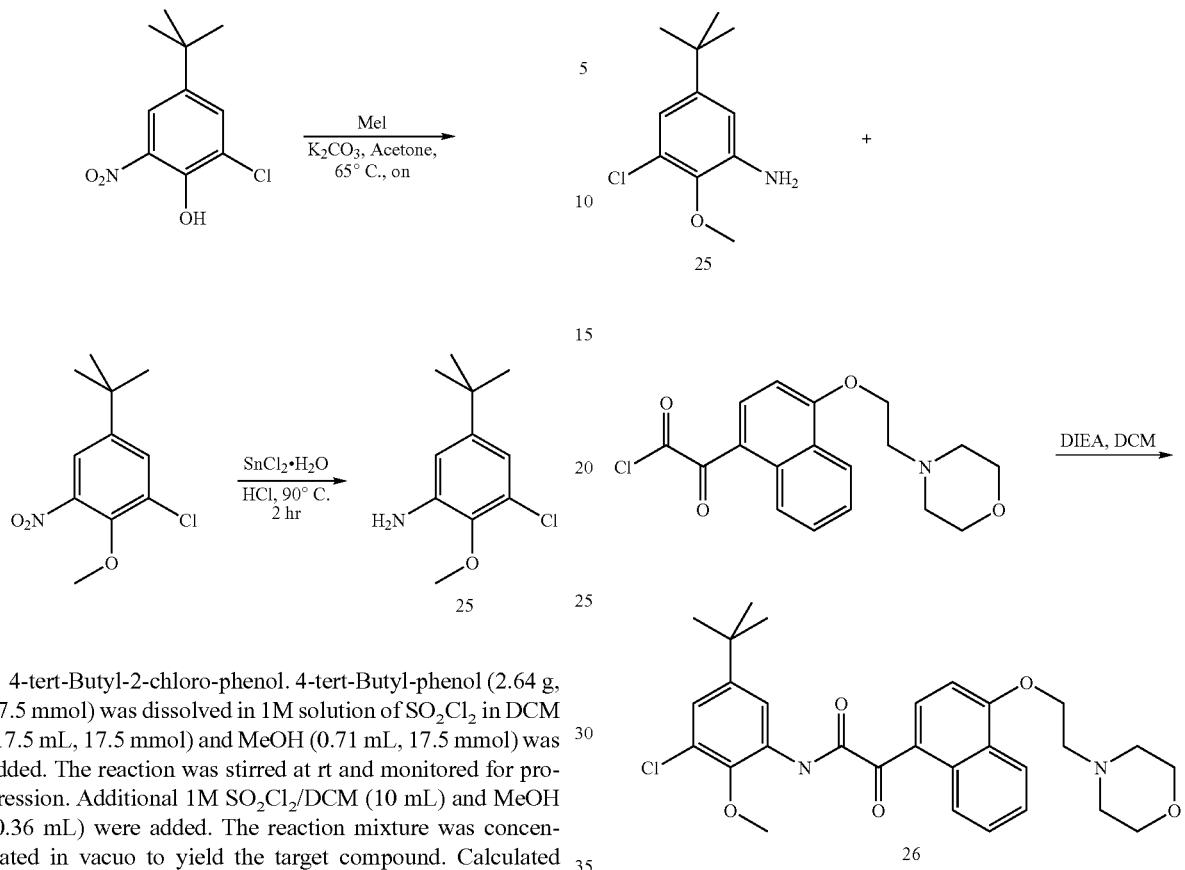

4-tert-Butyl-2-chloro-phenol. 4-tert-Butyl-phenol (2.64 g, 17.5 mmol) was dissolved in 1M solution of $SO_2Cl_2$ in DCM (17.5 mL, 17.5 mmol) and MeOH (0.71 mL, 17.5 mmol) was added. The reaction was stirred at rt and monitored for progression. Additional 1M $SO_2Cl_2$/DCM (10 mL) and MeOH (0.36 mL) were added. The reaction mixture was concentrated in vacuo to yield the target compound. Calculated mass=186. Observed mass=187

4-tert-Butyl-2-chloro-6-nitro-phenol. The product obtained above (0.585 g, 3.17 mmol) was dissolved in 6 mL AcOH, cooled to 0° C. and $HNO_3$ (0.16 mL, 3.5 mmol) was added. The reaction was allowed to warm up to room temperature, after which water was added and the compound was extracted into EtOAc. The organic layer was dried over $MgSO_4$, the solution was concentrated and the concentrate was filtered through silica gel to yield 0.306 g of target compound. Calculated mass=209. Observed mass=210

5-tert-Butyl-1-chloro-2-methoxy-3-nitro-benzene. 4-tert-Butyl-2-chloro-6-nitro-phenol (0.214 g, 0.934 mmol) was dissolved in 3 mL acetone and $K_2CO_3$ (0.65 g, 4.7 mmol) and MeI (0.58 mL, 9.3 mmol) were added. The reaction was stirred at 65° C. overnight, after which the solvent was removed under reduced pressure. The residue was taken up in DCM, the organic layer was washed with water, dried over $MgSO_4$ and concentrated to yield 0.15 g of target product.

5-tert-Butyl-3-chloro-2-methoxy-phenylamine (25). 5-tert-Butyl-1-chloro-2-methoxy-3-nitro-benzene (157 mg, 0.646 mmol) was dissolved in 3 mL concentrated HCl and $SnCl_2 \cdot 2H_2O$ (0.874 g, 3.87 mmol) was added. The reaction was stirred at 90° C. for 2 hrs, after which water was added and the product extracted into diethyl ether. The organic layer was dried over $MgSO_4$ and concentrated. The residue was purified by column chromatography (2/1 Hex/EtOAc) to yield 100 mg of final product. Calculated mass=213. Observed mass=214

N-(5-tert-Butyl-3-chloro-2-methoxy-phenyl)-2-[4-(2-morpholin-4-yl-ethoxy)-naphthalen-1-yl]-2-oxo-acetamide (26). 5-tert-Butyl-3-chloro-2-methoxy-phenylamine (25) (77 mg, 0.36 mmol) was dissolved in 10 mL DCM. [4-(2-Morpholin-4-yl-ethoxy)-naphthalen-1-yl]-oxo-acetyl chloride (0.54 mmol), prepared as described before, and DIEA (0.37 mL, 1.44 mmol) were added and the reaction was stirred on. The reaction mixture was evaporated and the residue was purified by LC/MS (10-100% AcN). Calculated mass=524. Observed mass=525

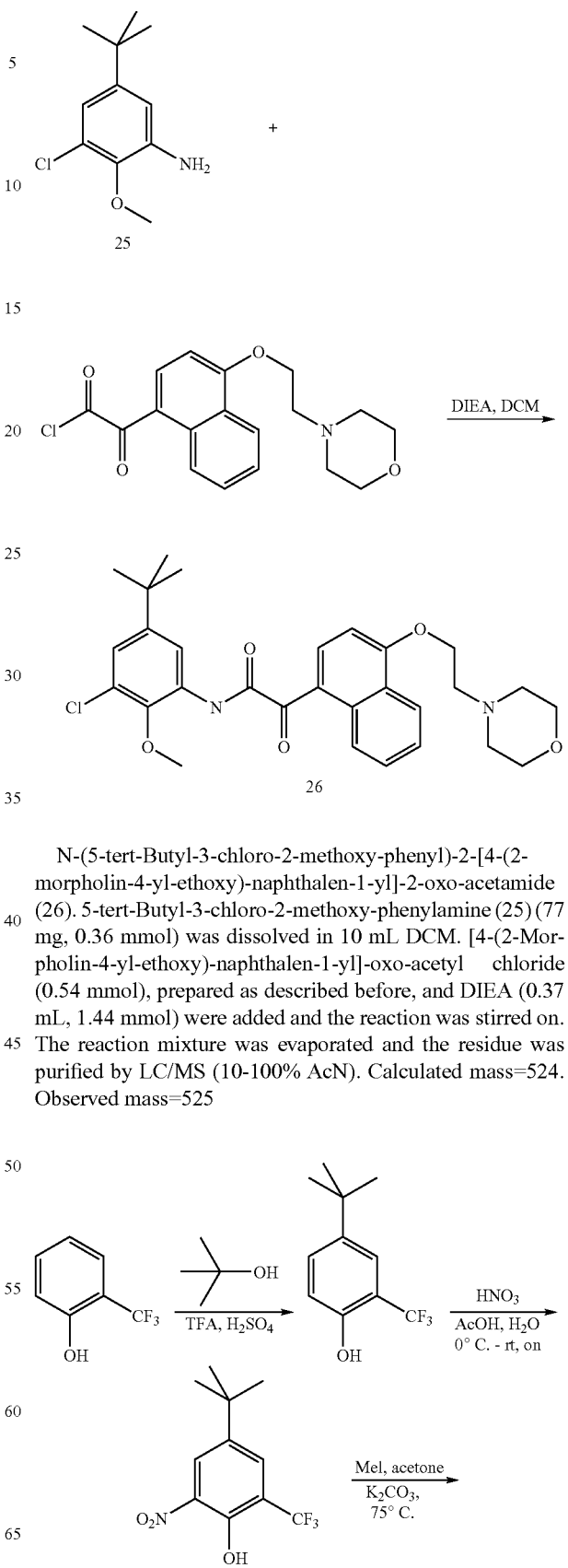

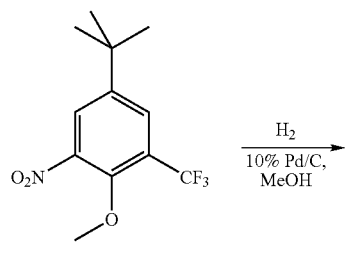

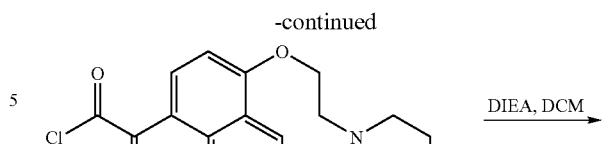

4-tert-Butyl-2-trifluoromethyl-phenol. 2-Trifluoromethyl-phenol (2.98 g, 18.3 mmol) was dissolved in 12 mL TFA and t-butanol (1.43 g, 19.3 mmol) and $H_2SO_4$ (0.24 mL) were added. The reaction was stirred at rt for 48 hrs, after which water was added and the compound was extracted into DCM. The organic layer was dried over $MgSO_4$ and concentrated in vacuo. The residue was purified by column chromatography (2/1 Hex/EtOAc) to yield 2.01 g of the target compound.

4-tert-Butyl-2-trifluoromethyl-6-nitro-phenol. 4-tert-Butyl-2-trifluoromethyl-phenol (70 mg, 0.32 mmol) was dissolved in 3 mL AcOH/1.5 mL water and cooled to 0° C. $HNO_3$ (1.5 mL) and catalytic $H_2SO_4$ were added and the reaction was allowed to warm to room temperature. Stirring was continued overnight, after which water was added and the compound was extracted into EtOAc. The organic layer was dried over $MgSO_4$ and concentrated to yield 34 mg of final compound. Calculated mass =263. Observed mass=264

5-tert-Butyl-2-methoxy-1-trifluoromethyl-3-nitro-benzene. The compound obtained above (34 mg, 0.163 mmol) was dissolved in 3 mL acetone and $K_2CO_3$ (112 mg, 0.81 mmol) and MeI (0.1 mL, 1.63 mmol) were added. The reaction was stirred at 75° C. The mixture was concentrated and the residue was dissolved in DCM. The organic layer was filtered, dried over $MgSO_4$ and concentrated. The residue was purified by column chromatography (10-30% EtOAc/Hex) to yield 30 mg target compound. Calculated mass=277. Observed mass=278

5-tert-Butyl-2-methoxy-3-trifluoromethyl-phenylamine (27). The compound obtained above (100 mg, 0.0.36 mmol) was dissolved in MeOH, 10% Pd/C (50 mg) was added and the compound was hydrogenated at 1 atm $H_2$. The reaction mixture was filtered and concentrated in vacuo. The resulting residue was dissolved in DCM and purified by column chromatography (4/1 EtOAc/Hex) to yield 72 mg of the target product. Calculated mass=247. Observed mass=248

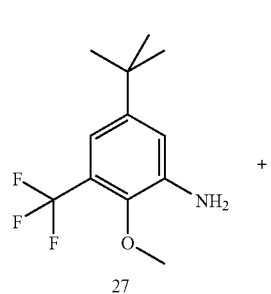

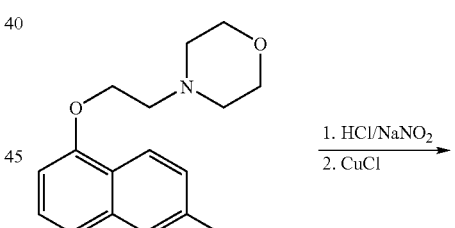

N-(5-tert-Butyl-2-methoxy-3-trifluoromethyl-phenyl)-2-[4-(2-morpholin-4-yl-ethoxy)-naphthalen-1-yl]-2-oxo-acetamide (28). 5-tert-Butyl-2-methoxy-3-trifluoromethyl-phenylamine (32 mg, 0.165 mmol) was dissolved in 2 mL DCM. [4-(2-Morpholin-4-yl-ethoxy)-naphthalen-1-yl]-oxo-acetyl chloride (0.232 mmol), prepared as described before, and DIEA (0.02 mL, 0.50 mmol) were added and the reaction was stirred on. The reaction mixture was evaporated and the residue was purified by LC/MS (10-100% AcN). Calculated mass=558. Observed mass=559

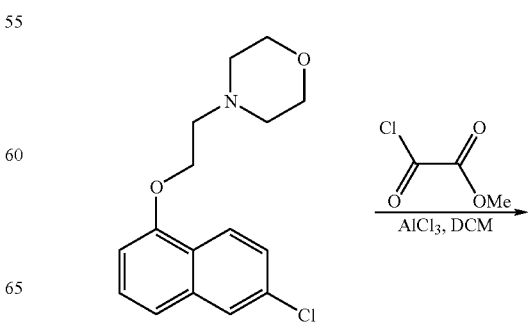

-continued

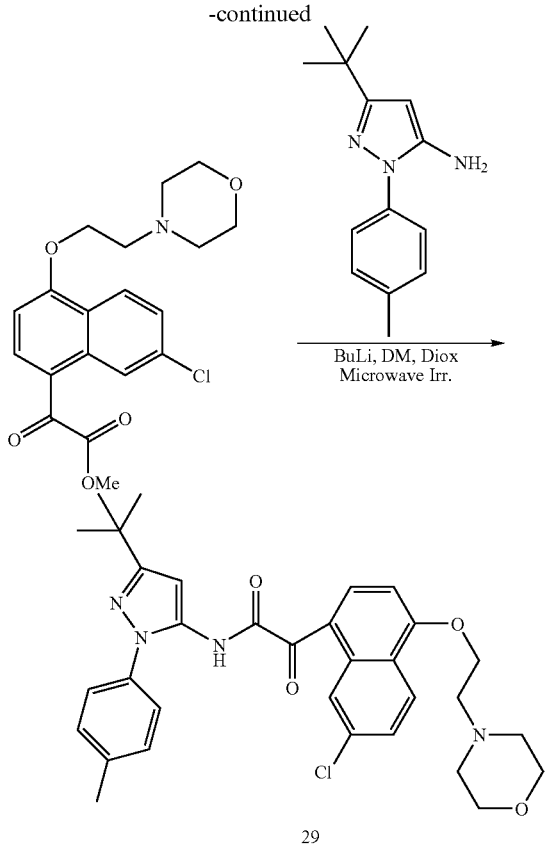

29

4-[2-(6-Chloro-naphthalen-1-yloxy)-ethyl]-morpholine. To a suspension of the amine (1.0 g, 3.67 mmol) in 6M HCl (1.8 mL, 11.01 mmol), NaNO₂ (253 mg, 3.67 mmol) was added and the reaction was stirred at 0° C. for 1 hr. To this mixture CuCl (363 mg, 3.67 mmol) was added, whereby gas evolved. The reaction was heated to 100° C. and stirred for 1 hr. The mixture was extracted with DCM, the organic layer was dried and evaporated to give 9% of the target product. Calculated mass=291. Observed mass=291.

[7-Chloro-4-(2-morpholin-4-yl-ethoxy)-naphthalen-1-yl]-oxo-acetic acid methyl ester. To a suspension of AlCl₃ (430 mg, 3.30 mmol) in DCM, methylchloroacetate (0.30 mL, 3.30 mmol) was added, whereby the AlCl₃ dissolved. To this solution 4-[2-(6-Chloro-naphthalen-1-yloxy)-ethyl]-morpholine (95 mg, 0.33 mmol) was added dropwise. The mixture was stirred overnight at room temperature. The mixture was diluted with DCM, the organic layer was washed with water, dried over MgSO₄ and evaporated to yield 83% of target material. Calculated mass=378. Observed mass=378.

N-(5-tert-Butyl-2-p-tolyl-2H-pyrazol-3-yl)-2-[7-chloro-4-(2-morpholin-4-yl-ethoxy)-naphthalen-1-yl]-2-oxo-acetamide (29). To a solution of 5--tert-butyl-2-p-tolyl-2H-pyrazol-3-ylamine (50 mg, 0.22 mmol) in 1 mL dioxane, BuLi (0.11 mL, 2M in cHex) was added and the mixture was left standing for 10 min. To this mixture a solution of the ester (83 mg, 0.22 mmol) in 1 mL DMF was added and the resulting mixture was heated in the microwave at 150° C. for 5 min. The mixture was washed with water, dried over MgSO₄ and evaporated. The residue was purified by LC/MS to yield 12% of the desired product. Calculated mass=575. Observed mass=575.

General Procedure for Synthesis of Amido-anisidine Derivatives

Method a.

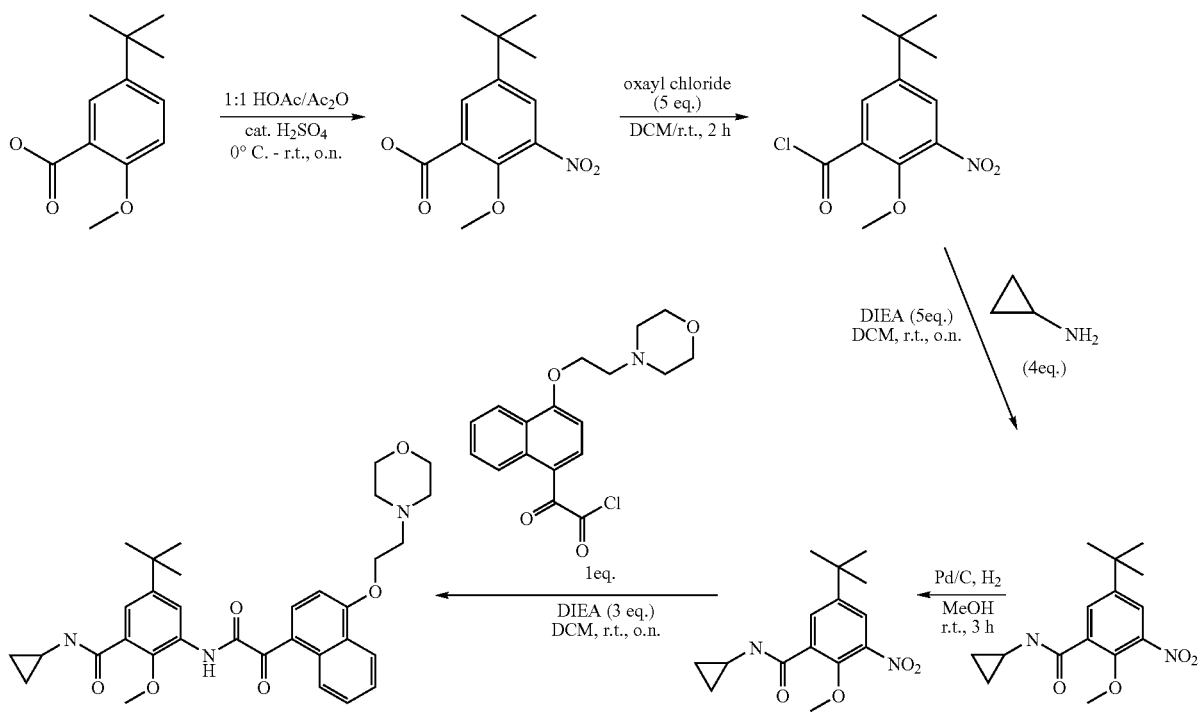

30

5-t-Butyl-2-methoxy-3-nitrobenzoic acid. To a solution of 5-t-butyl-2-methoxybenzoic acid (5.5 g, 26 mmol) in 30 mL AcOH and 30 mL acetic anhydride, a catalytic amount (ca. 5 drops) of conc. sulfuric acid was added. The resulting reaction was stirred at rt overnight. After the reaction, the reaction mixture was poured in ca. 1.2 L ice-water. A white precipitate formed which was filtered and washed with water. After drying under vacuum at 80° C., 5.98 g (91%) pure product as determined by NMR was obtained as white solid. $^1$H NMR (500 MHz, CDCl$_3$): 1.39 (s, 9H), 4.08 (s, 3H), 8.02 (s, 1H), 8.32 (s, 1H)

DCM. DIEA (1.0 mL, 6 mmol) was added, followed by addition of the acid chloride (2 mmol). The resulting suspension was stirred at rt overnight, after which DCM was added to the reaction. The organic layer was washed with aq. sodium bicarbonate and water. The organic phase was dried over sodium sulfate, concentrated and the residue was purified by silica gel column purification (ISCO Optix 7×12 gram column) to give 948 mg product as light yellow foam (yield: 82.6%). Calculated mass=574. Observed mass=574.

Method b.

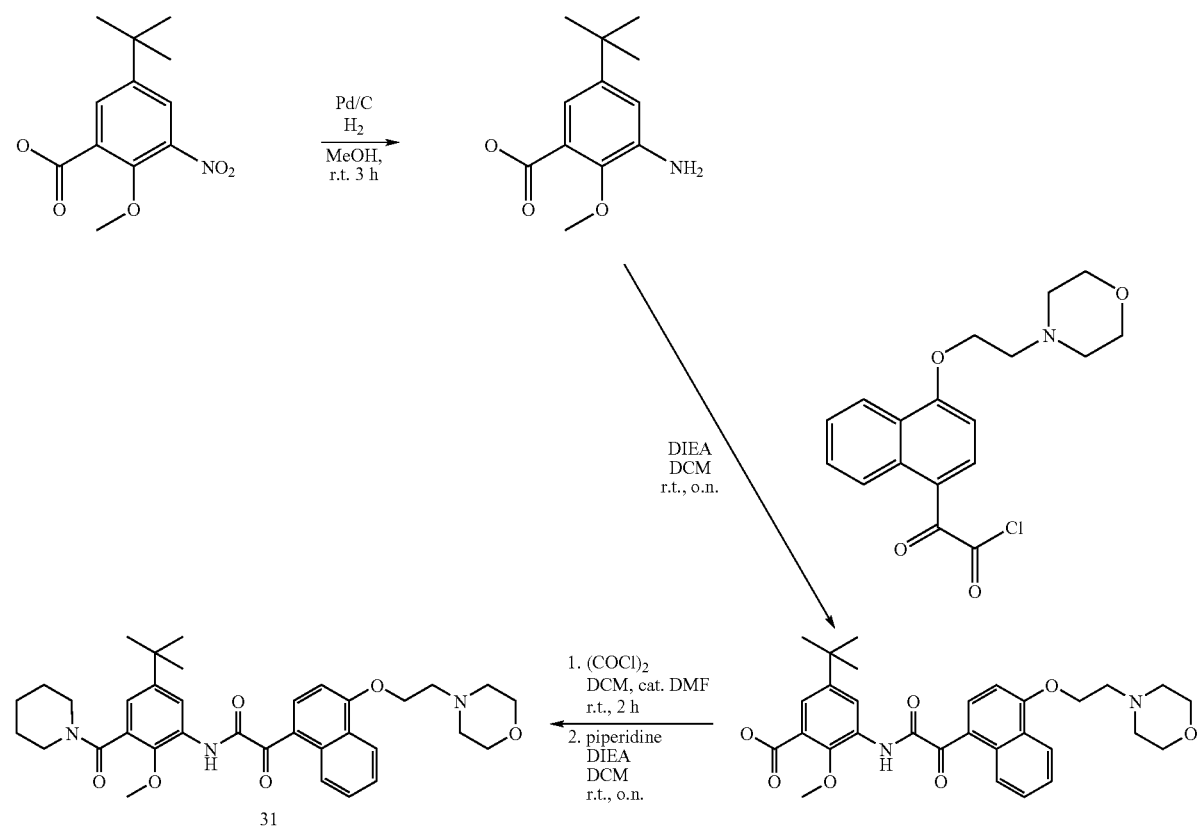

5-tert-Butyl-N-cyclopropyl-2-methoxy-3-nitro-benzamide. To a solution of 5-t-butyl-2-methoxy-3-nitrobenzoic acid (759 mg, 3 mmol) in 18 mL DCM, oxalyl chloride (1.8 mL, 15 mmol) was added. After stirring at rt for 2 hr the reaction mixture was concentrated to dryness. The resulting acid chloride was dissolved in 30 mL DCM, and DIEA (2.6 mL, 15 mmol) and cyclopropyl amine (0.83 mL, 12 mmol) were added. Stirring was continued overnight at rt, after which DCM was added to the reaction mixture. After aq. sodium bicarbonate work-up, column chromatography purification was performed on ISCO Optix (3×12 g silica gel column) using DCM. 678 mg pure product was isolated as pale yellow solid. Calculated mass=292. Observed mass=295

5-tert-Butyl-N-cyclopropyl-2-methoxy-3-{2-[4-(2-morpholin-4-yl-ethoxy)-naphthalen-1-yl]2-oxo-acetylamino}-benzamide (30). The compound obtained in the previous step (584 mg, 2 mmol) was reduced with Pd/C and H$_2$ in 30 mL MeOH at rt for 3 hr. After filtration, methanol was removed and the crude reduced intermediate was dissolved in 25 mL 3-Amino-5-tert-butyl-2-methoxy-benzoic acid. 5-t-Butyl-2-methoxy-3-nitrobenzoic acid (1.5 mmol) was reduced with Pd/C and H$_2$ in MeOH, and the obtained amine was coupled with acid chloride (1.5 mmol). The reaction was worked up as described above and column purification (3×12 g silica gel) gave 211 mg of the target compound.

N-[5-tert-Butyl-2-methoxy-3-(piperidine-1-carbonyl)-phenyl]-2-[4-(2-morpholin-4-yl-ethoxy)-naphthalen-1-yl]-2-oxo-acetamide (31) 26 mg (0.049 mmol) of the compound obtained above was converted to the acid chloride by reaction with oxalyl chloride (54 μl, 0.5 mmol) in 0.5 mL DCM in the presence of a catalytic amount of DMF (rt, 2h). After removal of the solvent, the crude acid chloride was dissolved in 1 mL DCM. DIEA (0.2 mmol) was added, followed by the addition of piperidine (0.1 mmol). The resulting mixture was stirred at rt overnight. Aqueous work-up and purification by LC-MS resulted in 7.6 mg pure product. Calculated mass=602. Observed mass=602

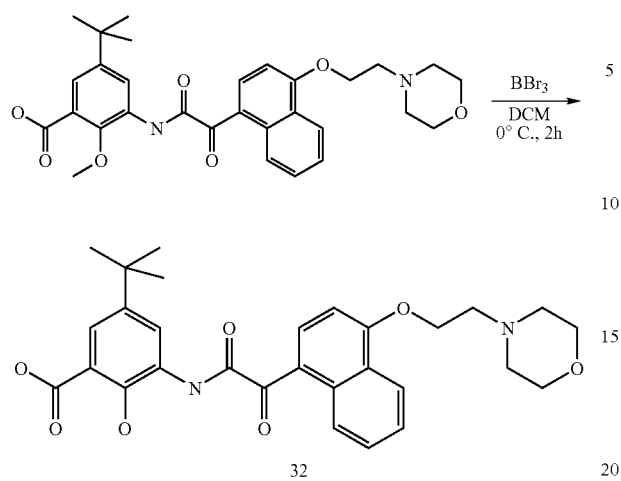

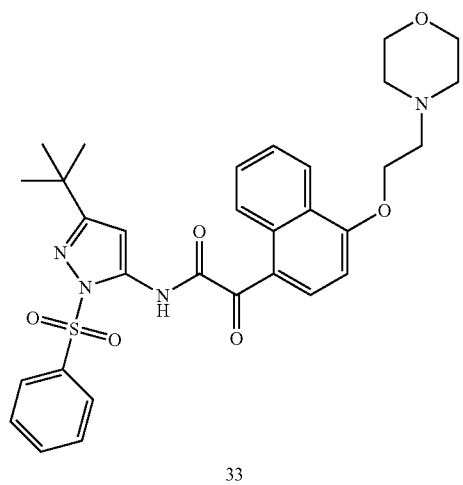

-continued 5-tert-Butyl-2-hydroxy-3-{2-[4-(2-morpholin-4-yl-ethoxy)-naphthalen-1-yl]-2-oxo-acetylamino}-benzoic acid (32). The starting material (11 mg, 0.02 mmol) was dissolved in 1 mL DCM. A solution of BBr$_3$ in DCM (0.1 mL, 1 M solution) was added at 0° C., and the reaction was allowed to continue at the same temperature for 2 hr before quenching with water. Aq. sodium bicarbonate work-up and purification by LC-MS resulted in 3.6 mg target compound. Calculated mass=521. Observed mass=521.

General Procedure for Derivatization of Pyrazolyl Containing Compounds

N-(5-tert-Butyl-2H-pyrazol-3-yl)-2-[4-(2-morpholin-4-yl-ethoxy)-naphthalen-1-yl]-2-oxo-acetamide. To a solution of the acid chloride prepared as before (695 mg, 2 mmol) in 10 mL BtOAc, 5-tert-butyl-2H-pyrazol-3-ylamine (278 mg, 2 mmol) and NaHCO$_3$ (504 mg, 6 mmol) in 2.5 mL H$_2$O were added. The solution was stirred at 60° C. for 15 hr. The layers were separated and the organic layer was purified by column chromatography (0-6% MeOH/DCM). The target compound was obtained as a pale yellow oil in 51% yield. Calculated mass 450. Observed mass=451.

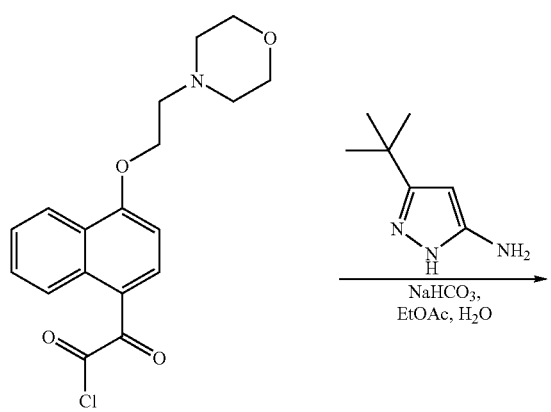

N-(5-tert-Butyl-2H-pyrazol-3-yl)-2-[4-(2-morpholin-4-yl-ethoxy)-naphthalen-1-yl]-2-oxo-acetamide (33). The compound obtained in the previous reaction (17 mg, 0.038 mmol) was treated for 15 hr at 60° C. with phenylsulfonyl chloride (9.8 mL, 0.076 mmol) in pyridine (1 mL) in the presence of DMAP (2 mg). The crude reaction mixture was purified by preparative LC/MS to yield 3.1 mg of target material. Calculated mass 591. Observed mass=591.

Additional derivatives, such as amide and urea derivatives, were synthesized by essentially the same methods.

Synthesis of Alpha-ketoamides

Method B: Via 2H-pyrazol-3-yl-oxo-acetic acid

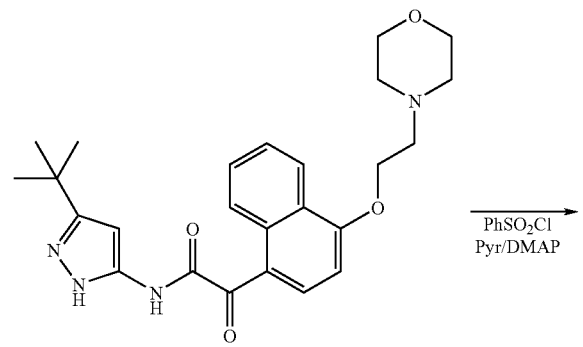

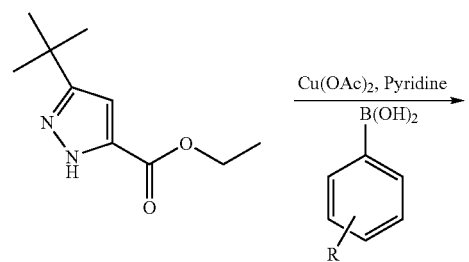

-continued

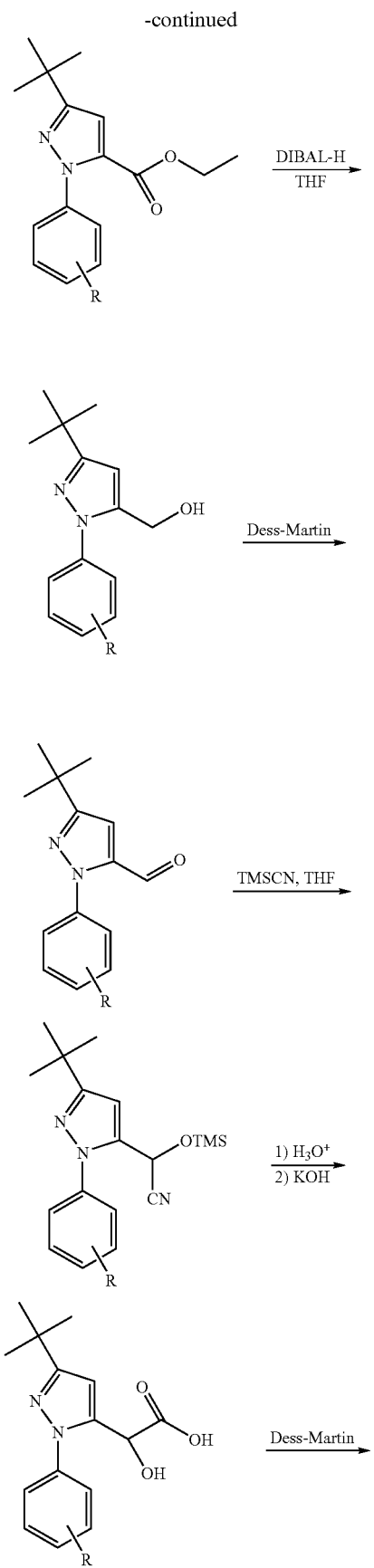

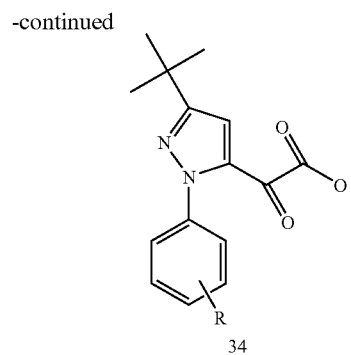

34

5-tert-Butyl-2-p-tolyl-2H-pyrazole-3-carboxylic acid ethyl ester (R=Me). To a round bottom flask containing 5-tert-Butyl-2H-pyrazole-3-carboxylic acid ethyl ester (0.5 g, 2.6 mmol) stirring in 25 mL DCM was added Pyridine (0.95 mL, 11.7 mmol), p-tolylboronic acid (1.1 g, 8.1 mmol), Cu(OAc)$_2$ (0.75 g, 4.1 mmol) and 4 A molecular sieves (0.75 g). The reaction stirred at room temperature for 14 h under air. The resulting mixture was filtered through a pad of diatomaceous earth and the filtrate concentrated in vacuo to afford a light green solid. The crude material was purified by Flash chromatography to afford (0.64 g, 83%) the desired product as a clear oil (0-50% EtOAc:hexanes on silica gel). Expected mass=286. Observed mass=287.

(5-tert-Butyl-2-p-tolyl-2H-pyrazol-3-yl)-methanol (R=Me). To an oven dried round bottom flask containing 5-tert-Butyl-2-p-tolyl-2H-pyrazole-3-carboxylic acid ethyl ester (0.64 g, 2.2 mmol) was added anhydrous THF (20 mL) followed by the drop wise addition of DIBAL-H (0.96 mL, 4.9 mmol) under nitrogen. After stirring at room temperature for 30 minutes the reaction was diluted with 100 mL diethyl ether and quenched with 5 mL Methanol stirring for an additional 30 minutes at room temperature. The resulting slurry was treated with 5 g MgSO$_4$ and filtered through a pad of diatomaceous earth. The filter cake was washed with 3×75 mL portions of ether and the combined filtrates concentrated under vacuo to afford the desired alcohol as a clear oil (0.515 g, 96%). No further purification was necessary. Expected mass=244. Observed mass=245.

5-tert-Butyl-2-p-tolyl-2H-pyrazole-3-carbaldehyde (R=Me). To a scintillation vial containing (5-tert-Butyl-2-p-tolyl-2H-pyrazol-3-yl)-methanol (0.515 g, 2.1 mmol) was added 15 mL DCM followed by the addition of Dess-Martin periodinane (1.1 g, 2.52 mmol). The reaction mixture was allowed to stir at room temperature for 20 minutes and poured into a separatory funnel containing 30 mL water. The layers separated and the aqueous layer extracted twice more with 50 mL DCM. The combined organic layers were washed with Brine, dried over MgSO$_4$ and concentrated under vacuum to afford the crude aldehyde. The crude material was purified by flash chromatography (0-50% EtOAc:Hexanes, silica gel) to yield the desired product as a clear oil (0.5 g, 97%). Expected mass=242. Observed mass=243.

(5-tert-Butyl-2-p-tolyl-2H-pyrazol-3-yl)-trimethylsilanyloxy-acetonitrile (R=Me). To and oven dried flask containing 5-tert-Butyl-2-p-tolyl-2H-pyrazole-3-carbaldehyde (0.5 g, 2.0 mmol) stirring in anhydrous THF at 0° C. under nitrogen was added neat trimethylsilyl cyanide (0.29 mL, 2.2 mmol), followed by addition of one drop of n-butyllithium (2.0 M in hexane). The mixture stirred at 0° C. for 1 h before warmed to room temperature and stirred overnight. The reaction mixture was concentrated under vacuum to afford the product as thick oil. No further purification was attempted. Expected mass=341. Observed mass=342.

(5-tert-Butyl-2-p-tolyl-2H-pyrazol-3-yl)-hydroxy-acetic acid (R=Me). To a round bottom flask containing (5-tert-Butyl-2-p-tolyl-2H-pyrazol-3-yl)-trimethylsilanyloxy-acetonitrile was added 100 mL concentrated HCl and heated to 80° C. After overnight heating, the reaction was diluted with 150 mL water and extracted with DCM (3×100 mL). The organic layers were washed with brine, dried over sodium sulfate, and concentrated under vacuum. The residue was then re-dissolved in about 75 mL methanol, followed by the addition of KOH (0.45 g, 8 mmol) and the solution was refluxed for 2 h. The reaction mixture was then cooled to room temperature, concentrated under vacuum. Several pieces of crushed ice were added to the flask with the reaction residue and acidified with 1N HCl. The mixture was then diluted with 100 mL water and extracted with DCM (3×100 mL). The organic layers were washed with brine, dried over MgSO₄, and concentrated under vacuum to yield 0.35 g (60%) of the desired product. No further purification was attempted. Expected mass=288. Observed mass=289.

(5-tert-Butyl-2-p-tolyl-2H-pyrazol-3-yl)-oxo-acetic acid (34, R=Me). To a scintillation vial containing (5-tert-Butyl-2-p-tolyl-2H-pyrazol-3-yl)-hydroxy-acetic acid (0.35 g, 1.2 mmol) was added 15 mL DCM followed by the addition of Dess-Martin periodinane (0.61 g, 1.44 mmol). The reaction mixture was allowed to stir at room temperature for 20 minutes and poured into a separatory funnel containing 30 mL 0.5 M HCl. The layers separated and the aqueous layer extracted twice more with 50 mL DCM. The combined organic layers were washed with Brine, dried over MgSO₄ and concentrated under vacuum to afford the desired product (purity >80% by NMR). No further purification was attempted. Expected mass=286. Observed mass=287.

2-(5-tert-Butyl-2-p-tolyl-2H-pyrazol-3-yl)-N-[4-(2-morpholin-4-yl-ethoxy)naphthalen-1-yl]-2-oxo-acetamide (35, R=Me): To the crude (5-tert-Butyl-2-p-tolyl-2H-pyrazol-3-yl)-oxo-acetic acid 34 (0.4 g, 1.4 mmol) in a 40 mL scintillation vial was added oxalyl Chloride (5 mL) and on drop of DMF. The suspension was stirred at rt for 1 h, and concentrated under vacuum. The resulting solid was dissolved in EtOAc (10 mL) and added to 4-(2-Morpholin-4-yl-ethoxy)-naphthalen-1-ylamine (0.45 g, 1.2 mmol) dissolved in EtOAc (10 mL)/50% NaHCO₃ (10 mL) and stirred overnight at rt. The mixture was diluted with EtOAc and extracted with NaHCO₃. The combined organic layers were washed with brine, dried over MgSO₄, filtered and the solvent removed affording a dark brown oil. The material was purified by column chromatography (50-100% EtOAc/Hexanes) providing 0.357 g (57%) of the desired compound as a yellow solid. Expected mass=540. Observed mass=541.

Synthesis of α-ketoamides

Method C: Via 2H-pyrazol-3-yl-3-oxo-2-(triphenyl-λ5-phosphanylidene)-propionitrile

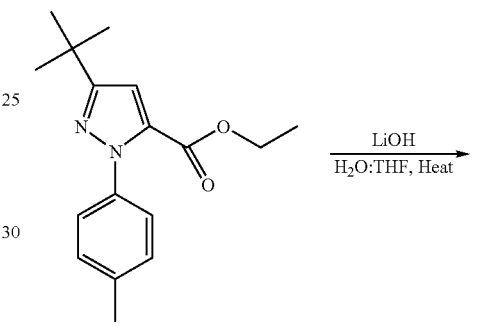

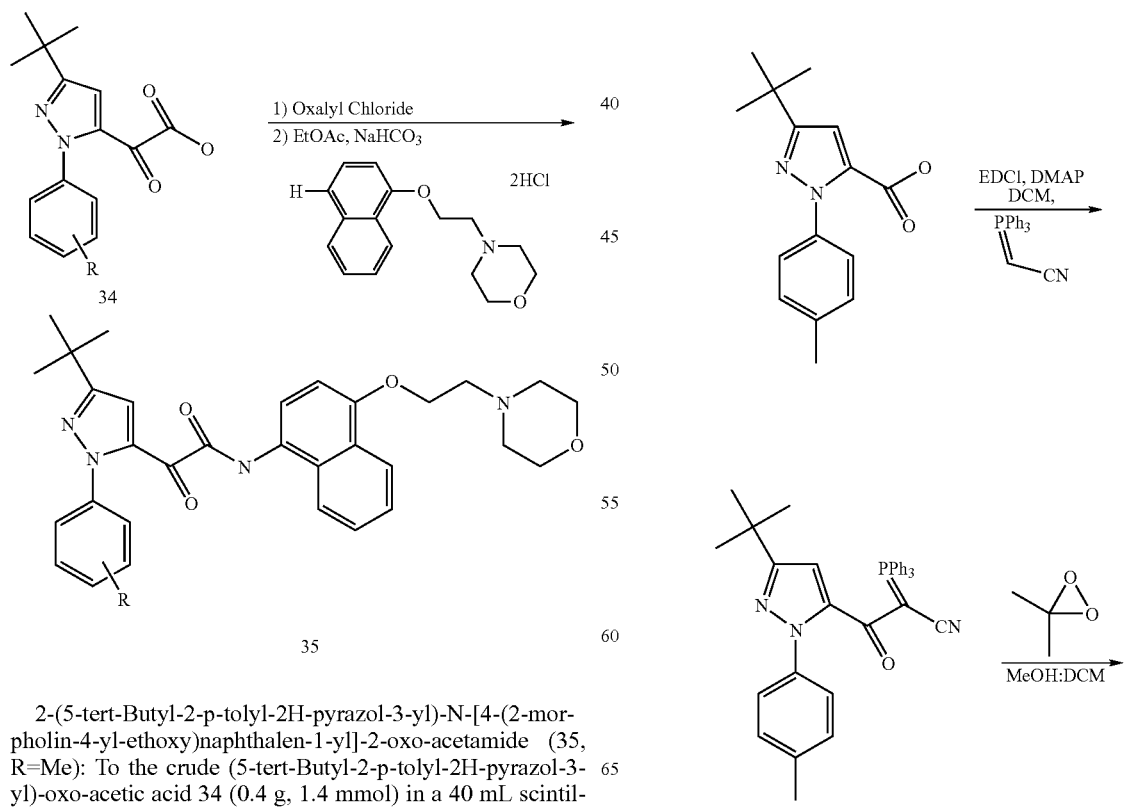

-continued

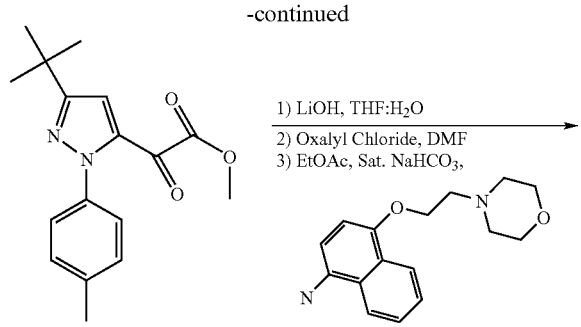

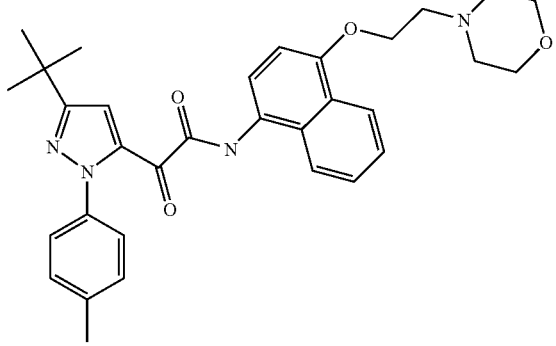

35 (R=Me)

5-tert-Butyl-2-p-tolyl-2H-pyrazole-3-carboxylic acid. To 5-tert-butyl-2-p-tolyl-2H-pyrazole-3-carboxylic acid ethyl ester (0.5 g, 1.75 mmol) in a 40 mL scintillation vial was added 2 mL THF and 2 mL 1N LiOH. The reaction was heated at 50° C. for 1 hr after which the reaction mixture was concentrated under vacuum and the crude residue was diluted with 5 mL 1N HCl. The reaction slurry was then extracted with DCM (3×25 mL) and the combined organic layers were washed with brine (10 mL) and dried over $MgSO_4$. The resulting solution was concentrated under vacuum to yield the desired product (0.432 g, 96%) in >95% purity. The isolated material was used without further purification.

3-(5-tert-Butyl-2-p-tolyl-2H-pyrazol-3-yl)-3-oxo-2-(triphenyl-λ5-phosphanylidene)-propionitrile. To a round bottomed flask containing 5-tert-Butyl-2-p-tolyl-2H-pyrazole-3-carboxylic acid (0.432 g, 1.67 mmol) was added 50 mL DCM, followed by the addition of (triphenyl-15-phosphanylidene)-acetonitrile (0.635 g, 2.0 mmol), EDCI (0.394 g, 2.0 mmol) and DMAP (0.024 g, 0.2 mmol). The reaction mixture was allowed to stir at room temperature for 16 hr and then concentrated under vacuum. The crude residue was purified by flash chromatography (0-20% EtOAc:DCM on Silica gel) to yield the desired product as a white powder (0.722 g, 81%).

(5-tert-Butyl-2-p-tolyl-2H-pyrazol-3-yl)-oxo-acetic acid methyl ester: In a 100 mL round bottom flask containing 3-(5-tert-Butyl-2-p-tolyl-2H-pyrazol-3-yl)-3-oxo-2-(triphenyl-15-phosphanylidene)-propionitrile (0.722 g, 1.3 mmol) was added 25 mL DCM and 25 mL methanol. The starting material was allowed to fully dissolve in the solvent mixture, after which dimethyl dioxirane (25 mL, 0.1M in acetone) was added to the reaction. The resulting solution was allowed to stir at room temperature for 30 min, after which the reaction mixture was concentrated under vacuum and the crude material was purified by flash chromatography (0-20% EtOAc: DCM on silica gel) to afford the desired keto-ester as a white solid (0.359 g, 92%).

2-(5-tert-Butyl-2-1)-tolyl-2H-pyrazol-3-yl)-N-[4-(2-morpholin-4-yl-ethoxy)-naphthalen-1-yl]-2-oxo-acetamide (35, R=Me). To (5-tert-butyl-2-p-tolyl-2H-pyrazol-3-yl)-oxoacetic acid methyl ester (0.359 g, 1.19 mmol) in a 40 mL scintillation vial was added 2 mL THF and 2 mL 1N LiOH. The reaction was heated at 50° C. for 1 hr after which the reaction mixture was concentrated under vacuum and the crude residue was diluted with 5 mL 1N HCl. The reaction slurry was then extracted with DCM (3×25 mL) and the combined organic layers were washed with brine (10 mL) and dried over $MgSO_4$. The resulting solution was concentrated under vacuum to afford the desired acid.

The neat acid was then dissolved in a minimal amount of DCM ~2 mL and oxalyl chloride (5 mL) was added, followed by the addition of one drop of DMF. The suspension was stirred at rt for 1 hr, and then concentrated under vacuum. The resulting solid was dissolved in EtOAc (10 mL) and added to 4-(2-morpholin-4-yl-ethoxy)-naphthalen-1-ylamine (0.41 g, 1.2 mmol) dissolved in EtOAc (10 mL)/50% $NaHCO_3$ (10 mL) and stirred overnight at rt. The mixture was diluted with EtOAc and washed with $NaHCO_3$. The aqueous layer was extracted twice more with 30 mL EtOAc and the combined organic layers were washed with brine, dried over $MgSO_4$, filtered and the solvent removed under vacuum to afford a dark brown oil. The material was purified by column chromatography (0-100% EtOAc/DCM) yielding 0.250 g (47%) of the desired compound as a yellow solid.

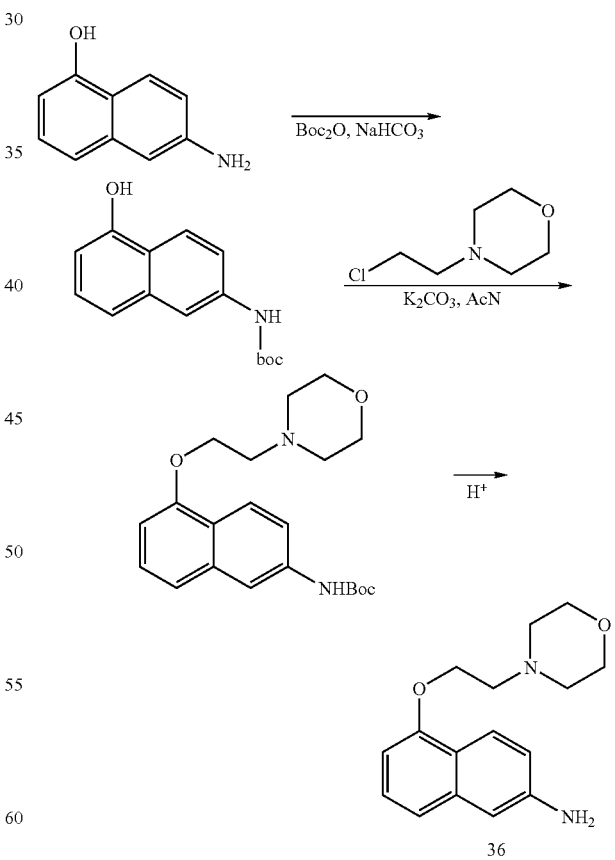

36

6-Boc-Amino-naphthalen-1-ol. 6-Amino-naphthalen-1-ol (5 g, 31.4 mmol) was suspended in 50 mL 0.5N $NaHCO_3$ and 50 mL EtOAc. $Boc_2O$ (6.85 g, 31.4 mmol) was added and the reaction mixture was stirred at 60° C. overnight. Complete conversion of starting material was achieved. The solvent layers were separated, the organic layer was washed with water, dried over MgSO$_4$ and evaporated to yield the target material.

[6-(2-Morpholin-4-yl-ethoxy)-naphthalen-1-yl]-carbamic acid tert-butyl ester. The compound obtained above (8.14 g, 31.4 mmol) was dissolved in 100 mL AcN and 4-(2-chloro-ethyl)-morpholine (5.80 g, 34.5 mmol) and K$_2$CO$_3$ (15.6 g, 0.11 mol) were added. The reaction was stirred at 75° C. overnight. The mixture was filtered, the solvent evaporated and the residue was purified by silica gel chromatography (DCM/MeOH: 15/1) to yield 0.51 g of target product. Calculated mass=372. Observed mass=372.

6-(2-Morpholin-4-yl-ethoxy)-naphthalen-1-yl-Boc-amine (36). The Boc protected material (1 g, 2.7 mmol) was stirred in 95% TFA/DCM/Et$_3$SiH at room temperature for several days. After evaporation the target material was obtained. Calculated mass=272. Observed mass=272.

Example 4

Synthesis of Imidazolonopyridines and Imidazolonopyrimidines

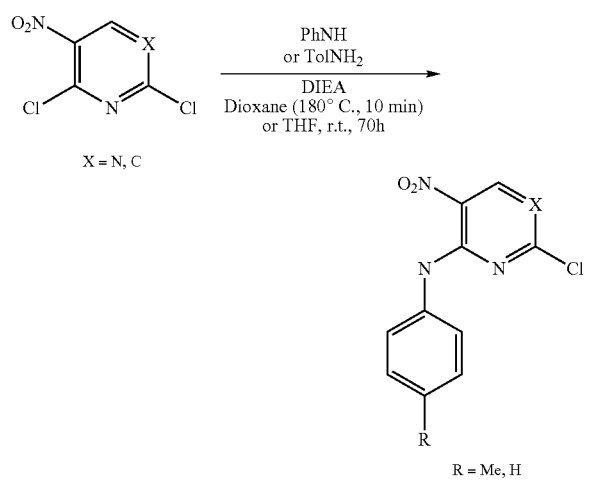

X = N, C

R = Me, H 2,6-Dichloro-nitro-pyridine or 2,4-dichloropyrimidine coupled smoothly with various amines in presence of DIEA either in microwave (dioxane, 180° C., 10 min) or at r.t. (THF, 70 h) as shown in the scheme above and as described in methods A and B.

Method A:

(6-Chloro-3-nitro-pyridin-2-yl)-phenyl-amine. A mixture of 2,6-dichloro-3-nitropyridine (386 mg, 2 mmol), aniline (182 µL, 2 mmol) and DIEA(419 µL, 2.4 mmol) in 3 mL dioxane was stirred in microwave at 180° C. for 10 min. After removal of the solvent, the residue was dissolved in 3 mL DCM, subjected to silica gel column purification to give 308 mg (yield 61.7%) (6-chloro-3-nitro-pyridin-2-yl)-phenyl-amine. Calculated mass=249. Observed mass=250.

Method B:

(6-Chloro-3-nitro-pyridin-2-yl)-phenyl-amine. A mixture of 2,6-dichloro-3-nitropyridine (772 mg, 4 mmol), aniline (364 µL, 4 mmol) and DIEA (838 µL, 24.8 mmol) in 10 mL THF was stirred at r.t. for 70 h. After removal of the solvent, the residue was dissolved in DCM, and subjected to silica gel column purification to give 735 mg (yield 74%) of the title compound. LC-MS: Calculated mass=249. Observed mass=250.

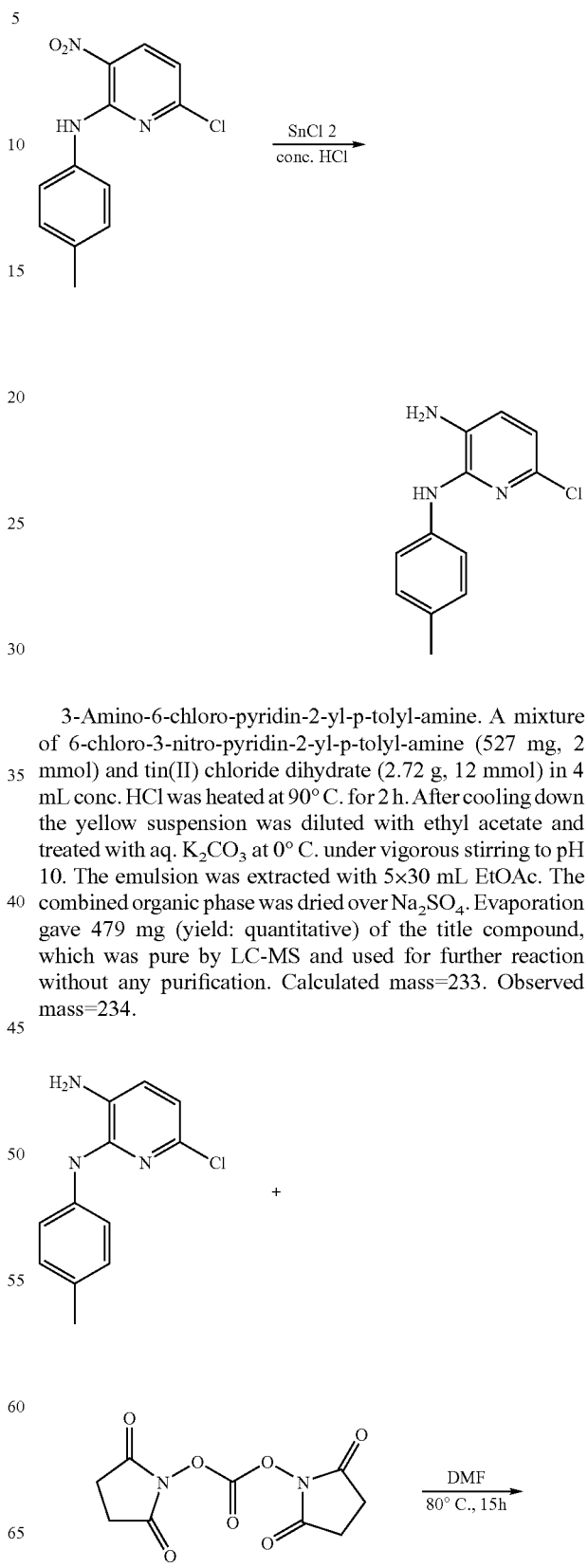

3-Amino-6-chloro-pyridin-2-yl-p-tolyl-amine. A mixture of 6-chloro-3-nitro-pyridin-2-yl-p-tolyl-amine (527 mg, 2 mmol) and tin(II) chloride dihydrate (2.72 g, 12 mmol) in 4 mL conc. HCl was heated at 90° C. for 2 h. After cooling down the yellow suspension was diluted with ethyl acetate and treated with aq. K$_2$CO$_3$ at 0° C. under vigorous stirring to pH 10. The emulsion was extracted with 5×30 mL EtOAc. The combined organic phase was dried over Na$_2$SO$_4$. Evaporation gave 479 mg (yield: quantitative) of the title compound, which was pure by LC-MS and used for further reaction without any purification. Calculated mass=233. Observed mass=234.

-continued

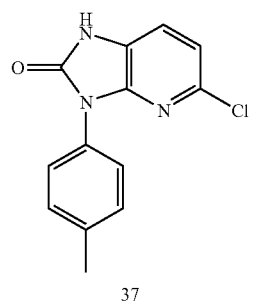

37

5-Chloro-3-p-tolyl-1,3-dihydro-imidazo[4,5-b]pyridine-2-one (37). A mixture of 3-amino-6-chloro-pyridin-2-yl-p-tolyl-amine (470 mg, 2 mmol) and DSC (768 mg, 3 mmol) in 10 mL DMF was heated at 80° C. for 15 h. After cooling down the red solution was diluted with EtOAc, washed 2× with sat. sodium bicarbonate solution, 2× with water. Org. phase was dried over sodium sulfate, evaporation gave 540 mg (quantitative yield) pink solid. TLC showed single spot (Rf=0.32 in DCM/MeOH (15:1)). LC-MS analysis indicates that the compound was pure and was used as is in the following step. Calculated mass=259. Observed mass=260.

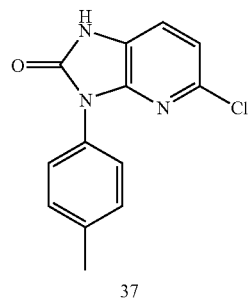

37

+

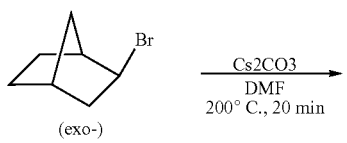

(exo-)

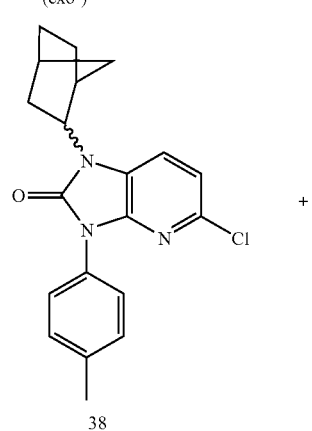

38

-continued

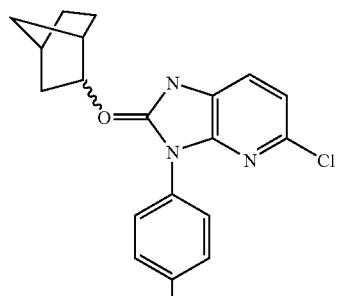

39

1-Bicyclo[2.2.1]hept-2-yl-5-chloro-3-p-tolyl-13-dihydro-imidazo[4,5-b]pyridine-2-one (38) and 2-(Bicyclo[2.2.1]hept-2-yloxy)-5-chloro-3-p-tolyl-3H-imidazo[4,5-b]pyridine (39). A mixture of 5-Chloro-3-p-tolyl-1,3-dihydro-imidazo[4,5-b]pyridine-2-one (52 mg, 0.2 mmol), exo-2-bromonorbornane (103 μL, 0.8 mmol) and Cs$_2$CO$_3$ (195 mg, 0.6 mmol) in 1.5 mL DMF was heated in microwave at 200° C. for 20 min. After filtration, the filtrate was diluted with EtOAc, washed with water. The organic phase was concentrated, the residue was dissolved in a minimum amount of DCM, and subjected to silica gel column purification to give 21.2 mg (yield: 30%) 1-Bicyclo[2.2.1]hept-2-yl-5-chloro-3-p-tolyl-1,3-dihydro-imidazo[4,5-b]pyridine-2-one (Rf=0.60 in DCM) and 6.2 mg (yield: 9%) 2-(Bicyclo[2.2.1]hept-2-yloxy)-5-chloro-3-p-tolyl-3H-imidazo[4,5-b]pyridine (Rf=0.49 in DCM). Calculated mass=353. Observed mass=354.

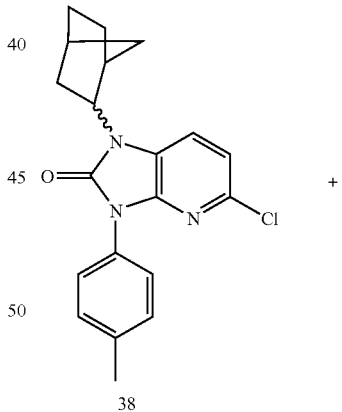

38

+

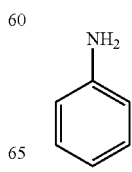

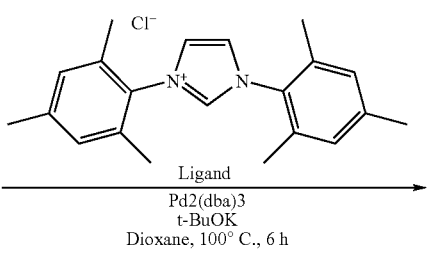

Ligand
Pd2(dba)3
t-BuOK
Dioxane, 100° C., 6 h

-continued

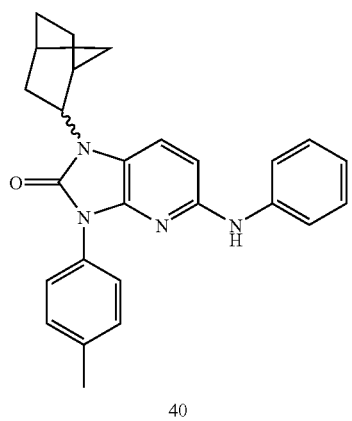

40

1-Bicyclo[2.2.1]hept-2-yl-5-phenylamino-3-p-tolyl-1,3-dihydro-imidazo[4,5-b]pyridine-2-one (40). A mixture of 1-bicyclo[2.2.1]hept-2-yl-5-chloro-3-p-tolyl-1,3-dihydro-imidazo[4,5-b]pyridine-2-one (19 mg, 0.054 mmol), 15 μL (0.16 mmol) aniline, Ligand (5.1 mg, 0.015 mmol), Pd$_2$(dba)$_3$ (6.9 mg, 0.0075 mmol), t-BuOK (56 mg, 0.162 mmol) in 1 mL dioxane was heated at 100° C. for 6 h. Prep LC-MS gave 3.2 mg TFA salt of the title compound. Calculated mass=410. Observed mass=411.

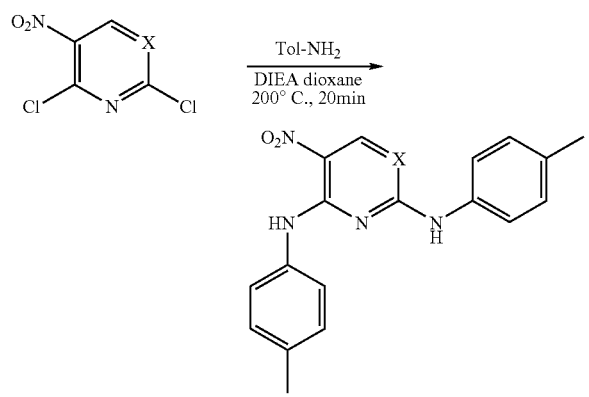

X=C, N 2,6-Bis(p-tolylamino)-3-nitro-pyridine (X=C). A mixture of 2,6-dichloro-3-nitropyridine (193 mg, 1 mmol), p-tolylamine (236 mg, 2.2 mmol) and DIEA (524 μL, 3 mmol) in 3 mL dioxane was stirred in microwave at 200° C. for 20 min. After removal of the solvent, the residue was dissolved in chloroform and subjected to silica gel column purification to give 291 mg (yield: 87%) title compound. Calculated mass=334. Observed mass=335.

2,6-Bis(p-tolylamino)-3-nitro-pyrimidine (X=N). A mixture of 2,6-dichloro-3-nitropyrimidine (194 mg, 1 mmol), p-tolylamine (236 mg, 2.2 mmol) and DIEA (524 μL, 3 mmol) in 3 mL dioxane was stirred in microwave at 200° C. for 20 min. After removal of the solvent, the residue was dissolved in chloroform and subjected to silica gel column purification to give 319 mg (yield: 95%) title compound. Calculated mass=335. Observed mass=336.

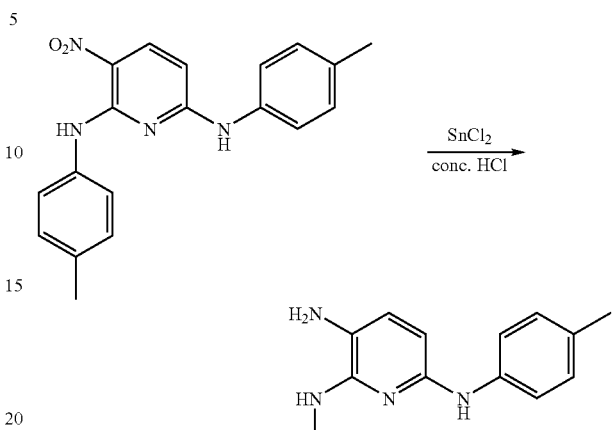

3-Amino-2,6-(bis-p-tolylamino)-pylidine. A mixture of 2,6-Bis(p-tolylamino)-3-nitro-pyridine (288 mg, 0.86 mmol) and Tin(II) chloride dihydrate (1.25 g, 5.5 mmol) in 3 mL conc. HCl was heated at 90° C. for 2 h. After cooling down the suspension was diluted with ethyl acetate and treated with aq. K$_2$CO$_3$ at 0° C. under vigorous stirring to pH 10. The emulsion was extracted with 5×30 mL EtOAc. The combined organic phase was dried over Na$_2$SO$_4$. Evaporation gave 254 mg (yield: 97%) title compound, which was pure by LC-MS and used for further reaction without any purification. Calculated mass=304. Observed mass=305.

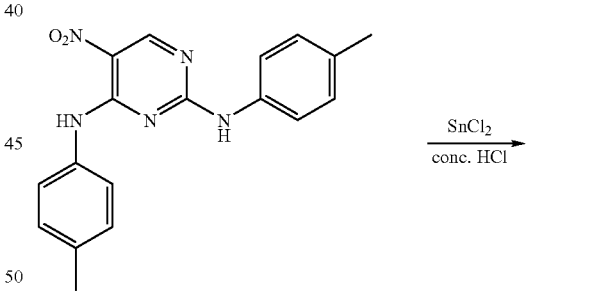

3-Amino-2,6-(bis-p-tolylamino)-pyrimidine. 2,6-Bis(p-tolylamino)-3-nitro-pyrimidine was treated as described in the previous procedure to yield the title compound, which was pure by LC-MS and used for further reaction without any purification. Calculated mass=305. Observed mass=306.

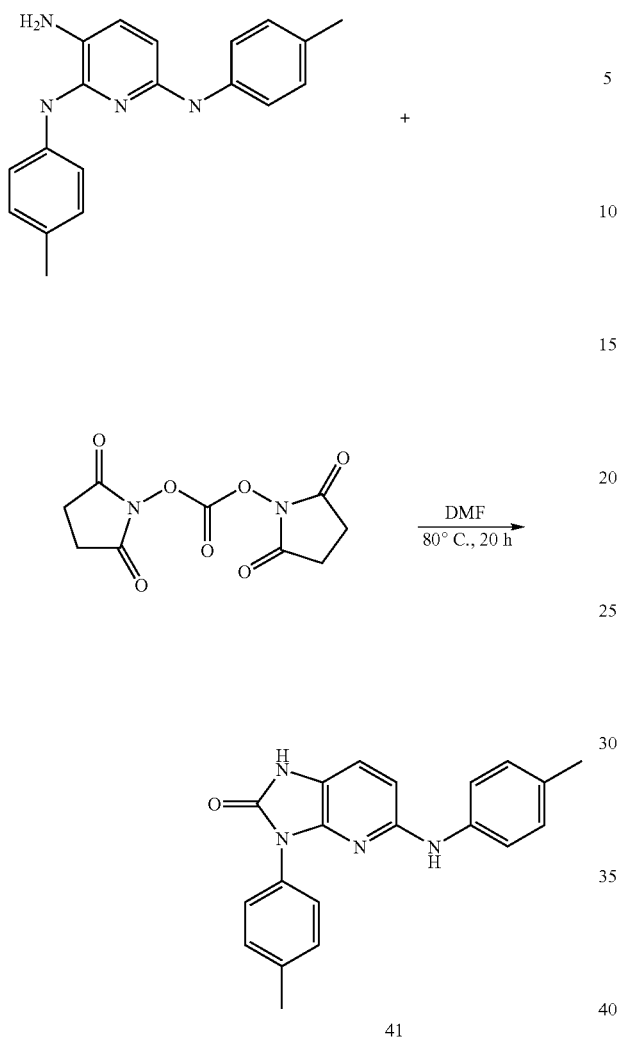

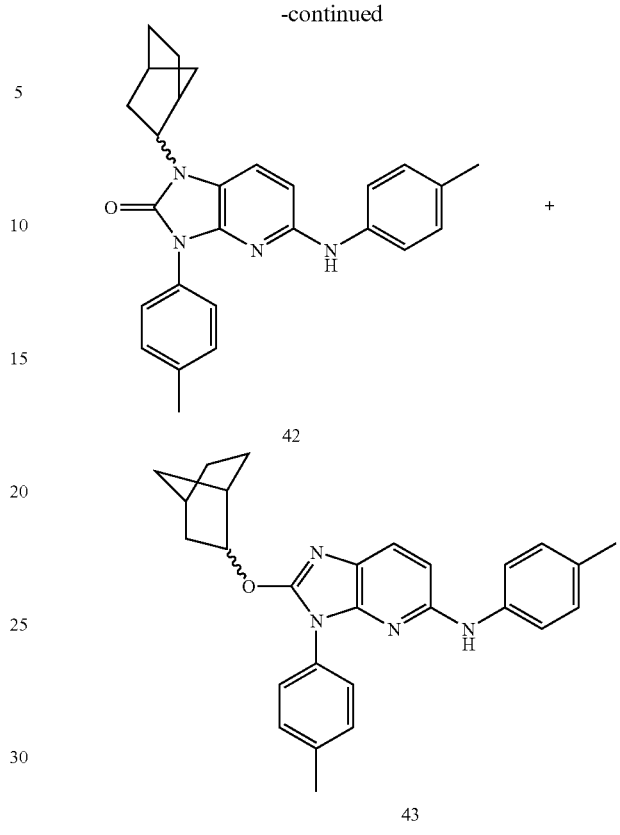

42

43

3-p-Tolyl-5-p-tolylamino-1,3-dihydro-imidazo[4,5-b]pyridine-2-one (41). A mixture of 3-Amino-2,6-(bis-p-tolylamino)-pyridine (254 mg, 0.84 mmol) and DSC (323 mg, 1.26 mmol) in 6 mL DMF was heated at 80° C. for 20 h. After cooling down the red solution was diluted with EtOAc, washed 2× with sat. sodium bicarbonate solution, 2× with water. The organic phase was dried over sodium sulfate, concentrated and subjected to silica gel column purification to give 266 mg (yield: 96%) of the title compound. LC-MS: Calculated mass=330. Observed mass=331.

1-Bicyclo[2.2.1]hept-2-yl-3-p-tolyl-5-p-tolylamino-1,3-dihydro-imidazo[4,5-b]pyridine-2-one (42) and [2-(Bicyclo[2.2.1]hept-2-yloxy)-3-p-tolyl-3H-imidazo[4,5-b]pyridine-5-yl]-p-tolyl-amine (43). A mixture of 3-p-Tolyl-5-p-tolylamino-1,3-dihydro-imidazo[4,5-b]pyridine-2-one (33 mg, 0.1 mmol), exo-2-bromonorbornane (19 μL, 0.15 mmol) and Cs$_2$CO$_3$ (65 mg, 0.2 mmol) in 0.5 mL DMF was heated at 180° C. for 3 h. After cooling down EtOAc was added, and the organic layer was washed with water. The organic phase was concentrated, the residue was dissolved in a minimum amount of DCM and subjected to silica gel column purification to give 13.4 mg (yield: 32%) 1-Bicyclo[2.2.1]hept-2-yl-3-p-tolyl-5-p-tolylamino-1,3-dihydro-imidazo[4,5-b]pyridine-2-one (Rf=0.44 in DCM) and 4.8 mg (yield: 11%) [2-(Bicyclo[2.2.1]hept-2-yloxy)-3-p-tolyl-3H-imidazo[4,5-b]pyridine-5-yl]-p-tolyl-amine (Rf=0.27 in DCM).

Example 5

General Procedure for Difluoro-acetic Acid Derivatives

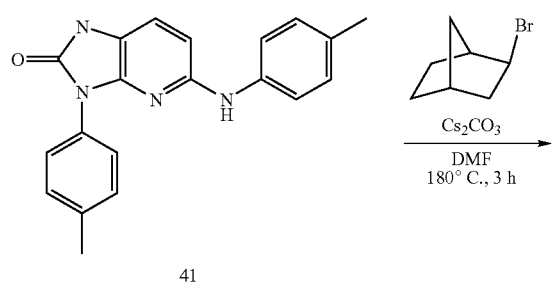

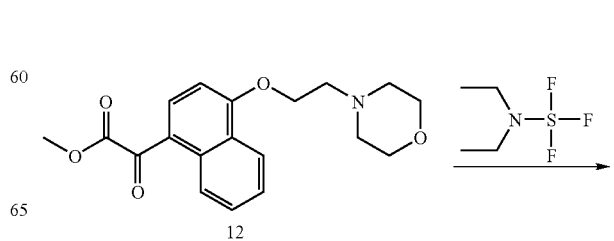

155

-continued

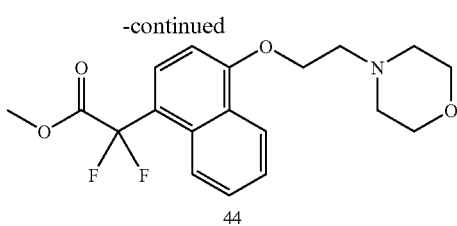

44

Difluoro-[4-(2-morpholin-4-yl-ethoxy)-naphthalen-1-yl]-acetic acid methyl ester (44). To a solution of keto-ethyl ester 12 (0.618 g, 1.80 mmol) in $CH_2Cl_2$ (20 mL) was added Diethylaminosulfur trifluoride (1.70 mL, 13.8 mmol) and EtOH (3 drops). The solution was stirred at rt for 3 days. The mixture was neutralized with saturated $NaHCO_3$ and extracted with $CH_2Cl_2$ (3×20 mL). The combined organic layers were washed with brine, dried over $MgSO_4$, filtered and the solvent removed. The crude material was purified by preparative LCMS yielding 70 mgs (10% yield) as an oil. Expected mass=365. Observed mass=366.

156

N-(5-tert-Butyl-2-p-tolyl-2H-pyrazol-3-yl)-2,2-difluoro-2-[4-(2-morpholin-4-yl-ethoxy)-naphthalen-1-yl]-acetamide (45). The Difluoro methyl ester 44 was saponified, converted to the acid chloride and coupled as described previously. Expected mass=562. Observed mass=563.

Example 6

Synthesis of Diamide Derivatives

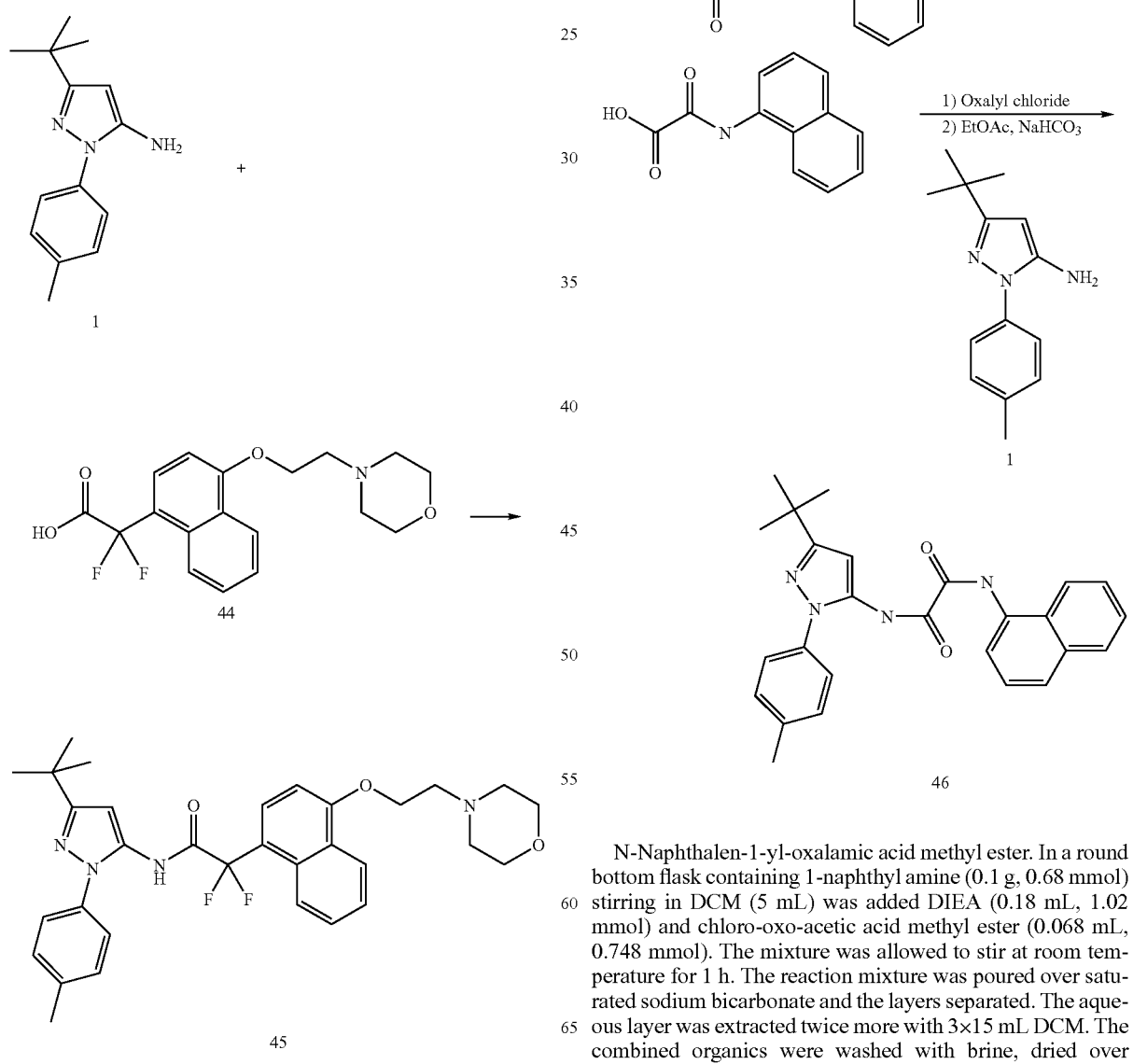

N-Naphthalen-1-yl-oxalamic acid methyl ester. In a round bottom flask containing 1-naphthyl amine (0.1 g, 0.68 mmol) stirring in DCM (5 mL) was added DIEA (0.18 mL, 1.02 mmol) and chloro-oxo-acetic acid methyl ester (0.068 mL, 0.748 mmol). The mixture was allowed to stir at room temperature for 1 h. The reaction mixture was poured over saturated sodium bicarbonate and the layers separated. The aqueous layer was extracted twice more with 3×15 mL DCM. The combined organics were washed with brine, dried over $MgSO_4$ and concentrated in vacuo to afford a brown solid.

The crude material was purified by flash chromatography (0-50% EtOAc:Hexanes on silica gel) to yield the desired product (0.14 g, 90%) as an off-white solid. Expected mass=229. Observed mass=230.

N-Naphthalen-1-yl-oxalamic acid. To N-Naphthalen-1-yl-oxalamic acid methyl ester (0.14 g, 0.61 mmol) stirring in THF (2 mL) was added 2 mL of a 1N lithium hydroxide solution. The reaction was heated to 50° C. and stirred for 2 h. The resulting mixture was concentrated in vacuo to afford a yellow residue that was acidified with 1N HCL. The resulting mixture was extracted with DCM (3×50 mL), dried over $MgSO_4$ and concentrated under vacuum to afford crude product. The crude material was purified by flash chromatography (0-20% MeOH:DCM, silica gel) to afford the desired product (0.128 g, 98%) as a thick oil. Expected mass=215. Observed mass=216.

N-(5-tert-Butyl-2-p-tolyl-2H-pyrazol-3-yl)-N'-naphthalen-1-yl-oxalamide (46). In a round bottom flask containing the N-Naphthalen-1-yl-oxalamic acid (0.128 g, 0.6 mmol) stirring in DCM (5 mL) was added diisopropylcarbodiimide (0.09 g, 0.72 mmol) and DIEA (0.19 mL, 1.08 mmol). The reaction was allowed to stir at room temperature overnight and quenched with 10 mL saturated $NaHCO_3$. The layers separated and the aqueous layer extracted twice more with 2×25 mL DCM. The combined organics were washed with brine, dried over $MgSO_4$ and concentrated under vacuum to afford a brown oil. The crude mixture was purified by flash chromatography (50-100 EtOAc:hexanes, silica gel) to afford the desired product (184 g, 72%) as an off-white solid. Expected mass=426. Observed mass=427.

Example 7

General Procedure for Formation of Oxime Derivatives

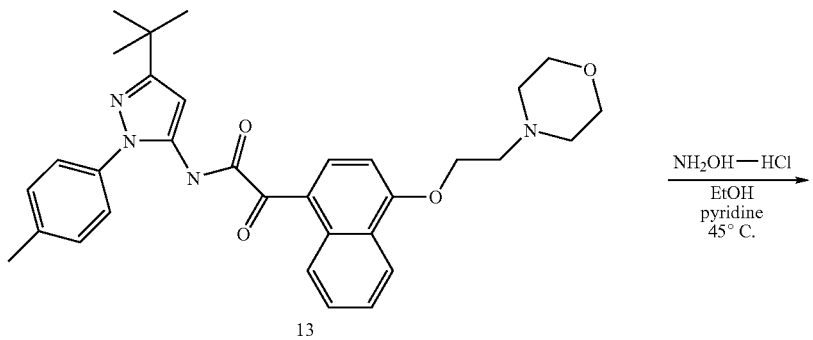

13

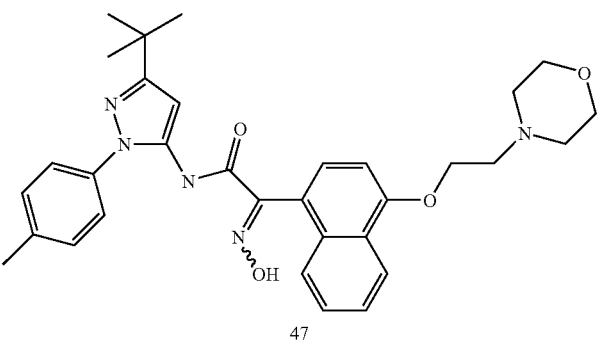

47

N-(5-tert-Butyl-2-p-tolyl-2H-pyrazol-3-yl)-2-hydroxy-imino-2-[4-(2-morpholin-4-yl-ethoxy)-naphthalen-1-yl]-acetamide (47). Compound 13 (10 mg, 0.018 mmol) and hydroxylamine hydrochloride (50 eqv., 0.92 mmol, 64 mg) were dissolved in 2 mL of EtOH. Pyridine (0.1 mL) was added and the mixture was stirred at 45° C. for 12 h. The solvent was then removed in vacuo and the crude solid was purified via LCMS to yield 6 mg of a white solid (58% yield; mixture of isomers). Expected mass=555. Observed mass=556.

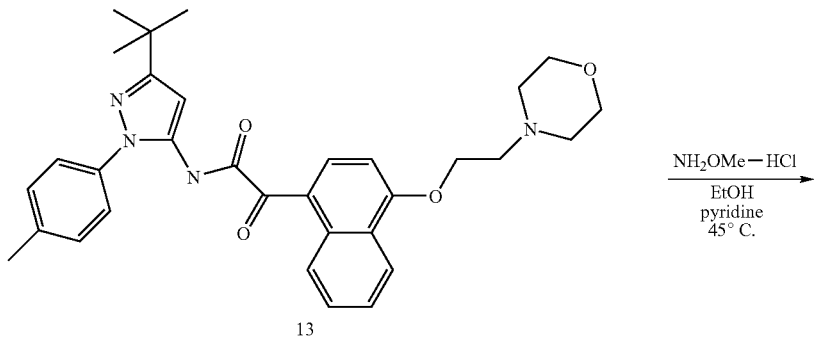

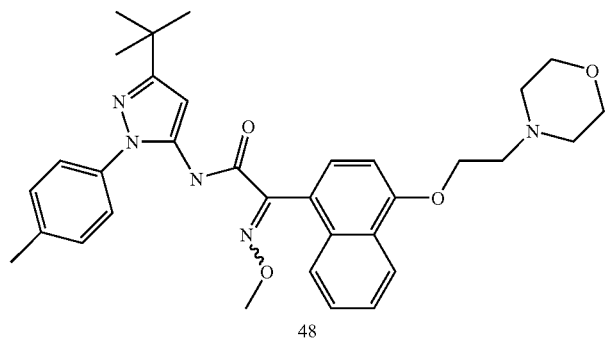

N-(5-tert-Butyl-2-p-tolyl-2H-pyrazol-3-yl)-2-methoxy-imino-2-[4-(2-morpholin-4-yl-ethoxy)-naphthalen-1-yl]-acetamide (48). Compound 13 (10 mg, 0.018 mmol) and methoxyamine hydrochloride (50 eqv., 0.92 mmol, 77 mg) were dissolved in 2 mL of EtOH. Pyridine (0.1 mL) was added and the mixture was stirred at 45° C. for 12 h. The solvent was then removed in vacuo and the crude solid was purified via LCMS to yield 8 mg of a white solid (76% yield; mixture of isomers). Expected mass=569. Observed mass=570.

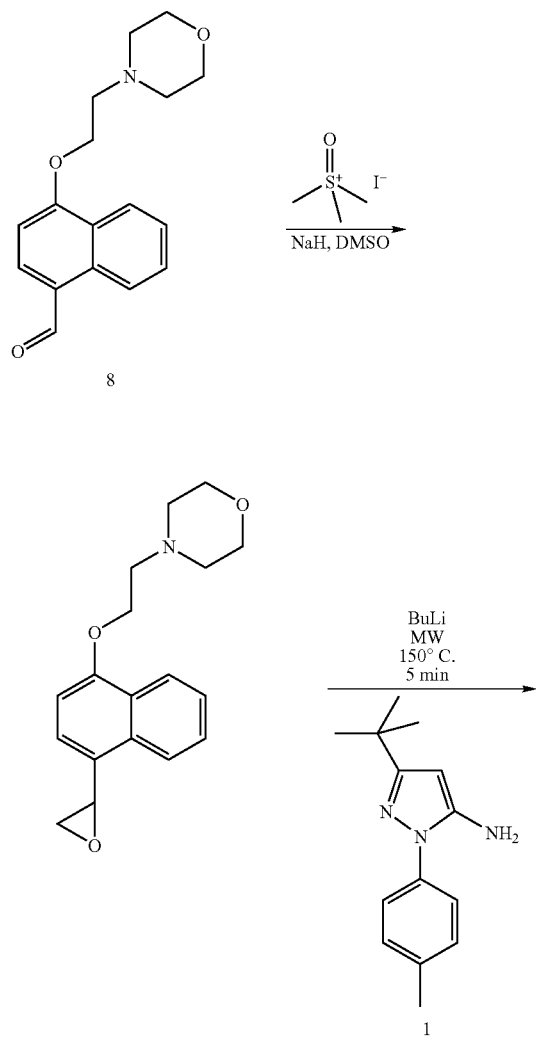

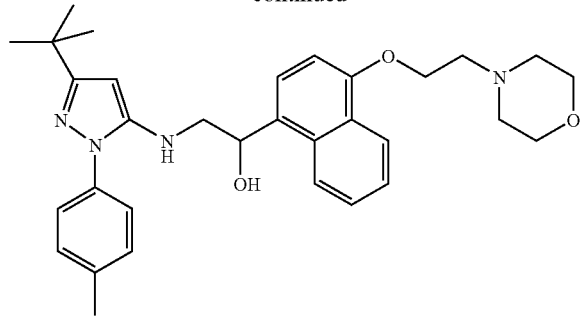

49

4-(Morpholin-4-yl-ethyloxy)-1-naphthylepoxide. To a suspension of NaH (24 mg, 1.0 mmol) in DMSO (1 mL), trimethylsulfoxonium iodide (220 mg, 1.0 mmol) was added. After the $H_2$ evolution ceased, a solution of aldehyde 8 (285 mg, 1.0 mmol) in DMSO (0.5 mL) was added and the mixture stirred at 20° C. for 12 h. The mixture was diluted with $H_2O$, extracted with $Et_2O$ and the combined organic layers dried ($MgSO_4$) and rotary evaporated to give a yellow oil which was used in the next step without any further purification. Expected mass=299. Observed mass=300.

N-(5-tert-Butyl-2-p-tolyl-2H-pyrazol-3-yl)-2-hydroxy-2-[4-(2-morpholin-4-yl-ethoxy)-naphthalen-1-yl]-ethylamine (49). To a solution of 5-amino-3-t-butyl-1-(4 methylphenyl) pyrazole (1) (50 mg, 0.2 mmol) in 1,4-dioxane (2 mL), n-BuLi (0.1 mL, 0.2 mmol, 2.0 M in cyclohexane) was added at 20° C. under $N_2$. A solution of the compound obtained in the previous reaction in DMF (1 mL) was added and the brown mixture heated for 5 min in the microwave at 150° C. The mixture was diluted with $CH_2Cl_2$, washed with water and the organic layer dried ($MgSO_4$) and rotary evaporated to give a brown oil which was purified by preparative LC-MS to give the title compound (8.3 mg, 8%) as a yellow waxy solid: Calculated mass=528. Observed mass=529.

Example 9

Synthesis of Triazolidine-dione Derivatives

Route A:

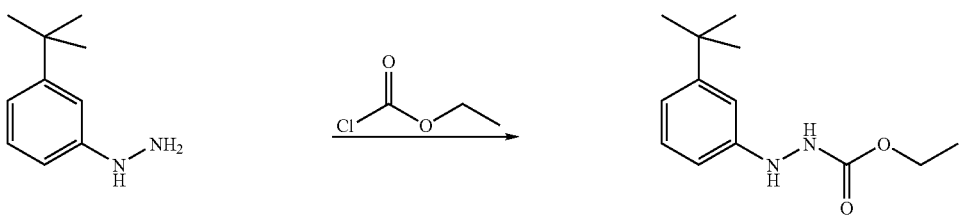

-continued

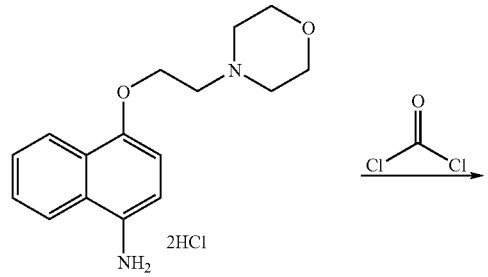

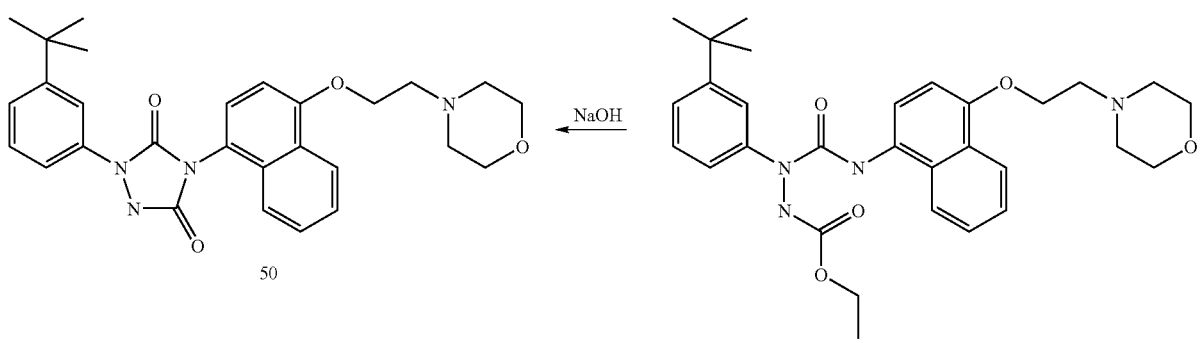

N'-(3-tert-Butyl-phenyl)-hydrazinecarboxylic acid ethyl ester. 3-t-Butylhydrazine hydrochloride (600 mg, 3 mmol) was dissolved in 15 mL DCM, DIEA (1.7 mL, 10 mmol) was added, followed by addition of ethyl chloroformate (3 mmol). The reaction mixture was stirred at rt overnight, followed by aq. sodium bicarbonate work-up. The organic phase was dried over Na$_2$SO$_4$, concentrated and subjected to ISCO column (4×12 g) purification to give 437 mg product as brown oil.

1-(3-tert-Butyl-phenyl)-4-[4-(2-morpholin-4-yl-ethoxy)-naphthalen-1-yl]-[1 2,4]triazolidine-3,5-dione (50). 4-(2-N-morpholinoethoxy)naphthylamine dihydrochloride (70 mg, 0.2 mmol) was dissolved in a cold (0° C.) mixture of 4 mL DCM and 4 mL saturated NaHCO$_3$ solution. Stirring was stopped. After addition of 0.36 mL ca. 20% phosgene in toluene to the DCM layer, vigorous stirring was resumed. Reaction was continued at 0° C. for 30 min. The organic layer was separated, and the aqueous layer was extracted once with DCM. The combined organic layers were evaporated. A solution of N'-(3-tert-Butyl-phenyl)-hydrazinecarboxylic acid ethyl ester (47 mg, 0.2 mmol) in 1 mL DCM was added to this crude isocyanate. The reaction mixture was stirred at rt overnight. After removal of the solvent, the residue was dissolved in DMSO and subjected to preparative LC-MS purification to afford 8.4 mg of the target compound. The compound obtained in the previous step (8.4 mg, 0.016 mmol) was dissolved in 1 mL EtOH, and a solution of NaOH (2 mg, 0.05 mmol) in 0.2 mL water was added. The resulting mixture was stirred at rt for 2 hr, before it was neutralized with conc. HCl to pH 4. Purification of the crude material was achieved by preparative LC-MS to give 6 mg final product.

Route B:

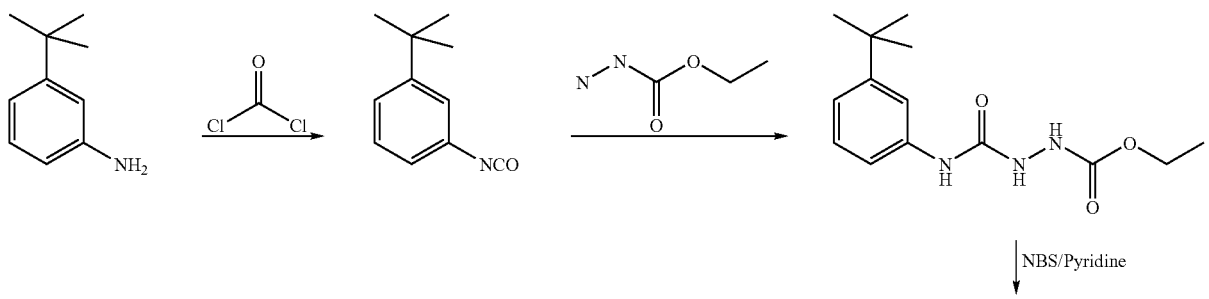

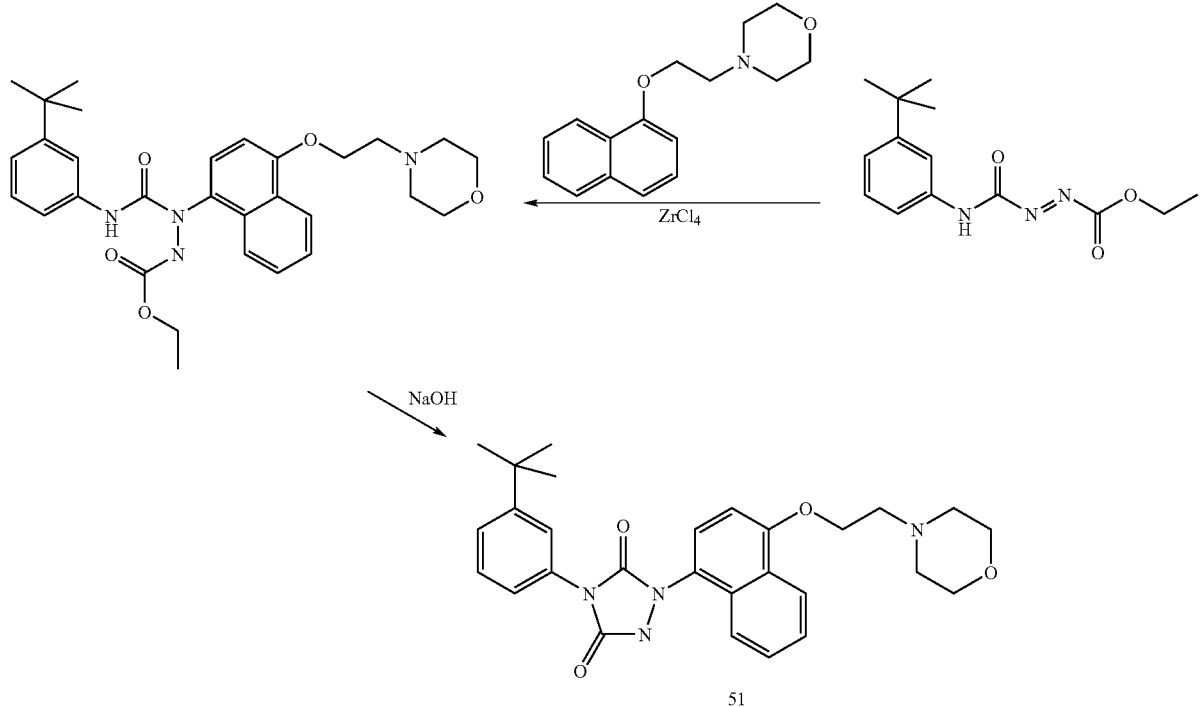

1-tert-Butyl-3-isocyanato-benzene. 3-t-Butyl-aniline (150 mg, 1 mmol) was converted to the isocyanate as described above and then dissolved in 4 mL DCM. Hydrazate (104 mg, 1 mmol) was added and the reaction was continued at rt overnight. Preparative LC-MS purification afforded 181 mg of the target compound as a white solid.

Ethyl 2-[(tolylamino)carbonyl]hydrazinecarboxylate. NBS (121 mg, 0.68 mmol) was added to a stirred suspension of 1-tert-Butyl-3-isocyanato-benzene (181 mg, 0.65 mmol) in 3 mL DCM and 105 gl pyridine at rt. After stirring for another 2 hr, 2 mL of water was added, followed by addition of 1 mL conc. HCl. The organic phase was separated, and washed with a solution of $Na_2S_2O_3$ (65 mg) in 3 mL water, saturated $NaHCO_3$ and water. The organic phase was dried over $Na_2SO_4$ and concentrated to give 182 mg of the target compound as a pale red thick oil.

4-(3-tert-Butyl-phenyl)-1-[4-(2-morpholin-4-yl-ethoxy)-naphthalen-1-yl]-[1,2,4]triazolidine-3,5-dione. (51). A cold solution of the compound obtained above (55 mg, 0.2 mmol) and 1-(2-morpholinoethoxy)-naphthalene (51 mg, 0.2 mmol) in 1.5 mL DCM was added drop wise to a stirred suspension of $ZrCl_4$ in 0.5 mL DCM at −30° C. The reaction was continued at −30° C. for 45 min, then it was allowed to warm up to rt and 1 mL of water was added to quench the reaction. Neutralization was done with saturated $NaHCO_3$. The organic phase was separated and the aqueous phase was extracted with DCM. The combined organic phases were dried over $Na_2SO_4$, concentrated and subjected to preparative LC-MS purification to give 22.8 mg of target compound.

The compound obtained above (22.8 mg, 0.43 mmol) was dissolved in 2 mL EtOH. A solution of NaOH (4 mg, 1 mmol) in 0.4 mL water was added. After stirring at rt for 2 hr, the reaction mixture was neutralized with conc. HCl (to pH=4) and subjected directly to preparative LC-MS purification to afford 7 mg final product.

Example 10

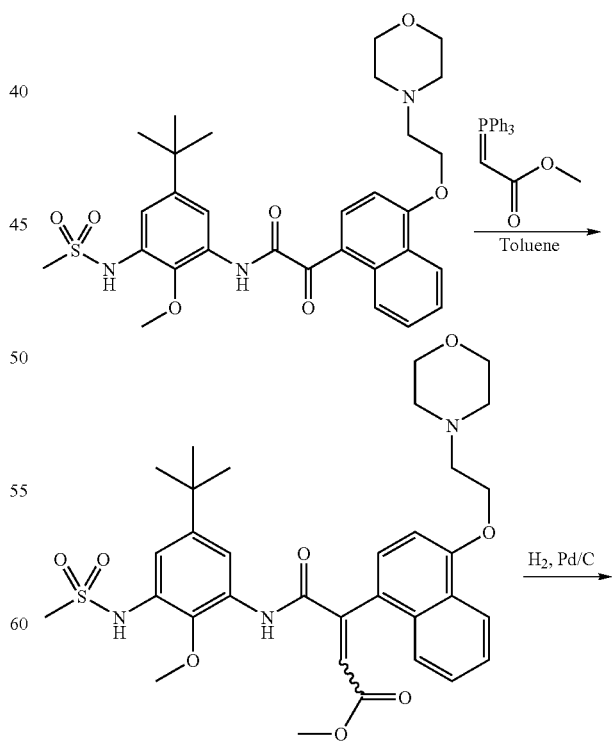

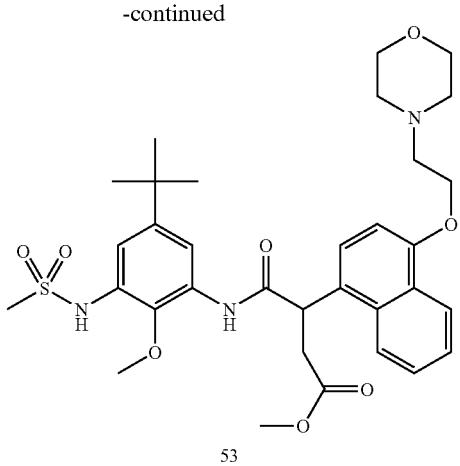

53

N-(5-tert-Butyl-3-methanesulfonylamino-2-methoxy-phenyl)-3-[4-(2-morpholin-4-yl-ethoxy)-naphthalen-1-yl]-succinamic acid methyl ester (52). To the ketoamide (13b) (250 mg, 0.43 mmol) stirring in toluene was added the ylide (156 mg, 0.52 mmol) and two drops of diisopropylethyl amine. The reaction was sealed and heated to 100° C. overnight. The reaction was cooled to room temperature and concentrated under vacuum. The crude residue was purified by LCMS, yielding two isomers independently isolated as white solids (105 mg, 84%). Both isomers were carried on in the next step.

N-(5-tert-Butyl-3-methanesulfonylamino-2-methoxy-phenyl)-3-[4-(2-morpholin-4-yl-ethoxy)-naphthalen-1-yl]-succinamic acid methyl ester (53). A 50 mL round bottom flask containing ethyl acetate and the succinamic acid obtained in the reaction above (75 mg, 0.12 mmol) was sparged with nitrogen for 5 min. The resulting solution was placed under nitrogen and treated with 10% Pd/C (10 mole %). The atmosphere was then exchanged with hydrogen via a balloon, and the reaction was stirred at room temperature for 16 h. The resulting solution was filtered through a pad of celite and the filtrate concentrated under vacuum to yield crude product. The crude material was purified by flash chromatography to yield the desired product as a white solid (65 mg) in 87% yield.

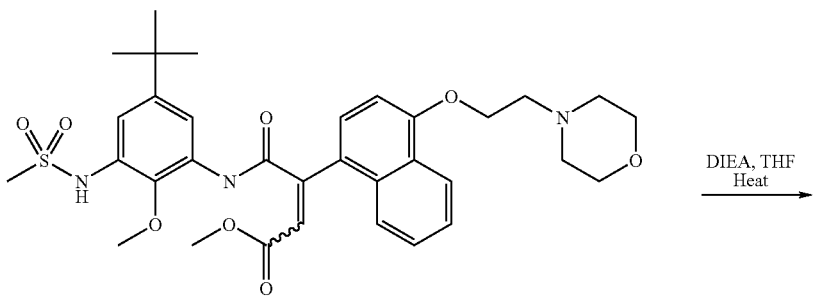

52

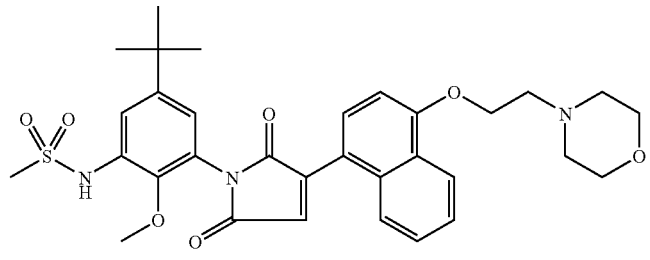

54

N-(5-tert-butyl-2-methoxy-3-{3-[4-(2-morpholin-4-yl-ethoxy)-naphthalen-1-yl]-2,5-dioxo-2,5-dihydro-pyrrol-1-yl}-phenyl)-methanesulfonamide (54). In a 40 mL scintillation vial was placed 3-(5-tert-butyl-3-methanesulfonylamino-2-methoxy-phenylcarbamoyl)-3-[4-(2-morpholin-4-yl-ethoxy)-naphthalen-1-yl]-acrylic acid methyl ester 51 (25 mg, 0.04 mmol), DIEA (13.6 mL, 0.08 mmol), and 5 mL THF. The reaction was heated to 80° C., stirring for 16 hours. The resulting reaction mixture was concentrated under vacuum and the crude residue purified by reverse phase preparative LC-MS to afford (10.2 mg, 39%) of the desired compound. Calculated mass=607. Observed mass=608.

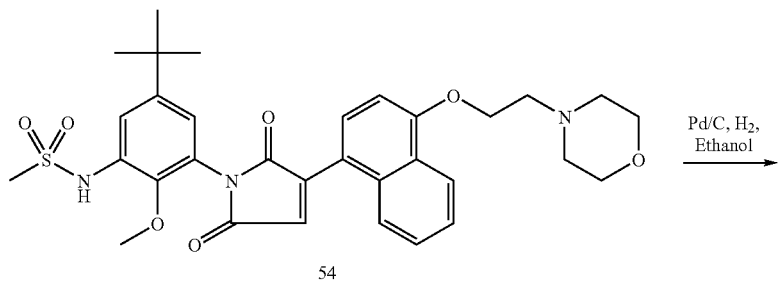

54

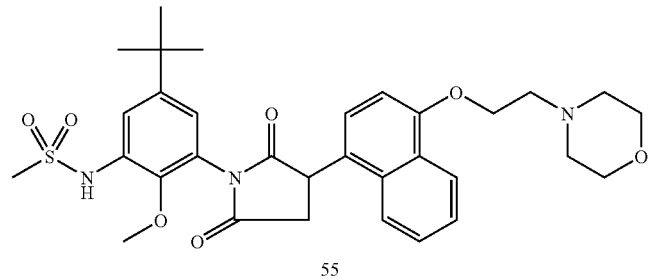

55

N-(5-tert-Butyl-2-methoxy-3-{3-[4-(2-morpholin-4-yl-ethoxy)-naphthalen-1-yl]-2,5-dioxo-pyrrolidin-1-yl}-phenyl)-methanesulfonamide (55). In a 20 mL scintillation vial was placed (28 mg, 0.046 mmol) N-(5-tert-butyl-2-methoxy-3-{3-[4-(2-morpholin-4-yl-ethoxy)-naphthalen-1-yl]-2,5-dioxo-2,5-dihydro-pyrrol-1-yl}-phenyl)-methanesulfonamide, 5 mL ethanol, and Pd/C (15 mg, 10 mole%). The vial was sealed with a septum and the reaction mixture was sparged with house nitrogen for 10 minutes. The resulting solution was then sparged with hydrogen gas via a balloon for 5 minutes. After recharging the balloon with hydrogen gas the reaction was allowed to stir at room temp for 2 hours. The resulting solution was filtered through a pad of celite and concentrated under vacuum to afford the desired product (27 mg, 100%). Calculated mass=610. Observed mass=611.

Example 11

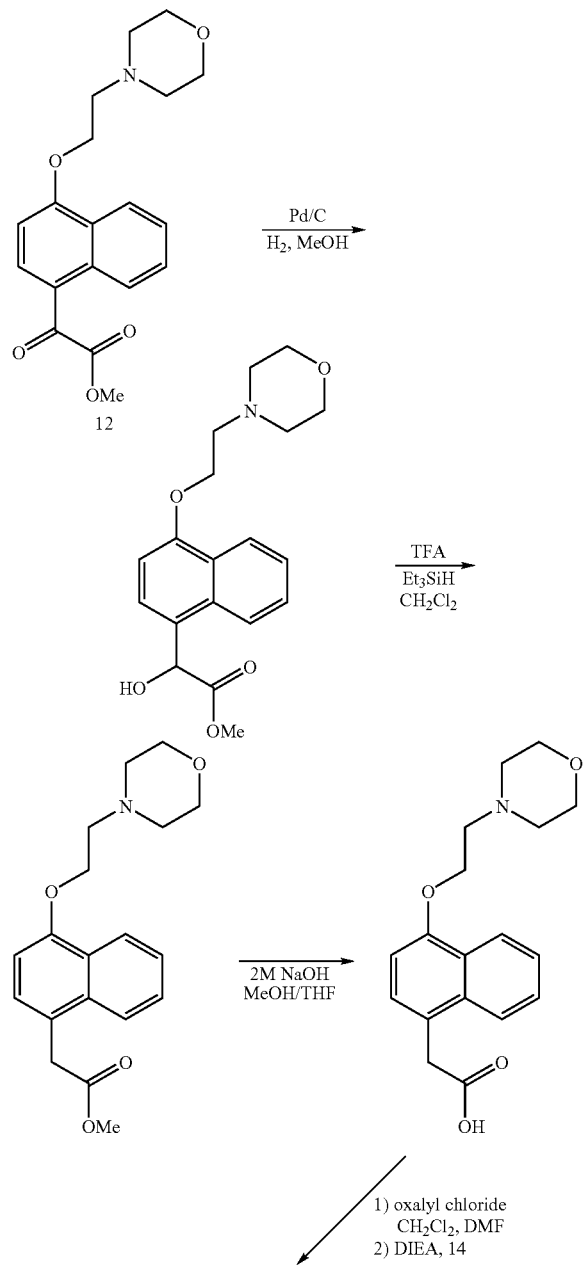

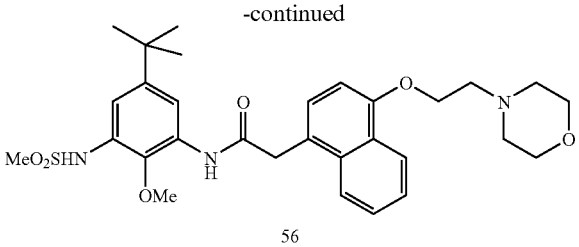

Hydroxy-[4-(2-morpholin-4-yl-ethoxy)-naphthalen-1-yl]-acetic acid methyl ester. To a solution of 12 (1 g, 2.9 mmol) in MeOH (10 mL), Pd/C (10 wt %) was added and the mixture stirred at rt under $H_2$ atmosphere. Upon completion of the reaction (monitored by LCMS), the mixture was filtered through celite and the filtrate evaporated to give a yellow oil which solidified upon standing. Calculated mass=345. Observed mass=345.

[4-(2-Morpholin-4-yl-ethoxy)-naphthalen-1-yl]-acetic acid. The yellow solid (0.5 g) was dissolved in $CH_2Cl_2$ (10 mL). To this solution TFA (10 mL) and $Et_3SiH$ (10 eq., 30 mmol) were added and the mixture was stirred at rt until the reaction was complete (after further addition of 10 eq. of $Et_3SiH$ as indicated by LCMS). The solvent was evaporated and the residue triturated with hexane. The product which precipitated was filtered, washed with hexane, dried in vacuo and taken up in MeOH/THF (1:1, 10 mL). To this solution, 2M NaOH (2.2 mL) was added and the mixture was stirred at rt for 4 h. The mixture was neutralized with 6 M HCl and evaporated to give a brown residue. The residue was repeatedly taken up in a minimum amount of MeOH and filtered from residual NaCl. The solvent was evaporated and the acid dried in vacuo at 50° C. Calculated mass=315. Observed mass=315.

N-(5-tert-Butyl-3-methanesulfonylamino-2-methoxy-phenyl)-2-[4-(2-morpholin-4-yl-ethoxy)-naphthalen-1-yl]-acetamide (56). To a suspension of the acid in $CH_2Cl_2$ (5 mL), oxalyl chloride (10 eq) and a drop of DMF were added. The mixture cleared rapidly under the evolution of gas and was left stirring at rt for 4 h. The solvent was evaporated to give a foamy residue which was dried in vacuo and taken up again in $CH_2Cl_2$ (5 mL). To this solution, DIEA (3 eq) and 14 (1.2 eq) were added and the mixture was stirred at rt for 60 h. The brown solution was washed with $H_2O$, dried ($MgSO_4$) and evaporated. The brown residue was purified by column chromatography on silica with EtOAc as eluent to give the final product as a pale yellow solid. Calculated mass=569. Observed mass=569.

Example 12

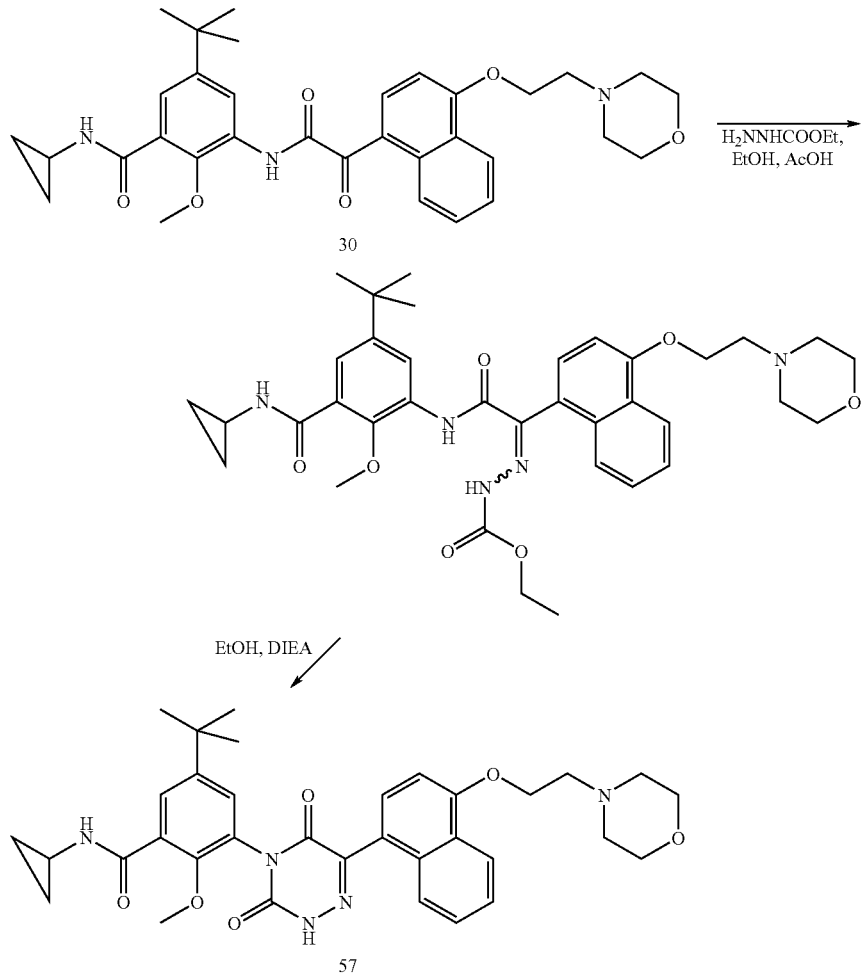

N'-{(5-tert-Butyl-3-sec-butylcarbamoyl-2-methoxy-phenylcarbamoyl)-[4-(2-morpholin-4-yl-ethoxy)-naphthalen-1-yl]-methylene}-hydrazinecarboxylic acid ethyl ester. Compound 30 (44 mg, 0.077 mmol) was dissolved in EtOH (1 mL) and hydrazinecarboxylic acid ethyl ester (24 mg, 0.231 mmol) and 1 drop of AcOH were added. The reaction mixture was stirred at 120° C. for 15 hrs, after which the crude mixture was purified by LC/MS. The isomers separated and the desired isomer was taken on into the next step. Calculated mass=660. Observed mass=660.

5-tert-Butyl-N-cyclopropyl-2-methoxy-3-{6-[4-(2-morpholin-4-yl-ethoxy)-naphthalen-1-yl]-3,5-dioxo-2,5-dihydro-3H-1,2,4-triazin-4-yl}-benzamide (57). The compound obtained in the previous step (~8 mg, 0.1 mmol) was dissolved in EtOH, and DIEA (0.1 ml, 0.6 mmol) was added. The mixture was stirred at 120° C. overnight and then purified by LC/MS to yield 2.5 mg of target product. Calculated mass=614. Observed mass=614.

Example 13

Inhibition of TNFa Production in THP Cells

The inhibition of cytokine production can be observed by measuring inhibition of TNFa in lipopolysaccharide-stimulated THP-1 cells (see Prichett et al. J. Inflammation, 1995, 45, 97). THP-1 cells (ATCC TIB 202, American Type Culture Collection, Rockville, Md.) were maintained at 37° C., 5% $CO_2$ in RPMI 1640 media with 10% fetal bovine serum, 10 mM Hepes, 1 mM sodium pyruvate, 4.5 g/L glucose and 0.05 mM 2-mercaptoethanol as suggested by ATCC. For the assay the cells and compounds were diluted in the media above except with 1% fetal bovine serum (assay media). Test compound stocks in DMSO were diluted into assay media to 6× the final assay concentration, with a final DMSO concentration of 0.3% in the assay. THP-1 cells were plated at $1 \times 10^5$/well in 96 well tissue culture plates. Diluted compounds (or DMSO control) were added and allowed to preincubate with the cells at 37° C., 5% CO$_2$ for 30 minutes prior to the addition of LPS (Sigma) to a final concentration of 1 μg/mL. Cells were then incubated 18-20 h at 37° C./5% CO$_2$. The assay was terminated by centrifuging the plates for 10 min at room temperature. Supernatants were removed to clean culture plates and aliquots removed for analysis for TNFa by a commercially available ELISA kit (R&D Systems #DY210, Minneapolis, Minn.). Data was analyzed by non-linear regression using PRISM 4 software from Graphpad Software (San Diego, Calif.). The calculated IC$_{50}$ is the concentration of the test compound that caused a 50% decrease in the maximal TNFa production.

Example 14

Table 1 lists compounds of the invention prepared using the methods of Examples 1-13. Each compound was analyzed by LC-MS and displayed the expected molecular ion. Each of the compounds in Table 1 was tested in the TNFa ELISA assay (Example 13) and found to have activity therein, with some compounds having IC$_{50}$s below 10 μM in this assay.

TABLE 1

| Compound number | Compound Name | Calculated MW |
| --- | --- | --- |
| 2 | 1H-Indazole-3-carboxylic acid (5-tert-butyl-2-p-tolyl-2H-pyrazol-3-yl)-amide | 373 |
| 7 | 3-tert-Butyl-5-phenyl-1-p-tolyl-1,6-dihydro-imidazo[4,5-c]pyrazole | 330 |
| 13 | N-(5-tert-Butyl-2-p-tolyl-2H-pyrazol-3-yl)-2-[4-(2-morpholin-4-yl-ethoxy)-naphthalen-1-yl]-2-oxo-acetamide | 541 |
| 15 | N-(5-tert-Butyl-3-methanesulfonylamino-2-methoxy-phenyl)-2-[4-(2-morpholin-4-yl-ethoxy)-naphthalen-1-yl]-2-oxo-acetamide | 584 |
| 17 | N-(5-tert-Butyl-3-methanesulfonylamino-2-methoxy-phenyl)-2-[4-(2-morpholin-4-yl-pyrimidin-4-yloxy)-naphthalen-1-yl]-2-oxo-acetamide | 634 |
| 22 | N-(5-tert-Butyl-2-hydroxy-3-morpholin-4-ylmethyl-phenyl)-2-[4-(2-morpholin-4-yl-ethoxy)-naphthalen-1-yl]-2-oxo-acetamide | 576 |
| 23 | N-(5-tert-Butyl-2-hydroxy-3-methyl-phenyl)-2-[4-(2-morpholin-4-yl-ethoxy)-naphthalen-1-yl]-2-oxo-acetamide | 491 |
| 24 | N-(5-tert-Butyl-2-methoxy-3-methyl-phenyl)-2-[4-(2-morpholin-4-yl-ethoxy)-naphthalen-1-yl]-2-oxo-acetamide | 505 |
| 26 | N-(5-tert-Butyl-3-chloro-2-methoxy-phenyl)-2-[4-(2-morpholin-4-yl-ethoxy)-naphthalen-1-yl]-2-oxo-acetamide | 525 |
| 28 | N-(5-tert-Butyl-2-methoxy-3-trifluoromethyl-phenyl)-2-[4-(2-morpholin-4-yl-ethoxy)-naphthalen-1-yl]-2-oxo-acetamide | 559 |
| 29 | N-(5-tert-Butyl-2-p-tolyl-2H-pyrazol-3-yl)-2-[7-chloro-4-(2-morpholin-4-yl-ethoxy)-naphthalen-1-yl]-2-oxo-acetamide | 575 |
| 30 | 5-tert-Butyl-N-cyclopropyl-2-methoxy-3-{2-[4-(2-morpholin-4-yl-ethoxy)-naphthalen-1-yl]-2-oxo-acetylamino}-benzamide | 574 |
| 31 | N-[5-tert-Butyl-2-methoxy-3-(piperidine-1-carbonyl)-phenyl]-2-[4-(2-morpholin-4-yl-ethoxy)-naphthalen-1-yl]-2-oxo-acetamide | 602 |
| 32 | 5-tert-Butyl-2-hydroxy-3-{2-[4-(2-morpholin-4-yl-ethoxy)-naphthalen-1-yl]-2-oxo-acetylamino}-benzoic acid | 521 |
| 33 | N-(2-Benzenesulfonyl-5-tert-butyl-2H-pyrazol-3-yl)-2-[4-(2-morpholin-4-yl-ethoxy)-naphthalen-1-yl]-2-oxo-acetamide | 591 |
| 35 | 2-(5-tert-Butyl-2-p-tolyl-2H-pyrazol-3-yl)-N-[4-(2-morpholin-4-yl-ethoxy)-naphthalen-1-yl]-2-oxo-acetamide | 541 |
| 40 | 1-Bicyclo[2.2.1]hept-2-yl-5-phenylamino-3-p-tolyl-1,3-dihydro-imidazo[4,5-b]pyridin-2-one | 411 |
| 41 | 3-p-Tolyl-5-p-tolylamino-1,3-dihydro-imidazo[4,5-b]pyridin-2-one | 330 |
| 42 | 1-Bicyclo[2.2.1]hept-2-yl-3-p-tolyl-5-p-tolylamino-1,3-dihydro-imidazo[4,5-b]pyridin-2-one | 425 |
| 45 | N-(5-tert-Butyl-2-p-tolyl-2H-pyrazol-3-yl)-2,2-difluoro-2-[4-(2-morpholin-4-yl-ethoxy)-naphthalen-1-yl]-acetamide | 563 |
| 46 | N-(5-tert-Butyl-2-p-tolyl-2H-pyrazol-3-yl)-N'-naphthalen-1-yl-oxalamide | 427 |

TABLE 1-continued

| Compound number | Compound Name | Calculated MW |
|---|---|---|
| 47 | N-(5-tert-Butyl-2-p-tolyl-2H-pyrazol-3-yl)-2-[(Z)-hydroxyimino]-2-[4-(2-morpholin-4-yl-ethoxy)-naphthalen-1-yl]-acetamide | 556 |
| 48 | N-(5-tert-Butyl-2-p-tolyl-2H-pyrazol-3-yl)-2-[(Z)-methoxyimino]-2-[4-(2-morpholin-4-yl-ethoxy)-naphthalen-1-yl]-acetamide | 570 |
| 49 | 2-(5-tert-Butyl-2-p-tolyl-2H-pyrazol-3-ylamino)-1-[4-(2-morpholin-4-yl-ethoxy)-naphthalen-1-yl]-ethanol | 529 |
| 50 | 1-(3-tert-Butyl-phenyl)-4-[4-(2-morpholin-4-yl-ethoxy)-naphthalen-1-yl]-[1,2,4]triazolidine-3,5-dione | 489 |
| 51 | 4-(3-tert-Butyl-phenyl)-1-[4-(2-morpholin-4-yl-ethoxy)-naphthalen-1-yl]-[1,2,4]triazolidine-3,5-dione | 489 |
| 52 | (E)-3-(5-tert-Butyl-3-methanesulfonylamino-2-methoxy-phenylcarbamoyl)-3-[4-(2-morpholin-4-yl-ethoxy)-naphthalen-1-yl]-acrylic acid methyl ester | 640 |
| 54 | N-(5-tert-Butyl-2-methoxy-3-{3-[4-(2-morpholin-4-yl-ethoxy)-naphthalen-1-yl]-2,5-dioxo-2,5-dihydro-pyrrol-1-yl}-phenyl)-methanesulfonamide | 608 |
| 55 | N-(5-tert-Butyl-2-methoxy-3-{3-[4-(2-morpholin-4-yl-ethoxy)-naphthalen-1-yl]-2,5-dioxo-pyrrolidin-1-yl}-phenyl)-methanesulfonamide | 610 |
| 56 | N-(5-tert-Butyl-3-methanesulfonylamino-2-methoxy-phenyl)-2-[4-(2-morpholin-4-yl-ethoxy)-naphthalen-1-yl]-acetamide | 570 |
| 57 | N-(5-tert-Butyl-3-methanesulfonylamino-2-methoxy-phenyl)-2-oxo-2-[4-(2-piperidin-1-yl-pyrimidin-4-yloxy)-naphthalen-1-yl]-acetamide | 632 |
| 58 | 3-tert-Butyl-1-p-tolyl-5-(3-trifluoromethyl-phenyl)-1,6-dihydro-imidazo[4,5-c]pyrazole | 398 |
| 59 | 1-(2-Morpholin-4-yl-ethyl)-1H-indazole-3-carboxylic acid (5-tert-butyl-3-methanesulfonylamino-2-methoxy-phenyl)-amide | 530 |
| 60 | N-[4-(2-Morpholin-4-yl-ethoxy)-naphthalen-1-yl]-2-oxo-2-(2,4,6-trimethyl-phenyl)-acetamide | 447 |
| 61 | 1-Phenyl-cyclopropanecarboxylic acid (5-tert-butyl-2-p-tolyl-2H-pyrazol-3-yl)-amide | 373 |
| 62 | N-[5-tert-Butyl-2-(2,5-difluoro-phenyl)-2H-pyrazol-3-yl]-2-[4-(2-morpholin-4-yl-ethoxy)-naphthalen-1-yl]-2-oxo-acetamide | 563 |
| 63 | N-(5-tert-Butyl-2-methoxy-phenyl)-2-[4-(2-morpholin-4-yl-ethoxy)-naphthalen-1-yl]-2-oxo-acetamide | 491 |
| 64 | N-(5-tert-Butyl-3-methanesulfonylamino-2-methoxy-phenyl)-2-(4-methoxy-naphthalen-1-yl)-2-oxo-acetamide | 485 |
| 65 | N-[5-tert-Butyl-2-(3-chloro-benzoyl)-2H-pyrazol-3-yl]-2-[4-(2-morpholin-4-yl-ethoxy)-naphthalen-1-yl]-2-oxo-acetamide | 589 |
| 66 | N-[5-tert-Butyl-2-(3-methanesulfonyl-phenyl)-2H-pyrazol-3-yl]-2-[4-(2-morpholin-4-yl-ethoxy)-naphthalen-1-yl]-2-oxo-acetamide | 605 |
| 67 | 4-[[(5-tert-Butyl-2-p-tolyl-2H-pyrazol-3-ylcarbamoyl)-methyl]-piperidine-1-carboxylic acid tert-butyl ester | 455 |
| 68 | N-[3-(Benzenesulfonyl-carbamoylmethyl-amino)-5-tert-butyl-2-methoxy-phenyl]-2-naphthalen-1-yl-2-oxo-acetamide | 574 |
| 69 | N-(3-tert-Butyl-isoxazol-5-yl)-2-[4-(2-morpholin-4-yl-ethoxy)-naphthalen-1-yl]-2-oxo-acetamide | 452 |
| 70 | N-(5-tert-Butyl-3-ethanesulfonylamino-2-methoxy-phenyl)-3-[4-(2-morpholin-4-yl-ethoxy)-naphthalen-1-yl]-succinamic acid methyl ester | 656 |
| 71 | 2-(2-Benzyl-5-tert-butyl-2H-pyrazol-3-yl)-N-[4-(2-morpholin-4-yl-ethoxy)-naphthalen-1-yl]-2-oxo-acetamide | 541 |
| 72 | N-(5-tert-Butyl-2-p-tolyl-2H-pyrazol-3-yl)-2-[4-(2-morpholin-4-yl-pyrimidin-4-ylamino)-naphthalen-1-yl]-2-oxo-acetamide | 590 |
| 73 | 5-tert-Butyl-2-(3-chloro-phenyl)-2H-pyrazole-3-carboxylic acid [4-(2-morpholin-4-yl-ethoxy)-naphthalen-1-yl]-amide | 533 |
| 74 | 2-(3-Bromo-4-methoxy-phenyl)-N-(5-tert-butyl-2-p-tolyl-2H-pyrazol-3-yl)-acetamide | 456 |
| 75 | N-(5-tert-Butyl-2-p-tolyl-2H-pyrazol-3-yl)-2-[3-fluoro-4-(2-morpholin-4-yl-ethoxy)-phenyl]-acetamide | 495 |
| 76 | (5-tert-Butyl-2-p-tolyl-2H-pyrazol-3-yl)-(2,2-dimethyl-propyl)-amine | 299 |
| 77 | 2-(4-Benzyloxy-phenyl)-N-(5-tert-butyl-2-p-tolyl-2H-pyrazol-3-yl)-acetamide | 454 |

TABLE 1-continued

| Compound number | Compound Name | Calculated MW |
|---|---|---|
| 78 | N-(5-tert-Butyl-2-p-tolyl-2H-pyrazol-3-yl)-2-hydroxy-2-[4-(2-morpholin-4-yl-ethoxy)-naphthalen-1-yl]-acetamide | 543 |
| 79 | N-[5-tert-Butyl-2-(4-sulfamoyl-phenyl)-2H-pyrazol-3-yl]-2-[4-(2-morpholin-4-yl-ethoxy)-naphthalen-1-yl]-2-oxo-acetamide | 606 |
| 80 | 5-tert-Butyl-2-methoxy-3-(1-naphthalen-1-yl-3,5-dioxo-[1,2,4]triazolidin-4-yl)-benzamide | 432 |
| 81 | 2-(4-Bromo-naphthalen-1-yl)-N-(5-tert-butyl-2-methyl-2H-pyrazol-3-yl)-2-oxo-acetamide | 414 |
| 82 | 5-tert-Butyl-2-hydroxy-3-{2-[4-(2-morpholin-4-yl-ethoxy)-naphthalen-1-yl]-2-oxo-acetylamino}-benzamide | 520 |
| 83 | N-(5-tert-Butyl-2-p-tolyl-2H-pyrazol-3-yl)-2-hydroxy-2-(4-methoxy-naphthalen-1-yl)-acetamide | 444 |
| 84 | N-(5-tert-Butyl-3-methanesulfonylamino-2-methoxy-phenyl)-2-[4-(6-morpholin-4-ylmethyl-pyridin-3-yl)-naphthalen-1-yl]-2-oxo-acetamide | 631 |
| 85 | N-(5-tert-Butyl-2-methoxy-phenyl)-2-[4-(2-methylamino-pyrimidin-4-ylamino)-naphthalen-1-yl]-2-oxo-acetamide | 484 |
| 86 | N-(5-tert-Butyl-2-methoxy-phenyl)-2-[4-(2-dimethylamino-pyrimidin-4-ylamino)-naphthalen-1-yl]-2-oxo-acetamide | 498 |
| 87 | N-(5-tert-Butyl-2-p-tolyl-2H-pyrazol-3-yl)-2-oxo-2-{4-[2-(1-oxo-1$\lambda^4$-thiomorpholin-4-yl)-ethoxy]-naphthalen-1-yl}-acetamide | 573 |
| 88 | 5-tert-Butyl-3-{2-[(Z)-hydroxyimino]-2-[4-(2-morpholin-4-yl-ethoxy)-naphthalen-1-yl]-acetylamino}-thiophene-2-carboxylic acid methyl ester | 540 |
| 89 | N-[5-tert-Butyl-2-(3-methanesulfonyl-phenyl)-2H-pyrazol-3-yl]-2-hydroxy-2-[4-(2-morpholin-4-yl-ethoxy)-naphthalen-1-yl]-acetamide | 607 |
| 90 | N-(5-tert-Butyl-2-p-tolyl-2H-pyrazol-3-yl)-2-{4-[2-((2R,6R)-2,6-dimethyl-morpholin-4-yl)-ethoxy]-naphthalen-1-yl}-2-oxo-acetamide | 569 |
| 91 | N-(5-tert-Butyl-2-methyl-2H-pyrazol-3-yl)-2-[4-(6-morpholin-4-ylmethyl-pyridin-3-yl)-naphthalen-1-yl]-2-oxo-acetamide | 512 |
| 92 | N-(5-tert-Butyl-3-methanesulfonylamino-2-methoxy-phenyl)-2-[7-chloro-4-(2-morpholin-4-yl-ethoxy)-naphthalen-1-yl]-2-oxo-acetamide | 618 |
| 93 | N-(5-tert-Butyl-3-methanesulfonylamino-2-methoxy-phenyl)-2-[(Z)-hydroxyimino]-2-[4-(2-morpholin-4-yl-ethoxy)-naphthalen-1-yl]-acetamide | 599 |
| 94 | N-(5-tert-Butyl-2-methoxy-phenyl)-2-[4-(6-morpholin-4-ylmethyl-pyridin-3-yl)-naphthalen-1-yl]-2-oxo-acetamide | 538 |
| 95 | 5-tert-Butyl-N-cyclopropyl-2-methoxy-3-[2-(4-methoxy-naphthalen-1-yl)-2-oxo-acetylamino]-benzamide | 475 |
| 96 | 4-tert-Butyl-N-[4-(2-piperidin-1-yl-ethoxy)-naphthalen-1-yl]-benzamide | 431 |
| 97 | N-(2-Acetyl-5-tert-butyl-2H-pyrazol-3-yl)-2-[4-(2-morpholin-4-yl-ethoxy)-naphthalen-1-yl]-2-oxo-acetamide | 493 |
| 98 | 5-tert-Butyl-N-cyclopropyl-3-{2-hydrazono-2-[4-(2-morpholin-4-yl-ethoxy)-naphthalen-1-yl]-acetylamino}-2-methoxy-benzamide | 588 |
| 99 | N-(5-tert-Butyl-2-methoxy-phenyl)-2-hydroxy-2-(4-methoxy-naphthalen-1-yl)-propionamide | 408 |
| 100 | N-(5-tert-Butyl-2-p-tolyl-2H-pyrazol-3-yl)-2-oxo-2-phenyl-acetamide | 361 |
| 101 | N-(5-tert-Butyl-3-methanesulfonylamino-2-methoxy-phenyl)-2-hydrazono-2-[4-(2-morpholin-4-yl-ethoxy)-naphthalen-1-yl]-acetamide | 598 |
| 102 | 2,3-Dihydro-indole-1-carboxylic acid (5-tert-butyl-2-p-tolyl-2H-pyrazol-3-yl)-amide | 374 |
| 103 | N-(3,4-Dimethyl-phenyl)-2-[4-(2-morpholin-4-yl-ethoxy)-naphthalen-1-yl]-2-oxo-acetamide | 433 |
| 104 | N-(5-tert-Butyl-2-cyclohexyl-2H-pyrazol-3-yl)-2-[4-(2-morpholin-4-yl-ethoxy)-naphthalen-1-yl]-2-oxo-acetamide | 533 |
| 105 | N-(5-tert-Butyl-2-p-tolyl-2H-pyrazol-3-yl)-2-(3,5-difluoro-phenyl)-acetamide | 383 |
| 106 | N-(5-tert-Butyl-2-methoxy-phenyl)-2-oxo-2-(4-pyridin-3-yl-naphthalen-1-yl)-acetamide | 439 |

TABLE 1-continued

| Compound number | Compound Name | Calculated MW |
| --- | --- | --- |
| 107 | N-(5-tert-Butyl-isoxazol-3-yl)-2-[(Z)-hydroxyimino]-2-[4-(2-morpholin-4-yl-ethoxy)-naphthalen-1-yl]-acetamide | 467 |
| 108 | N-(5-tert-Butyl-3-methanesulfonylamino-2-methoxy-phenyl)-2-[4-(2-diethylamino-ethoxy)-naphthalen-1-yl]-2-oxo-acetamide | 570 |
| 109 | N-(5-tert-Butyl-2-p-tolyl-2H-pyrazol-3-yl)-2-oxo-2-{4-[2-(3-oxo-[1,4]diazepan-1-yl)-ethyl]-naphthalen-1-yl}-acetamide | 552 |
| 110 | 5-tert-Butyl-N-ethyl-2-methoxy-3-[2-(4-methoxy-naphthalen-1-yl)-2-oxo-acetylamino]-benzamide | 463 |
| 111 | N-(5-tert-Butyl-2-methoxy-phenyl)-2-oxo-2-{4-[6-(tetrahydro-pyran-4-ylamino)-pyridin-3-yl]-naphthalen-1-yl}-acetamide | 538 |
| 112 | 5-tert-Butyl-3-ethanesulfonylamino-2-methoxy-N-[4-(2-morpholin-4-yl-ethoxy)-naphthalen-1-yl]-benzamide | 570 |
| 113 | 2-(5-tert-Butyl-2-methyl-2H-pyrazol-3-yl)-2-oxo-N-m-tolyl-acetamide | 299 |
| 114 | N-(2,5-Dimethyl-phenyl)-2-[4-(2-morpholin-4-yl-ethoxy)-naphthalen-1-yl]-2-oxo-acetamide | 433 |
| 115 | Pyrrolidine-1-carboxylic acid (5-tert-butyl-2-methoxy-3-{2-[4-(2-morpholin-4-yl-ethoxy)-naphthalen-1-yl]-2-oxo-acetylamino}-phenyl)-amide | 603 |
| 116 | 2-(4-Bromo-phenyl)-N-(5-tert-butyl-2-methoxy-phenyl)-acetamide | 376 |
| 117 | N-(3-Amino-5-tert-butyl-2-methoxy-phenyl)-2-oxo-2-{4-[2-((S)-1-phenyl-ethylamino)-pyrimidin-4-ylamino]-naphthalen-1-yl}-acetamide | 589 |
| 118 | 5-tert-Butyl-3-[1-(2,3-dimethyl-phenyl)-3,5-dioxo-[1,2,4]triazolidin-4-yl]-2-methoxy-benzamide | 410 |
| 119 | N-(5-tert-Butyl-2-p-tolyl-2H-pyrazol-3-yl)-2-naphthalen-2-yl-acetamide | 398 |
| 120 | 5-tert-Butyl-2-methoxy-3-{2-[4-(2-morpholin-4-yl-ethoxy)-naphthalen-1-yl]-2-oxo-acetylamino}-benzamide | 534 |
| 121 | N-(5-tert-Butyl-2-p-tolyl-2H-pyrazol-3-yl)-2-methoxy-2-(4-methoxy-naphthalen-1-yl)-propionamide | 472 |
| 122 | 5-tert-Butyl-2-methoxy-N-[4-(2-morpholin-4-yl-ethoxy)-naphthalen-1-ylmethyl]-3-nitro-benzamide | 522 |
| 123 | N-(5-tert-Butyl-2-methoxy-3-{2-[4-(2-morpholin-4-yl-ethoxy)-naphthalen-1-yl]-2-oxo-acetylamino}-phenyl)-benzamide | 610 |
| 124 | N-(5-tert-Butyl-2-p-tolyl-2H-pyrazol-3-yl)-2-(2,5-difluoro-phenyl)-acetamide | 383 |
| 125 | N-(3,5-Di-tert-butyl-2-methoxy-phenyl)-2-[(Z)-hydroxyimino]-2-[4-(2-morpholin-4-yl-ethoxy)-naphthalen-1-yl]-acetamide | 562 |
| 126 | N'-[1-(5-tert-Butyl-2-methyl-2H-pyrazol-3-ylcarbamoyl)-1-[4-(2-morpholin-4-yl-ethoxy)-naphthalen-1-yl]-meth-(E)-ylidene]-hydrazinecarboxamide | 522 |
| 127 | N-[2-(4-Amino-phenyl)-5-tert-butyl-2H-pyrazol-3-yl]-2-hydroxy-2-[4-(2-morpholin-4-yl-ethoxy)-naphthalen-1-yl]-acetamide | 544 |
| 128 | 5-tert-Butyl-3-{2-[(Z)-methoxyimino]-2-[4-(2-morpholin-4-yl-ethoxy)-naphthalen-1-yl]-acetylamino}-thiophene-2-carboxylic acid amide | 539 |
| 129 | Ethanesulfonic acid (5-tert-butyl-2-methoxy-3-{3-[4-(2-morpholin-4-yl-ethoxy)-naphthalen-1-yl]-2,5-dioxo-2,5-dihydro-pyrrol-1-yl}-phenyl)-amide | 622 |
| 130 | 5-tert-Butyl-N-cyclopropylmethyl-2-methoxy-3-{2-[4-(2-morpholin-4-yl-ethoxy)-naphthalen-1-yl]-2-oxo-acetylamino}-benzamide | 588 |
| 131 | 5-Fluoro-1H-indazole-3-carboxylic acid (5-tert-butyl-2-p-tolyl-2H-pyrazol-3-yl)-amide | 391 |
| 132 | N-[5-tert-Butyl-2-methoxy-3-(2-methoxy-acetylamino)-phenyl]-2-[4-(2-morpholin-4-yl-ethoxy)-naphthalen-1-yl]-2-oxo-acetamide | 578 |
| 133 | 7-Bicyclo[2.2.1]hept-2-yl-9-p-tolyl-2-p-tolylamino-7,9-dihydro-purin-8-one | 426 |
| 134 | N-(5-tert-Butyl-2-isopropoxy-3-methanesulfonylamino-phenyl)-2-[4-(2-morpholin-4-yl-ethoxy)-naphthalen-1-yl]-2-oxo-acetamide | 612 |
| 135 | N-[5-tert-Butyl-2-(3,4-dimethyl-phenyl)-2H-pyrazol-3-yl]-2-[4-(2-morpholin-4-yl-ethoxy)-naphthalen-1-yl]-2-oxo-acetamide | 555 |

TABLE 1-continued

| Compound number | Compound Name | Calculated MW |
|---|---|---|
| 136 | 3-tert-Butyl-1-(3,4-dichloro-phenyl)-5-phenyl-1,6-dihydro-imidazo[4,5-c]pyrazole | 385 |
| 137 | N-(5-tert-Butyl-2-p-tolyl-2H-pyrazol-3-yl)-2-oxo-2-[4-(2-thiomorpholin-4-yl-ethoxy)-naphthalen-1-yl]-acetamide | 557 |
| 138 | 5-Nitro-1H-pyrazole-3-carboxylic acid (5-tert-butyl-2-p-tolyl-2H-pyrazol-3-yl)-amide | 368 |
| 139 | N-(5-tert-Butyl-3-methanesulfonylamino-2-methoxy-phenyl)-2-[4-(2-dimethylamino-pyrimidin-4-ylamino)-naphthalen-1-yl]-2-oxo-acetamide | 591 |
| 140 | 1-(2-Amino-4-tert-butyl-6-{2-[4-(2-morpholin-4-yl-ethoxy)-naphthalen-1-yl]-2-oxo-acetylamino}-phenyl)-pyridinium | 554 |
| 141 | N-(5-tert-Butyl-2-isopropoxy-phenyl)-2-[4-(2-morpholin-4-yl-ethoxy)-naphthalen-1-yl]-2-oxo-acetamide | 519 |
| 142 | N-[4-(2-Morpholin-4-yl-ethoxy)-naphthalen-1-yl]-2,5-bis-trifluoromethyl-benzamide | 512 |
| 143 | 2-(tert-Butyl-dimethyl-silanyloxy)-N-(5-tert-butyl-2-p-tolyl-2H-pyrazol-3-yl)-2-(4-methoxy-phenyl)-acetamide | 508 |
| 144 | N-(5-tert-Butyl-2-m-tolyl-2H-pyrazol-3-yl)-2-[(Z)-hydroxyimino]-2-[4-(2-morpholin-4-yl-ethoxy)-naphthalen-1-yl]-acetamide | 556 |
| 145 | 5-tert-Butyl-2-methoxy-3-[2-(4-methoxy-naphthalen-1-yl)-2-oxo-acetylamino]-benzamide | 434 |
| 146 | N-(5-tert-Butyl-2-p-tolyl-2H-pyrazol-3-yl)-2-oxo-2-phenyl-acetamide | 361 |
| 147 | 5-tert-Butyl-2-methoxy-N-(2-methoxy-ethyl)-3-{2-[4-(2-morpholin-4-yl-ethoxy)-naphthalen-1-yl]-2-oxo-acetylamino}-benzamide | 592 |
| 148 | (E)-3-(5-tert-Butyl-3-ethanesulfonylamino-2-methoxy-phenylcarbamoyl)-3-[4-(2-morpholin-4-yl-ethoxy)-naphthalen-1-yl]-acrylic acid methyl ester | 654 |
| 149 | 1-Isopropyl-3-phenyl-5-phenylamino-1,3-dihydro-imidazo[4,5-b]pyridin-2-one | 344 |
| 150 | N-(5-tert-Butyl-isoxazol-3-yl)-2-[4-(2-morpholin-4-yl-pyrimidin-4-ylamino)-naphthalen-1-yl]-2-oxo-acetamide | 501 |
| 151 | 2-(2-Benzyl-5-tert-butyl-2H-pyrazol-3-yl)-2-[(Z)-hydroxyimino]-N-[4-(2-morpholin-4-yl-ethoxy)-naphthalen-1-yl]-acetamide | 556 |
| 152 | 2-(5-tert-Butyl-2-methoxy-phenyl)-N-[4-(2-morpholin-4-yl-ethoxy)-naphthalen-1-yl]-2-oxo-acetamide | 491 |
| 153 | N-(5-tert-Butyl-2-p-tolyl-2H-pyrazol-3-yl)-2-(2,4-dimethoxy-phenyl)-acetamide | 408 |
| 154 | (5-tert-Butyl-2-methoxy-3-{2-[4-(2-morpholin-4-yl-ethoxy)-naphthalen-1-yl]-2-oxo-acetylamino}-phenyl)-carbamic acid methyl ester | 564 |
| 155 | 3-tert-Butyl-5-{2-[4-(2-morpholin-4-yl-ethoxy)-naphthalen-1-yl]-2-oxo-acetylamino}-pyrazole-1-carboxylic acid adamantan-1-ylamide | 628 |
| 156 | 3-tert-Butyl-5-phenyl-1-(4-trifluoromethyl-phenyl)-1,6-dihydro-imidazo[4,5-c]pyrazole | 384 |
| 157 | N-(5-tert-Butyl-2-methoxy-3-{3-[4-(2-morpholin-4-yl-ethoxy)-naphthalen-1-yl]-2,4,5-trioxo-imidazolidin-1-yl}-phenyl)-methanesulfonamide | 625 |
| 158 | 3-tert-Butyl-1-(3-chloro-phenyl)-5-phenyl-1,6-dihydro-imidazo[4,5-c]pyrazole | 351 |
| 159 | 5-tert-Butyl-3-{2-[4-(2-morpholin-4-yl-ethoxy)-naphthalen-1-yl]-2-oxo-acetylamino}-thiophene-2-carboxylic acid amide | 510 |
| 160 | 2-(5-tert-Butyl-2-p-tolyl-2H-pyrazol-3-yl)-2-hydroxy-N-[4-(2-morpholin-4-yl-ethoxy)-naphthalen-1-yl]-acetamide | 543 |
| 161 | N-(5-tert-Butyl-2-p-tolyl-2H-pyrazol-3-yl)-2-{4-[2-(2,6-dimethyl-morpholin-4-yl)-ethyl]-naphthalen-1-yl}-2-oxo-acetamide | 553 |
| 162 | N-(5-tert-Butyl-2H-pyrazol-3-yl)-2-[4-(2-morpholin-4-yl-ethoxy)-naphthalen-1-yl]-2-oxo-acetamide | 451 |
| 163 | N-[5-tert-Butyl-2-methoxy-3-(propane-1-sulfonylamino)-phenyl]-2-[4-(2-morpholin-4-yl-ethoxy)-naphthalen-1-yl]-acetamide | 598 |
| 164 | 3-tert-Butyl-5-{2-[4-(2-morpholin-4-yl-ethoxy)-naphthalen-1-yl]-2-oxo-acetylamino}-pyrazole-1-carboxylic acid tert-butylamide | 550 |
| 165 | 1-(5-tert-Butyl-2-methyl-2H-pyrazol-3-yl)-3-(2,3-dichlorophenyl)-3'-(carbamic acid ethyl ester)-urea | 428 |

TABLE 1-continued

| Compound number | Compound Name | Calculated MW |
|---|---|---|
| 166 | 2-(3,5-Difluoro-phenyl)-N-[4-(2-morpholin-4-yl-ethoxy)-naphthalen-1-yl]-2-oxo-acetamide | 440 |
| 167 | 3-tert-Butyl-5-{2-[4-(2-morpholin-4-yl-ethoxy)-naphthalen-1-yl]-2-oxo-acetylamino}-pyrazole-1-carboxylic acid amide | 494 |
| 168 | N-Allyl-5-tert-butyl-2-methoxy-3-{2-[4-(2-morpholin-4-yl-ethoxy)-naphthalen-1-yl]-2-oxo-acetylamino}-benzamide | 574 |
| 169 | N-(5-tert-Butyl-isoxazol-3-yl)-2-[(Z)-methoxyimino]-2-[4-(2-morpholin-4-yl-ethoxy)-naphthalen-1-yl]-acetamide | 481 |
| 170 | 3-(5-tert-Butyl-2-methyl-2H-pyrazol-3-yl)-1-[4-(2-morpholin-4-yl-ethoxy)-naphthalen-1-yl]-pyrrole-2,5-dione | 489 |
| 171 | 2-(5-tert-Butyl-2-methyl-2H-pyrazol-3-yl)-2-[(Z)-hydroxyimino]-N-[4-(2-morpholin-4-yl-ethoxy)-naphthalen-1-yl]-acetamide | 480 |
| 172 | 3-tert-Butyl-5-o-tolyl-1-p-tolyl-1,6-dihydro-imidazo[4,5-c]pyrazole | 344 |
| 173 | N-(5-tert-Butyl-2-p-tolyl-2H-pyrazol-3-yl)-2-[(E)-hydroxyimino]-2-phenyl-acetamide | 376 |
| 174 | N-(5-tert-Butyl-2-methoxy-phenyl)-2-hydroxy-2-phenyl-acetamide | 313 |
| 175 | N-(3-Acetylamino-5-tert-butyl-2-methoxy-phenyl)-2-[4-(2-morpholin-4-yl-ethoxy)-naphthalen-1-yl]-2-oxo-acetamide | 548 |
| 176 | 1H-Indazole-3-carboxylic acid (5-tert-butyl-3-methanesulfonylamino-2-methoxy-phenyl)-amide | 417 |
| 177 | 5-tert-Butyl-2-methoxy-N-[4-(2-morpholin-4-yl-ethoxy)-naphthalen-1-yl]-3-nitro-benzamide | 508 |
| 178 | 5-tert-Butyl-3-{2-[(Z)-hydroxyimino]-2-[4-(2-morpholin-4-yl-pyrimidin-4-yloxy)-naphthalen-1-yl]-acetylamino}-thiophene-2-carboxylic acid amide | 575 |
| 179 | N-[3-(4-Acetyl-piperazine-1-carbonyl)-5-tert-butyl-2-methoxy-phenyl]-2-[4-(2-morpholin-4-yl-ethoxy)-naphthalen-1-yl]-2-oxo-acetamide | 645 |
| 180 | 2-(5-tert-Butyl-2-methyl-2H-pyrazol-3-yl)-N-[4-(2-morpholin-4-yl-pyrimidin-4-yloxy)-naphthalen-1-yl]-2-oxo-acetamide | 515 |
| 181 | N-(5-tert-Butyl-4-methyl-2-p-tolyl-2H-pyrazol-3-yl)-2-[(Z)-hydroxyimino]-2-[4-(2-morpholin-4-yl-ethoxy)-naphthalen-1-yl]-acetamide | 570 |
| 182 | 2-[4-(2-Morpholin-4-yl-ethoxy)-naphthalen-1-yl]-2-oxo-N-(2-phenyl-cyclopropyl)-acetamide | 445 |
| 183 | N-(5-tert-Butyl-isoxazol-3-yl)-2-[4-(6-morpholin-4-ylmethyl-pyridin-3-yl)-naphthalen-1-yl]-2-oxo-acetamide | 499 |
| 184 | N-(5-tert-Butyl-2,3-dimethoxy-phenyl)-2-[(Z)-hydroxyimino]-2-[4-(2-morpholin-4-yl-ethoxy)-naphthalen-1-yl]-acetamide | 536 |
| 185 | N-(5-tert-Butyl-2-p-tolyl-2H-pyrazol-3-yl)-2-(2-chloro-phenyl)-acetamide | 382 |
| 186 | N-(5-tert-Butyl-2-p-tolyl-2H-pyrazol-3-yl)-2-{4-[2-(4-methyl-piperazin-1-yl)-ethyl]-naphthalen-1-yl}-2-oxo-acetamide | 538 |
| 187 | N-(5-tert-Butyl-3-methanesulfonylamino-2-methoxy-phenyl)-2-(1H-indol-3-yl)-2-oxo-acetamide | 444 |
| 188 | N-(5-tert-Butyl-2-methoxy-phenyl)-2-[4-(2-morpholin-4-yl-pyridin-4-ylamino)-naphthalen-1-yl]-2-oxo-acetamide | 539 |
| 189 | N-(4-tert-Butyl-6-trifluoromethyl-pyrimidin-2-yl)-2-[4-(2-morpholin-4-yl-ethoxy)-naphthalen-1-yl]-2-oxo-acetamide | 531 |
| 190 | N-(5-tert-Butyl-2-p-tolyl-2H-pyrazol-3-yl)-2-o-tolyl-acetamide | 361 |
| 191 | 5-tert-Butyl-3-{2-[(Z)-hydroxyimino]-2-[4-(2-morpholin-4-yl-ethoxy)-naphthalen-1-yl]-acetylamino}-thiophene-2-carboxylic acid methylamide | 539 |
| 192 | N-[5-tert-Butyl-2-(3,5-dichloro-phenyl)-2H-pyrazol-3-yl]-2-[4-(2-morpholin-4-yl-ethoxy)-naphthalen-1-yl]-2-oxo-acetamide | 596 |
| 193 | N-(5-tert-Butyl-2-p-tolyl-2H-pyrazol-3-yl)-2-{4-[2-((2R,6S)-2,6-dimethyl-morpholin-4-yl)-ethoxy]-naphthalen-1-yl}-2-oxo-acetamide | 569 |
| 194 | 3-tert-Butyl-1,5-diphenyl-1,6-dihydro-imidazo[4,5-c]pyrazole | 316 |

TABLE 1-continued

| Compound number | Compound Name | Calculated MW |
| --- | --- | --- |
| 195 | N-(5-tert-Butyl-2-p-tolyl-2H-pyrazol-3-yl)-2-[4-(2-imidazol-1-yl-ethyl)-naphthalen-1-yl]-2-oxo-acetamide | 506 |
| 196 | 3-tert-Butyl-5-(3-chloro-phenyl)-1-p-tolyl-1,6-dihydro-imidazo[4,5-c]pyrazole | 365 |
| 197 | N-(5-tert-Butyl-2-methoxy-3-phenylmethanesulfonylamino-phenyl)-2-[4-(2-morpholin-4-yl-ethoxy)-naphthalen-1-yl]-2-oxo-acetamide | 660 |
| 198 | N-(5-tert-Butyl-2-p-tolyl-2H-pyrazol-3-yl)-2-oxo-2-[4-(2-pyridin-4-yl-ethoxy)-naphthalen-1-yl]-acetamide | 533 |
| 199 | 1-(5-tert-Butyl-2-methoxy-phenyl)-3-(4-{2-[(pyridin-2-ylmethyl)-amino]-pyrimidin-4-yloxy}-naphthalen-1-yl)-imidazolidine-2,4,5-trione | 603 |
| 200 | N-[5-tert-Butyl-2-(3-chloro-phenyl)-2H-pyrazol-3-yl]-2-[4-(2-morpholin-4-yl-ethoxy)-naphthalen-1-yl]-2-oxo-acetamide | 561 |
| 201 | 5-Methoxy-1H-indazole-3-carboxylic acid (5-tert-butyl-2-p-tolyl-2H-pyrazol-3-yl)-amide | 403 |
| 202 | N-[5-tert-Butyl-2-(6-chloro-pyridazin-3-yl)-2H-pyrazol-3-yl]-2-[4-(2-morpholin-4-yl-ethoxy)-naphthalen-1-yl]-2-oxo-acetamide | 563 |
| 203 | N-(5-tert-Butyl-2-m-tolyl-2H-pyrazol-3-yl)-2-[4-(2-morpholin-4-yl-ethoxy)-naphthalen-1-yl]-2-oxo-acetamide | 541 |
| 204 | N-(5-tert-Butyl-2-p-tolyl-2H-pyrazol-3-yl)-2-(2-methoxy-phenyl)-acetamide | 377 |
| 205 | 5-tert-Butyl-N-cyclopropyl-2-methoxy-3-{2-[4-(2-morpholin-4-yl-pyrimidin-4-ylamino)-naphthalen-1-yl]-2-oxo-acetylamino}-benzamide | 623 |
| 206 | [(5-tert-Butyl-2-methoxy-3-{2-[4-(2-morpholin-4-yl-ethoxy)-naphthalen-1-yl]-2-oxo-acetylamino}-phenyl)-methanesulfonyl-amino]-acetic acid ethyl ester | 670 |
| 207 | N-(5-tert-Butyl-4-methyl-2-m-tolyl-2H-pyrazol-3-yl)-2-[(Z)-hydroxyimino]-2-[4-(2-morpholin-4-yl-ethoxy)-naphthalen-1-yl]-acetamide | 570 |
| 208 | N-[5-tert-Butyl-2-(2,5-dichloro-phenyl)-2H-pyrazol-3-yl]-2-[4-(2-morpholin-4-yl-ethoxy)-naphthalen-1-yl]-2-oxo-acetamide | 596 |
| 209 | N-(5-tert-Butyl-2-p-tolyl-2H-pyrazol-3-yl)-2-[4-(2-[1,4]oxazepan-4-yl-ethoxy)-naphthalen-1-yl]-2-oxo-acetamide | 555 |
| 210 | 1-(5-tert-Butyl-2-methoxy-3-benzamide)-3-(4-methoxy-phenyl)-3'-(carbamic acid ethyl ester)-urea | 459 |
| 211 | N-[5-tert-Butyl-2-(4-methoxy-phenyl)-2H-pyrazol-3-yl]-2-(4-methoxy-naphthalen-1-yl)-acetamide | 444 |
| 212 | N-(5-tert-Butyl-2-p-tolyl-2H-pyrazol-3-yl)-4-chloro-benzamide | 368 |
| 213 | N-(2-Bromo-5-trifluoromethyl-phenyl)-2-[4-(2-morpholin-4-yl-ethoxy)-naphthalen-1-yl]-2-oxo-acetamide | 551 |
| 214 | 3-Isopropyl-5-phenyl-1-p-tolyl-1,6-dihydro-imidazo[4,5-c]pyrazole | 316 |
| 215 | 3,5-Di-tert-butyl-1-p-tolyl-1,6-dihydro-imidazo[4,5-c]pyrazole | 310 |
| 216 | 5-tert-Butyl-N-cyclopentyl-2-methoxy-3-{2-[4-(2-morpholin-4-yl-ethoxy)-naphthalen-1-yl]-2-oxo-acetylamino}-benzamide | 602 |
| 217 | 2-[5-tert-Butyl-2-(3-fluoro-4-methyl-phenyl)-2H-pyrazol-3-yl]-N-[4-(2-morpholin-4-yl-ethoxy)-naphthalen-1-yl]-2-oxo-acetamide | 559 |
| 218 | N-(5-tert-Butyl-2-p-tolyl-2H-pyrazol-3-yl)-2-(4-methoxy-phenyl)-2-oxo-acetamide | 391 |
| 219 | 1,3-Di-tert-butyl-5-phenyl-1,6-dihydro-imidazo[4,5-c]pyrazole | 296 |
| 220 | 4-(4-Bromo-naphthalen-1-yl)-1-(3-tert-butyl-phenyl)-[1,2,4]triazolidine-3,5-dione | 438 |
| 221 | N-[5-tert-Butyl-2-(morpholine-4-carbonyl)-thiophen-3-yl]-2-[4-(2-morpholin-4-yl-ethoxy)-naphthalen-1-yl]-2-oxo-acetamide | 580 |
| 222 | 3-tert-Butyl-5-(3-methoxy-phenyl)-1-p-tolyl-1,6-dihydro-imidazo[4,5-c]pyrazole | 360 |
| 223 | N-(5-tert-Butyl-2-methoxy-phenyl)-2-[4-(2-morpholin-4-yl-pyrimidin-4-yloxy)-naphthalen-1-yl]-2-oxo-acetamide | 541 |
| 224 | 1-tert-Butyl-5-[4-(2-morpholin-4-yl-ethoxy)-naphthalen-1-ylamino]-3-p-tolyl-1,3-dihydro-imidazo[4,5-b]pyridin-2-one | 552 |

TABLE 1-continued

| Compound number | Compound Name | Calculated MW |
|---|---|---|
| 225 | 2-[5-tert-Butyl-2-(3-fluoro-phenyl)-2H-pyrazol-3-yl]-2-[(Z)-hydroxyimino]-N-[4-(2-morpholin-4-yl-ethoxy)-naphthalen-1-yl]-acetamide | 560 |
| 226 | 5-tert-Butyl-2-p-tolyl-2H-pyrazole-3-carboxylic acid [4-(2-morpholin-4-yl-ethoxy)-naphthalen-1-ylmethyl]-amide | 527 |
| 227 | 2-[5-tert-Butyl-2-(3-fluoro-phenyl)-2H-pyrazol-3-yl]-N-[4-(2-morpholin-4-yl-ethoxy)-naphthalen-1-yl]-2-oxo-acetamide | 545 |
| 228 | 5-tert-Butyl-N-cyclopropylmethyl-2-methoxy-3-[2-(4-methoxy-naphthalen-1-yl)-2-oxo-acetylamino]-benzamide | 489 |
| 229 | N-[5-tert-Butyl-3-(3,3-diethyl-ureido)-2-methoxy-phenyl]-2-[4-(2-morpholin-4-yl-ethoxy)-naphthalen-1-yl]-2-oxo-acetamide | 605 |
| 230 | N-[5-tert-Butyl-2-(4-fluoro-phenyl)-2H-pyrazol-3-yl]-2-[4-(2-morpholin-4-yl-ethoxy)-naphthalen-1-yl]-2-oxo-acetamide | 545 |
| 231 | N-(2-Benzyl-5-tert-butyl-2H-pyrazol-3-yl)-2-[4-(2-morpholin-4-yl-ethoxy)-naphthalen-1-yl]-2-oxo-acetamide | 541 |
| 232 | N-(5-tert-Butyl-3-methanesulfonylamino-2-methoxy-phenyl)-2-oxo-2-[4-(2-piperazin-1-yl-ethoxy)-naphthalen-1-yl]-acetamide | 583 |
| 233 | N-(5-tert-Butyl-3-methanesulfonylamino-2-methoxy-phenyl)-2-[4-(2-morpholin-4-yl-pyridin-4-ylamino)-naphthalen-1-yl]-2-oxo-acetamide | 632 |
| 234 | (5-tert-Butyl-2-methoxy-3-{2-[4-(2-morpholin-4-yl-ethoxy)-naphthalen-1-yl-2-oxo-acetylamino}-phenyl)-carbamic acid isopropyl ester | 592 |
| 235 | 1-(5-tert-Butyl-2-methoxy-phenyl)-3-[4-(2-dimethylamino-pyrimidin-4-yloxy)-naphthalen-1-yl]-imidazolidine-2,4,5-trione | 540 |
| 236 | N-(5-tert-Butyl-3-methanesulfonylamino-2-methoxy-phenyl)-2-[4-(2-morpholin-4-yl-pyrimidin-4-ylamino)-naphthalen-1-yl]-2-oxo-acetamide | 633 |
| 237 | 4-(3-tert-Butyl-1-p-tolyl-1,6-dihydro-imidazo[4,5-c]pyrazol-5-yl)-2-methoxy-phenol | 376 |
| 238 | N-(5-tert-Butyl-2-p-tolyl-2H-pyrazol-3-yl)-2-(3,4-dichloro-phenyl)-acetamide | 416 |
| 239 | N-[3-(3-Allyl-ureido)-5-tert-butyl-2-methoxy-phenyl]-2-[4-(2-morpholin-4-yl-ethoxy)-naphthalen-1-yl]-2-oxo-acetamide | 589 |
| 240 | 5-tert-Butyl-N,N-diethyl-2-methoxy-3-{2-[4-(2-morpholin-4-yl-ethoxy)-naphthalen-1-yl]-2-oxo-acetylamino}-benzamide | 590 |
| 241 | N-(5-tert-Butyl-3-methanesulfonylamino-2-methoxy-phenyl)-2-[4-(2-[1,4]oxazepan-4-yl-ethoxy)-naphthalen-1-yl]-2-oxo-acetamide | 598 |
| 242 | N-(3-tert-Butyl-phenyl)-2-[4-(2-morpholin-4-yl-ethoxy)-naphthalen-1-yl]-2-oxo-acetamide | 461 |
| 243 | 5-tert-Butyl-N-ethyl-2-methoxy-3-{2-[4-(2-morpholin-4-yl-ethoxy)-naphthalen-1-yl]-acetylamino}-benzamide | 548 |
| 244 | N-[5-tert-Butyl-2-(6-methyl-pyridin-3-yl)-2H-pyrazol-3-yl]-2-[4-(2-morpholin-4-yl-ethoxy)-naphthalen-1-yl]-2-oxo-acetamide | 542 |
| 245 | N-[5-tert-Butyl-2-(4-ureido-phenyl)-2H-pyrazol-3-yl]-2-[4-(2-morpholin-4-yl-ethoxy)-naphthalen-1-yl]-2-oxo-acetamide | 585 |
| 246 | N-(5-tert-Butyl-2-m-tolyl-2H-pyrazol-3-yl)-2-[4-(2-dimethylamino-ethoxy)-naphthalen-1-yl]-2-oxo-acetamide | 499 |
| 247 | N-(5-tert-Butyl-2-methoxy-phenyl)-2-oxo-2-[4-(2-piperidin-1-yl-pyrimidin-4-yloxy)-naphthalen-1-yl]-acetamide | 539 |
| 248 | N-[5-tert-Butyl-2-(3-fluoro-4-methyl-phenyl)-2H-pyrazol-3-yl]-2-[4-(2-morpholin-4-yl-ethoxy)-naphthalen-1-yl]-2-oxo-acetamide | 559 |
| 249 | Indazole-1-carboxylic acid (5-tert-butyl-2-p-tolyl-2H-pyrazol-3-yl)-amide | 373 |
| 250 | N-[3,5-Bis-(1,1-dimethyl-propyl)-2-methoxy-phenyl]-2-[4-(2-morpholin-4-yl-ethoxy)-naphthalen-1-yl]-2-oxo-acetamide | 575 |
| 251 | 1-Benzyl-3-tert-butyl-5-phenyl-1,6-dihydro-imidazo[4,5-c]pyrazole | 330 |

TABLE 1-continued

| Compound number | Compound Name | Calculated MW |
|---|---|---|
| 252 | 2-(5-tert-Butyl-2-methoxy-3-nitro-phenyl)-N-[4-(2-morpholin-4-yl-ethoxy)-naphthalen-1-yl]-2-oxo-acetamide | 536 |
| 253 | 4-{2-[4-(5-tert-Butyl-3-methanesulfonylamino-2-methoxy-phenylaminooxalyl)-naphthalen-1-yloxy]-ethyl}-piperazine-1-carboxylic acid ethyl ester | 655 |
| 254 | 2-Hydroxy-N-(5-isopropyl-2-p-tolyl-2H-pyrazol-3-yl)-2-[4-(2-morpholin-4-yl-ethoxy)-naphthalen-1-yl]-acetamide | 529 |
| 255 | 1-Bicyclo[2.2.1]hept-2-yl-3-phenyl-5-phenylamino-1,3-dihydro-imidazo[4,5-b]pyridin-2-one | 396 |
| 256 | N-(3-Amino-5-tert-butyl-2-methoxy-phenyl)-2-[4-(2-morpholin-4-yl-pyrimidin-4-ylamino)-naphthalen-1-yl]-2-oxo-acetamide | 555 |
| 257 | N-[5-tert-Butyl-3-(2-dimethylamino-acetylamino)-2-methoxy-phenyl]-2-[4-(2-morpholin-4-yl-ethoxy)-naphthalen-1-yl]-2-oxo-acetamide | 591 |
| 258 | N-(5-tert-Butyl-2-methoxy-3-{6-[4-(2-morpholin-4-yl-ethoxy)-naphthalen-1-yl]-3,5-dioxo-2,5-dihydro-3H-[1,2,4]triazin-4-yl}-phenyl)-methanesulfonamide | 624 |
| 259 | N-(5-tert-Butyl-2-methyl-2H-pyrazol-3-yl)-2-[4-(2-morpholin-4-yl-ethoxy)-naphthalen-1-yl]-2-oxo-acetamide | 465 |
| 260 | (R)-N-(5-tert-Butyl-2-p-tolyl-2H-pyrazol-3-yl)-2-hydroxy-2-phenyl-acetamide | 363 |
| 261 | N-(5-tert-Butyl-3-methanesulfonylamino-2-methoxy-phenyl)-2-[4-(2-dimethylamino-ethoxy)-naphthalen-1-yl]-2-oxo-acetamide | 542 |
| 262 | 2-(5-tert-Butyl-2-methyl-2H-pyrazol-3-yl)-N-[4-(2-morpholin-4-yl-ethoxy)-naphthalen-1-yl]-2-oxo-acetamide | 465 |
| 263 | N-[2-(3-Amino-phenyl)-5-tert-butyl-2H-pyrazol-3-yl]-2-hydroxy-2-[4-(2-morpholin-4-yl-ethoxy)-naphthalen-1-yl]-acetamide | 544 |
| 264 | 2-[5-tert-Butyl-2-(3-chloro-phenyl)-2H-pyrazol-3-yl]-N-[4-(2-morpholin-4-yl-ethoxy)-naphthalen-1-yl]-2-oxo-acetamide | 561 |
| 265 | 1,5-Diphenyl-1,6-dihydro-imidazo[4,5-c]pyrazole | 260 |
| 266 | N-(5-tert-Butyl-[1,3,4]thiadiazol-2-yl)-2-[(Z)-hydroxyimino]-2-[4-(2-morpholin-4-yl-ethoxy)-naphthalen-1-yl]-acetamide | 484 |
| 267 | N-(5-tert-Butyl-3-{2-hydroxy-2-[4-(2-morpholin-4-yl-pyrimidin-4-yloxy)-naphthalen-1-yl]-ethylamino}-2-methoxy-phenyl)-methanesulfonamide | 622 |
| 268 | N-(5-tert-Butyl-2-p-tolyl-2H-pyrazol-3-yl)-4-chloro-benzamide | 368 |
| 269 | N-(5-tert-Butyl-2-ethoxy-phenyl)-2-[4-(2-morpholin-4-yl-ethoxy)-naphthalen-1-yl]-2-oxo-acetamide | 505 |
| 270 | (5-tert-Butyl-2-methoxy-3-{2-[4-(2-morpholin-4-yl-ethoxy)-naphthalen-1-yl]-2-oxo-acetylamino}-phenyl)-carbamic acid 2-methoxy-ethyl ester | 608 |
| 271 | (R)-N-(5-tert-Butyl-2-p-tolyl-2H-pyrazol-3-yl)-2-methoxy-2-phenyl-acetamide | 377 |
| 272 | 2-(5-tert-Butyl-2-m-tolyl-2H-pyrazol-3-yl)-2-hydroxy-N-[4-(2-morpholin-4-yl-ethoxy)-naphthalen-1-yl]-acetamide | 543 |
| 273 | 2-Amino-N-(5-tert-butyl-2-p-tolyl-2H-pyrazol-3-yl)-2-naphthalen-1-yl-acetamide | 413 |
| 274 | N-(5-tert-Butyl-3-methanesulfonylamino-2-methoxy-phenyl)-2-[4-(2-morpholin-4-yl-ethoxy)-naphthalen-1-yl]-acrylamide | 582 |
| 275 | N-(5-tert-Butyl-2-p-tolyl-2H-pyrazol-3-yl)-2-[4-(2-imidazol-1-yl-ethoxy)-naphthalen-1-yl]-2-oxo-acetamide | 522 |
| 276 | N-(4-Bromo-3-trifluoromethyl-phenyl)-2-[4-(2-morpholin-4-yl-ethoxy)-naphthalen-1-yl]-2-oxo-acetamide | 551 |
| 277 | 4-(4-Benzyloxy-phenyl)-1-(3-tert-butyl-phenyl)-[1,2,4]triazolidine-3,5-dione | 415 |
| 278 | N-(5-tert-Butyl-3-methanesulfonylamino-2-methoxy-phenyl)-2-[8-chloro-4-(2-morpholin-4-yl-ethoxy)-naphthalen-1-yl]-2-oxo-acetamide | 618 |
| 279 | N-(5-tert-Butyl-3-methanesulfonylamino-2-methoxy-phenyl)-2-[4-(2-chloro-ethoxy)-naphthalen-1-yl]-2-oxo-acetamide | 533 |

TABLE 1-continued

| Compound number | Compound Name | Calculated MW |
|---|---|---|
| 280 | 5-tert-Butyl-3-{2-[4-(2-morpholin-4-yl-ethoxy)-naphthalen-1-yl]-2-oxo-acetylamino}-thiophene-2-carboxylic acid dimethylamide | 538 |
| 281 | 1-(5-tert-Butyl-isoxazol-3-yl)-3-[4-(2-morpholin-4-yl-ethoxy)-naphthalen-1-yl]-imidazolidine-2,4,5-trione | 493 |
| 282 | N-(4-Chloro-3-trifluoromethyl-phenyl)-2-[4-(2-morpholin-4-yl-ethoxy)-naphthalen-1-yl]-2-oxo-acetamide | 507 |
| 283 | 1-Benzoyl-3-(5-tert-butyl-2-methoxy-phenyl)-urea | 326 |
| 284 | N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(Z)-ylidene]-hydrazinecarboxylic acid ethyl ester | 648 |
| 285 | 3-tert-Butyl-5-(3-fluoro-phenyl)-1-p-tolyl-1,6-dihydro-imidazo[4,5-c]pyrazole | 348 |
| 286 | 2-[3-Bromo-4-(2-morpholin-4-yl-ethoxy)-phenyl]-N-(5-tert-butyl-2-p-tolyl-2H-pyrazol-3-yl)-acetamide | 556 |
| 287 | 2-(2-Chloro-5-trifluoromethyl-phenyl)-N-[4-(2-morpholin-4-yl-ethoxy)-naphthalen-1-yl]-2-oxo-acetamide | 507 |
| 288 | N-[5-tert-Butyl-2-(3-chloro-benzenesulfonyl)-2H-pyrazol-3-yl]-2-[4-(2-morpholin-4-yl-ethoxy)-naphthalen-1-yl]-2-oxo-acetamide | 625 |
| 289 | (5-tert-Butyl-2-p-tolyl-2H-pyrazol-3-yl)-carbamic acid p-tolyl ester | 363 |
| 290 | N-(5-tert-Butyl-2-diethylamino-3-methanesulfonylamino-phenyl)-2-[4-(2-morpholin-4-yl-ethoxy)-naphthalen-1-yl]-2-oxo-acetamide | 625 |
| 291 | N-(5-tert-Butyl-2-p-tolyl-2H-pyrazol-3-yl)-2-[4-(2-morpholin-4-yl-ethoxy)-naphthalen-1-yl]-acetamide | 527 |
| 292 | N-[5-tert-Butyl-2-methoxy-3-(propane-1-sulfonylamino)-phenyl]-2-(4-methoxy-naphthalen-1-yl)-2-oxo-acetamide | 513 |
| 293 | Propane-1-sulfonic acid (5-tert-butyl-2-methoxy-3-{4-[4-(2-morpholin-4-yl-ethoxy)-naphthalen-1-yl]-3,5-dioxo-[1,2,4]triazolidin-1-yl}-phenyl)-amide | 640 |
| 294 | 3-Amino-5-tert-butyl-2-methoxy-N-[4-(2-morpholin-4-yl-ethoxy)-naphthalen-1-ylmethyl]-benzamide | 492 |
| 295 | 2-[4-(2-Morpholin-4-yl-ethoxy)-naphthalen-1-yl]-2-oxo-N-(3-trifluoromethyl-phenyl)-acetamide | 472 |
| 296 | 4-(5-tert-Butyl-2-methyl-2H-pyrazol-3-yl)-6-[4-(2-morpholin-4-yl-ethoxy)-naphthalen-1-yl]-2H-[1,2,4]triazine-3,5-dione | 505 |
| 297 | N-[5-tert-Butyl-2-(4-trifluoromethyl-phenyl)-2H-pyrazol-3-yl]-2-[4-(2-morpholin-4-yl-ethoxy)-naphthalen-1-yl]-2-oxo-acetamide | 595 |
| 298 | N-[5-tert-Butyl-2-methoxy-3-(propane-1-sulfonylamino)-phenyl]-2-[4-(2-dimethylamino-pyrimidin-4-ylamino)-naphthalen-1-yl]-2-oxo-acetamide | 619 |
| 299 | N-(5-tert-Butyl-2-p-tolyl-2H-pyrazol-3-yl)-2-phenyl-acetamide | 347 |
| 300 | N-[5-tert-Butyl-2-methoxy-3-(propane-1-sulfonylamino)-phenyl]-2-[4-(2-morpholin-4-yl-pyrimidin-4-yloxy)-naphthalen-1-yl]-2-oxo-acetamide | 662 |
| 301 | N-(5-tert-Butyl-3-methanesulfonylamino-2-methoxy-phenyl)-2-{4-[2-(2,6-dimethyl-morpholin-4-yl)-ethoxy]-naphthalen-1-yl}-2-oxo-acetamide | 612 |
| 302 | N-(5-tert-Butyl-2-p-tolyl-2H-pyrazol-3-yl)-2-(4-methoxy-naphthalen-1-yl)-acetamide | 428 |
| 303 | 3-tert-Butyl-1-cyclohexyl-5-phenyl-1,6-dihydro-imidazo[4,5-c]pyrazole | 322 |
| 304 | 3-tert-Butyl-5-(4-fluoro-phenyl)-1-p-tolyl-1,6-dihydro-imidazo[4,5-c]pyrazole | 348 |
| 305 | N-(5-tert-Butyl-2-methoxy-3-{4-[4-(2-morpholin-4-yl-ethoxy)-naphthalen-1-yl]-3,5-dioxo-[1,2,4]triazolidin-1-yl}-phenyl)-methanesulfonamide | 612 |
| 306 | N-(5-tert-Butyl-2-p-tolyl-2H-pyrazol-3-yl)-2-oxo-2-{4-[2-(3-oxo-piperazin-1-yl)-ethyl]-naphthalen-1-yl}-acetamide | 538 |
| 307 | N-(5-tert-Butyl-2-p-tolyl-2H-pyrazol-3-yl)-2-oxo-2-[4-(3-pyridin-4-yl-propoxy)-naphthalen-1-yl]-acetamide | 547 |
| 308 | N-(5-tert-Butyl-3-methanesulfonylamino-2-methoxy-phenyl)-2-[(Z)-hydroxyimino]-2-[4-(2-morpholin-4-yl-ethoxy)-5,6,7,8-tetrahydro-naphthalen-1-yl]-acetamide | 603 |

TABLE 1-continued

| Compound number | Compound Name | Calculated MW |
|---|---|---|
| 309 | N-[5-tert-Butyl-2-(4-methanesulfonyl-phenyl)-2H-pyrazol-3-yl]-2-[4-(2-morpholin-4-yl-ethoxy)-naphthalen-1-yl]-2-oxo-acetamide | 605 |
| 310 | 2-(5-tert-Butyl-2-p-tolyl-2H-pyrazol-3-ylcarbamoyl)-2,5-dihydro-pyrrole-1-carboxylic acid tert-butyl ester | 425 |
| 311 | N-(5-tert-Butyl-3-methanesulfonylamino-2-methoxy-phenyl)-2-[4-(2-imidazol-1-yl-ethoxy)-naphthalen-1-yl]-2-oxo-acetamide | 565 |
| 312 | N-[5-tert-Butyl-2-(3,5-dimethyl-phenyl)-2H-pyrazol-3-yl]-2-[4-(2-morpholin-4-yl-ethoxy)-naphthalen-1-yl]-2-oxo-acetamide | 555 |
| 313 | N-(5-tert-Butyl-2-p-tolyl-2H-pyrazol-3-yl)-2-[4-(2-morpholin-4-yl-pyridin-4-ylamino)-naphthalen-1-yl]-2-oxo-acetamide | 589 |
| 314 | N-{5-tert-Butyl-3-[carbamoylmethyl-(propane-1-sulfonyl)-amino]-2-methoxy-phenyl}-2-naphthalen-1-yl-2-oxo-acetamide | 540 |
| 315 | N'-[1-(5-tert-Butyl-2-methyl-2H-pyrazol-3-ylcarbamoyl)-1-[4-(2-morpholin-4-yl-ethoxy)-naphthalen-1-yl]-meth-(Z)-ylidene]-hydrazinecarboxylic acid ethyl ester | 551 |
| 316 | 5-tert-Butyl-N-cyclopropyl-2-methoxy-3-{2-[4-(2-morpholin-4-yl-ethoxy)-naphthalen-1-yl]-acetylamino}-benzamide | 560 |
| 317 | N-[5-tert-Butyl-2-(3-nitro-phenyl)-2H-pyrazol-3-yl]-2-[4-(2-morpholin-4-yl-ethoxy)-naphthalen-1-yl]-2-oxo-acetamide | 572 |
| 318 | N-(5-tert-Butyl-2-p-tolyl-2H-pyrazol-3-yl)-2-[3-chloro-4-(2-morpholin-4-yl-ethoxy)-phenyl]-2-oxo-acetamide | 525 |
| 319 | N-(3-Benzenesulfonylamino-5-tert-butyl-2-methoxy-phenyl)-2-[4-(2-morpholin-4-yl-ethoxy)-naphthalen-1-yl]-2-oxo-acetamide | 646 |
| 320 | 3-tert-Butyl-5-{2-[4-(2-morpholin-4-yl-ethoxy)-naphthalen-1-yl]-2-oxo-acetylamino}-pyrazole-1-carboxylic acid cyclohexylamide | 576 |
| 321 | N-[5-tert-Butyl-2-methoxy-3-(2,2,2-trifluoro-ethanesulfonylamino)-phenyl]-2-[4-(2-morpholin-4-yl-ethoxy)-naphthalen-1-yl]-2-oxo-acetamide | 652 |
| 322 | N'-[1-(5-tert-Butyl-3-carbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester | 620 |
| 323 | 5-tert-Butyl-2-methoxy-N-[4-(2-morpholin-4-yl-ethoxy)-naphthalen-1-yl]-3-(propane-1-sulfonylamino)-benzamide | 584 |
| 324 | N-(5-tert-Butyl-2-methoxy-phenyl)-2-hydroxy-2-(4-methoxy-naphthalen-1-yl)-acetamide | 393 |
| 325 | (5-tert-Butyl-2-methoxy-3-{2-[4-(2-morpholin-4-yl-ethoxy)-naphthalen-1-yl]-2-oxo-acetylamino}-phenyl)-carbamic acid 2-dimethylamino-ethyl ester | 621 |
| 326 | N-(5-tert-Butyl-3-methanesulfonylamino-2-methoxy-phenyl)-2-[7-fluoro-4-(2-morpholin-4-yl-ethoxy)-naphthalen-1-yl]-2-oxo-acetamide | 602 |
| 327 | N-(5-tert-Butyl-isoxazol-3-yl)-2-[4-(2-morpholin-4-yl-pyridin-4-ylamino)-naphthalen-1-yl]-2-oxo-acetamide | 500 |
| 328 | 3-tert-Butyl-1-(4-chloro-phenyl)-5-phenyl-1,6-dihydro-imidazo[4,5-c]pyrazole | 351 |
| 329 | N-(5-tert-Butyl-2-methyl-2H-pyrazol-3-yl)-2-(4-methoxy-naphthalen-1-yl)-2-oxo-acetamide | 365 |
| 330 | 2-[5-tert-Butyl-2-(3,4-dimethyl-phenyl)-2H-pyrazol-3-yl]-2-[(Z)-hydroxyimino]-N-[4-(2-morpholin-4-yl-ethoxy)-naphthalen-1-yl]-acetamide | 570 |
| 331 | N-(5-tert-Butyl-isoxazol-3-yl)-2-(4-methoxy-naphthalen-1-yl)-2-oxo-acetamide | 352 |
| 332 | N-[5-(1,1-Dimethyl-propyl)-2-p-tolyl-2H-pyrazol-3-yl]-2-hydroxy-2-[4-(2-morpholin-4-yl-ethoxy)-naphthalen-1-yl]-acetamide | 557 |
| 333 | N-[5-tert-Butyl-2-(3-methoxy-phenyl)-2H-pyrazol-3-yl]-2-[4-(2-dimethylamino-pyrimidin-4-ylamino)-naphthalen-1-yl]-2-oxo-acetamide | 564 |
| 334 | N-(2-Chloro-5-trifluoromethyl-phenyl)-2-[4-(2-morpholin-4-yl-ethoxy)-naphthalen-1-yl]-2-oxo-acetamide | 507 |
| 335 | N-(5-tert-Butyl-3-methanesulfonylamino-2-methoxy-phenyl)-2-[2,3-dichloro-4-(2-morpholin-4-yl-ethoxy)-phenyl]-2-oxo-acetamide | 603 |

TABLE 1-continued

| Compound number | Compound Name | Calculated MW |
|---|---|---|
| 336 | N-(3-Methanesulfonylamino-2-methoxy-5-methyl-phenyl)-2-[4-(2-morpholin-4-yl-ethoxy)-naphthalen-1-yl]-2-oxo-acetamide | 542 |
| 337 | 4-{2-[4-(5-tert-Butyl-2-p-tolyl-2H-pyrazol-3-ylaminooxalyl)-naphthalen-1-yl]-ethyl}-piperazine-1-carboxylic acid ethyl ester | 596 |
| 338 | (1-Benzyl-1H-benzoimidazol-2-yl)-(5-tert-butyl-2-p-tolyl-2H-pyrazol-3-yl)-amine | 436 |
| 339 | N-(3,5-Di-tert-butyl-2-hydroxy-phenyl)-2-[4-(2-morpholin-4-yl-ethoxy)-naphthalen-1-yl]-2-oxo-acetamide | 533 |
| 340 | N-(5-tert-Butyl-2-naphthalen-1-yl-2H-pyrazol-3-yl)-2-[4-(2-morpholin-4-yl-ethoxy)-naphthalen-1-yl]-2-oxo-acetamide | 577 |
| 341 | N-(5-tert-Butyl-2-methoxy-phenyl)-2-[4-(2-morpholin-4-yl-pyrimidin-4-ylamino)-naphthalen-1-yl]-2-oxo-acetamide | 540 |
| 342 | 4-{2-[4-(5-tert-Butyl-2-p-tolyl-2H-pyrazol-3-ylaminooxalyl)-naphthalen-1-yloxy]-ethyl}-piperazine-1-carboxylic acid ethyl ester | 612 |
| 343 | 5-tert-Butyl-2-methoxy-3-{2-[4-(2-morpholin-4-yl-pyrimidin-4-ylamino)-naphthalen-1-yl]-2-oxo-acetylamino}-benzamide | 583 |
| 344 | N-(5-tert-Butyl-3-methanesulfonylamino-2-methoxy-phenyl)-2-(1-methyl-1H-indol-3-yl)-2-oxo-acetamide | 458 |
| 345 | 4-Phenyl-piperidine-4-carboxylic acid (5-tert-butyl-2-methoxy-phenyl)-amide | 367 |
| 346 | 5-tert-Butyl-2-methoxy-3-{2-[4-(2-morpholin-4-yl-ethoxy)-naphthalen-1-yl]-acetylamino}-benzamide | 520 |
| 347 | N-[2-(4-Acetyl-phenyl)-5-tert-butyl-2H-pyrazol-3-yl]-2-[4-(2-morpholin-4-yl-ethoxy)-naphthalen-1-yl]-2-oxo-acetamide | 569 |
| 348 | 1-(5-tert-Butyl-2-p-tolyl-2H-pyrazol-3-yl)-3-[4-(2-morpholin-4-yl-ethoxy)-naphthalen-1-yl]-imidazolidine-2,4,5-trione | 582 |
| 349 | N-(5-tert-Butyl-2-p-tolyl-2H-pyrazol-3-yl)-2-(2,3-difluoro-phenyl)-acetamide | 383 |
| 350 | N-[5-tert-Butyl-3-(carbamoylmethyl-methanesulfonyl-amino)-2-methoxy-phenyl]-2-naphthalen-1-yl-2-oxo-acetamide | 512 |
| 351 | N-(5-tert-Butyl-2-methyl-2H-pyrazol-3-yl)-2-[2-methyl-4-(2-morpholin-4-yl-ethoxy)-phenyl]-2-oxo-acetamide | 429 |
| 352 | N-[2-(4-Amino-phenyl)-5-tert-butyl-2H-pyrazol-3-yl]-2-[4-(2-morpholin-4-yl-ethoxy)-naphthalen-1-yl]-2-oxo-acetamide | 542 |
| 353 | (5-tert-Butyl-2-methoxy-3-{2-[4-(2-morpholin-4-yl-ethoxy)-naphthalen-1-yl]-2-oxo-acetylamino}-phenyl)-carbamic acid phenyl ester | 626 |
| 354 | N-(5-tert-Butyl-2-methyl-2H-pyrazol-3-yl)-2-[4-(2-morpholin-4-yl-ethoxy)-naphthalen-1-yl]-acetamide | 451 |
| 355 | N-(5-tert-Butyl-2-isobutoxy-phenyl)-2-[4-(2-morpholin-4-yl-ethoxy)-naphthalen-1-yl]-2-oxo-acetamide | 533 |
| 356 | N-(4-tert-Butyl-phenyl)-2-[4-(2-morpholin-4-yl-ethoxy)-naphthalen-1-yl]-2-oxo-acetamide | 461 |
| 357 | N-[5-tert-Butyl-2-(3-methyl-benzoyl)-2H-pyrazol-3-yl]-2-[4-(2-morpholin-4-yl-ethoxy)-naphthalen-1-yl]-2-oxo-acetamide | 569 |
| 358 | 5-tert-Butyl-3-{2-[(Z)-hydroxyimino]-2-[4-(2-morpholin-4-yl-ethoxy)-naphthalen-1-yl]-acetylamino}-thiophene-2-carboxylic acid amide | 525 |
| 359 | 1-(5-tert-Butyl-2-methoxy-phenyl)-3-[4-(2-chloro-pyrimidin-4-yloxy)-naphthalen-1-yl]-imidazolidine-2,4,5-trione | 531 |
| 360 | (S)-N-(5-tert-Butyl-2-p-tolyl-2H-pyrazol-3-yl)-2-hydroxy-2-phenyl-acetamide | 363 |
| 361 | N-[5-tert-Butyl-2-(2,3-dimethyl-phenyl)-2H-pyrazol-3-yl]-2-[4-(2-morpholin-4-yl-ethoxy)-naphthalen-1-yl]-2-oxo-acetamide | 555 |
| 362 | N-[5-tert-Butyl-2-(4-nitro-phenyl)-2H-pyrazol-3-yl]-2-[4-(2-morpholin-4-yl-ethoxy)-naphthalen-1-yl]-2-oxo-acetamide | 572 |
| 363 | 2-(5-tert-Butyl-2-m-tolyl-2H-pyrazol-3-yl)-N-[4-(2-morpholin-4-yl-ethoxy)-naphthalen-1-yl]-2-oxo-acetamide | 541 |
| 364 | 2-[(Z)-Hydroxyimino]-N-(3-methanesulfonylamino-2-methoxy-5-methyl-phenyl)-2-[4-(2-morpholin-4-yl-ethoxy)-naphthalen-1-yl]-acetamide | 557 |

TABLE 1-continued

| Compound number | Compound Name | Calculated MW |
|---|---|---|
| 365 | N-[5-tert-Butyl-2-(morpholine-4-carbonyl)-thiophen-3-yl]-2-[(Z)-hydroxyimino]-2-[4-(2-morpholin-4-yl-ethoxy)-naphthalen-1-yl]-acetamide | 595 |
| 366 | N-(5-tert-Butyl-2-phenyl-2H-pyrazol-3-yl)-2-[4-(2-morpholin-4-yl-ethoxy)-naphthalen-1-yl]-2-oxo-acetamide | 527 |
| 367 | N'-[1-(5-tert-Butyl-2-methyl-2H-pyrazol-3-ylcarbamoyl)-1-[4-(2-morpholin-4-yl-ethoxy)-naphthalen-1-yl]-meth-(E)-ylidene]-hydrazinecarboxylic acid ethyl ester | 551 |
| 368 | N'-[1-(5-tert-Butyl-2-methyl-2H-pyrazol-3-ylcarbamoyl)-1-[4-(2-morpholin-4-yl-ethoxy)-naphthalen-1-yl]-meth-(Z)-ylidene]-hydrazinecarboxamide | 522 |
| 369 | N-[5-tert-Butyl-2-(3-methoxy-phenyl)-2H-pyrazol-3-yl]-2-[4-(2-morpholin-4-yl-ethoxy)-naphthalen-1-yl]-2-oxo-acetamide | 557 |
| 370 | 5-tert-Butyl-2-methoxy-3-{2-[4-(2-morpholin-4-yl-ethoxy)-naphthalen-1-yl]-2-oxo-acetylamino}-N-pyridin-2-yl-benzamide | 611 |
| 371 | N-[5-tert-Butyl-3-(3,3-dimethyl-ureido)-2-methoxy-phenyl]-2-[4-(2-morpholin-4-yl-ethoxy)-naphthalen-1-yl]-2-oxo-acetamide | 577 |
| 372 | 5-tert-Butyl-3-{2-[7-chloro-4-(2-morpholin-4-yl-ethoxy)-naphthalen-1-yl]-2-oxo-acetylamino}-2-methoxy-benzamide | 568 |
| 373 | N-(5-tert-Butyl-2-p-tolyl-2H-pyrazol-3-yl)-2-m-tolyl-acetamide | 361 |
| 374 | 1-(5-tert-Butyl-2-methoxy-phenyl)-3-[4-(2-pyrrolidin-1-yl-pyrimidin-4-yloxy)-naphthalen-1-yl]-imidazolidine-2,4,5-trione | 566 |
| 375 | N-(5-tert-Butyl-2-p-tolyl-2H-pyrazol-3-yl)-2-hydroxy-2-phenyl-propionamide | 377 |
| 376 | 2-[4-(2-Morpholin-4-yl-ethoxy)-naphthalen-1-yl]-2-oxo-N-quinolin-3-yl-acetamide | 456 |
| 377 | 1-(5-tert-Butyl-2-m-tolyl-2H-pyrazol-3-yl)-3-[4-(2-morpholin-4-yl-ethoxy)-naphthalen-1-yl]-imidazolidine-2,4,5-trione | 582 |
| 378 | (5-tert-Butyl-2-p-tolyl-2H-pyrazol-3-yl)-(3-trifluoromethyl-benzyl)-amine | 387 |
| 379 | N-[5-tert-Butyl-2-methoxy-3-(morpholine-4-carbonyl)-phenyl]-2-[4-(2-morpholin-4-yl-ethoxy)-naphthalen-1-yl]-2-oxo-acetamide | 604 |
| 380 | N-[5-tert-Butyl-3-(3-isopropyl-ureido)-2-methoxy-phenyl]-2-[4-(2-morpholin-4-yl-ethoxy)-naphthalen-1-yl]-2-oxo-acetamide | 591 |
| 381 | N-(5-tert-Butyl-2-p-tolyl-2H-pyrazol-3-yl)-2-methoxy-2-(4-methoxy-naphthalen-1-yl)-acetamide | 458 |
| 382 | N-(3-Amino-5-trifluoromethyl-phenyl)-2-[4-(2-morpholin-4-yl-ethoxy)-naphthalen-1-yl]-2-oxo-acetamide | 487 |
| 383 | N-(5-tert-Butyl-2-methyl-2H-pyrazol-3-yl)-2-[4-(2-morpholin-4-yl-pyrimidin-4-yloxy)-naphthalen-1-yl]-2-oxo-acetamide | 515 |
| 384 | 3-Methyl-1,5-diphenyl-1,6-dihydro-imidazo[4,5-c]pyrazole | 274 |
| 385 | N-(5-tert-Butyl-isoxazol-3-yl)-2-hydroxy-2-[4-(2-morpholin-4-yl-ethoxy)-naphthalen-1-yl]-acetamide | 454 |
| 386 | N-[4-(2-Morpholin-4-yl-ethoxy)-naphthalen-1-yl]-2-oxo-2-(2-phenyl-cyclopropyl)-acetamide | 445 |
| 387 | 2-{4-[2-(4-Acetyl-piperazin-1-yl)-ethoxy]-naphthalen-1-yl}-N-(5-tert-butyl-3-methanesulfonylamino-2-methoxy-phenyl)-2-oxo-acetamide | 625 |
| 388 | 2-(1H-Indol-3-yl)-N-[4-(2-morpholin-4-yl-ethoxy)-naphthalen-1-yl]-2-oxo-acetamide | 444 |
| 389 | N-[5-tert-Butyl-2-(3-fluoro-phenyl)-2H-pyrazol-3-yl]-2-[4-(2-morpholin-4-yl-ethoxy)-naphthalen-1-yl]-2-oxo-acetamide | 545 |
| 390 | 2-(3-Amino-5-tert-butyl-2-methoxy-phenyl)-N-[4-(2-morpholin-4-yl-ethoxy)-naphthalen-1-yl]-2-oxo-acetamide | 506 |
| 391 | N-[5-tert-Butyl-2-(3,4-dichloro-phenyl)-2H-pyrazol-3-yl]-2-[4-(2-morpholin-4-yl-ethoxy)-naphthalen-1-yl]-2-oxo-acetamide | 596 |
| 392 | N-(5-tert-Butyl-isoxazol-3-yl)-2-[4-(2-morpholin-4-yl-pyrimidin-4-yloxy)-naphthalen-1-yl]-2-oxo-acetamide | 502 |

TABLE 1-continued

| Compound number | Compound Name | Calculated MW |
|---|---|---|
| 393 | N-[5-tert-Butyl-2-(2,5-dimethyl-phenyl)-2H-pyrazol-3-yl]-2-[4-(2-morpholin-4-yl-ethoxy)-naphthalen-1-yl]-2-oxo-acetamide | 555 |
| 394 | N-(5-tert-Butyl-3-methanesulfonylamino-2-methoxy-phenyl)-2-[4-(2-morpholin-4-yl-ethoxy)-5,6,7,8-tetrahydro-naphthalen-1-yl]-2-oxo-acetamide | 588 |
| 395 | 1H-Indazole-3-carboxylic acid (5-tert-butyl-2-pyridin-2-yl-2H-pyrazol-3-yl)-amide | 360 |
| 396 | N-(4-Chloro-3-trifluoromethyl-phenyl)-2-(4-methoxy-naphthalen-1-yl)-2-oxo-acetamide | 408 |
| 397 | N-[5-(1,1-Dimethyl-butyl)-2-p-tolyl-2H-pyrazol-3-yl]-2-[4-(2-morpholin-4-yl-ethoxy)-naphthalen-1-yl]-2-oxo-acetamide | 569 |
| 398 | 1H-Indazole-3-carboxylic acid [5-tert-butyl-2-(4-methoxy-phenyl)-2H-pyrazol-3-yl]-amide | 389 |
| 399 | 1H-Indazole-3-carboxylic acid [5-tert-butyl-2-(4-hydroxy-phenyl)-2H-pyrazol-3-yl]-amide | 375 |
| 400 | N'-[1-(5-tert-Butyl-3-methanesulfonylamino-2-methoxy-phenylcarbamoyl)-1-[4-(2-morpholin-4-yl-ethoxy)-naphthalen-1-yl]-meth-(E)-ylidene]-hydrazinecarboxamide | 641 |
| 401 | N-(5-tert-Butyl-2-p-tolyl-2H-pyrazol-3-yl)-N'-[4-(2-morpholin-4-yl-ethoxy)-naphthalen-1-yl]-oxalamide | 556 |
| 402 | N-(5-tert-Butyl-3-methanesulfonylamino-2-methoxy-phenyl)-2-[4-(2-methylamino-pyrimidin-4-ylamino)-naphthalen-1-yl]-2-oxo-acetamide | 577 |
| 403 | N-(5-tert-Butyl-2-m-tolyl-2H-pyrazol-3-yl)-2-[(Z)-methoxyimino]-2-[4-(2-morpholin-4-yl-ethoxy)-naphthalen-1-yl]-acetamide | 570 |
| 404 | 5-tert-Butyl-N-cyclopropyl-3-[2-[(E)-hydroxyimino]-2-(4-methoxy-naphthalen-1-yl)-acetylamino]-2-methoxy-benzamide | 490 |
| 405 | N-(5-tert-Butyl-2-p-tolyl-2H-pyrazol-3-yl)-2-{4-[2-(2,6-dimethyl-morpholin-4-yl)-ethoxy]-naphthalen-1-yl}-2-oxo-acetamide | 569 |
| 406 | N-(5-tert-Butyl-3-methanesulfonylamino-2-methoxy-phenyl)-2-[8-fluoro-4-(2-morpholin-4-yl-ethoxy)-naphthalen-1-yl]-2-oxo-acetamide | 602 |
| 407 | N-(5-tert-Butyl-2-p-tolyl-2H-pyrazol-3-yl)-2-(3-fluoro-phenyl)-acetamide | 365 |
| 408 | 5-tert-Butyl-N-furan-2-ylmethyl-2-methoxy-3-{2-[4-(2-morpholin-4-yl-ethoxy)-naphthalen-1-yl]-2-oxo-acetylamino}-benzamide | 614 |
| 409 | N-[5-tert-Butyl-2-(3-trifluoromethyl-benzoyl)-2H-pyrazol-3-yl]-2-[4-(2-morpholin-4-yl-ethoxy)-naphthalen-1-yl]-2-oxo-acetamide | 623 |
| 410 | N-[5-tert-Butyl-2-methoxy-3-(propane-1-sulfonylamino)-phenyl]-2-[4-(2-morpholin-4-yl-pyrimidin-4-ylamino)-naphthalen-1-yl]-2-oxo-acetamide | 661 |
| 411 | 1-(5-tert-Butyl-isoxazol-3-yl)-3-[4-(2-morpholin-4-yl-pyrimidin-4-yloxy)-naphthalen-1-yl]-imidazolidine-2,4,5-trione | 543 |
| 412 | 1-(5-tert-Butyl-2-methyl-2H-pyrazol-3-yl)-3-[4-(2-morpholin-4-yl-ethoxy)-naphthalen-1-yl]-3'-(carbamic acid ethyl ester)-urea | 539 |
| 413 | N-(5-tert-Butyl-3-methanesulfonylamino-2-methoxy-phenyl)-2-oxo-2-{4-[2-(3-oxo-piperazin-1-yl)-ethoxy]-naphthalen-1-yl}-acetamide | 597 |
| 414 | 2-{4-[2-(4-Acetyl-piperazin-1-yl)-ethyl]-naphthalen-1-yl}-N-(5-tert-butyl-2-p-tolyl-2H-pyrazol-3-yl)-2-oxo-acetamide | 566 |
| 415 | N-(5-tert-Butyl-2-phenylacetyl-2H-pyrazol-3-yl)-2-[4-(2-morpholin-4-yl-ethoxy)-naphthalen-1-yl]-2-oxo-acetamide | 569 |
| 416 | N-(5-tert-Butyl-2-p-tolyl-2H-pyrazol-3-yl)-2-oxo-2-{4-[2-(3-oxo-piperazin-1-yl)-ethoxy]-naphthalen-1-yl}-acetamide | 554 |
| 417 | 2-(5-tert-Butyl-2-m-tolyl-2H-pyrazol-3-yl)-2-[(Z)-hydroxyimino]-N-[4-(2-morpholin-4-yl-ethoxy)-naphthalen-1-yl]-acetamide | 556 |
| 418 | N-[5-tert-Butyl-2-(3-ureido-phenyl)-2H-pyrazol-3-yl]-2-[4-(2-morpholin-4-yl-ethoxy)-naphthalen-1-yl]-2-oxo-acetamide | 585 |
| 419 | N-(5-tert-Butyl-3-methanesulfonylamino-2-methoxy-phenyl)-2-[(Z)-methoxyimino]-2-[4-(2-morpholin-4-yl-pyrimidin-4-yloxy)-naphthalen-1-yl]-acetamide | 663 |

TABLE 1-continued

| Compound number | Compound Name | Calculated MW |
|---|---|---|
| 420 | N-[5-tert-Butyl-2-methoxy-3-(3-oxo-piperazine-1-carbonyl)-phenyl]-2-[4-(2-morpholin-4-yl-ethoxy)-naphthalen-1-yl]-2-oxo-acetamide | 617 |
| 421 | 3-tert-Butyl-5-{2-[4-(2-morpholin-4-yl-ethoxy)-naphthalen-1-yl]-2-oxo-acetylamino}-pyrazole-1-carboxylic acid propylamide | 536 |
| 422 | 5-tert-Butyl-N-cyclopropyl-2-methoxy-3-{2-[4-(2-morpholin-4-yl-pyrimidin-4-yloxy)-naphthalen-1-yl]-2-oxo-acetylamino}-benzamide | 624 |
| 423 | N-(5-tert-Butyl-2-p-tolyl-2H-pyrazol-3-yl)-2-{4-[2-(4-methyl-piperazin-1-yl)-ethoxy]-naphthalen-1-yl}-2-oxo-acetamide | 554 |
| 424 | N-(3-Amino-5-tert-butyl-2-methoxy-phenyl)-2-[4-(2-morpholin-4-yl-pyrimidin-4-yloxy)-naphthalen-1-yl]-2-oxo-acetamide | 556 |
| 425 | 5-tert-Butyl-2-methoxy-3-{2-[4-(2-morpholin-4-yl-ethoxy)-naphthalen-1-yl]-2-oxo-acetylamino}-N-propyl-benzamide | 576 |
| 426 | N-(5-tert-Butyl-2-p-tolyl-2H-pyrazol-3-yl)-2-hydroxy-2-(4-methoxy-phenyl)-acetamide | 393 |
| 427 | N-(5-tert-Butyl-2-methyl-2H-pyrazol-3-yl)-2-[(Z)-hydroxyimino]-2-[4-(2-rnorpholin-4-yl-ethoxy)-naphthalen-1-yl]-acetamide | 480 |
| 428 | N-(5-tert-Butyl-2-p-tolyl-2H-pyrazol-3-yl)-2-(3-phenoxy-phenyl)-acetamide | 440 |
| 429 | N-(5-Isopropyl-2-methyl-phenyl)-2-[4-(2-morpholin-4-yl-ethoxy)-naphthalen-1-yl]-2-oxo-acetamide | 461 |
| 430 | 7-Isopropyl-9-phenyl-2-phenylamino-7,9-dihydro-purin-8-one | 345 |
| 431 | (5-tert-Butyl-2-methoxy-3-{2-[4-(2-morpholin-4-yl-ethoxy)-naphthalen-1-yl]-2-oxo-acetylamino}-phenyl)-carbamic acid pyridin-3-ylmethyl ester | 641 |
| 432 | N-(5-tert-Butyl-3-methanesulfonylamino-2-methoxy-phenyl)-2-[4-(2-ethylamino-ethoxy)-naphthalen-1-yl]-2-oxo-acetamide | 542 |
| 433 | N-(3,5-Di-tert-butyl-phenyl)-2-[4-(2-morpholin-4-yl-ethoxy)-naphthalen-1-yl]-2-oxo-acetamide | 517 |
| 434 | 2-Amino-N-(5-tert-butyl-2-p-tolyl-2H-pyrazol-3-yl)-2-naphthalen-2-yl-acetamide | 413 |
| 435 | N-[5-tert-Butyl-2-(3-fluoro-4-methyl-phenyl)-2H-pyrazol-3-yl]-2-hydroxy-2-[4-(2-morpholin-4-yl-ethoxy)-naphthalen-1-yl]-acetamide | 561 |
| 436 | 2-[5-tert-Butyl-2-(3,4-difluoro-phenyl)-2H-pyrazol-3-yl]-N-[4-(2-morpholin-4-yl-ethoxy)-naphthalen-1-yl]-2-oxo-acetamide | 563 |
| 437 | N-(3-Amino-5-tert-butyl-2-methoxy-phenyl)-2-[4-(2-methylamino-pyrimidin-4-ylamino)-naphthalen-1-yl]-2-oxo-acetamide | 499 |
| 438 | N-(5-tert-Butyl-2-p-tolyl-2H-pyrazol-3-yl)-2-[4-(2-morpholin-4-yl-pyrimidin-4-yloxy)-naphthalen-1-yl]-2-oxo-acetamide | 591 |
| 439 | N-[5-tert-Butyl-2-(2,3-dichloro-phenyl)-2H-pyrazol-3-yl]-2-[4-(2-morpholin-4-yl-ethoxy)-naphthalen-1-yl]-2-oxo-acetamide | 596 |
| 440 | N-[3,5-Bis-(1,1-dimethyl-propyl)-2-hydroxy-phenyl]-2-[4-(2-morpholin-4-yl-ethoxy)-naphthalen-1-yl]-2-oxo-acetamide | 561 |
| 441 | 4-{2-[4-(5-tert-Butyl-3-methanesulfonylamino-2-methoxy-phenylaminooxalyl)-naphthalen-1-yloxy]-ethyl}-piperazine-1-carboxylic acid tert-butyl ester | 683 |
| 442 | 3-tert-Butyl-1-naphthalen-2-yl-5-phenyl-1,6-dihydro-imidazo[4,5-c]pyrazole | 366 |
| 443 | 2-Biphenyl-4-yl-N-(5-tert-butyl-2-p-tolyl-2H-pyrazol-3-yl)-acetamide | 424 |
| 444 | 5-tert-Butyl-N-isopropyl-2-methoxy-3-{2-[4-(2-morpholin-4-yl-ethoxy)-naphthalen-1-yl]-2-oxo-acetylamino}-benzamide | 576 |
| 445 | N-(5-tert-Butyl-3-diethylaminomethyl-2-hydroxy-phenyl)-2-[4-(2-morpholin-4-yl-ethoxy)-naphthalen-1-yl]-2-oxo-acetamide | 562 |
| 446 | 6-Hydroxy-nicotinic acid 3-[5-tert-butyl-2-methoxy-3-(propane-1-sulfonylamino)-phenylcarbamoyl]-1H-indazol-5-yl ester | 582 |
| 447 | N-(5-tert-Butyl-2-m-tolyl-2H-pyrazol-3-yl)-2-[4-(2-morpholin-4-yl-pyrimidin-4-ylamino)-naphthalen-1-yl]-2-oxo-acetamide | 590 |

TABLE 1-continued

| Compound number | Compound Name | Calculated MW |
|---|---|---|
| 448 | N-(5-tert-Butyl-2-methyl-2H-pyrazol-3-yl)-2-[4-(2-morpholin-4-yl-pyrimidin-4-ylamino)-naphthalen-1-yl]-2-oxo-acetamide | 514 |
| 449 | N-(5-tert-Butyl-3-methanesulfonylamino-2-methoxy-phenyl)-2-[4-(4-morpholin-4-yl-pyrimidin-2-ylamino)-naphthalen-1-yl]-2-oxo-acetamide | 633 |
| 450 | N-(3-Amino-5-tert-butyl-2-methoxy-phenyl)-2-[4-(2-morpholin-4-yl-ethoxy)-naphthalen-1-yl]-2-oxo-acetamide | 506 |
| 451 | 1,3,5-Triphenyl-1,6-dihydro-imidazo[4,5-c]pyrazole | 336 |
| 452 | N-(5-tert-Butyl-2-p-tolyl-2H-pyrazol-3-yl)-2-cyclohexyl-acetamide | 354 |
| 453 | 2-[5-tert-Butyl-2-(2-chloro-phenyl)-2H-pyrazol-3-yl]-N-[4-(2-morpholin-4-yl-ethoxy)-naphthalen-1-yl]-2-oxo-acetamide | 561 |
| 454 | 7-Cyclohexylmethyl-9-phenyl-2-phenylamino-7,9-dihydro-purin-8-one | 399 |
| 455 | 5-tert-Butyl-3-{2-[4-(2-morpholin-4-yl-ethoxy)-naphthalen-1-yl]-2-oxo-acetylamino}-thiophene-2-carboxylic acid methylamide | 524 |
| 456 | 5-tert-Butyl-N-cyclopropylmethyl-2-methoxy-3-{2-[4-(2-morpholin-4-yl-ethoxy)-naphthalen-1-yl]-acetylamino}-benzamide | 574 |
| 457 | N-[5-tert-Butyl-2-(3-methoxy-phenyl)-2H-pyrazol-3-yl]-2-[4-(2-morpholin-4-yl-pyrimidin-4-ylamino)-naphthalen-1-yl]-2-oxo-acetamide | 606 |
| 458 | N'-[1-(5-tert-Butyl-3-carbamoyl-2-methoxy-phenylcarbamoyl)-1-[4-(2-morpholin-4-yl-ethoxy)-naphthalen-1-yl]-meth-(Z)-ylidene]-hydrazinecarboxylic acid ethyl ester | 620 |
| 459 | 4-(5-tert-Butyl-2-methyl-2H-pyrazol-3-yl)-1-(2,3-dimethyl-phenyl)-[1,2,4]triazolidine-3,5-dione | 341 |
| 460 | N-(4-Fluoro-3-trifluoromethyl-phenyl)-2-[4-(2-morpholin-4-yl-ethoxy)-naphthalen-1-yl]-2-oxo-acetamide | 490 |
| 461 | 1-Benzyl-3-phenyl-5-phenylamino-1,3-dihydro-imidazo[4,5-b]pyridin-2-one | 392 |
| 462 | N-(5-tert-Butyl-2-methoxy-phenyl)-2-naphthalen-2-yl-acetamide | 347 |
| 463 | 2-[4-(2-Morpholin-4-yl-ethoxy)-naphthalen-1-ylcarbamoyl]-pyrrole-1-carboxylic acid tert-butyl ester | 466 |
| 464 | N-(2,5-Di-tert-butyl-phenyl)-2-[4-(2-morpholin-4-yl-ethoxy)-naphthalen-1-yl]-2-oxo-acetamide | 517 |
| 465 | 2-[4-(2-Morpholin-4-yl-ethoxy)-naphthalen-1-yl]-2-oxo-N-((1S,2R)-2-phenyl-cyclopropyl)-acetamide | 445 |
| 466 | 2-Oxo-2,3-dihydro-benzoimidazole-1-carboxylic acid (5-tert-butyl-2-p-tolyl-2H-pyrazol-3-yl)-amide | 389 |
| 467 | N-(2-Methoxy-5-trifluoromethyl-phenyl)-2-[4-(2-morpholin-4-yl-ethoxy)-naphthalen-1-yl]-2-oxo-acetamide | 502 |
| 468 | N-[2-(4-Bromo-phenyl)-5-tert-butyl-2H-pyrazol-3-yl]-2-[4-(2-morpholin-4-yl-ethoxy)-naphthalen-1-yl]-2-oxo-acetamide | 606 |
| 469 | 1-(5-tert-Butyl-2-methoxy-phenyl)-3-[4-(2-morpholin-4-yl-pyrimidin-4-yloxy)-naphthalen-1-yl]-imidazolidine-2,4,5-trione | 582 |
| 470 | 5-tert-Butyl-2-methoxy-N-methyl-3-{2-[4-(2-morpholin-4-yl-ethoxy)-naphthalen-1-yl]-2-oxo-acetylamino}-benzamide | 548 |
| 471 | N-(5-tert-Butyl-2-methoxy-3-piperidin-1-ylmethyl-phenyl)-2-[4-(2-morpholin-4-yl-ethoxy)-naphthalen-1-yl]-2-oxo-acetamide | 588 |
| 472 | N-(5-tert-Butyl-2-methoxy-phenyl)-2-naphthalen-1-yl-2-oxo-acetamide | 361 |
| 473 | N-(2,5-Di-tert-butyl-2H-pyrazol-3-yl)-2-[4-(2-morpholin-4-yl-ethoxy)-naphthalen-1-yl]-2-oxo-acetamide | 507 |
| 474 | (5-tert-Butyl-2-p-tolyl-2H-pyrazol-3-yl)-carbamic acid 4-methoxy-phenyl ester | 379 |
| 475 | N-(3-Amino-5-tert-butyl-2-methoxy-phenyl)-2-naphthalen-1-yl-2-oxo-acetamide | 376 |
| 476 | 5-tert-Butyl-N-ethyl-3-{2-[(Z)-hydroxyimino]-2-[4-(2-morpholin-4-yl-ethoxy)-naphthalen-1-yl]-acetylamino}-2-methoxy-benzamide | 577 |
| 477 | 4-{2-[4-(5-tert-Butyl-2-p-tolyl-2H-pyrazol-3-ylaminooxalyl)-naphthalen-1-yl]-ethyl}-piperazine-1-carboxylic acid tert-butyl ester | 624 |

TABLE 1-continued

| Compound number | Compound Name | Calculated MW |
|---|---|---|
| 478 | 5-tert-Butyl-N-ethyl-2-hydroxy-3-{2-[4-(2-morpholin-4-yl-ethoxy)-naphthalen-1-yl]-2-oxo-acetylamino}-benzamide | 548 |
| 479 | N-(5-tert-Butyl-2-p-tolyl-2H-pyrazol-3-yl)-2-naphthalen-1-yl-acetamide | 398 |
| 480 | N-(5-tert-Butyl-2-ethoxy-3-methanesulfonylamino-phenyl)-2-[4-(2-morpholin-4-yl-ethoxy)-naphthalen-1-yl]-2-oxo-acetamide | 598 |
| 481 | N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(E)-ylidene]-hydrazinecarboxamide | 619 |
| 482 | 2-{4-[2-(4-Acetyl-piperazin-1-yl)-ethoxy]-naphthalen-1-yl}-N-(5-tert-butyl-2-p-tolyl-2H-pyrazol-3-yl)-2-oxo-acetamide | 582 |
| 483 | 5-tert-Butyl-N-ethyl-2-methoxy-3-{2-[4-(2-morpholin-4-yl-ethoxy)-naphthalen-1-yl]-2-oxo-acetylamino}-benzamide | 562 |
| 484 | 5-tert-Butyl-2-methoxy-3-{2-[4-(2-morpholin-4-yl-ethoxy)-naphthalen-1-yl]-2-oxo-acetylamino}-benzoic acid | 535 |
| 485 | N-(5-tert-Butyl-3-methanesulfonylamino-2-methoxy-phenyl)-2-hydroxy-2-[4-(2-morpholin-4-yl-ethoxy)-5,6,7,8-tetrahydro-naphthalen-1-yl]-acetamide | 590 |
| 486 | N-(5-tert-Butyl-isoxazol-3-yl)-2-[4-(2-dimethylamino-pyrimidin-4-ylamino)-naphthalen-1-yl]-2-oxo-acetamide | 459 |
| 487 | 5-tert-Butyl-3-{2-[4-(2-morpholin-4-yl-pyridin-4-ylamino)-naphthalen-1-yl]-2-oxo-acetylamino}-thiophene-2-carboxylic acid amide | 558 |
| 488 | 2-[4-(2-Morpholin-4-yl-ethoxy)-naphthalen-1-yl]-2-oxo-N-m-tolyl-acetamide | 418 |
| 489 | 5-tert-Butyl-3-{2-[4-(2-morpholin-4-yl-ethoxy)-naphthalen-1-yl]-2-oxo-acetylamino}-thiophene-2-carboxylic acid methyl ester | 525 |
| 490 | N'-[1-(5-tert-Butyl-3-methanesulfonylamino-2-methoxy-phenylcarbamoyl)-1-[4-(2-morpholin-4-yl-ethoxy)-naphthalen-1-yl]-meth-(Z)-ylidene]-hydrazinecarboxamide | 641 |
| 491 | N-[5-tert-Butyl-2-(3-methoxy-phenyl)-2H-pyrazol-3-yl]-2-[4-(2-morpholin-4-yl-pyridin-4-ylamino)-naphthalen-1-yl]-2-oxo-acetamide | 605 |
| 492 | N-(5-Isopropyl-2-p-tolyl-2H-pyrazol-3-yl)-2-[4-(2-morpholin-4-yl-ethoxy)-naphthalen-1-yl]-2-oxo-acetamide | 527 |
| 493 | N-(5-tert-Butyl-isoxazol-3-yl)-2-[4-(2-morpholin-4-yl-ethoxy)-naphthalen-1-yl]-2-oxo-acetamide | 452 |
| 494 | N-(2-Benzoyl-5-tert-butyl-2H-pyrazol-3-yl)-2-[4-(2-morpholin-4-yl-ethoxy)-naphthalen-1-yl]-2-oxo-acetamide | 555 |
| 495 | 6-Bromo-1H-indazole-3-carboxylic acid (5-tert-butyl-2-p-tolyl-2H-pyrazol-3-yl)-amide | 452 |
| 496 | 5-tert-Butyl-N-ethyl-3-{2-hydrazono-2-[4-(2-morpholin-4-yl-ethoxy)-naphthalen-1-yl]-acetylamino}-2-methoxy-benzamide | 576 |
| 497 | N-(5-tert-Butyl-3-ethanesulfonylamino-2-methoxy-phenyl)-2-[(Z)-hydroxyimino]-2-[4-(2-morpholin-4-yl-ethoxy)-naphthalen-1-yl]-acetamide | 613 |
| 498 | N-(3-Amino-5-tert-butyl-2-methoxy-phenyl)-2-[4-(2-dimethylamino-pyrimidin-4-ylamino)-naphthalen-1-yl]-2-oxo-acetamide | 513 |
| 499 | N-(5-tert-Butyl-thiophen-3-yl)-2-[4-(2-morpholin-4-yl-ethoxy)-naphthalen-1-yl]-2-oxo-acetamide | 467 |
| 500 | N-[5-tert-Butyl-2-(4-chloro-phenyl)-2H-pyrazol-3-yl]-2-[4-(2-morpholin-4-yl-ethoxy)-naphthalen-1-yl]-2-oxo-acetamide | 561 |
| 501 | N'-[1-(5-tert-Butyl-3-carbamoyl-2-methoxy-phenylcarbamoyl)-1-[4-(2-morpholin-4-yl-ethoxy)-naphthalen-1-yl]-meth-(E)-ylidene]-hydrazinecarboxamide | 591 |
| 502 | N-[5-tert-Butyl-2-(4-methoxy-phenyl)-2H-pyrazol-3-yl]-2-[4-(2-morpholin-4-yl-ethoxy)-naphthalen-1-yl]-2-oxo-acetamide | 557 |
| 503 | 5-tert-Butyl-3-{2-[7-chloro-4-(2-morpholin-4-yl-ethoxy)-naphthalen-1-yl]-2-oxo-acetylamino}-N-cyclopropyl-2-methoxy-benzamide | 608 |

TABLE 1-continued

| Compound number | Compound Name | Calculated MW |
|---|---|---|
| 504 | N-(5-tert-Butyl-3-methanesulfonylamino-2-methoxy-phenyl)-2-{4-[2-(4-methyl-piperazin-1-yl)-ethoxy]-naphthalen-1-yl}-2-oxo-acetamide | 597 |
| 505 | 1-(5-tert-Butyl-2-p-tolyl-2H-pyrazol-3-yl)-3-[4-(2-morpholin-4-yl-ethoxy)-naphthalen-1-yl]-imidazolidin-2-one | 554 |
| 506 | N-(5-tert-Butyl-thiophen-3-yl)-2-[(Z)-hydroxyimino]-2-[4-(2-morpholin-4-yl-ethoxy)-naphthalen-1-yl]-acetamide | 482 |
| 507 | 5-tert-Butyl-N-cyclopropyl-3-[2-[(Z)-hydroxyimino]-2-(4-methoxy-naphthalen-1-yl)-acetylamino]-2-methoxy-benzamide | 490 |
| 508 | N-(5-tert-Butyl-2-methyl-2H-pyrazol-3-yl)-2-[4-(4-morpholin-4-yl-pyrimidin-2-ylamino)-naphthalen-1-yl]-2-oxo-acetamide | 514 |
| 509 | N-[5-tert-Butyl-2-(3-methoxy-phenyl)-2H-pyrazol-3-yl]-2-[(Z)-hydroxyimino]-2-[4-(2-morpholin-4-yl-ethoxy)-naphthalen-1-yl]-acetamide | 572 |
| 510 | N-[2-Methoxy-5-(1-methyl-1-phenyl-ethyl)-phenyl]-2-[4-(2-morpholin-4-yl-ethoxy)-naphthalen-1-yl]-2-oxo-acetamide | 553 |
| 511 | 2-[5-tert-Butyl-2-(3,4-dimethyl-phenyl)-2H-pyrazol-3-yl]-N-[4-(2-morpholin-4-yl-ethoxy)-naphthalen-1-yl]-2-oxo-acetamide | 555 |
| 512 | 5-tert-Butyl-3-{2-[4-(2-morpholin-4-yl-pyrimidin-4-ylamino)-naphthalen-1-yl]-2-oxo-acetylamino}-thiophene-2-carboxylic acid amide | 559 |
| 513 | 5-tert-Butyl-N-isobutyl-2-methoxy-3-{2-[4-(2-morpholin-4-yl-ethoxy)-naphthalen-1-yl]-2-oxo-acetylamino}-benzamide | 590 |
| 514 | 2-(5-tert-Butyl-2-p-tolyl-2H-pyrazol-3-yl)-2-[(Z)-hydroxyimino]-N-[4-(2-morpholin-4-yl-ethoxy)-naphthalen-1-yl]-acetamide | 556 |
| 515 | 3-tert-Butyl-1-(2,3-dichloro-phenyl)-5-phenyl-1,6-dihydro-imidazo[4,5-c]pyrazole | 385 |
| 516 | N-(3,5-Di-tert-butyl-2-methoxy-phenyl)-2-[4-(2-morpholin-4-yl-ethoxy)-naphthalen-1-yl]-2-oxo-acetamide | 547 |
| 517 | 5-tert-Butyl-3-{2-[(Z)-hydroxyimino]-2-[4-(2-morpholin-4-yl-ethoxy)-naphthalen-1-yl]-acetylamino}-thiophene-2-carboxylic acid dimethylamide | 553 |
| 518 | N-(5-tert-Butyl-2-methoxy-3-methyl-phenyl)-2-[(Z)-hydroxyimino]-2-[4-(2-morpholin-4-yl-ethoxy)-naphthalen-1-yl]-acetamide | 520 |
| 519 | N'-[1-(5-tert-Butyl-3-cyclopropylcarbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester | 660 |
| 520 | N-Indan-5-yl-2-[4-(2-morpholin-4-yl-ethoxy)-naphthalen-1-yl]-2-oxo-acetamide | 445 |
| 521 | N-[5-tert-Butyl-2-(3-chloro-4-fluoro-phenyl)-2H-pyrazol-3-yl]-2-[4-(2-morpholin-4-yl-ethoxy)-naphthalen-1-yl]-2-oxo-acetamide | 579 |
| 522 | N-[5-tert-Butyl-3-(imidazole-1-carbonyl)-2-methoxy-phenyl]-2-[4-(2-morpholin-4-yl-ethoxy)-naphthalen-1-yl]-2-oxo-acetamide | 585 |
| 523 | 2-(2,5-Bis-trifluoromethyl-phenyl)-N-[4-(2-morpholin-4-yl-ethoxy)-naphthalen-1-yl]-2-oxo-acetamide | 540 |
| 524 | N-[5-tert-Butyl-2-(2,4-difluoro-phenyl)-2H-pyrazol-3-yl]-2-[4-(2-morpholin-4-yl-ethoxy)-naphthalen-1-yl]-2-oxo-acetamide | 563 |
| 525 | 1H-Indazole-3-carboxylic acid (5-tert-butyl-2-methoxy-phenyl)-amide | 323 |
| 526 | N-(5-tert-Butyl-2-p-tolyl-2H-pyrazol-3-yl)-2-oxo-2-{4-[2-(5-oxo-[1,4]diazepan-1-yl)-ethoxy]-naphthalen-1-yl}-acetamide | 568 |
| 527 | 3-tert-Butyl-1-p-tolyl-5-(4-trifluoromethyl-phenyl)-1,6-dihydro-imidazo[4,5-c]pyrazole | 398 |
| 528 | N-(5-tert-Butyl-3-ethanesulfonylamino-2-methoxy-phenyl)-2-[4-(2-morpholin-4-yl-ethoxy)-naphthalen-1-yl]-2-oxo-acetamide | 598 |
| 529 | 3-tert-Butyl-5-{2-[4-(2-morpholin-4-yl-ethoxy)-naphthalen-1-yl]-2-oxo-acetylamino}-pyrazole-1-carboxylic acid isopropylamide | 536 |
| 530 | N-(5-tert-Butyl-[1,3,4]thiadiazol-2-yl)-2-hydroxy-2-[4-(2-morpholin-4-yl-ethoxy)-naphthalen-1-yl]-acetamide | 471 |

TABLE 1-continued

| Compound number | Compound Name | Calculated MW |
|---|---|---|
| 531 | N-(5-tert-Butyl-3-methanesulfonylamino-2-methoxy-phenyl)-2-[(Z)-hydroxyimino]-2-[4-(2-morpholin-4-yl-pyrimidin-4-yloxy)-naphthalen-1-yl]-acetamide | 649 |
| 532 | N-[2-(3-Amino-phenyl)-5-tert-butyl-2H-pyrazol-3-yl]-2-[4-(2-morpholin-4-yl-ethoxy)-naphthalen-1-yl]-2-oxo-acetamide | 542 |
| 533 | 3-tert-Butyl-5-{2-[4-(2-morpholin-4-yl-ethoxy)-naphthalen-1-yl]-2-oxo-acetylamino}-pyrazole-1-carboxylic acid phenylamide | 570 |
| 534 | 2-(5-tert-Butyl-2-methyl-furan-3-yl)-N-[4-(2-morpholin-4-yl-ethoxy)-naphthalen-1-yl]-2-oxo-acetamide | 465 |
| 535 | N-(5-tert-Butyl-2-o-tolyl-2H-pyrazol-3-yl)-2-[4-(2-morpholin-4-yl-ethoxy)-naphthalen-1-yl]-2-oxo-acetamide | 541 |
| 536 | N-(5-tert-Butyl-isoxazol-3-yl)-2-[4-(2-morpholin-4-yl-ethoxy)-naphthalen-1-yl]-acetamide | 438 |
| 537 | N-(5-tert-Butyl-2-methoxy-phenyl)-2-(3-methoxy-phenyl)-acetamide | 327 |
| 538 | 5-tert-Butyl-3-{2-[4-(2-morpholin-4-yl-pyrimidin-4-yloxy)-naphthalen-1-yl]-2-oxo-acetylamino}-thiophene-2-carboxylic acid amide | 560 |
| 539 | N-(5-tert-Butyl-3-methanesulfonylamino-2-methoxy-phenyl)-2-hydroxy-2-[4-(2-morpholin-4-yl-ethoxy)-naphthalen-1-yl]-acetamide | 586 |
| 540 | N-[5-tert-Butyl-2-(2,4-dichloro-phenyl)-2H-pyrazol-3-yl]-2-[4-(2-morpholin-4-yl-ethoxy)-naphthalen-1-yl]-2-oxo-acetamide | 596 |
| 541 | N-(5-tert-Butyl-isoxazol-3-yl)-2-[4-(3-hydroxy-propoxy)-naphthalen-1-yl]-2-oxo-acetamide | 396 |
| 542 | N-(3-tert-Butyl-isoxazol-5-yl)-2-[(Z)-hydroxyimino]-2-[4-(2-morpholin-4-yl-ethoxy)-naphthalen-1-yl]-acetamide | 467 |
| 543 | 1H-Indole-3-carboxylic acid (5-tert-butyl-2-methoxy-phenyl)-amide | 322 |
| 544 | N-[5-tert-Butyl-2-methoxy-3-(propane-1-sulfonylamino)-phenyl]-2-[4-(2-morpholin-4-yl-ethoxy)-naphthalen-1-yl]-2-oxo-acetamide | 612 |
| 545 | 7-Bicyclo[2.2.1]hept-2-yl-9-phenyl-2-phenylamino-7,9-dihydro-purin-8-one | 397 |
| 546 | N-(5-tert-Butyl-2-p-tolyl-2H-pyrazol-3-yl)-2-(2,4-dichloro-phenyl)-acetamide | 416 |
| 547 | 5-tert-Butyl-2-methoxy-N-[4-(2-morpholin-4-yl-ethoxy)-naphthalen-1-yl]-benzamide | 463 |
| 548 | N-(5-tert-Butyl-2-methyl-2H-pyrazol-3-yl)-2-[2,3-dimethyl-4-(2-morpholin-4-yl-ethoxy)-phenyl]-2-oxo-acetamide | 443 |
| 549 | N-(5-tert-Butyl-2-methoxy-phenyl)-2-(3-fluoro-phenyl)-acetamide | 315 |
| 550 | 1-(5-tert-Butyl-2-methoxy-3-benzamide)-3-(2,3-dimethylphenyl)-3'-(carbamic acid ethyl ester)-urea | 457 |
| 551 | 2-(5-tert-Butyl-2-methyl-2H-pyrazol-3-yl)-2-oxo-N-(3-trifluoromethyl-phenyl)-acetamide | 353 |
| 552 | 7-Benzyl-9-phenyl-2-phenylamino-7,9-dihydro-purin-8-one | 393 |
| 553 | 2,5-Dihydro-1H-pyrrole-2-carboxylic acid (5-tert-butyl-2-p-tolyl-2H-pyrazol-3-yl)-amide | 324 |
| 554 | N-(5-tert-Butyl-3-methanesulfonylamino-2-methoxy-phenyl)-2-oxo-2-{4-[2-(5-oxo-[1,4]diazepan-1-yl)-ethoxy]-naphthalen-1-yl}-acetamide | 611 |
| 555 | N-[5-tert-Butyl-2-(3-cyano-phenyl)-2H-pyrazol-3-yl]-2-[4-(2-morpholin-4-yl-ethoxy)-naphthalen-1-yl]-2-oxo-acetamide | 552 |
| 556 | N-(5-tert-Butyl-2-methoxy-3-phenylacetylamino-phenyl)-2-[4-(2-morpholin-4-yl-ethoxy)-naphthalen-1-yl]-2-oxo-acetamide | 624 |
| 557 | 2-(2-Chloro-5-trifluoromethyl-phenyl)-N-[4-(2-morpholin-4-yl-pyrimidin-4-yloxy)-naphthalen-1-yl]-2-oxo-acetamide | 557 |
| 558 | 1-(5-tert-Butyl-2-methoxy-phenyl)-3-[4-(2-piperidin-1-yl-pyrimidin-4-yloxy)-naphthalen-1-yl]-imidazolidine-2,4,5-trione | 580 |
| 559 | 2-(2-Benzyl-5-tert-butyl-2H-pyrazol-3-yl)-2-hydroxy-N-[4-(2-morpholin-4-yl-ethoxy)-naphthalen-1-yl]-acetamide | 543 |
| 560 | 5-tert-Butyl-3-{2-[4-(2-dimethylamino-pyrimidin-4-ylamino)-naphthalen-1-yl]-2-oxo-acetylamino}-thiophene-2-carboxylic acid amide | 517 |

TABLE 1-continued

| Compound number | Compound Name | Calculated MW |
|---|---|---|
| 561 | N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester | 648 |
| 562 | N-(3-Methanesulfonylamino-5-trifluoromethyl-phenyl)-2-[4-(2-morpholin-4-yl-ethoxy)-naphthalen-1-yl]-2-oxo-acetamide | 566 |
| 563 | N-(5-tert-Butyl-2-hydroxy-3-piperidin-1-ylmethyl-phenyl)-2-[4-(2-morpholin-4-yl-ethoxy)-naphthalen-1-yl]-2-oxo-acetamide | 574 |
| 564 | 2-(1-Methyl-1H-indol-3-yl)-N-[4-(2-morpholin-4-yl-ethoxy)-naphthalen-1-yl]-2-oxo-acetamide | 458 |
| 565 | N-(5-tert-Butyl-2-methoxy-phenyl)-2-oxo-2-{4-[2-((S)-1-phenyl-ethylamino)-pyrimidin-4-ylamino]-naphthalen-1-yl}-acetamide | 574 |
| 566 | N-[5-tert-Butyl-2-(4-cyano-phenyl)-2H-pyrazol-3-yl]-2-[4-(2-morpholin-4-yl-ethoxy)-naphthalen-1-yl]-2-oxo-acetamide | 552 |
| 567 | N'-[1-(5-tert-Butyl-3-methanesulfonylamino-2-methoxy-phenylcarbamoyl)-1-[4-(2-morpholin-4-yl-ethoxy)-naphthalen-1-yl]-meth-(E)-ylidene]-hydrazinecarboxylic acid ethyl ester | 670 |
| 568 | N-[5-tert-Butyl-2-(3-methoxy-phenyl)-2H-pyrazol-3-yl]-2-hydroxy-2-[4-(2-morpholin-4-yl-ethoxy)-naphthalen-1-yl]-acetamide | 559 |
| 569 | N-(5-tert-Butyl-2-methoxy-3-{2-[4-(2-morpholin-4-yl-ethoxy)-naphthalen-1-yl]-2-oxo-acetylamino}-phenyl)-isobutyramide | 576 |
| 570 | N-[5-tert-Butyl-2-(4-methyl-benzoyl)-2H-pyrazol-3-yl]-2-[4-(2-morpholin-4-yl-ethoxy)-naphthalen-1-yl]-2-oxo-acetamide | 569 |
| 571 | N-[5-tert-Butyl-2-(2-chloro-phenyl)-2H-pyrazol-3-yl]-2-[4-(2-morpholin-4-yl-ethoxy)-naphthalen-1-yl]-2-oxo-acetamide | 561 |
| 572 | N-[5-tert-Butyl-2-(3-chloro-4-methyl-phenyl)-2H-pyrazol-3-yl]-2-[4-(2-morpholin-4-yl-ethoxy)-naphthalen-1-yl]-2-oxo-acetamide | 575 |
| 573 | 2-(4-Bromo-phenyl)-N-(5-tert-butyl-2-p-tolyl-2H-pyrazol-3-yl)-acetamide | 426 |
| 574 | 2-(5-tert-Butyl-2-methyl-furan-3-yl)-N-[4-(6-morpholin-4-ylmethyl-pyridin-3-yl)-naphthalen-1-yl]-2-oxo-acetamide | 512 |
| 575 | 4-(4-{4-[2-(5-tert-Butyl-2-methyl-furan-3-yl)-2-oxo-acetylamino]-naphthalen-1-ylamino}-phenoxy)-pyridine-2-carboxylic acid methylamide | 577 |
| 576 | N-[5-tert-Butyl-2-methoxy-3-(propane-1-sulfonylamino)-phenyl]-2-[4-(2-morpholin-4-yl-pyridin-4-ylamino)-naphthalen-1-yl]-2-oxo-acetamide | 660 |
| 577 | 5-tert-Butyl-N-cyclopropyl-2-methoxy-3-{2-[4-(2-morpholin-4-yl-pyridin-4-ylamino)-naphthalen-1-yl]-2-oxo-acetylamino}-benzamide | 622 |
| 578 | N-(5-tert-Butyl-3-methanesulfonylamino-2-methoxy-phenyl)-2-oxo-2-{4-[6-(tetrahydro-pyran-4-ylamino)-pyridin-3-yl]-naphthalen-1-yl}-acetamide | 631 |
| 579 | 3-[2-(4-Bromo-naphthalen-1-yl)-2-oxo-acetylamino]-5-tert-butyl-N-cyclopropyl-2-methoxy-benzamide | 523 |
| 580 | N-(5-tert-Butyl-3-methanesulfonylamino-2-methoxy-phenyl)-2-[4-(6-morpholin-4-yl-pyridin-3-yl)-naphthalen-1-yl]-2-oxo-acetamide | 617 |
| 581 | N-(5-tert-Butyl-2-p-tolyl-2H-pyrazol-3-yl)-2-[4-(6-morpholin-4-ylmethyl-pyridin-3-yl)-naphthalen-1-yl]-2-oxo-acetamide | 588 |
| 582 | N-(5-tert-Butyl-3-methanesulfonylamino-2-methoxy-phenyl)-2-oxo-2-(4-pyridin-3-yl-naphthalen-1-yl)-acetamide | 532 |
| 583 | N-(5-tert-Butyl-2-methyl-2H-pyrazol-3-yl)-2-oxo-2-(4-pyridin-3-yl-naphthalen-1-yl)-acetamide | 412 |
| 584 | 2-(4-Chloro-3-trifluoromethyl-phenyl)-N-[4-(2-morpholin-4-yl-ethoxy)-naphthalen-1-yl]-2-oxo-acetamide | 507 |
| 585 | 4-{4-[2-(4-Chloro-3-trifluoromethyl-phenyl)-2-oxo-acetylamino]-phenoxy}-pyridine-2-carboxylic acid methylamide | 478 |

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

While certain embodiments have been illustrated and described, it should be understood that changes and modifications can be made therein in accordance with ordinary skill in the art without departing from the invention in its broader aspects as defined in the following claims.

What is claimed is:

1. A cytokine inhibitor having Formula IA:

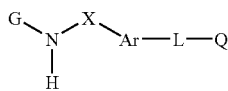

stereoisomers thereof; tautomers thereof, and pharmaceutically acceptable salts thereof, wherein:

X is C(O) or C(S);

G is a $C_{3-10}$ carbocyclyl, a 5-8 membered monocyclic heterocyclyl, or a 8-11 membered bicyclic heterocyclyl containing 1 or more heteroatoms selected from O, N or S; wherein G is substituted by one or more $R^1$, $R^2$ or $R^3$;

Ar is —(Y)—($C_{0-3}$ alkyl)-(bicyclic aryl) wherein the bicyclic aryl is naphthyl, tetrahydronaphthyl, dihydronaphthyl, indenyl, or indanyl, or Ar is —(Y)—($C_{0-3}$ alkyl)-(bicyclic heteroaryl), wherein the bicyclic heteroaryl is indazolyl, isoindolyl, quinolinyl, isoquinolinyl, phthalazinyl, dihydroindolyl, benzofuranyl, benzoxazolyl, benzoisoxazolyl, dihydrobenzoisoxoazolyl, dihydroisoindolyl, benzimidazolyl, benzothienyl, benzothiazolyl, benzoisothiazolyl, or benzoisothiazolyl dioxide, and wherein Ar is optionally substituted with one or more $R^4$ or $R^5$; provided however, that the bicyclic aryl is not 1,1,4,4-tetramethyl-1,2,3,4-tetrahydronaphthyl;

Y is —C(O)—, —C(NNRC(O)OR)—, —C(NNRR)—, —C(NNHC(O)NRR)— or —C(NOR)—;

L is a covalent bond or a saturated or unsaturated branched or unbranched $C_{1-10}$ carbon chain, wherein one or more methylene groups are optionally independently replaced by heteroatoms chosen from O, NR and S(O)$_m$; and wherein L is optionally substituted with 0-2 oxo groups and one or more $C_{1-4}$ branched or unbranched alkyl optionally substituted by one or more F, Cl, Br, or I;

each m is independently 0, 1 or 2;

Q is —NR'R', cycloalkyl, aryl, heterocyclyl, $C_{1-6}$ alkoxy, $C_{1-6}$ alkyl-S(O)$_m$, or phenyl-S(O)$_m$, wherein the cycloalkyl, aryl, heterocyclyl, $C_{1-6}$ alkoxy, $C_{1-6}$ alkyl-S(O)$_m$, or phenyl-S(O)$_m$ is each optionally substituted with one or more $R^{27}$;

each R is independently hydrogen or substituted or unsubstituted $C_{1-6}$ alkyl;

each R' is independently hydrogen, substituted or unsubstituted $C_{1-8}$ alkyl, substituted or unsubstituted ($C_{0-4}$ alkyl)-($C_{6-10}$ aryl) or substituted or unsubstituted ($C_{0-4}$ alkyl)-(5-10 member heterocyclyl);

each $R^1$ is independently F, Cl, Br, I, cyano, —C(O)R, —C(O)NR$_2$, —C(O)OR, —OR, —NR'R', —SiR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted saturated or unsaturated 3-11 member heterocyclyl or heterocyclylalkyl containing 1, 2, 3, or 4 heteroatoms selected independently from N, O, S(O)$_m$;

each $R^2$, $R^4$ and $R^5$ is independently F, Cl, Br, I, cyano, substituted or unsubstituted straight or branched $C_{1-6}$ alkyl, substituted or unsubstituted $C_{6-10}$ aryl, substituted or unsubstituted 5-10 member heteroaryl, —OR', —OR$^6$, —C(O)R', —C(O)OR', —C(O)NR'$_2$, —NR'$_2$, —NO$_2$, S(O)$_m$R", —NR'SO$_2$R", —NR'C(O)NR'R', —NR'C(S)NR'R', —NR'C(O)OR' or —SO$_2$NR'$_2$;

each R" is independently substituted or unsubstituted $C_{1-8}$ alkyl, substituted or unsubstituted $C_{0-4}$ alkyl-$C_{6-10}$ aryl or substituted or unsubstituted ($C_{0-4}$ alkyl)-(5-10 member heterocyclyl);

each $R^3$ is independently substituted or unsubstituted $C_{6-10}$ aryl, substituted or unsubstituted saturated or unsaturated 3-11 member heterocyclyl or heterocyclylalkyl containing 1, 2, 3, or 4 heteroatoms selected independently from N, O, S(O)$_m$, substituted or unsubstituted $C_{3-12}$ cycloalkyl, substituted or unsubstituted $C_{5-12}$ cycloalkenyl, substituted or unsubstituted $C_{7-20}$ aralkyl, substituted or unsubstituted straight or branched $C_{1-8}$ alkyl, $R^{20}$C(O)N($R^{21}$)—, $R^{22}$O—, $R^{23}R^{24}$NC(O)—, $R^{26}(CH_2)_mC(O)N(R^{21})$—, $R^{26}C(O)(CH_2)_mN(R^{21})$—, substituted or unsubstituted $C_{2-8}$ alkenyl, or substituted or unsubstituted $C_{2-8}$ alkynyl, wherein one or more methylene groups of the $C_{1-8}$ alkyl, $C_{2-8}$ alkenyl, or $C_{2-8}$ alkynyl are optionally replaced by O, NH, or S(O)$_m$;

each $R^6$ is a $C_{1-6}$ branched or unbranched alkyl optionally partially or fully halogenated and optionally substituted with $R^{26}$;

each $R^{26}$ is independently cyano, morpholino, piperidinyl, piperazinyl, imidazolyl, phenyl, pyridinyl, tetrazolyl, or mono or di-($C_{0-4}$ alkyl)amino optionally partially or fully halogenated;

$R^{20}$ is substituted or unsubstituted $C_{1-10}$ alkyl, substituted or unsubstituted $C_{0-6}$ alkyl-phenyl, substituted or unsubstituted $C_{0-6}$ alkyl-heterocyclyl, OR' or NR'$_2$;

$R^{21}$ is hydrogen or $C_{1-4}$ branched or unbranched alkyl optionally partially or fully halogenated; and each $R^{22}$, $R^{23}$ and $R^{24}$ is independently hydrogen, substituted or unsubstituted $C_{1-10}$ alkyl, wherein the $C_{1-10}$ alkyl is optionally interrupted by one or more O, N or S, substituted or unsubstituted $C_{0-6}$ alkyl-phenyl, substituted or unsubstituted $C_{0-6}$ alkyl-heterocyclyl; or $R^{23}$ and $R^{24}$ taken together optionally form a heterocyclic or heteroaryl ring;

each $R^{27}$ is independently F, Cl, Br, I, cyano, —C(O)R', —C(O)NR'$_2$, —C(O)OR', —OR', —NR'R', —SiR'$_3$, —S(O)$_m$R', substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ aralkyl, substituted or unsubstituted 3-11 member heterocyclyl or heterocyclylalkyl containing 1, 2, 3, or 4 heteroatoms selected independently from N, O, S(O)$_m$;

provided however that when Ar is —(Y)-(bicyclic aryl) and G is N-(substituted or unsubstituted phenyl)-pyrazolyl, the pyrazolyl is additionally substituted with one or more $R^1$, $R^2$ or $R^3$; and IA is not N-(4-chloro-3-methyl-isothiazol-5-yl)-2-[2-(2,2-dimethyl-propyl)-benzooxazol-5-yl]-2-oxo-acetamide.

2. The compound of claim 1, wherein G is phenyl, naphthyl, cyclopropyl, benzocyclobutanyl, dihydronaphthyl, tetrahydronaphthyl, benzocycloheptanyl, benzocycloheptenyl, indanyl, indenyl, or benzofuran-3-one.

3. The compound of claim 1, wherein G is pyrazolyl, pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzoxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, or phthalimidyl.

4. The compound of claim 1, wherein G is phenyl, naphthyl, cyclopropyl, pyrazolyl, pyrrolyl, pyrrolidinyl, imidazolyl, imidazolonyl, thiazolyl, oxazolyl, isoxazolyl, furanyl, thienyl, or pyridinyl.

5. The compound of claim 1, wherein Ar is —(Y)—($C_{0-3}$ alkyl)-(bicyclic aryl), and the bicyclic aryl is naphthyl.

6. The compound of claim 5, wherein Ar is substituted with at least one $R^4$ or $R^5$.

7. The compound of claim 5, wherein Y is —C(O)—, —C(NNRC(O)OR)— or —C(NOR)—.

8. The compound of claim 1, wherein Ar is —(Y)—($C_{0-3}$ alkyl)-(bicyclic heteroaryl).

9. The compound of claim 8, wherein Ar is substituted with at least one $R^4$ $R^5$.

10. The compound of claim 8, wherein Y is —C(O)—, —C(NNRC(O)OR)— or —C(NOR)—.

11. The compound of claim 8, wherein the bicyclic heteroaryl is quinolinyl, isoquinolinyl, phthalazinyl, or quinazolinyl.

12. The compound of claim 1 wherein L is a covalent bond, a $C_1$-$C_9$ alkoxy, —C(O)O—, —NH— or —O—.

13. The compound of claim 1, wherein Q is thiomorpholino sulfoxide, thiomorpholino sulfone, piperazinonyl, oxazepinyl, diazepinonyl, imidazolyl, pyridinyl or morpholino.

14. The compound of claim 1, wherein Q is morpholino, piperazinyl, pyrimidinyl or pyridinyl.

15. The compound of claim 14, wherein $R^{27}$ is —C(O)OR, —NR'R', substituted or unsubstituted straight or branched $C_{1-10}$ alkyl, substituted or unsubstituted $C_{7-20}$ aralkyl, or substituted or unsubstituted saturated or unsaturated 3-11 member heterocyclyl or heterocyclylalkyl containing 1, 2, 3, or 4 heteroatoms selected independently from N, O, S(O)$_m$.

16. The compound of claim 1, wherein each $R^1$ is independently $C_{3-10}$ branched or unbranched alkyl optionally partially or fully halogenated, and optionally substituted with one to three $C_{3-10}$ cycloalkyl, hydroxy phenyl, naphthyl, pyridinyl, pyrimidinyl, pyrazinyl, pyridazinyl, pyrrolyl, imidazolyl, pyrazolyl, thienyl, furyl, isoxazolyl, or isothiazolyl; each of which is optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di-$C_{1-3}$ alkyl) aminocarbonyl.

17. The compound of claim 1, wherein each $R^1$ is independently $C_{3-10}$ branched or unbranched alkyl.

18. The compound of claim 1, wherein each R is independently —OR', —OR$^6$, —C(O)R', —C(O)OR', —C(O)NR'$_2$, —NR'$_2$, —NO$_2$, —S(O)$_m$R", —NR'SO$_2$R", —NR'C(O)NR'R', —NR'C(S)NR'R', —NR'C(O)OR' or —SO$_2$NR'$_2$.

19. The compound of claim 1, wherein each $R^2$ is independently —NR'$_2$, —NO$_2$, —C(O)NR'$_2$, —NR'SO$_2$R", —NR'C(O)NR'R', —NR'C(S)NR'R', —NR'C(O)OR' or —SO$_2$NR'$_2$.

20. The compound of claim 1, wherein $R^3$ is phenyl, pyridazinyl or pyridyl, each of which is optionally partially or fully halogenated and optionally substituted with $C_{1-6}$ branched or unbranched alkyl which is optionally partially or fully halogenated, hydroxy, oxo, cyano, $C_{1-3}$ alkoxy optionally partially or fully halogenated, nitro, amino, or mono- or di-($C_{1-3}$ alkyl)amino;

$C_{1-6}$ alkyl or $C_{1-6}$ alkoxy, each optionally partially or fully halogenated or optionally substituted with $R^{17}$, amino, $OR^{18}$, $C_{1-5}$ mono- or di-alkylamino optionally substituted with $R^{19}$;

$R^{20}C(O)N(R^{21})$—, $R^{22}O$—, $R^{23}R^{24}NC(O)$—, $R^{26}(CH_2)_mC(O)N(R^{21})$— or $R^{26}C(O)(CH_2)_mN(R^{21})$—.

21. The compound of claim 1, wherein X is C=O.

22. The compound of claim 1, wherein Ar is —(Y)-naphthyl-, Y is —C(O)—, or —C(=NOH)— and G is phenyl, pyridinyl, pyrazolyl, pyrrolyl, imidazolyl, oxazolyl, isoxazolyl, furanyl or thienyl.

23. The compound of claim 1, wherein Ar is —(Y)-naphthyl-, Y is —C(O)—, or —C(=NOH)— and G is phenyl or pyridyl.

24. The compound of claim 23, wherein each $R^1$ is independently a substituted or unsubstituted straight or branched $C_{1-10}$ alkyl.

25. The compound of claim 24, wherein each $R^3$ is independently $R^{23}R^{24}N$—C(O)—, $R^{20}$—C(O)—NR$^{21}$—, or $OR^{22}$.

26. The compound of claim 25, wherein each $R^2$ is independently —NR'SO$_2$R", —Cl, —Br, —F, —C(O)—NR'$_2$ substituted or unsubstituted straight or branched $C_{1-6}$ alkyl, —NR'$_2$, or —OR'.

27. The compound of claim 1, wherein Ar is —(Y)-naphthyl-, Y is —C(O)—, or —C(=NOH)—, and G is pyrazolyl, thienyl or isoxazolyl.

28. The compound of claim 27, wherein each $R^1$ is independently a substituted or unsubstituted straight or branched $C_{1-10}$ alkyl.

29. The compound of claim 28, wherein each $R^3$ is independently phenyl or pyridinyl, optionally substituted with one, two, or three —F, —Cl, substituted or unsubstituted $C_{1-6}$ branched or unbranched alkyl or substituted or unsubstituted $C_{1-4}$ alkoxy.

30. A pharmaceutical composition comprising a compound of claim 1 and a pharmaceutically acceptable carrier.

31. A pharmaceutical composition comprising a compound of claim 1 and one or more active ingredients A, wherein A is a non-steroidal anti-inflammatory drug, immunosuppressive drug, immunomodulatory drug, cytostatic drug, angiogenesis inhibitor, biological agent, steroid, vitamin D3 or analog thereof retinoid, or inhibitor of cell adhesion molecule lymphocyte function-associated antigen-1 or intercellular adhesion molecule.

32. The composition according to claim 31, wherein the immunosuppressive drug, immunomodulatory drug, or cytostatic drug is methotrexate, infliximab, leflunomide, or combinations thereof.

33. A compound or a pharmaceutically acceptable salt thereof wherein the compound is selected from the group consisting of
- N-(5-tert-Butyl-2-p-tolyl-2H-pyrazol-3-yl)-2-[4-(2-morpholin-4-yl-ethoxy)-naphthalen-1-yl]-2-oxo-acetamide;
- N-(5-tert-Butyl-3-methanesulfonylamino-2-methoxy-phenyl)-2-[4-(2-morpholin-4-yl-ethoxy)-naphthalen-1-yl]-2-oxo-acetamide;
- N-(5-tert-Butyl-3-methanesulfonylamino-2-methoxy-phenyl)-2-[4-(2-morpholin-4-yl-pyrimidin-4-yloxy)-naphthalen-1-yl]-2-oxo-acetamide;
- N-(5-tert-Butyl-2-hydroxy-3-morpholin-4-ylmethyl-phenyl)-2-[4-(2-morpholin-4-yl-ethoxy)-naphthalen-1-yl]-2-oxo-acetamide;
- N-(5-tert-Butyl-2-hydroxy-3-methyl-phenyl)-2-[4-(2-morpholin-4-yl-ethoxy)-naphthalen-1-yl]-2-oxo-acetamide;
- N-(5-tert-Butyl-2-methoxy-3-methyl-phenyl)-2-[4-(2-morpholin-4-yl-ethoxy)-naphthalen-1-yl]-2-oxo-acetamide;
- N-(5-tert-Butyl -3-chloro-2-methoxy-phenyl)-2-[4-(2-morpholin-4-yl-ethoxy)-naphthalen-1-yl]-2-oxo-acetamide;
- N-(5-tert-Butyl-2-methoxy-3-trifluoromethyl-phenyl)-2-[4-(2-morpholin-4-yl-ethoxy)-naphthalen-1-yl]-2-oxo-acetamide;
- N-(5-tert-Butyl-2-p-tolyl-2H-pyrazol-3-yl)-2-[7-chloro-4-(2-morpholin-4-yl-ethoxy)-naphthalen-1-yl]-2-oxo-acetamide;
- 5-tert-Butyl-N-cyclopropyl-2-methoxy-3-{2-[4-(2-morpholin-4-yl-ethoxy)-naphthalen-1-yl]-2-oxo-acetylamino}-benzamide;
- N-[5-tert-Butyl-2-methoxy-3-(piperidine-1-carbonyl)-phenyl]-2-[4-(2-morpholin-4-yl-ethoxy)-naphthalen-1-yl]-2-oxo-acetamide;
- 5-tert-Butyl-2-hydroxy-3-{2-[4-(2-morpholin-4-yl-ethoxy)-naphthalen-1-yl]-2-oxo-acetylamino}-benzoic acid;
- N-(2-Benzenesulfonyl-5-tert-butyl-2H-pyrazol-3-yl)-2-[4-(2-morpholin-4-yl-ethoxy)-naphthalen-1-yl]-2-oxo-acetamide;
- N-(5-tert-Butyl-2-p-tolyl-2H-pyrazol-3-yl)-2-[(Z)-hydroxyimino]-2-[4-(2-morpholin-4-yl-ethoxy)-naphthalen-1-yl]-acetamide;
- N-(5-tert-Butyl-2-p-tolyl-2H-pyrazol-3-yl)-2-[(Z)-methoxyimino]-2-[4-(2-morpholin-4-yl-ethoxy)-naphthalen-1-yl]-acetamide;
- N-(5-tert-Butyl-3-methanesulfonylamino-2-methoxy-phenyl)-2-oxo-2-[4-(2-piperidin-1-yl-pyrimidin-4-yloxy)-naphthalen-1-yl]-acetamide;
- N-[5-tert-Butyl-2-(2,5-difluoro-phenyl)-2H-pyrazol-3-yl]-2-[4-(2-morpholin-4-yl-ethoxy)naphthalen-1-yl]-2-oxo-acetamide;
- N-(5-tert-Butyl-2-methoxy-phenyl)-2[4-(2-morpholin-4-yl-ethoxy)-naphthalen-1-yl]-2-oxo-acetamide;
- N-(5-tert-Butyl-3-methanesulfonylamino-2-methoxy-phenyl)-2-(4-methoxy-naphthalen-1-yl)-2-oxo-acetamide;
- N-[5-tert-Butyl-2-(3-chloro-benzoyl)-2H-pyrazol-3-yl]-2-[4-(2-morpholin-4-yl-ethoxy)-naphthalen-1-yl]-2-oxo-acetamide;
- N-[5-tert-Butyl-2-(3-methanesulfonyl-phenyl)-2H-pyrazol-3-yl]-2-[4-(2-morpholin-4-yl-ethoxy)-naphthalen-1-yl]-2-oxo-acetamide;
- N-[3-(Benzenesulfonyl-carbamoylmethyl-amino)-5-tert-butyl-2-methoxy-phenyl]-2-naphthalen-1-yl-2-oxo-acetamide;
- N-(3-tert-Butyl-isoxazol-5-yl)-2[4-(2-morpholin-4-yl-ethoxy)-naphthalen-1-yl]-2-oxo-acetamide;
- N-(5-tert-Butyl-2-p-tolyl-2H-pyrazol-3-yl)-2-[4-(2-morpholin-4-yl-pyrimidin-4-ylamino)-naphthalen-1-yl]-2-oxo-acetamide;
- N-[5-tert-Butyl-2-(4-sulfamoyl-phenyl)-2H-pyrazol-3-yl]-2-[4-(2-morpholin-4-yl-ethoxy)-naphthalen-1-yl]-2-oxo-acetamide;
- 2-(4-Bromo-naphthalen-1-yl)-N-(5-tert-butyl-2-methyl-2H-pyrazol-3-yl)-2-oxo-acetamide;
- 5-tert-Butyl-2-hydroxy-3-{2-[4-(2-morpholin-4-yl-ethoxy)-naphthalen-1-yl]-2-oxo-acetylamino}-benzamide;
- N-(5-tert-Butyl-3-methanesulfonylamino-2-methoxy-phenyl)-2-[4-(6-morpholin-4-ylmethyl-pyridin-3-yl)-naphthalen-1-yl]-2-oxo-acetamide;
- N-(5tert-Butyl-2-methoxy-phenyl)-2-[4-(2-methylamino-pyrimidin-4-ylamino)-naphthalen-1-yl]-2-oxo-acetamide;
- N-(5-tert-Butyl-2-methoxy-phenyl)-2-[4-(2-dimethylamino-pyrimidin-4-ylamino)-naphthalen-1-yl]-2-oxo-acetamide;
- N-(5-tert-Butyl-2-p-tolyl-2H-pyrazol-3-yl)-2-oxo-2-{4-[2-(1-oxo-1$\lambda^4$-thiomorpholin-4-yl)-ethoxy]-naphthalen-1-yl}-acetamide;
- 5-tert-Butyl-3-{2-[(Z)-hydroxyimino]-2-[4-(2-morpholin-4-yl-ethoxy)-naphthalen-1-yl]-acetylamino}-thiophene-2-carboxylic acid methyl ester;
- N-(5-tert-Butyl-2-p-tolyl-2H-pyrazol-3-yl)-2-{4-[2-((2R,6R)-2,6-dimethyl-morpholin-4-yl)-ethoxy]-naphthalen-1-yl}-2-oxo-acetamide;
- N-(5-tert-Butyl-2-methyl-2H-pyrazol-3-yl)-2-[4-(6-morpholin-4-ylmethyl-pyridin-3-yl)-naphthalen-1-yl]-2-oxo-acetamide;
- N-(5-tert-Butyl-3-methanesulfonylamino-2-methoxy-phenyl)-2-[7-chloro-4-(2morpholin-4-yl-ethoxy)-naphthalen-1-yl]-2-oxo-acetamide;
- N-(5-tert-Butyl-3-methanesulfonylamino-2-methoxy-phenyl)-2-[(Z)-hydroxyimino]-2-[4-(2-morpholin-4-yl-ethoxy)-naphthalen-1-yl]-acetamide;
- N-(5-tert-Butyl-2-methoxy-phenyl)-2-[4-(6-morpholin-4-ylmethyl-pyridin-3-yl)-naphthalen-1-yl]-2-oxo-acetamide;
- 5-tert-Butyl-N-cyclopropyl-2-methoxy-3-[2-(4-methoxy-naphthalen-1-yl)-2-oxo-acetylamino]-benzamide;
- N-(2-Acetyl-5-tert-butyl-2H-pyrazol-3-yl)-2-[4-(2-morpholin-4-yl-ethoxy)-naphthalen-1-yl]-2-oxo-acetamide;
- 5-tert-Butyl-N-cyclopropyl-3-{2-hydrazono-2-[4-(2-morpholin-4-yl-ethoxy)-naphthalen--1-yl]-acetylamino}-2-methoxy-benzamide;
- N-(5-tert-Butyl-3-methanesulfonylamino-2-methoxy-phenyl)-2-hydrazono-2-[4-(2-morpholin-4-yl-ethoxy)-naphthalen-1-yl]-acetamide;
- N-(3,4-Dimethyl-phenyl)-2-[4-(2-morpholin-4-yl-ethoxy)-naphthalen-1-yl]-2-oxo-acetamide;
- N-(5-tert-Butyl-2-cyclohexyl-2H-pyrazol-3-yl)-2-[4-(2-morpholin-4-yl-ethoxy)-naphthalen-1-yl]-2-oxo-acetamide;
- N-(5-tert-Butyl-2-methoxy-phenyl)-2-oxo-2-(4-pyridin-3-yl-naphthalen-1-yl)-acetamide;

N-(5-tert-Butyl-isoxazol-3-yl)-2-[(Z)-hydroxyimino]-2-[4-(2-morpholin-4-yl-ethoxy)naphthalen-1-yl]-acetamide;

N-(5-tert-Butyl-3-methanesulfonylamino-2-methoxy-phenyl)-2-[4-(2-diethylamino-ethoxy)-naphthalen-1-yl]-2-oxo-acetamide;

N-(5-tert-Butyl-2-p-tolyl-2H-pyrazol-3-yl)-2-oxo-2-{4-[2-(3-oxo-[1,4]diazepan-1-yl)-ethyl]-naphthalen-1-yl}-acetamide;

5-tert-Butyl-N-ethyl-2-methoxy-3-[2-(4-methoxy-naphthalen-1-yl)-2-oxo-acetylamino]-benzamide;

N-(5-tert-Butyl-2-methoxy-phenyl)-2-oxo-2-{4-[6-(tetrahydro-pyran-4-ylamino)-pyridin-3-yl]-naphthalen-1-yl}-acetamide;

N-(2,5Dimethyl-phenyl)-2-[4-(2morpholin-4yl-ethoxy)-naphthalen-1-yl]-2-oxo-acetamide;

Pyrrolidine-1-carboxylic acid (5-tert-butyl-2-methoxy-3-{2-[4-(2-morpholin-4-yl-ethoxy)-naphthalen-1-yl]-2-oxo-acetylamino}-phenyl)-amide;

N-(3-Amino-5-tert-butyl-2-methoxy-phenyl)-2-oxo-2-{4-[2-((S)-1-phenyl-ethylamino)-pyrimidin-4-ylamino]-naphthalen-1-yl}-acetamide;

5-tert-Butyl-2-methoxy-3-{2-[4-(2-morpholin-4-yl-ethoxy)-naphthalen-1-yl]-2-oxo-acetylamino}-benzamide;

N-(5-tert-Butyl-2-methoxy-3-{2-[4-(2-morpholin-4-yl-ethoxy)-naphthalen-1-yl]-2-oxo-acetylamino}-phenyl)-benzamide;

N-(3,5-Di-tert-butyl-2-methoxy-phenyl)2-[(Z)hydroxyimino]-2-[4-(2-morpholin-4-yl-ethoxy)-naphthalen-1-yl]-acetamide;

N'-[1-(5-tert-Butyl-2-methyl-2H-pyrazol-3-ylcarbamoyl)-1-[4-(2-morpholin-4-yl-ethoxy)-naphthalen-1-yl]-meth-(E)-ylidene]-hydrazinecarboxamide;

5-tert-Butyl-3-{2-[(Z)-methoxyimino]-2-[4-(2-morpholin-4-yl-ethoxy)--naphthalen-1-yl]-acetylamino}-thiophene-2-carboxylic acid amide;

5-tert-Butyl-N-cyclopropylmethyl-2-methoxy-3-{2-[4-(2-morpholin-4-yl-ethoxy)-naphthalen-1-yl]-2-oxo-acetylamino}-benzamide;

N-[5-tert-Butyl-2-methoxy-3-(2-methoxy-acetylamino)-phenyl]-2-[4-(2-morpholin-4-yl-ethoxy)-naphthalen-1-yl]-2-oxo-acetamide;

N-(5-tert-Butyl-2-isopropoxy-3-methanesulfonylamino-phenyl)-2-[4-(2-morpholin-4-yl -ethoxy)-naphthalen-1-yl]-2-oxo-acetamide;

N-[5-tert-Butyl-2-(3,4-dimethyl-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-oxo-2-[4-(2-thiomorpholin-4-yl-ethoxy)-naphthalen-1-yl]-acetamide;

N-(5-tert-Butyl-3-methanesulfonylamino-2-methoxy-phenyl)-2-[4-(2-dimethylamino-pyrimidin-4-ylamino)-naphthalen-1-yl]-2-oxo-acetamide;

1-(2-Amino-4-tert-butyl-6-{2-[4-(2-morpholin-4-yl-ethoxy)-naphthalen-1-yl]-2-oxo-acetylamino}-phenyl)-pyridinium;

N-(5-tert-Butyl-2-isopropoxy-phenyl)-2-[4-(2-morpholin-4-yl-ethoxy)-naphthalen-1-yl]-2-oxo-acetamide;

N-(5-tert-Butyl-2-m-tolyl-2H-pyrazol-3-yl)-2-[(Z)-hydroxyimino]-2-[4-(2-morpholin-4-yl-ethoxy)-naphthalen-1-yl]-acetamide;

5-tert-Butyl-2-methoxy-3-[2-(4-methoxy-naphthalen-1-yl)-2-oxo-acetylamino]benzamide;

5-tert-Butyl-2-methoxy-N-(2-methoxy-ethyl)-3-{2-[4-(2-morpholin-4-yl-ethoxy)-naphthalen-1-yl]-2-oxo-acetylamino}-benzamide;

N-(5-tert-Butyl-isoxazol-3-yl)-2-[4-(2-morpholin-4-yl-pyrimidin-4-ylamino)-naphthalen-1-yl]-2-oxo-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid methyl ester;

3-tert-Butyl-5-{2-[4-(2-morpholin-4-yl-ethoxy)-naphthalen-1-yl]-2-oxo-acetylamino}-pyrazole-1-carboxylic acid adamantan-1-ylamide;

5-tert-Butyl-3-{2-[4-(2-morpholin-4-yl-ethoxy)-naphthalen-1-yl]-2-oxo-acetylamino}-thiophene-2-carboxylic acid amide;

N-(5-tert-Butyl-2-p-tolyl-2H-pyrazol-3-yl)-2-{4-[2-(2,6-dimethyl-morpholin-4-yl)-ethyl]-naphthalen-1-yl}-2-oxo-acetamide;

N-(5-tert-Butyl-2H-pyrazol-3-yl)-2-[4-(2-morpholin-4-yl-ethoxy)-naphthalen-1-yl ]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid tert-butylamide;

3-tert-Butyl-5-{2-[4-(2-morpholin-4-yl-ethoxy)-naphthalen-1-yl]-2-oxo-acetylamino}-pyrazole-1-carboxylic acid amide;

N-Allyl-5-tert-butyl-2-methoxy-3-{2-[4-(2-morpholin-4-yl-ethoxy)-naphthalen-1-yl]-2-oxo-acetylamino}-benzamide;

N-(5-tert-Butyl-isoxazol-3-yl)-2-[(Z)-methoxylmino]-2-[4-(2-morpholin-4-yl-ethoxy)-naphthalen-1-yl]-acetamide;

N-(3-Acetylamino-5-tert-butyl-2-methoxy-phenyl)-2-[4-(2morpholin-4-yl-ethoxy)-naphthalen-1-yl]-2-oxo-acetamide;

5-tert-Butyl-3-{2-[(Z)-hydroxyimino]-2-[4-(2-morpholin-4-yl-pyrimidin-4-yloxy)-naphthalen-1-yl]-acetylamino}-thiophene-2-carboxylic acid amide;

N-[3-(4-Acetyl-piperazine-1-carbonyl)-5-tert-butyl-2-methoxy-phenyl]-2-[4-(2-morpholin-4-yl-ethoxy)-naphthalen-1-yl]-2-oxo-acetamide;

N-(5-tert-Butyl-4-methyl-2-p-tolyl-2H-pyrazol-3-yl)-2-[(Z)-hydroxyimino]-2-[4-(2-morpholin-4-yl-ethoxy)-naphthalen-1-yl]-acetamide;

2-[4-(2-Morpholin-4-yl-ethoxy)-naphthalen-1-yl]-2-oxo-N-(2-phenyl-cyclopropyl)-acetamide;

N-(5-tert-Butyl-isoxazol-3-yl)-2-[4-(6-morpholin-4-ylmethyl-pyridin-3-yl)-naphthalen-1-yl]-2-oxo-acetamide;

N-(5-tert-Butyl-2,3-dimethoxy-phenyl)-2-[(Z)-hydroxyimino]-2-[4-(2-morpholin-4-yl-ethoxy)-naphthalen-1-yl]-acetamide;

N-(5-tert-Butyl-2-p-tolyl-2H-pyrazol-3-yl)-2-{4-[2-(4-methyl-piperazin-1-yl)-ethyl]-naphthalen-1-yl}-2-oxo-acetamide;

N-(5-tert-Butyl-3-methanesulfonylamino-2-methoxy-phenyl)-2-(1H-indol-3-yl)-2-oxo-acetamide;

N-(5-tert-Butyl-2-methoxy-phenyl)-2-[4-(2-morpholin-4-yl-pyridin-4-ylamino)naphthalen-1-yl]-2-oxo-acetamide;

N-(4-tert-Butyl-6-trifluoromethyl-pyrimidin-2-yl)-2-[4-(2-morpholin-4-yl-ethoxy)-naphthalen-1-yl]-2-oxo-acetamide;

5-tert-Butyl-3-{2-[(Z)-hydroxyimino]-2[4-(2-morpholin-4-yl-ethoxy)-naphthalen-1-yl]-acetylamino}-thiophene-2-carboxylic acid methylamide;

N-[5-tert-Butyl-2-(3,5-dichloro-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-{4-[2-((2R,6S)-2,6-dimethyl-morpholin-4-yl)-ethoxy]-naphthalen-1-yl}-2-oxo-acetamide;

N-(5-tert-Butyl-2-p-tolyl-2H-pyrazol-3-yl)-2-[4-(2-imidazol-1-yl-ethyl)-naphthalen-1-yl]-2-oxo-acetamide;

N-(5-tert-Butyl-2-methoxy-3-phenylmethanesulfonylamino-phenyl)-2-[4-(2-morpholin-4-yl-ethoxy)-naphthalen-1-yl]-2-oxo-acetamide;

N-(5-tert-Butyl-2-p-tolyl-2H-pyrazol-3-yl-oxo-2-[4-(2-pyridin-4-yl-ethoxy)naphthalen-1-yl]-acetamide;

N-[5-tert-Butyl-2-(3-chloro-phenyl)-2H-pyrazol-3-yl]-2-[4-(2-morpholin-4-yl-ethoxy)-naphthalen-1-yl]-2-oxo-acetamide;

N-[5-tert-Butyl-2-(6-chloro-pyridazin-3-yl)-2H-Pyrazol-3-yl]-2-[4-(2morpholin-4-yl-ethoxy)-naphthalen-1-yl]-2-oxo-acetamide;

N-[5-tert-Butyl-2-m-tolyl-2H-pyrazol-3-yl)-2-[4-(2-morpholin-4-yl-ethoxy)naphthalen-1-yl]-2-oxo-acetamide;

5-tert-Butyl-N-cyclopropyl-2-methoxy-3-{2-[4-(2-morpholin-4-yl-pyrimidin-4-ylamino)-naphthalen-1-yl]-2-oxo-acetylamino}-benzamide;

[(5-tert-Butyl-2-methoxy-3-{2-[4-(2-morpholin-4-yl-ethoxy)-naphthalen-1-yl]-2-oxo-acetylamino}-phenyl)-methanesulfonyl-amino]-acetic acid ethyl ester;

N-[5-tert-Butyl-4-methyl-2-m-tolyl-2H-pyrazol-3-yl)-2-[(Z)-hydroxyimino]-2-[4-(2-morpholin-4-yl-ethoxy)-naphthalen-1-yl]-acetamide;

N-[5-tert-Butyl-2-(2,5-dichloro-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[4-(2-[1,4]oxazepan-4-yl-ethoxy)-naphthalen-1-yl]-2-oxo-acetamide;

N-(2-Bromo-5-trifluoromethyl-phenyl)-2-[4-(2morpholin-4-yl-ethoxy)-naphthalen-1-yl]-2-oxo-acetamide;

5-tert-Butyl-N-cyclopentyl-2-methoxy-3-{2-[4-(2-morpholin-4-yl-ethoxy)naphthalen-1-yl]-2-oxo-acetylamino}-benzamide;

N-[5-tert-Butyl-2-(morpholine-4-carbonyl)-thiophen-3-yl]-2-[4-(2-morpholin-4-yl-ethoxy)-naphthalen-1-yl]-2-oxo-acetamide;

N-(5-tert-Butyl-2-methoxy-phenyl)-2-[4-(2-morpholin-4-yl-pyrimidin-4-yloxy)-naphthalen-1-yl]-2-oxo-acetamide;

5-tert-Butyl-N-cyclopropylmethyl-2-methoxy-3-[2-(4-methoxy-naphthalen-1-yl)-2-oxo-acetylamino]-benzamide;

N- [5-tert-Butyl-3-(3,3-diethyl-ureido)-2-methoxy-phenyl]-2-[4-(2-morpholin-4-yl-ethoxy)-naphthalen-1-yl]-2-oxo-acetamide;

N-[5-tert-Butyl-2-(4-fluoro-phenyl)-2H-pyrazol-3-yl]-2-[4-(2-morpholin-4-yl-ethoxy)-naphthalen-1-yl]-2-oxo-acetamide;

N-(2-Benzyl-5-tert-butyl-2H-pyrazol-3-yl)-2-[4-(2-morpholin-4-yl-ethoxy)-naphthalen-1-yl]-2-oxo-acetamide;

N-(5-tert-Butyl-3-methanesulfonylamino-2-methoxyphenyl)-2-oxo-2-[4-(2-piperazin-1-yl-ethoxy)-naphthalen-1-yl]-acetamide;

N-(5-tert-Butyl-3-methanesulfonylamino-2-methoxyphenyl)-2-[4-(2-morpholin-4-yl-pyridin-4-ylamino)-naphthalen-1-yl]-2-oxo-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid isopropyl ester;

N-(5-tert-Butyl-3-methanesulfonylamino-2-methoxyphenyl)-2-[4-(2-morpholin-4-yl-pyrimidin-4-ylamino)-naphthalen-1-yl]-2-oxo-acetamide;

N-[3-(3-Allyl-ureido)-5-tert-butyl-2-methoxy-phenyl]-2-[4-(2-morpholin-4-yl-ethoxy)-naphthalen-1-yl]-2-oxo-acetamide;

5-tert-Butyl-N,N-diethyl-2-methoxy-3-{2-[4-(2-morpholin-4-yl-ethoxy)-naphthalen-1-yl]-2-oxo-acetylamino}-benzamide;

N-(5-tert-Butyl-3-methanesulfonylamino-2-methoxyphenyl)-2-[4-(2-[1,4]oxazepan-4-yl-ethoxy)-naphthalen-1-yl]-2-oxo-acetamide;

N-(3-tert-Butyl-phenyl)-2-[4-(2-morpholin-4-yl-ethoxy)-naphthalen-1-yl]-2-oxo-acetamide;

N-[5-tert-Butyl-2-(6-methyl-pyridin-3-yl)-2H-pyrazol-3-yl]-2-[4-(2-morpholin-4-yl-ethoxy)-naphthalen-1-yl]-2-oxo-acetamide;

N-[5-tert-Butyl-2-(4-ureido-phenyl)-2H-pyrazol-3-yl]-2-[4-(2-morpholin-4-yl-ethoxy)-naphthalen-1-yl]-2-oxo-acetamide;

N-(5-tert-Butyl-2-m-tolyl-2H-pyrazol-3-yl)-2-[4-(2-dimethylamino-ethoxy)naphthalen-1-yl]-2-oxo-acetamide;

N-(5-tert-Butyl-2-methoxy-phenyl)-2-oxo-2-[4-(2-piperidin-1-yl-pyrimidin-4-yloxy)-naphthalen-1-yl]-acetamide;

N-[5-tert-Butyl-2-(3-fluoro-4-methyl-phenyl)-2H-pyrazol-3-yl]-2-[4-(2-morpholin-4-yl-ethoxy)-naphthalen-1-yl]-2-oxo-acetamide;

N-[3,5-Bis-(1,1-dimethyl-propyl)-2methoxy-phenyl]-2-[4-(2-morpholin-4-yl-ethoxy)-naphthalen-1-yl]-2-oxo-acetamide;

4-{2-[4-(5-tert-Butyl-3-methanesulfonylamino-2-methoxy-phenylaminooxalyl)-naphthalen-1-yloxy]-ethyl}-piperazine-1-carboxylic acid ethyl ester;

N-(3-Amino-5-tert-butyl-2-methoxy-phenyl)-2-[4-(2-morpholin-4-yl-pyrimidin-4-ylamino)-naphthalen-1-yl]-2-oxo-acetamide;

N-[5-tert-Butyl-3-(2-dimethylamino-acetylamino)-2-methoxy-phenyl]-2-[4-(2-morpholin-4-yl-ethoxy)-naphthalen-1-yl]-2-oxo-acetamide;

N-(5-tert-Butyl-2-methyl-2H-pyrazol-3-yl)-2-[4-(2-morpholin-4-yl-ethoxy)-naphthalen-1-yl]-2-oxo-acetamide;

N-(5-tert-Butyl-3-methanesulfonylamino-2-methoxyphenyl)-2-[4(2-dimethylamino-ethoxy)-naphthalen-1-yl]-2-oxo-acetamide;

N-(5-tert-Butyl-[1,3,4]thiadiazol-2-yl)-2-[(Z)-hydroxyimino]-2-[4-(2-morpholin-4-yl-ethoxy)-naphthalen-1-yl]-acetamide;

N-(5-tert-Butyl-2-ethoxy-phenyl)-2-[4-(2-morpholin-4-yl-ethoxy)-naphthalen-1-yl]-2-oxo-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid 2-methoxy-ethyl ester;

N-(5-tert-Butyl-2-p-tolyl-2H-pyrazol-3-yl)-2-[4-(2-imidazol-1-yl-ethoxy)-naphthalen-1-yl]-2-oxo-acetamide;

N-(4-Bromo-3-trifluoromethyl-phenyl)-2-[4-(2-morpholin-4-yl-ethoxy)-naphthalen-1-yl]-2-oxo-acetamide;

N-(5-tert-Butyl-3-methanesulfonylamino-2-methoxyphenyl)-2-[8-chloro-4-(2-morpholin-4-yl-ethoxy)-naphthalen-1-yl]-2-oxo-acetamide;

N-(5-tert-Butyl-3-methanesulfonylamino-2-methoxyphenyl)-2-[4-(2-chloro-ethoxy)-naphthalen-1-yl]-2-oxo-acetamide;

5-tert-Butyl-3-{2-[4-(2-morpholin-4-yl-ethoxy)-naphthalen-1-yl]-2-oxo-acetylamino}-thiophene-2-carboxylic acid dimethylamide;

N-(4-Chloro-3-trifluoromethyl-phenyl)-2-[4-(2-morpholin-4-yl-ethoxy)-naphthalen-1-yl]-2-oxo-acetamide;

N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(Z)-ylidene]-hydrazinecarboxylic acid ethyl ester;

N-[5-tert-Butyl-2-(3-chloro-benzenesulfonyl)-2H-pyrazol-3-yl]-2-[4-(2-morpholin-4-yl-ethoxy)-naphthalen-1-yl]-2-oxo-acetamide;

N-(5-tert-Butyl-2-diethylamino-3-methanesulfonylamino-phenyl)-2-[4-(2-morpholin-4-yl-ethoxy)-naphthalen-1-yl]-2-oxo-acetamide;

N-[5-tert-Butyl-2-methoxy-3-(propane-1-sulfonylamino)-phenyl]-2-(4-methoxy-naphthalen-1-yl)-2-oxo-acetamide;

2-[4-(2-Morpholin-4-yl-ethoxy)-naphthalen-1-yl]-2-oxo-N-(3-trifluoromethyl-phenyl)-acetamide;

N-[5-tert-Butyl-2-(4-trifluoromethyl-phenyl)-2H-pyrazol-3-yl]-2-[4-(2-morpholin-4-yl-ethoxy)-naphthalen-1-yl]-2-oxo-acetamide;

N-[5-tert-Butyl-2-methoxy-3-(propane-1-sulfonylamino)-phenyl]-2-[4-(2-dimethylamino-pyrimidin-4-ylamino)-naphthalen-1-yl]-2-oxo-acetamide;

N-[5-tert-Butyl-2-methoxy-3-(propane-1-sulfonylamino)-phenyl]-2-[4-(2-morpholin-4-yl-pyrimidin-4-yloxy)-naphthalen-1-yl]-2-oxo-acetamide;

N-(5-tert-Butyl-3-methanesulfonylamino-2-methoxyphenyl)-2-{4-[2-(2,6-dimethyl-morpholin-4-yl)-ethoxy]-naphthalen-1-yl}-2-oxo-acetamide;

N-(5-tert-Butyl-2-p-tolyl-2H-pyrazol-3-yl)-2-oxo-2-{4-[2-(3-oxo-piperazin-1-yl)-ethyl]-naphthalen-1-yl}-acetamide;

N-(5-tert-Butyl-2-p-tolyl-2H-pyrazol-3-yl)-2-oxo-2-[4-(3-pyridin-4-yl-propoxy)-naphthalen-1-yl]-acetamide;

N-(5-tert-Butyl-3-methanesulfonylamino-2-methoxyphenyl)-2-[(Z)-hydroxyimino]-2-[4-(2-morpholin-4-yl-ethoxy)-5,6,7,8-tetrahydro-naphthalen-1-yl]-acetamide;

N-[5-tert-Butyl-2-(4-methanesulfonyl-phenyl)-2H-pyrazol-3-yl]-2-[4-(2-morpholin-4-yl-ethoxy)-naphthalen-1-yl]-2-oxo-acetamide;

N-(5-tert-Butyl-3-methanesulfonylamino-2-methoxyphenyl)-2-[4-(2-imidazol-1-yl-ethoxy)-naphthalen-1-yl]-2-oxo-acetamide;

N-[5-tert-Butyl-2-(3,5-dimethyl-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[4-(2-morpholin-4-yl-pyridin-4-ylamino)-naphthalen-1-yl]-2-oxo-acetamide;

N-{5-tert-Butyl-3-[carbamoylmethyl-(propane-1-sulfonyl)-amino]-2-methoxy-phenyl}-2-naphthalen-1-yl-2-oxo-acetamide;

N'-[1-(5-tert-Butyl-2-methyl-2H-pyrazol-3-ylcarbamoyl)-1-[4-(2-morpholin-4-yl-ethoxy)-naphthalen-1-yl]-meth-(Z)-ylidene]-hydrazinecarboxylic acid ethyl ester;

N-[5-tert-Butyl-2-(3-nitro-phenyl)-2H-pyrazol-3-yl]-2-[4-(2-morpholin-4-yl-ethoxy)-naphthalen-1-yl]-2-oxo-acetamide;

N-(5-tert-Butyl-2-p-tolyl-2H-pyrazol-3-yl)-2-[3-chloro-4-(2-morpholin-4-yl-ethoxy)-phenyl]-2-oxo-acetamide;

N-(3-Benzenesulfonylamino-5-tert-butyl-2-methoxyphenyl)-2-[4-(2-morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid cyclohexylamide;

N-[5-tert-Butyl-2-methoxy-3-(2,2,2-trifluoro-ethanesulfonylamino)-phenyl]-2-[4-(2-morpholin-4-yl-ethoxy)-naphthalen-1-yl]-2-oxo-acetamide;

N'-[1-(5-tert-Butyl-3-carbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;

(5-tert-Butyl-2-methoxy-3-{2-[4-(2-morpholin-4-yl-ethoxy)-naphthalen-1-yl]-2-oxo-acetylamino}-phenyl)-carbamic acid 2-dimethylamino-ethyl ester;

N-(5-tert-Butyl-3-methanesulfonylamino-2-methoxyphenyl)-2-[7-fluoro-4-(2-morpholin-4-yl-ethoxy)-naphthalen-1-yl]-2-oxo-acetamide;

N-(5-tert-Butyl-isoxazol-3-yl)-2-[4-(2-morpholin-4-yl-pyridin-4-ylamino)-naphthalen-1-yl]-2-oxo-acetamide;

N-(5-tert-Butyl-2-methyl-2H-pyrazol-3-yl)-2-(4-methoxy-naphthalen-1-yl)-2-oxo-acetamide;

N-(5-tert-Butyl-isoxazol-3-yl)-2-(4-methoxy-naphthalen-1-yl)-2-oxo-acetamide;

N-[5-tert-Butyl-2-(3-methoxy-phenyl)-2H-pyrazol-3-yl]-2-[4-(2-dimethylamino-pyrimidin-4-ylamino)-naphthalen-1-yl]-2-oxo-acetamide;

N-(2-Chloro-5-trifluoromethyl-phenyl)-2-[4-(2-morpholin-4-yl-ethoxy)-naphthalen-1-yl]-2-oxo-acetamide;

N-(3-Methanesulfonylamino-2-methoxy-5-methyl-phenyl)-2-[4-(2-morpholin-4-yl-ethoxy)-naphthalen-1-yl]-2-oxo-acetamide;

4-{2-[4-(5-tert-Butyl-2-p-tolyl-2H-pyrazol-3-ylaminooxalyl)-naphthalen-1-yl]-ethyl}-piperazine-1-carboxylic acid ethyl ester;

N-(3,5-Di-tert-butyl-2-hydroxy-phenyl)-2-[4-(2-morpholin-4-yl-ethoxy)-naphthalen-1-yl]-2-oxo-acetamide;

N-(5-tert-Butyl-2-naphthalen-1-yl-2H-pyrazol-3-yl)-2-[4-(2-morpholin-4-yl-ethoxy)-naphthalen-1-yl]-2-oxo-acetamide;

N-(5-tert-Butyl-2-methoxy-phenyl)-2-[4-(2-morpholin-4-yl-pyrimidin-4-ylamino)-naphthalen-1-yl]-2-oxo-acetamide;

4-{2-[4-(5-tert-Butyl-2-p-tolyl-2H-pyrazol-3-ylaminooxalyl)-naphthalen-1-yloxy]-ethyl}-piperazine-1-carboxylic acid ethyl ester;

5-tert-Butyl-2-methoxy-3-{2-[4-(2-morpholin-4-yl-pyrimidin-4-ylamino)-naphthalen-1-yl]-2-oxo-acetylamino}-benzamide;

N-(5-tert-Butyl-3-methanesulfonylamino-2-methoxyphenyl)-2-(1-methyl-1H-indol-3-yl)-2-oxo-acetamide;

N-[2-(4-Acetyl-phenyl)-5-tert-butyl-2H-pyrazol-3-yl]-2-[4-(2-morpholin-4-yl-ethoxy)-naphthalen-1-yl]-2-oxo-acetamide;

N-[5-tert-Butyl-3-(carbamoylmethyl-methanesulfonylamino)-2-methoxy-phenyl]-2-naphthalen-1-yl-2-oxo-acetamide;

N-[2-(4-Amino-phenyl)-5-tert-butyl-2H-pyrazol-3-yl]-2-[4-(2-morpholin-4-yl-ethoxy)-naphthalen-1-yl]-2-oxo-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid phenyl ester;

N-(5-tert-Butyl-2-isobutoxy-phenyl)-2-[4-(2-morpholin-4-yl-ethoxy)-naphthalen-1-yl]-2-oxo-acetamide;

N-(4-tert-Butyl-phenyl)-2-[4-(2-morpholin-4-yl-ethoxy)-naphthalen-1-yl]-2-oxo-acetamide;

N-[5-tert-Butyl-2-(3-methyl-benzoyl)-2H-pyrazol-3-yl]-2-[4-(2-morpholin-4-yl-ethoxy)-naphthalen-1-yl]-2-oxo-acetamide;

5-tert-Butyl-3-{2-[(Z)-hydroxyimino]-2-[4-(2-morpholin-4-yl-ethoxy)-naphthalen-1-yl]-acetylamino}-thiophene-2-carboxylic acid amide;

N-[5-tert-Butyl-2-(2,3-dimethyl-phenyl)-2H-pyrazol-3-yl]-2-[4-(2-morpholin-4-yl-ethoxy)-naphthalen-1-yl]-2-oxo-acetamide;

N-[5-tert-Butyl-2-(4-nitro-phenyl)-2H-pyrazol-3-yl]-2-[4-(2-morpholin-4-yl-ethoxy)-naphthalen-1-yl]-2-oxo-acetamide;

2-[(Z)-Hydroxyimino]-N-(3-methanesulfonylamino-2-methoxy-5-methyl-phenyl)-2-[4-(2-morpholin-4-yl-ethoxy)-naphthalen-1-yl]-acetamide;

N-[5-tert-Butyl-2-(morpholine-4-carbonyl)-thiophen-3-yl]-2-[(Z)-hydroxyimino]-2-[4-(2-morpholin-4-yl-ethoxy)-naphthalen-1-yl]-acetamide;

N-(5-tert-Butyl-2-phenyl-2H-pyrazol-3-yl)-2-[4-(2-morpholin-4-yl-ethoxy)-naphthalen-1-yl]-2-oxo-acetamide;

N'-[1-(5-tert-Butyl-2-methyl-2H-pyrazol-3-ylcarbamoyl)-1-[4-(2-morpholin-4-yl-ethoxy)-naphthalen-1-yl]-meth-(E)-ylidene]-hydrazinecarboxylic acid ethyl ester;

N'-[1-(5-tert-Butyl-2-methyl-2H-pyrazol-3-ylcarbamoyl)-1-[4-(2-morpholin-4-yl-ethoxy)-naphthalen-1-yl]-meth-(Z)-ylidene]-hydrazinecarboxamide;

N-[5-tert-Butyl-2-(3-methoxy-phenyl)-2H-pyrazol-3-yl]-2-[4-(2-morpholin-4-yl-ethoxy)-naphthalen-1-yl]-2-oxo-acetamide;

5-tert-Butyl-2-methoxy-3-{2-[4-(2-morpholin-4-yl-ethoxy)-naphthalen-1-yl]-2-oxo-acetylamino}-N-pyridin-2-yl-benzamide;

N-[5-tert-Butyl-3-(3,3-dimethyl-ureido)-2-methoxy-phenyl]-2-[4-(2-morpholin-4-yl-ethoxy)-naphthalen-1-yl]-2-oxo-acetamide;

5-tert-Butyl-3-{2-[7-chloro-4-(2-morpholin-4-yl-ethoxy)-1-yl]-2-oxo-acetylamino}-2-methoxy-benzamide;

2-[4-(2-Morpholin-4-yl-ethoxy)-naphthalen-1-yl]-2-oxo-N-quinolin-3-yl-acetamide;

N-[5-tert-Butyl-2-methoxy-3-morpholine-4-carbonyl)-phenyl]-2-[4-(2-morpholin-4-yl-ethoxy)-naphthalen-1-yl]-2-oxo-acetamide;

N-[5-tert-Butyl-3-(3-isopropyl-ureido)-2-methoxy-phenyl]-2-[4-yl-ethoxy)-naphthalen-1-yl]-2-oxo-acetamide;

N-(3-Amino-5-trifluoromethyl-phenyl)-2-[4-(2-morpholin-4-yl-ethoxy)-naphthalen-1-yl]-2-oxo-acetamide;

5-tert-Butyl-2-methyl-2H-pyrazol-3-yl)2[4-(2-morpholin-4-yl-pyrimidin-4-yloxy)-naphthalen-1-yl]-2-oxo-acetamide;

2-{4-[2-(4-Acetyl-piperazin-1-yl)-ethoxy]-naphthalen-1-yl}-N-(5-tert-butyl-3-methanesulfonylamino-2-methoxy-phenyl)-2-oxo-acetamide;

N-[5-tert-Butyl-2-(3-fluoro-phenyl)-2H-pyrazol-3-yl]-2-[4-(2-morpholin-4-yl-ethoxy)-naphthalen-1-yl]-2-oxo-acetamide;

N-[5-tert-Butyl-2-(3,4-dichloro-phenyl)-2H-pyrazol-3-yl]2-[4-(2-morpholin-4-yl-ethoxy)-naphthalen-1-yl]-2-oxo-acetamide;

5-tert-Butyl-isoxazol-3-yl)-2-[4-(2-morpholin-4-yl-pyrimidin-4-yloxy)-naphthalen-1-yl]-2-oxo-acetamide;

N-[5-tert-Butyl-2-(2,5-dimethyl-phenyl)-2H-pyrazol-3-yl]-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-[4-(2-morpholin-4-yl-ethoxy)-5,6,7,8-tetrahydro-naphthalen-1-yl]-2-oxo-acetamide;

N-(4-Chloro-3-trifluoromethyl-phenyl)-2-(4methoxy-naphthalen-1-yl)-2-oxo-acetamide;

N-[5-(1,1-Dimethyl-butyl)-2-p-tolyl-2H-pyrazol-3-yl]-2-[4-(2-morpholin-4-yl-ethoxy)-naphthalen-1-yl]-2-oxo-acetamide;

N'-[1-(5-tert-Butyl-3-methanesulfonylamino-2-methoxy-phenylcarbamoyl)-1-[4-(2-morpholin-4-yl-ethoxy)-naphthalen-1-yl]-meth-(E)-ylidene]-hydrazinecarboxamide;

N-(5-tert-Butyl-3-methanesulfonylamino-2-methoxy-phenyl)-2-[4(2-methylamino-pyrimidin-4-ylamino)-naphthalen-1-yl]-2-oxo-acetamide;

5-tert-Butyl-2-m-tolyl-2H-pyrazol-3-yl)-2-[(Z)-methoxyimino]-2-[4-(2-morpholin-4-yl-ethoxy)-naphthalen-1-yl]-acetamide;

5-tert-Butyl-N-cyclopropyl-3-[2-[(E)-hydroxyimino]-2-(4-methoxy-naphthalen-1-yl)-acetylamino]-2-methoxy-benzamide;

N-(5-tert-Butyl-2-p-tolyl-2H-pyrazol-3-yl)-2-{4-[2-(2,6-dimethyl-morpholin-4-yl)-ethoxy]-naphthalen-1-yl}-2-oxo-acetamide;

N-(5-tert-Butyl-3-methanesulfonylamino-2-methoxy-phenyl)-2-[8-fluoro-4-(2-morpholin-4-yl-ethoxy)-naphthalen-1-yl]-2-oxo-acetamide;

5-tert-Butyl-N-furan-2-ylmethyl-2-methoxy-3-{2-[4-(2-morpholin-4-yl-ethoxy)-naphthalen-1-yl]-2-oxo-acetylamino}-benzamide;

N-[5-tert-Butyl-2-(3-trifluoromethyl-benzoyl)-2H-pyrazol-3-yl]-2-[4-(2-morpholin-4-yl-ethoxy)-naphthalen-1-yl]-2-oxo-acetamide;

N-[5-tert-Butyl-2-methoxy-3-(propane-1-sulfonylamino)-phenyl]-2-[4-(2-morpholin-4-yl-pyrimidin-4-ylamino)-naphthalen-1-yl]-2-oxo-acetamide;

N-(5-tert-Butyl-3-methanesulfonylamino-2-methoxy-phenyl)-2-oxo-2-{4-[2-(3-oxo-piperazin-1-yl)-ethoxy]-naphthalen-1-yl}-acetamide;

2-{4-[2-(4-Acetyl-piperazin-1-yl)-ethyl]-naphthalen-1-yl}-N-(5-tert-butyl-2-p-tolyl-2H-pyrazol-3-yl)-2-oxo-acetamide;

N-(5-tert-Butyl-2-phenylacetyl-2H-pyrazol-3-yl)-2-[4-(2-morpholin-4-yl-ethoxy)-naphthalen-1-yl]-2-oxo-acetamide;

N-(5-tert-Butyl-2-p-tolyl-2H-pyrazol-3-yl)-2-oxo-2-{4-[2-(3-oxo-piperazin-1-yl)-ethoxy]-naphthalen-1-yl}-acetamide;

N-[5-tert-Butyl-2-(3-ureido-phenyl)-2H-pyrazol-3-yl]-2-[4-(2-morpholin-4-yl-ethoxy)-naphthalen-1-yl]-2-oxo-acetamide;

N-(5-tert-Butyl-3-methanesulfonylamino-2-methoxy-phenyl)-2-[(Z)-methoxyimino]-2-[4-(2-morpholin-4-yl-pyrimidin-4-yloxy)-naphthalen-1-yl]-acetamide;

N-[5-tert-Butyl-2-methoxy-3-(3-oxo-piperazine-1-carbonyl)-phenyl]-2-[4-(2morpholin-4-yl-ethoxy)-naphthalen-1-yl]-2-oxo-acetamide;

3-tert-Butyl-5-{2-[4-(2-morpholin-4-yl-ethoxy)-naphthalen-1-yl]-2-oxo-acetylamino}-pyrazole-1-carboxylic acid propylamide;

5-tert-4-Butyl-N-cyclopropyl-2-methoxy-3-{2-[4-(2-morpholin-4-yl-pyrimidin-4-yloxy)-naphthalen-1-yl]-2-oxo-acetylamino}-benzamide;

N-(5-tert-Butyl-2-p-tolyl-2H-pyrazol-3-yl)-2-{4-[2-(4-methyl-piperazin-1-yl)-ethoxy]-naphthalen-1-yl}-2-oxo-acetamide;

N-(3-Amino-5-tert-butyl-2-methoxy-phenyl)-2[4-(2-morpholin-4-yl-pyrimidin-4-yloxy)-naphthalen-1-yl]-2-oxo-acetamide;

5-tert-Butyl-2-methoxy-3-{2-[4-(2-morpholin-4-yl-ethoxy)-naphthalen-1-yl]-2-oxo-acetylamino}-N-propyl-benzamide;

N-(5-tert-Butyl-2-methyl-2H-pyrazol-3-yl)-2-[(Z)-hydroxyimino]-2-[4-(2-morpholin-4-yl-ethoxy)-naphthalen-1-yl]-acetamide;

N-5-Isopropyl-2-methyl-phenyl)-2-[4-(2-morpholin-4-yl-ethoxy)-naphthalen-1-yl]-2-oxo-acetamide;

(5-tert-Butyl-2-methoxy-3-{2-[4-(2-morpholin-4-yl-ethoxy)-naphthalen-1-yl]-2-oxo-acetylamino}-phenyl)-carbamic acid pyridin-3-ylmethyl ester;

N-(5-tert-Butyl-3-methanesulfonylamino-2-methoxy-phenyl)-2-[4-(2-ethylamino-ethoxy)-naphthalen-1-yl]-2-oxo-acetamide;

N-(3,5-Di-tert-butyl-phenyl)-2-[4-(2-morpholin-4-yl-ethoxy)-naphthalen-1-yl]-2-oxo-acetamide;

N-(3-Amino-5-tert-butyl-2-methoxy-phenyl)-2-[4-(2-methylamino-pyrimidin-4-ylamino)-naphthalen-1-yl]-2-oxo-acetamide;

N-(5-tert-Butyl-2-p-tolyl-2H-pyrazol-3-yl)-2-[4-(2-morpholin-4-yl-pyrimidin-4-yloxy)-naphthalen-1-yl]-2-oxo-acetamide;

N-[5-tert-Butyl-2-(2,3-dichloro-phenyl)-2H-pyrazol-3-yl]-2-[4-(2-morpholin-4-yl-ethoxy)-naphthalen-1-yl]-2-oxo-acetamide;

N-[3,5-Bis-(1,1-dimethyl-propyl)-2-hydroxy-phenyl]2[4-(2-morpholin-4-yl-ethoxy)-naphthalen-1-yl]-2-oxo-acetamide;

4-{2-[4-(5-tert-Butyl-3-methanesulfonylamino-2-methoxy-phenylaminooxalyl)-naphthalen-1-yloxy]-ethyl}-piperazine-1-carboxylic acid tert-butyl ester;

5-tert-Butyl-N-isopropyl-2-methoxy-3-{2-[4-(2-morpholin-4-yl-ethoxy)-naphthalen-1-yl]-2-oxo-acetylamino}-benzamide;

N-(5-tert-Butyl-3-diethylaminomethyl-2-hydroxy-phenyl)-2-[4-(2-morpholin-4-yl-ethoxy)-naphthalen-1-yl]-2-oxo-acetamide;

N-(5-tert-Butyl-2-m-tolyl-2H-pyrazol-3-yl)-2-[4-(2-morpholin-4-yl-pyrimidin-4-ylamino)-1-yl]-2-oxo-acetamide;

N-(5-tert-Butyl-2-methyl-2H-pyrazol-3-yl)-2-[4-(2-morpholin-4-yl-pyrimidin-4-ylamino)-naphthalen-1-yl]-2-oxo-acetamide;

N-(5-tert-Butyl-3-methanesulfonylamino-2-methoxy-phenyl)-2-[4-(4-morpholin-4-yl-pyrimidin-2-ylamino)-naphthalen-1-yl]-2-oxo-acetamide;

N-(3-Amino-5-tert-butyl-2-methoxy-phenyl)-2-[4-(2-morpholin-4-yl-ethoxy)-naphthalen-1-yl]-2-oxo-acetamide;

5-tert-Butyl-3-{2-[4-(2-morpholin-4-yl-ethoxy)-naphthalen-1-yl]-2-oxo-acetylamino}-thiophene-2-carboxylic acid methylamide;

N-[5-tert-Butyl-2-(3-methoxy-phenyl)-2H-pyrazol-3-yl]-2-[4-(2-morpholin-4-yl-pyrimidin-4-ylamino)-naphthalen-1-yl]-2-oxo-acetamide;

N'-[1-(5-tert-Butyl-3-carbamoyl-2-methoxy-phenylcarbamoyl)-1-[4-(2-morpholin-4-yl-ethoxy)-naphthalen-1-yl]-meth-(Z)-ylidene]-hydrazinecarboxylic acid ethyl ester;

N-(4-Fluoro-3-trifluoromethyl-phenyl)-2-[4-(2-morpholin-4-yl-ethoxy)-naphthalen-1-yl]-2-oxo-acetamide;

N-(2,5-Di-tert-butyl-phenyl)-2-[4-(2-morpholin-4-yl-ethoxy)-naphthalen-1-yl]-2-oxo-acetamide;

2-[4-(2-Morpholin-4-yl-ethoxy)-naphthalen-1-yl]-2-oxo-N-((1S,2R)-2-phenyl-cyclopropyl)-acetamide;

N-(2-Methoxy-5-trifluoromethyl-phenyl)-2-[4-(2-morpholin-4-yl-ethoxy)-naphthalen-1-yl]-2-oxo-acetamide;

N-[2-(4-Bromo-phenyl)-5-tert-butyl-2H-pyrazol-3-yl]-2-[4-(2-morpholin-4-yl-ethoxy)-naphthalen-1-yl]-2-oxo-acetamide;

5-tert-Butyl-2-methoxy-N-methyl-3-{2-[4-(2-morpholin-4-yl-ethoxy)-naphthalen-1-yl]-2-oxo-acetylamino}-benzamide;

N-(5-tert-Butyl-2-methoxy-3-piperidin-1-ylmethyl-phenyl)-2-[4-(2-morpholin-4-yl-ethoxy)-naphthalen-1-yl]-2-oxo-acetamide;

N-(5-tert-Butyl-2-methoxy-phenyl)-2-naphthalen-1-yl-2-oxo-acetamide;

N-(2,5-Di-tert-butyl-2H-pyrazol-3-yl)-2-[4-(2-morpholin-4-yl-ethoxy)-naphthalen-1-yl]-2-oxo-acetamide;

N-(3-Amino-5-tert-butyl-2-methoxy-phenyl)-2naphthalen-1-yl-2-oxo-acetamide;

5-tert-Butyl-N-ethyl-3-{2-[(Z)-hydroxyimino]-2-[4-(2-morpholin-4-yl-ethoxy)-naphthalen-1-yl]-acetylamino}-2-methoxy-benzamide;

4-{2-[4-(5-tert-Butyl-2-p-tolyl-2H-pyrazol-3-ylaminooxalyl)-naphthalen-1-yl]-ethyl}-piperazine-1-carboxylic acid tert-butyl ester;

5-tert-Butyl-N-ethyl-2-hydroxy-3-{2-[4-(2-morpholin-4-yl-ethoxy)-naphthalen-1-yl]-2-oxo-acetylamino}-benzamide;

N-(5-tert-Butyl-2-ethoxy-3-methanesulfonylamino-phenyl)-2[4-(2-morpholin-4-yl-ethoxy)-naphthalen-1-yl]-2-oxo-acetamide;

N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(E)-ylidene]-hydrazinecarboxamide;

2-{4-[2-(4-Acetyl-piperazin-1-yl)-ethoxy]-naphthalen-1-yl}-N-(5-tert-butyl-2-p-tolyl-2H-pyrazol-3-yl)-2-oxo-acetamide;

5-tert-Butyl-N-ethyl-2-methoxy-3-{2-[4-(2-morpholin-4-yl-ethoxy)-naphthalen-1-yl]-2-oxo-acetylamino}-benzamide;

5-tert-Butyl-2-methoxy-3-{2-[4-(2-morpholin-4-yl-ethoxy)-naphthalen-1-yl]-2-oxo-acetylamino}-benzoic acid;

N-(5-tert-Butyl-isoxazol-3-yl)-2-[4-(2-dimethylamino-pyrimidin-4-ylamino)-naphthalen-1-yl]-2-oxo-acetamide;

5-tert-Butyl-3-{2-[4-(2-morpholin-4-yl-pyridin-4-ylamino)-naphthalen-1-yl]-2-oxo-acetylamino}-thiophene-2-carboxylic acid amide;

2-[4-(2-Morpholin-4-yl-ethoxy)-naphthalen-1-yl]-2-oxo-N-m-tolyl-acetamide;

5-tert-Butyl-3-{2-[4-(2-morpholin-4-yl-ethoxy)-naphthalen-1-yl]-2-oxo-acetylamino}-thiophene-2-carboxylic acid methyl ester;

N'-[1-(5-tert-Butyl-3-methanesulfonylamino-2-methoxy-phenylcarbamoyly-1-[4-(2-morpholin-4-yl-ethoxy)-naphthalen-1-yl]-meth-(Z)-ylidene]-hydrazinecarboxamide;

N-[5-tert-Butyl-2-(3-methoxy-phenyl)-2H-pyrazol-3-yl]-2-[4-(2-morpholin-4-yl-pyridin-4-ylamino)-naphthalen-1-yl]-2-oxo-acetamide;

N-(5-Isopropyl-2-p-tolyl-2H-pyrazol-3-yl)-2-[4-(2-morpholin-4-yl-ethoxy)-naphthalen-1-yl]-2-oxo-acetamide;

N-(5-tert-Butyl-isoxazol-3-yl)-2-[4-(2-morpholin-4-yl-ethoxy)-naphthalen-1-yl]-2-oxo-acetamide;
N-(2-Benzoyl-5-tert-butyl-2H-pyrazol-3-yl)-2-[4-(2-morpholin-4-yl-ethoxy)-naphthalen-1-yl]-2-oxo-acetamide;
5-tert-Butyl-N-ethyl-3-{2-hydrazono-2-[4-(2-morpholin-4-yl-ethoxy)-naphthalen-1-yl]-acetylamino)}-2-methoxy-benzamide;
N-(5-tert-Butyl-3-ethanesulfonylamino-2-methoxy-phenyl)-2-[(Z)-hydroxyimino]-2-[4-(2-morpholin-4-yl-ethoxy)-naphthalen-1-yl]-acetamide;
N-(3-Amino-5-tert-butyl-2-methoxy-phenyl)-2-[4-(2-dimethylamino-pyrimidin-4-ylamino)-naphthalen-1-yl]-2-oxo-acetamide;
N-(5-tert-Butyl-thiophen-3-yl)-2-[4-(2-morpholin-4-yl-ethoxy)-naphthalen-1-yl]-2-oxo-acetamide;
N-[5-tert-Butyl-2-(4-chloro-phenyl)-2H-pyrazol-3-yl]-2-[4-(2-morpholin-4-yl-ethoxy)-naphthalen-1-yl]-2-oxo-acetamide;
N'-[1-(5-tert-Butyl-3-carbamoyl-2-methoxy-phenylcarbamoyl)-1-[4-(2-morpholin-4-yl-ethoxy)-naphthalen-1-yl]-meth-(E)-ylidene]-hydrazinecarboxamide;
N-[5-tert-Butyl-2-(4-methoxy-phenyl)-2H-pyrazol-3-yl]-2-[4-(2-morpholin-4-yl-ethoxy)-naphthalen-1-yl]-2-oxo-acetamide;
5-tert-Butyl-3-{2-[7-chloro-4-(2-morpholin-4-yl-ethoxy)-naphthalen-1-yl]-2-oxo-acetylamino}-N-cyclopropyl-2-methoxy-benzamide;
N-(5-tert-Butyl-3-methanesulfonylamino-2-methoxy-phenyl)-2-{4-[2-(4-methyl-piperazin-1-yl)-ethoxy]-naphthalen-1-yl}-2-oxo-acetamide;
N-(5-tert-Butyl-thiophen-3-yl)-2-[(Z)-hydroxyimino]-2-[4-(2-morpholin-4-yl-ethoxy)-naphthalen-1-yl]-acetamide;
5-tert-Butyl-N-cyclopropyl-3-[2-[(Z)-hydroxyimino]-2-(4-methoxy-naphthalen-1-yl)-acetylamino]-2-methoxy-benzamide;
N-(5-tert-Butyl-2-methyl-2H-pyrazol-3-yl)-2-[4-(4-morpholin-4-yl-pyrimidin-2-ylamino)-naphthalen-1-yl]-2-oxo-acetamide;
N-[5-tert-Butyl-2-(3-methoxy-phenyl)-2H-pyrazol-3-yl]-2-[(Z)-hydroxyimino]-2-[4-(2-morpholin-4-yl-ethoxy)-naphthalen-1-yl]-acetamide;
N-[2-Methoxy-5-(1-methyl-1-phenyl-ethyl)-phenyl]-2-[4-(2-morpholin-4-yl-ethoxy)-naphthalen-1-yl]-2-oxo-acetamide;
5-tert-Butyl-3-{2-[4-(2-morpholin-4-yl-pyrimidin-4-ylamino)-naphthalen-1-yl]-2-oxo-acetylamino}-thiophene-2-carboxylic acid amide;
5-tert-Butyl-N-isobutyl-2-methoxy-3-{2-[4-(2-morpholin-4-yl-ethoxy)-naphthalen-1-yl]-2-oxo-acetylamino}-benzamide;
N-(3,5-Di-tert-butyl-2-methoxy-phenyl)-2-[4-(2-morpholin-4-yl-ethoxy)-naphthalen-1-yl]-2-oxo-acetamide;
5-tert-Butyl-3-{2-[(Z)-hydroxyimino]-2-[4-(2-morpholin-4-yl-ethoxy)-naphthalen-1-yl]-acetylamino}-thiophene-2-carboxylic acid dimethylamide;
N-(5-tert-Butyl-2-methoxy-3-methyl-phenyl)-2-[(Z)-hydroxyimino]-2-[4-(2-morpholin-4-yl-ethoxy)-naphthalen-1-yl]-acetamide;
N'-[1-(5-tert-Butyl-3-cyclopropylcarbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;
N-Indan-5-yl-2-[4-(2-morpholin-4-yl-ethoxy)-naphthalen-1-yl]-2-oxo-acetamide;
N-[5-tert-Butyl-2-(3-chloro-4-fluoro-phenyl)-2H-pyrazol-3-yl]-2-[4-(2-morpholin-4-yl-ethoxy)-naphthalen-1-yl]-2-oxo-acetamide;
N-[5-tert-Butyl-3-(imidazole-1-carbonyl)-2-methoxy-phenyl]-2-[4-(2-morpholin-4-yl-ethoxy)-naphthalen-1-yl]-2-oxo-acetamide;
N-[5-tert-Butyl-2-(2,4-difluoro-phenyl)-2H-pyrazol-3-yl]-2-[4-(2-morpholin-4-yl-ethoxy)-naphthalen-1-yl]-2-oxo-acetamide;
N(5-tert-Butyl-2-p-tolyl-2H-pyrazol-3-yl)-2-oxo-2-{4-[2-(5-oxo-[1,4]diazepan-1-yl)-ethoxy]-naphthalen-1-yl}-acetamide;
N-(5-tert-Butyl-3-ethanesulfonylamino-2-methoxy-phenyl)-2-[4-(2-morpholin-4-yl-ethoxy)-naphthalen-1-yl]-2-oxo-acetamide;
3-tert-Butyl-5-{2-[4-(2-morpholin-4-yl-ethoxy)-naphthalen-1-yl]-2-oxo-acetylamino}-pyrazole-1-carboxylic acid isopropylamide;
N-(5-tert-Butyl-3-methanesulfonylamino-2-methoxy-phenyl)-2-[(Z)-hydroxyimino]-2-[4-(2-morpholin-4-yl-pyrimidin-4-yloxy)-naphthalen-1-yl]-acetamide;
N-[2-(3-Amino-phenyl)-5-tert-butyl-2H-pyrazol-3-yl]-2-[4-(2-morpholin-4-yl-ethoxy)-naphthalen-1-yl]-2-oxo-acetamide;
3-tert-Butyl-5-{2-[4-(2-morpholin-4-yl-ethoxy)-naphthalen-1-yl]-2-oxo-acetylamino}-pyrazole-1-carboxylic acid phenylamide;
N-(5-tert-Butyl-2-o-tolyl-2H-pyrazol-3-yl)-2-[4-(2-morpholin-4-yl-ethoxy)-naphthalen-1-yl]-2-oxo-acetamide;
5-tert-Butyl-3-{2-[4-(2-morpholin-4-yl-pyrimidin-4-yloxy)-naphthalen-1-yl]-2-oxo-acetylamino}-thiophene-2-carboxylic acid amide;
N-[5-tert-Butyl-2-(2,2,4-dichloro-phenyl)-2H-pyrazol-3-yl]-2-[4-(2-morpholin-4-yl-ethoxy)-naphthalen-1-yl]-2-oxo-acetamide;
N-(5-tert-Butyl-isoxazol-3-yl)-2-[4-(3-hydroxy-propoxy)-naphthalen-1-yl]-2-oxo-acetamide;
N-(3-tert-Butyl-isoxazol-5-yl)-2[(Z)-hydroxyimino]-2[-4-(2-morpholin-4-yl-ethoxy)-naphthalen-1-yl]-acetamide;
N-[5-tert-Butyl-2-methoxy-3-(propane-1-sulfonylamino)-phenyl]-2-[4-(2-morpholin-4-yl-ethoxy)-naphthalen-1-yl]-2-oxo-acetamide;
N-(5-tert-Butyl-3-methanesulfonylamino-2-methoxy-phenyl)-2-oxo-2-{4-[2-(5-oxo-[1,4]diazepan-1-yl)-ethoxy]-naphthalen-1-yl}-acetamide;
N-[5-tert-Butyl-2-(3-cyano-phenyl)-2H-pyrazol-3-yl]-2-[4-(2-morpholin-4-yl-ethoxy)-naphthalen-1-yl]-2-oxo-acetamide;
N-(5-tert-Butyl-2-methoxy-3-phenylacetylamino-phenyl)-2-[4-(2-morpholin-4-yl-ethoxy)-naphthalen-1-yl]-2-oxo-acetamide;
5-tert-Butyl-3-{2-[4-(2-dimethylamino-pyrimidin-4-ylamino)-naphthalen-1-yl]-2-oxo-acetylamino}-thiophene-2-carboxylic acid amide;
N'-[1-(5-tert-Butyl-3-ethylcarbamoyl-2-methoxy-phenylcarbamoyl)-1-[4-(2-morpholin-4-yl-ethoxy)-naphthalen-1-yl]-meth-(E)-ylidene]-hydrazinecarboxylic acid ethyl ester;
N-(3-Methanesulfonylamino-5-trifluoromethyl-phenyl)-2-[4(2morpholin-4-yl-ethoxy)-naphthalen-1-yl]-2-oxo-acetamide;
N-(5-tert-Butyl-2-hydroxy-3-piperidin-1-ylmethyl-phenyl)-2-[4-(2-morpholin-4-yl-ethoxy)-naphthalen-1-yl]-2-oxo-acetamide;

N-(5-tert-Butyl-2-methoxy-phenyl)-2-oxo-2-{4-[2-((S)-1-phenyl-ethylamino)-pyrimidin-4-ylamino]-naphthalen-1-yl}-acetamide;

N-[5-tert-Butyl-2-(4-cyano-phenyl)-2H-pyrazol-3-yl]-2-[4-(2-morpholin-4-yl-ethoxy)-naphthalen-1-yl]-2-oxo-acetamide;

N'-[1-(5-tert-Butyl-3-methanesulfonylamino-2-methoxy-phenylcarbamoyl)-1-[4-(2-morpholin-4-yl -ethoxy)-naphthalen-1-yl]-meth-(E)-ylidene]-hydrazinecarboxylic acid ethyl ester;

N-(5-tert-Butyl-2-methoxy-3-{2-[4-(2-morpholin-4-yl-ethoxy)-naphthalen-1-yl]-2-oxo-acetylamino}-phenyl)-isobutyramide;

N-[5-tert-Butyl-2-(4-methyl-benzoyl)-2H-pyrazol-3-yl]-2-[4-(2-morpholin-4-yl-ethoxy)-naphthalen-1-yl]-2-oxo-acetamide;

N-[5-tert-Butyl-2-(2-chloro-phenyl)-2H-pyrazol-3-yl]-2-[4-(2-morpholin-4-yl-ethoxy)-naphthalen-1-yl]-2-oxo-acetamide;

N-[5-tert-Butyl-2-(3-chloro-4-methyl-phenyl)-2H-pyrazol-3-yl]-2-[4-(2-morpholin-4-yl-ethoxy)-naphthalen-1-yl]-2-oxo-acetamide;

N-[5-tert-Butyl-2-methoxy-3-(propane-1-sulfonylamino)-phenyl]-2-[4-(2-morpholin-4-yl-pyridin-4-ylamino)-naphthalen-1-yl]-2-oxo-acetamide;

5-tert-Butyl-N-cyclopropyl-2-methoxy-3-{2-[4-(2-morpholin-4-yl-pyridin-4-ylamino)-naphthalen-1-yl]-2-oxo-acetylamino}-benzamide;

N-(5-tert-Butyl-3-methanesulfonylamino-2-methoxy-phenyl)-2-oxo-2-{4-[6-(tetrahydro-pyran-4-ylamino)-pyridin-3-yl]-naphthalen-1-yl}-acetamide;

3-[2-(4-Bromo-naphthalen-1-yl)-2-oxo-acetylamino]-5-tert-butyl-N-cyclopropyl-2-methoxy-benzamide;

N-(5-tert-Butyl-3-methanesulfonylamino-2-methoxy-phenyl)-2-[4-(6-morpholin-4-yl-pyridin-3-yl)-naphthalen-1-yl]-2-oxo-acetamide;

N-(5-tert-Butyl-2-p-tolyl-2H-pyrazol-3-yl)-2-[4-(6-morpholin-4-ylmethyl-pyridin-3-yl)-naphthalen-1-yl]-2-oxo-acetamide;

N-(5-tert-Butyl-3-methanesulfonylamino-2-methoxy-phenyl)-2-oxo-2-(4-pyridin-3-yl-naphthalen-1-yl)-acetamide; or N-(5-tert-Butyl-2-methyl-2H-pyrazol-3-yl)-2-oxo-2-(4-pyridin-3-yl-naphthalen-1-yl)-acetamide.

34. The compound or pharmaceutical salt thereof of claim 33 wherein the compound is N-(5-tert-Butyl-3-methanesulfonylamino-2-methoxy-phenyl)-2-[4-(2-morpholin-4-yl-ethoxy)-naphthalen-1-yl]-2-oxo-acetamide.

35. The compound or pharmaceutical salt thereof of claim 33 wherein the compound is N-(5-tert-Butyl-2-methoxy-phenyl)-2-[4-(2-morpholin-4-yl-ethoxy)-naphthalen-1-yl]-2-oxo-acetamide.

* * * * *